United States Patent
Krishna et al.

(10) Patent No.: US 10,933,053 B2
(45) Date of Patent: *Mar. 2, 2021

(54) TREATING INFECTIONS WITH CEFTOLOZANE/TAZOBACTAM IN SUBJECTS HAVING IMPAIRED RENAL FUNCTION

(71) Applicant: MERCK SHARP & DOHME CORP., Rahway, NJ (US)

(72) Inventors: Gopal Krishna, Stow, MA (US); Gurudatt Chandorkar, Waltham, MA (US); Elham Hershberger, Lexington, MA (US); Benjamin Miller, Cambridge, MA (US); Alan Xiao, Lexington, MA (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/525,458

(22) Filed: Jul. 29, 2019

(65) Prior Publication Data

US 2020/0093803 A1 Mar. 26, 2020

Related U.S. Application Data

(63) Continuation of application No. 14/481,496, filed on Sep. 9, 2014, now Pat. No. 10,376,496.

(60) Provisional application No. 62/046,417, filed on Sep. 5, 2014, provisional application No. 62/002,457, filed on May 23, 2014, provisional application No. 61/988,085, filed on May 2, 2014, provisional application No. 61/984,299, filed on Apr. 25, 2014, provisional application No. 61/883,579, filed on Sep. 27, 2013, provisional application No. 61/875,358, filed on Sep. 9, 2013.

(51) Int. Cl.
| | |
|---|---|
| *A61K 31/431* | (2006.01) |
| *A61K 31/546* | (2006.01) |
| *A61K 9/00* | (2006.01) |
| *A61K 47/18* | (2017.01) |
| *A61K 9/19* | (2006.01) |
| *A61K 9/08* | (2006.01) |
| *A61K 31/4164* | (2006.01) |
| *A61M 1/14* | (2006.01) |

(52) U.S. Cl.
CPC .......... *A61K 31/431* (2013.01); *A61K 9/0019* (2013.01); *A61K 9/08* (2013.01); *A61K 9/19* (2013.01); *A61K 31/4164* (2013.01); *A61K 31/546* (2013.01); *A61K 47/183* (2013.01); *A61M 1/14* (2013.01); *Y02A 50/30* (2018.01)

(58) Field of Classification Search
CPC .................................................. A61K 31/431
USPC ...................................................... 514/192
See application file for complete search history.

(56) References Cited

U.S. PATENT DOCUMENTS

| | | |
|---|---|---|
| 4,200,575 A | 4/1980 | Numata et al. |
| 4,246,405 A | 1/1981 | Takaya et al. |
| 4,255,431 A | 3/1981 | Junggren et al. |
| 4,264,597 A | 4/1981 | Hashimoto et al. |
| 4,267,176 A | 5/1981 | Kamiya et al. |
| 4,268,509 A | 5/1981 | Teraji et al. |
| 4,284,631 A | 8/1981 | Talcaya et al. |
| 4,291,031 A | 9/1981 | Talcaya et al. |
| 4,298,529 A | 11/1981 | Ueda et al. |
| 4,299,829 A | 11/1981 | Kamiya et al. |
| 4,305,937 A | 12/1981 | Kamiya et al. |
| 4,327,093 A | 4/1982 | Ueda et al. |
| 4,331,665 A | 5/1982 | Teraji et al. |
| 4,332,798 A | 6/1982 | Teraji et al. |
| 4,332,800 A | 6/1982 | Teraji et al. |
| 4,336,253 A | 6/1982 | Lunn |
| 4,338,313 A | 7/1982 | Teraji et al. |
| 4,339,449 A | 7/1982 | Hashimoto et al. |
| 4,363,807 A | 12/1982 | Takaya et al. |
| 4,367,228 A | 1/1983 | Takaya et al. |
| 4,368,325 A | 1/1983 | Ueda et al. |
| 4,369,312 A | 1/1983 | Hashimoto et al. |
| 4,370,326 A | 1/1983 | Takaya et al. |
| 4,381,299 A | 4/1983 | Teraji et al. |
| 4,390,534 A | 6/1983 | Teraji et al. |
| 4,394,384 A | 7/1983 | Takaya et al. |
| 4,402,955 A | 9/1983 | Lunn |
| 4,405,617 A | 9/1983 | Takaya et al. |
| 4,407,798 A | 10/1983 | Kamiya et al. |
| 4,409,214 A | 10/1983 | Takaya et al. |
| 4,409,215 A | 10/1983 | Takaya et al. |
| 4,409,217 A | 10/1983 | Takaya et al. |
| 4,416,879 A | 11/1983 | Takaya et al. |
| 4,418,058 A | 11/1983 | Hirai et al. |

(Continued)

FOREIGN PATENT DOCUMENTS

| | | |
|---|---|---|
| AU | 614793 | 5/1989 |
| AU | 707730 | 5/1996 |

(Continued)

OTHER PUBLICATIONS

Adnan et al., Pharmacokinetics of Beta-Lactam Antibiotics in Patients with Intra-Abdominal Disease: A Structured Review. Surgical Infections. 2012, vol. 13, No. 1, pp. 9-17.

(Continued)

*Primary Examiner* — Taofiq A Solola
(74) *Attorney, Agent, or Firm* — Dechert LLP

(57) ABSTRACT

Disclosed are methods of administering cephalosporin/tazobactam to human patients with end stage renal disease undergoing hemodialysis and suffering from a complicated intra-abdominal infection or a complicated urinary tract infection.

34 Claims, 72 Drawing Sheets

(56) References Cited

U.S. PATENT DOCUMENTS

| | | |
|---|---|---|
| 4,420,477 A | 12/1983 | Takaya et al. |
| 4,423,213 A | 12/1983 | Takaya et al. |
| 4,425,340 A | 1/1984 | Teraji et al. |
| 4,425,341 A | 1/1984 | Takaya et al. |
| 4,427,677 A | 1/1984 | Takaya et al. |
| 4,430,499 A | 2/1984 | Wheeler |
| 4,431,642 A | 2/1984 | Teraji et al. |
| 4,436,912 A | 3/1984 | Wheeler |
| 4,438,113 A | 3/1984 | Takaya et al. |
| 4,443,443 A | 4/1984 | Ueda et al. |
| 4,443,444 A | 4/1984 | Takaya et al. |
| 4,447,429 A | 5/1984 | Teraji et al. |
| 4,450,270 A | 5/1984 | Lunn |
| 4,452,851 A | 6/1984 | Takaya et al. |
| 4,457,928 A | 7/1984 | Teraji et al. |
| 4,462,999 A | 7/1984 | Takaya et al. |
| 4,463,000 A | 7/1984 | Teraji et al. |
| 4,463,002 A | 7/1984 | Takaya et al. |
| 4,463,003 A | 7/1984 | Takaya et al. |
| 4,464,369 A | 8/1984 | Takaya et al. |
| 4,470,980 A | 9/1984 | Higuchi et al. |
| 4,474,779 A | 10/1984 | Nagano et al. |
| 4,477,447 A | 10/1984 | Ueda et al. |
| 4,487,768 A | 12/1984 | Takaya et al. |
| 4,495,182 A | 1/1985 | Teraji et al. |
| 4,496,562 A | 1/1985 | Takaya et al. |
| 4,499,088 A | 2/1985 | Takaya et al. |
| 4,501,739 A | 2/1985 | Lunn et al. |
| 4,515,788 A | 5/1985 | Takaya et al. |
| 4,521,413 A | 6/1985 | Teraji et al. |
| 4,529,592 A | 7/1985 | Micetich et al. |
| 4,546,101 A | 10/1985 | Takaya et al. |
| 4,550,102 A | 10/1985 | Teraji et al. |
| 4,559,334 A | 12/1985 | Takaya et al. |
| 4,562,073 A | 12/1985 | Micetich et al. |
| 4,563,449 A | 1/1986 | Teraji et al. |
| 4,577,014 A | 3/1986 | Lunn et al. |
| 4,584,290 A | 4/1986 | Takaya et al. |
| 4,585,872 A | 4/1986 | Teraji et al. |
| 4,590,186 A | 5/1986 | Takaya et al. |
| 4,600,772 A | 7/1986 | O'Callaghan et al. |
| 4,608,373 A | 8/1986 | Shibanuma et al. |
| 4,609,730 A | 9/1986 | Takaya et al. |
| 4,616,083 A | 10/1986 | Shima et al. |
| 4,622,318 A | 11/1986 | Takaya et al. |
| 4,626,384 A | 12/1986 | Tanaka et al. |
| 4,631,274 A | 12/1986 | Takaya et al. |
| 4,640,915 A | 2/1987 | Hashimoto et al. |
| 4,647,556 A | 3/1987 | Lattrell et al. |
| 4,667,028 A | 5/1987 | Schwab et al. |
| 4,690,921 A | 9/1987 | Shibanuma et al. |
| 4,692,443 A | 9/1987 | Katner |
| 4,698,337 A | 10/1987 | Takaya et al. |
| 4,699,980 A | 10/1987 | Shibanuma et al. |
| 4,703,046 A | 10/1987 | Ueda et al. |
| 4,705,851 A | 11/1987 | Takaya et al. |
| 4,735,937 A | 4/1988 | Hensler et al. |
| 4,748,172 A | 5/1988 | Katner |
| 4,761,410 A | 8/1988 | Takaya et al. |
| 4,764,606 A | 8/1988 | Imai et al. |
| 4,769,183 A | 9/1988 | Kawamata et al. |
| 4,808,617 A | 2/1989 | Kaplan et al. |
| 4,808,711 A | 2/1989 | Shimizu et al. |
| 4,822,787 A | 4/1989 | Murata et al. |
| 4,833,134 A | 5/1989 | Kishimoto et al. |
| 4,861,769 A | 8/1989 | Takaya et al. |
| 4,868,174 A | 9/1989 | Takaya et al. |
| 4,871,730 A | 10/1989 | Takaya et al. |
| 4,882,434 A | 11/1989 | Yoshioka |
| 4,921,852 A | 5/1990 | Murata et al. |
| 4,923,857 A | 5/1990 | Murata et al. |
| 4,925,934 A | 5/1990 | Taniguchi et al. |
| 4,927,818 A | 5/1990 | Takaya et al. |
| 4,935,507 A | 6/1990 | Takaya et al. |
| 4,943,567 A | 7/1990 | Nishizawa et al. |
| 4,952,578 A | 8/1990 | Sakane et al. |
| 4,960,766 A | 10/1990 | Takaya et al. |
| 4,963,543 A | 10/1990 | Murata et al. |
| 4,963,544 A | 10/1990 | Murata et al. |
| 4,971,962 A | 11/1990 | Oh et al. |
| 4,982,596 A | 1/1991 | Peterson et al. |
| 5,036,064 A | 7/1991 | Gotschi |
| RE33,778 E | 12/1991 | Iwanami et al. |
| 5,071,979 A | 12/1991 | Lattrell et al. |
| 5,073,550 A | 12/1991 | Gotschi |
| 5,079,241 A | 1/1992 | Olliero et al. |
| 5,081,116 A | 1/1992 | Nagano et al. |
| 5,095,012 A | 3/1992 | Okita et al. |
| 5,102,877 A | 4/1992 | Murata et al. |
| 5,104,866 A | 4/1992 | Sakane et al. |
| 5,108,997 A | 4/1992 | Takaya et al. |
| 5,109,130 A | 4/1992 | Sakane et al. |
| 5,138,066 A | 8/1992 | Gotschi |
| 5,159,070 A | 10/1992 | Heymes et al. |
| 5,162,520 A | 11/1992 | Takaya et al. |
| 5,173,485 A | 12/1992 | Sakane et al. |
| 5,179,485 A | 1/1993 | Tamayama |
| 5,187,160 A | 2/1993 | Sakane et al. |
| 5,194,432 A | 3/1993 | Takaya et al. |
| 5,210,080 A | 5/1993 | Takaya et al. |
| 5,215,982 A | 6/1993 | Sakane et al. |
| 5,215,983 A | 6/1993 | Murata et al. |
| 5,219,848 A | 6/1993 | Hennequin et al. |
| 5,234,920 A | 8/1993 | Okita et al. |
| 5,244,890 A | 9/1993 | Yamanaka et al. |
| 5,281,589 A | 1/1994 | Kim et al. |
| 5,286,721 A | 2/1994 | Murata et al. |
| 5,319,140 A | 6/1994 | Gotschi |
| 5,329,002 A | 7/1994 | Albrecht et al. |
| 5,336,768 A | 8/1994 | Albrecht et al. |
| 5,366,970 A | 11/1994 | Sakane et al. |
| 5,389,627 A | 2/1995 | Kim et al. |
| 5,498,787 A | 3/1996 | Wang et al. |
| 5,523,400 A | 6/1996 | Wei et al. |
| 5,637,580 A | 6/1997 | White et al. |
| 5,646,139 A | 7/1997 | White et al. |
| 5,648,346 A | 7/1997 | White et al. |
| 5,656,623 A | 8/1997 | White et al. |
| 5,661,144 A | 8/1997 | Tsushima et al. |
| 5,663,163 A | 9/1997 | Takaya et al. |
| 5,763,603 A | 6/1998 | Trickes |
| 6,207,661 B1 | 3/2001 | Thompson et al. |
| 6,214,818 B1 | 4/2001 | Nishitani et al. |
| 6,458,950 B1 | 10/2002 | Nishitani et al. |
| 6,518,263 B1 | 2/2003 | Nishitani et al. |
| 6,660,855 B2 | 12/2003 | Shimabayashi et al. |
| 6,774,104 B1 | 8/2004 | Sawai et al. |
| 6,800,621 B2 | 10/2004 | Nishitani et al. |
| 6,878,686 B2 | 4/2005 | Marquess et al. |
| 6,936,711 B2 | 8/2005 | Deshpande et al. |
| 6,974,797 B2 | 12/2005 | Fatheree et al. |
| 6,995,138 B2 | 2/2006 | Marquess et al. |
| 7,067,481 B2 | 6/2006 | Fatheree et al. |
| 7,067,482 B2 | 6/2006 | Fatheree et al. |
| 7,112,565 B2 | 9/2006 | Sawai et al. |
| 7,129,232 B2 | 10/2006 | Ohki et al. |
| 7,179,801 B2 | 2/2007 | Ohki et al. |
| 7,192,943 B2 | 3/2007 | Yamanaka et al. |
| 7,273,935 B2 | 9/2007 | Deshpande et al. |
| 7,279,458 B2 | 10/2007 | Fatheree et al. |
| 7,304,075 B2 | 12/2007 | Araki et al. |
| 7,332,471 B2 | 2/2008 | Fatheree et al. |
| 7,341,993 B2 | 3/2008 | Fatheree et al. |
| 7,384,928 B2 | 6/2008 | Nishitani et al. |
| 7,417,143 B2 | 8/2008 | Gnanaprakasam et al. |
| 7,547,777 B2 | 6/2009 | Tokumaru et al. |
| 7,553,962 B2 | 6/2009 | Fatheree et al. |
| 7,601,690 B2 | 10/2009 | Fatheree et al. |
| 7,612,037 B2 | 11/2009 | Fatheree et al. |
| 7,649,080 B2 | 1/2010 | Fatheree et al. |
| 7,655,621 B2 | 2/2010 | Fatheree et al. |
| 7,674,898 B2 | 3/2010 | Shimabayashi et al. |
| 7,728,127 B2 | 6/2010 | Fatheree et al. |
| 7,842,683 B2 | 11/2010 | Koppel |

(56) References Cited

U.S. PATENT DOCUMENTS

| | | |
|---|---|---|
| 7,915,229 B2 | 3/2011 | Cohen et al. |
| 8,133,883 B2 | 3/2012 | Cohen et al. |
| 8,476,245 B2 | 7/2013 | Pourmotabbed et al. |
| 8,809,314 B1 | 8/2014 | He et al. |
| 9,006,421 B2 | 4/2015 | Lai et al. |
| 2002/0115650 A1 | 8/2002 | Glinka |
| 2002/0193587 A1 | 12/2002 | Shimabayashi et al. |
| 2003/0130173 A1 | 7/2003 | Fatheree et al. |
| 2003/0232983 A1 | 12/2003 | Deshpande |
| 2004/0248875 A1 | 12/2004 | Ohki et al. |
| 2005/0004094 A1 | 1/2005 | Yamanaka et al. |
| 2005/0096306 A1 | 5/2005 | Yamanaka et al. |
| 2005/0171077 A1 | 8/2005 | Ruppen et al. |
| 2005/0228176 A1 | 10/2005 | Gnanaprakasam et al. |
| 2006/0051412 A1 | 3/2006 | Petereit et al. |
| 2006/0084639 A1 | 4/2006 | Cohen et al. |
| 2006/0099253 A1 | 5/2006 | Becker et al. |
| 2006/0173177 A1 | 8/2006 | Gego et al. |
| 2006/0241017 A1 | 10/2006 | Chandran |
| 2006/0269485 A1 | 11/2006 | Friedman et al. |
| 2006/0287244 A1 | 12/2006 | Chandran |
| 2006/0293516 A1 | 12/2006 | Wada et al. |
| 2007/0054899 A1 | 3/2007 | Park et al. |
| 2007/0116770 A1 | 5/2007 | Garms et al. |
| 2007/0219191 A1 | 9/2007 | Nishitani et al. |
| 2007/0286817 A1 | 12/2007 | Tatapudy et al. |
| 2007/0286818 A1 | 12/2007 | Tatapudy et al. |
| 2008/0015156 A1 | 1/2008 | Udayampalayam Palanisamy et al. |
| 2008/0160067 A1 | 7/2008 | Boeckh et al. |
| 2008/0233196 A1 | 9/2008 | Cattaneo et al. |
| 2009/0098088 A1 | 4/2009 | Taylor et al. |
| 2009/0137460 A1 | 5/2009 | Marquess et al. |
| 2009/0155387 A1 | 6/2009 | Zhang |
| 2009/0156517 A1 | 6/2009 | Zhang |
| 2009/0156518 A1 | 6/2009 | Zhang |
| 2009/0186865 A1 | 7/2009 | Diago et al. |
| 2009/0227554 A1 | 9/2009 | Liversidge et al. |
| 2009/0274662 A1 | 11/2009 | Magowan et al. |
| 2009/0275552 A1 | 11/2009 | Patel et al. |
| 2009/0291102 A1 | 11/2009 | Fortin |
| 2009/0311234 A1 | 12/2009 | Koski et al. |
| 2010/0040548 A1 | 2/2010 | Yu |
| 2010/0286031 A1 | 11/2010 | Charan et al. |
| 2011/0044917 A1 | 2/2011 | Tosetti |
| 2011/0136763 A1 | 6/2011 | Xia et al. |
| 2011/0190252 A1 | 8/2011 | Watson et al. |
| 2011/0190254 A1 | 8/2011 | Nishitani |
| 2011/0257079 A1 | 10/2011 | Chaudhary et al. |
| 2013/0065874 A1 | 3/2013 | Chandorkar et al. |
| 2014/0187528 A1 | 7/2014 | Lai et al. |
| 2014/0262868 A1 | 9/2014 | Terracciano et al. |
| 2014/0274958 A1 | 9/2014 | Lai et al. |
| 2014/0274989 A1 | 9/2014 | Terracciano et al. |
| 2014/0274990 A1 | 9/2014 | Terracciano et al. |
| 2014/0274991 A1 | 9/2014 | Damour et al. |
| 2014/0274992 A1 | 9/2014 | Damour et al. |
| 2014/0274993 A1 | 9/2014 | Terracciano et al. |
| 2014/0274994 A1 | 9/2014 | Damour et al. |
| 2014/0274995 A1 | 9/2014 | Zhou et al. |
| 2014/0274996 A1 | 9/2014 | Damour et al. |
| 2014/0274997 A1 | 9/2014 | Zhou et al. |
| 2014/0274999 A1 | 9/2014 | Lai et al. |
| 2015/0025053 A1 | 1/2015 | He et al. |
| 2015/0072968 A1 | 3/2015 | Krishna et al. |

FOREIGN PATENT DOCUMENTS

| | | |
|---|---|---|
| AU | 2002952355 | 10/2002 |
| AU | 2003904813 | 9/2003 |
| AU | 2003905084 | 9/2003 |
| CA | 1235689 | 4/1988 |
| CA | 2140701 | 7/1995 |
| CN | 1236781 | 12/1999 |
| CN | 1763046 | 4/2006 |
| CN | 1763046 | 10/2008 |
| CN | 101434610 | 5/2009 |
| CN | 101696212 | 4/2010 |
| CN | 102020663 | 4/2011 |
| CN | 102382123 | 3/2012 |
| EP | 047977 | 9/1981 |
| EP | 0097446 | 1/1984 |
| EP | 0137440 | 4/1985 |
| EP | 0137442 | 4/1985 |
| EP | 0138552 | 4/1985 |
| EP | 0111934 | 8/1988 |
| EP | 0318767 | 6/1989 |
| EP | 0664117 | 7/1995 |
| EP | 0711774 | 5/1996 |
| EP | 0771803 | 5/1997 |
| EP | 1273586 | 1/2003 |
| EP | 1285923 | 2/2003 |
| EP | 1468697 | 10/2004 |
| EP | 1134222 | 4/2005 |
| EP | 1554287 | 7/2005 |
| EP | 1671974 | 6/2006 |
| EP | 1686131 | 8/2006 |
| EP | 1759697 | 3/2007 |
| EP | 1787641 | 5/2007 |
| EP | 1959933 | 8/2008 |
| EP | 1974721 | 10/2008 |
| EP | 2015755 | 1/2009 |
| EP | 2062581 | 5/2009 |
| EP | 2062582 | 5/2009 |
| EP | 2062585 | 5/2009 |
| EP | 2136844 | 12/2009 |
| EP | 2305251 | 4/2011 |
| EP | 1154770 | 11/2011 |
| JP | 62103092 | 5/1987 |
| JP | 62158290 | 7/1987 |
| JP | 63051388 | 3/1988 |
| JP | 63051389 | 3/1988 |
| JP | 2088582 | 3/1990 |
| JP | 2117678 | 5/1990 |
| JP | 4288086 A | 10/1992 |
| JP | 5222058 | 8/1993 |
| JP | 6056848 | 3/1994 |
| JP | 6128268 | 5/1994 |
| JP | 2005162670 | 6/2005 |
| WO | WO-1995012601 | 5/1995 |
| WO | WO-1997041128 | 11/1997 |
| WO | WO-1999028308 | 6/1999 |
| WO | WO-1999064049 | 12/1999 |
| WO | WO-2000004915 | 2/2000 |
| WO | WO-2000050035 | 8/2000 |
| WO | WO-2002090363 | 11/2002 |
| WO | WO-2002090364 | 11/2002 |
| WO | WO-2002092605 | 11/2002 |
| WO | WO-2002102378 | 12/2002 |
| WO | WO-2003066053 | 8/2003 |
| WO | WO-2003078440 | 9/2003 |
| WO | WO-2003104241 | 12/2003 |
| WO | WO-2004019901 | 3/2004 |
| WO | WO-2004039776 | 5/2004 |
| WO | WO-2004048551 | 6/2004 |
| WO | WO-2004066976 | 8/2004 |
| WO | WO-2004098643 | 11/2004 |
| WO | WO-2005005436 | 1/2005 |
| WO | WO-2005074925 | 8/2005 |
| WO | WO-2006044600 | 4/2006 |
| WO | WO-2006045006 | 4/2006 |
| WO | WO-2006088305 | 8/2006 |
| WO | WO-2007065862 | 6/2007 |
| WO | WO-2007086011 | 8/2007 |
| WO | WO-2007086013 | 8/2007 |
| WO | WO-2007086014 | 8/2007 |
| WO | WO-2007099396 | 9/2007 |
| WO | WO-2007129176 | 11/2007 |
| WO | WO-2007145866 | 12/2007 |
| WO | WO-2007145868 | 12/2007 |
| WO | WO-2008030469 | 3/2008 |
| WO | WO-2008065247 | 6/2008 |
| WO | WO-2008075207 | 6/2008 |

(56) References Cited

FOREIGN PATENT DOCUMENTS

| | | |
|---|---|---|
| WO | WO-2008101743 | 8/2008 |
| WO | WO-2008113177 | 9/2008 |
| WO | WO-2009048603 | 4/2009 |
| WO | WO-2009105782 | 8/2009 |
| WO | WO-2009122252 | 10/2009 |
| WO | WO-2009134948 | 11/2009 |
| WO | WO-2010014285 | 2/2010 |
| WO | WO-2010142241 | 12/2010 |
| WO | WO-2011101710 | 8/2011 |
| WO | WO-2011112435 | 9/2011 |
| WO | WO-2011127200 | 10/2011 |
| WO | WO-2013036783 | 3/2013 |

OTHER PUBLICATIONS

Alexov et al., Efficacy of Ampicillin-Sulbactam Is not Dependent upon Maintenance of a Critical Ratio between Components: Sulbactam Pharmacokinetics in Pharmacodynamic Interactions. Antimcirobial Agents Chemotherapy 1996;40:2468.

Ambrose et al., Pharmacokinetic-pharmacodynamic considerations in the design of hospital-acquired or ventilator—associated bacterial pneumonia studies: look before you leap!; Clin Infect Dis, 2010, vol. 51, Suppl 1, pp. 5103-S110.

American Thoracic Society; Infectious Diseases Society of America; Guidelines for the management of adults with 2 hospital-acquired, ventilator-associated, and healthcare-associated pneumonia; Am J Respir Crit Care Med., 2005, vol. 171(4), pp. 388-416.

Anderegg et al., Quality Control Guidelines for BAL9141 (Ro 63-9141), an Investigational Cephalosporin, When Reference MIC and Standardized Disk Diffusion Susceptibility Test Methods Are Used; Journal of Clinical Microbiology. (2004), pp. 3356-3358.

Arin et al., The Comparative Stability of Different Types of Penicillin and Cephalosporin N-pyrryl derivatives. Pharmazie 1988, vol. 43, pp. 18-19.

Baughman et al., The diagnosis and treatment challenges in nosocomial pneumonia; Diagn Microbiol Infect Dis, vol. 33(2), pp. 131-139.

Bergogne-Berezin, Predicting the efficacy of antimicrobial agents in respiratory infections: is tissue concentration valid measure?; J Antimicrob Chemother, 1995, vol. 35, pp. 363-371.

Boselli et al., Alveolar concentrations of piperacillin/tazobactam administered in continuous infusion to patients with—associated pneumonia; Crit Care Med, 2008, vol. 36, pp. 1500-1506.

Boselli et al., Steady-state plasma and intrapulmonary concentrations of piperacillin/tazobactam 4 g10.5 g administered to critically ill patients with severe nosocomial pneumonia; Intensive Care Med, 2004, vol. 30, pp. 976-979.

Brown et al., Activity profile of CXA-101 against gram-positive and gram-negative pathogens by broth and agar dilution. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-354; This poster is obtainable at: http://www.eurofins.com/media/694466/Calixe/020F1-354%20broth%20agar°/020v6.pdf (Abstract).

Brown et al., Activity profile of CXA-101 and CXA-101/tazobactam against target gram-positive and gram-negative pathogens. 49th Annual Interscience Conference on Antimicrobial Agents and Chemotherapy (ICAAC 2009); 12th-15th, 2009. Poster F1-1986; This poster is obtainable at: http://www.eurofins.com/media/767069/Final%20F1-1986.pdf (Abstract).

Brown et al., Disk diffusion testing of CXA-101 and CXA-101 in combination with tazobactam against target pathogens. 49th Annual Interscience Conference on Antimicrobial Agents and Chemotherapy (ICAAC 2009); 12th-15th, 2009. Poster F1-1998; This poster is obtainable at: http://www.eurofins.com/media/767072/Final%20F1-1998.pdf (Abstract).

Brown et al., Effect of various testing parameters on the activity of CXA-101 by broth microdilution. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-357; This poster is obtainable at: http://www.eurofins.com/media/694469/CW/020F1-357%20parameter%20v6.pdf (Abstract).

Brown et al., Mode of action of CXA-101 based on minimum bactericidal concentration analysis and time-kill kinetic analysis. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-358; This poster is obtainable at: http://www.eurofins.com/media/694472/CXA%20F1-358°/020tV/020mbe/020v5.pdf (Abstract).

Brown et al., Quality control parameters for CXA-101 broth microdilution susceptibility tests. 49th Annual Interscience Conference on Antimicrobial Agents and Chemotherapy (ICAAC 2009); Sep. 12-15, 2009. Poster F1-1997 (Abstract).

Brown et al., Synthesis and Biological Evaluation of a Series of Parental 3'-Quaternary Ammonium Cephalosporins.sup.1 Journal of Medicinal Chemistry. 1990, vol. 33, No. 8, pp. 2114-2121.

Bulik et al., In vitro activity of CXA-101, a novel cephalosporin, against resistant phenotypes of Pseudomonas aeruginosa. 47th Annual Meeting of the Infectious Diseases Society (IDSA 2009); Oct. 29-Nov. 1, 2009; Philadelphia, PA. Poster 209. (Abstract).

Bulik et al., In vitro potency of CXA-101, a novel cephalosporin, against Pseudomonas aeruginosa displaying various resistance phenotypes, including multidrug resistance. Antimicrob Agents Chemother. 2010;54(1):557-9.

Bulik et al., In vivo Comparison of CXA-101 (FR264205) with and without Tazobactam verus Piperacillin-Tazobactam Using Human Simulated Exposures against Phenotypically Diverse Gram-Negative Organisms. ICAAC 2010. Poster A1-1381; This poster is obtainable at: http://www.cubist.com/downloads/Bulik_PP_ICAAC_2010_in_vivo_CXA-101_vs_TZP_against_gram_neg.pdf (Abstract).

Bulik et al., In vivo comparison of CXA-101 with and without tazobactam versus piperacillin-tazobactam using human simulated exposures against phenotypically diverse gram-negative organisms. Antimicrobial Agents and Chemotherapy 2012, 56(1):544-9.

Bush et al., Kinetic Interactions of Tazobactam with Beta-Lactamases from All Major Structural Classes. Antimicrobial Agents and Chemotherapy 1993;37:851.

Cabot et al., Activity of CXA-101 Against a Large Collection of P. aeruginosa Blood Stream Isolates Overexpressing AmpC and the Major Efflux Pumps. 50th Annual Interscience Conference on Antimicrobial Agents and Chemotherapy (ICAAC 2010); Sep. 12-15, 2010. Poster E-816 (Abstract).

Cabot et al., Dynamics and mechanisms of resistance development to ceftazidime, meropenem and ceftolozane-/tazobactam in wild-type and mutator P. aeruginosa strains. 52nd Annual Interscience Conference on Antimicrobial Agents and Chemotherapy (ICAAC 2012); Sep. 9-12, 2012; San Francisco, CA. Poster C1-1970. (Abstract).

Cabot et al., Pseudomonas aeruginosa Ceftolozane/Tazobactam Resistance Development Requires Multiple Mutations Leading to Overexpression and Structural Modification of AmpC. 53rd Annual Interscience Conference on Antimicrobial Agents and Chemotherapy (ICAAC 2013); Sep. 10-13, 2013; Denver, CO. Poster C1-060. (Abstract).

Cabot et al., Pseudomonas aeruginosa Ceftolozane-Tazobactam Resistance Development Requires Multiple Mutations Leading to Overexpression and Structural Modification of AmpC. Antimicrob Agents Chemother. Mar. 17, 2014. [Epub ahead of print] PubMed PMID: 24637685.

Cefazolin, (For Injection USP) Approved Dec. 1988, Product Label, B. Braun Medical Inc. Revised Jan. 2012.

Ceftazidime, (Systemic) Approved Nov. 1985, Product Label. American Society of Health-System Pharmacists Inc. 2004.

Chandorkar et al., Intrapulmonary penetration of ceftolozaneltazobactam and piperacillin/tazobactam in healthy adult subjects. J Antimicrob Chemother. 2012, 67, 2463-2469.

Chandorkar et al., Intrapulmonary penetration of CXA-201 and Piperacillin/tazobactam in healthy adult subjects. 49th Annual Meeting of the Infectious Diseases Society of America (IDSA 2011); Oct. 20-23, 2011. Poster 611 (Abstract).

(56) References Cited

OTHER PUBLICATIONS

Chandorkar et al., Penetration of Ceftolozane/Tazobactam and Piperacillinffazobactam into the Epithelial lining of Fluid of Healthy Volunteers. 22nd Annual Meeting of the European Congress of Clinical Microbiology (ECCMID 2012); Mar. 31-Apr. 3, 2012. Poster P1627 (Abstract).

Chandorkar et al., Pharmacokinetics and Safety of Ceftolozane/ Tazobactam in Subjects with Severe Renal Impairment or End Stage Renal Disease on Hemodialysis. To be presented at the 2nd Annual IDWeek (IDWeek 2013); Oct. 2-6, 2013; San Francisco, CA. Poster #723. (Abstract).

Chandorkar et al., Population Pharmacokinetics Analysis of Ceftolozane/ Tazobactam in Healthy Volunteers and Patients. Presented at the Annual Meeting of the American College of Clinical Pharmacy (ACCP 2013); Oct. 13-16, 2013; Albuquerque, NM. Poster # 120. (Abstract).

Chandorkar et al., Target Attainment Rates (TAR) and Cumulative Fraction of Response (CFR) in Plasma for Ceftolozane in a Simulated Population of Patients with Complicated Intra-abdominal (cIAI) and Urinary Tract Infection (cUTI). 23rd Annual Meeting of the European Congress of Clinical Microbiology (ECCMID 2013); Apr. 27-30, 2013; Berlin, Germany. Poster P2742. (Abstract).

Chastre et al., Comparison of 8 vs 15 days of antibiotic therapy for ventilator-associated pneumonia in adults: a randomized trial; JAMA, 2003, vol. 290(19), pp. 2588-2598.

Chastre et al., Ventilator-associated pneumonia; Am J Respir Crit Care Med, 2002, vol. 165(7), pp. 867-903.

Claforan, (Sterile- Cefotaxime for injection, USP & Injection-Cefotaxime injection) Approved Prior to Jan. 1982, Product Label. Sanofi-Aventis U.S. LLC 2011.

Clinical and Laboratory Standards Institute CLSI Document M07-A9.

Clinical and Laboratory Standards Institute CLSI Document M100-S22.

Cockcroft et al., Prediction of Creatinine Clearance from Serum Creatinine. Nephron. 1976, vol. 16, No. 1, pp. 31-41.

Committee for Medicinal Products for Human Use (CHMP). Guideline on reporting the results of population pharmacokinetic analyses. European Medicines Agency Web site. http://www.ema.europa.eu/docs/en_GB/document_library/Scientific_guideline/2009/09/WC500003067.pdf. Accessed May 29, 2014.

Concordet et al., Population PK/PD analysis. New York, NY: Marcel Dekker, Inc; 2004.

Coque et al., Teresa M. Dissemination of Clonally Related *Escherichia coli* Strains Expressing Extended-Spectrum β-Lactamase CTX-M-15-Emerging Infectious Disease journal-CDC, 2008. vol. 14, No. 2, pp. 195-200.

Craig et al., In Vivo Activities of Ceftolozane, a New Cephalosporin, with and without Tazobactam against Pseudomonas aeruginosa and Enterobacteriaceae, Including Strains with Extended Spectrum Beta-Lactamases, in the Thighs of Neutropenic Mice, Animicrobial Agents and Chemotherapy, (Apr. 2013) vol. 57 No. 4, pp. 1577-1582.

Craig et al., In vivo activity of CXA-101 plus a 2:1, 4:1, or 8:1 ratio of tazobactam against various Enterobacteriaceae producing Extended-spectrum beta-lactamases in the thighs of neutropenic mice. 49th Annual Interscience Conference on Antimicrobial Agents and Chemotherapy (ICAAC 2009); Sep. 12-15, 2009. Poster F1-1999 (Abstract).

Craig et al., In vivo activity of CXA-101, a new cephalosporin, against Pseudomonas aeruginosa and other Enterobacteriaceae in the thighs of neutropenic mice. 49th Annual Interscience Conference on Antimicrobial Agents and Chemotherapy (ICAAC 2009); Sep. 12-15, 2009. Poster F1-2002 (Abstract).

Cubist Pharmaceuticals, Cubist Announces Positive Results from Two Phase 2 Trials, CXA-201 and CDAD Program. Cubist Press Release. Jun. 2011.

Doribax, Approved Oct. 2007, Product Label. Ortho-McNeil-Janssen Pharmaceuticals, Inc. 2007.

El Solh et al., Update on the treatment of Pseudomonas aeruginosa pneumonia; J Antimicrob Chemother, 2009, vol. 64, pp. 229-238.

Estabrook et al., In vitro Activity of CXA-201 (Ceftolozane-Tazobactam) Against 200 CTX M-Producing *Escherichia coli* Clinical Isolates. 53rd Annual Interscience Conference on Antimicrobial Agents and Chemotherapy (ICAAC 2013); Sep. 10-13, 2013; Denver, CO. Poster E-1169. (Abstract).

European Committee on Antimicrobial Susceptibility Testing 2012.

Farrell et al., Antimicrobial Activity of Ceftolozane-Tazobactam Tested against Enterobacteriaceae with Various Resistance Patterns Isolated in U.S. Hospitals; Antimicrobial Agents and Chemotherapy; (2013) vol. 57 No. 12 pp. 6305-6310.

Fenneteau et al., Population PK/PD Modeling and Simulations of a Fixed-Dose Combination of CXA-101 and Tazobactam to Optimize Dosing Strategies in Renally Impaired Patients with Complicated Urinary Tract Infection. 3rd Biennial American Conference on Pharmacometrics (ACoP 2011); Apr. 3-6, 2011; This poster is obtainable at: http://www.go-acop.org/sites/default/files/webform/posters/ACOP2011%20-%20Dosing%20Strategies%20of%20CXA-101%20and%20Taz%20in%20cUTI%20Patients.pdf (Abstract).

Fiaccadori et al., Does haemodialysis significantly affect serum linezolid concentrations in critically ill patients with renal failure? A pilot investigation. Nephrology Dialysis Transplantation 21.5 (2006): 1402-1406.

Fortaz, (ceftazidime for Injection) (Ceftazidime Injection) Approved Jul. 1985, Product Label. GlaxoSmithKline 2007.

Freeman et al., Once-Daily Dosing of Aminoglycosides: Review and Recommendations for Clinical Practice. Journal of Antimicrobial Chemotherapy. 1997, vol. 39, No. 6, pp. 677-686.

Freire et al., Comparison of tigecycline with imipenem/cilastatin for the treatment of hospital-acquired penumonia; Diag Microbio and Infec Dis, 2010, vol. 68, pp. 140-151.

Ge et al., CXA-101 population PK analysis and Monte Carlo simulation for PK/PD target attainment and dose regimen selection. 49th Annual Interscience Conference on Antimicrobial Agents and Chemotherapy (ICAAC 2009); Sep. 12-15, 2009. Poster F1-2003 (Abstract).

Ge et al., Pharmacokinetics (PK) and safety of CXA-101, a new anti-pseudomonal cephalosporin, in healthy adult subjects after single intravenous dosing. 49th Annual Interscience Conference on Antimicrobial Agents and Chemotherapy (ICAAC 2009); Sep. 12-15, 2009. Poster F1-2004 (Abstract).

Ge et al., Pharmacokinetics (PK) study of CXA-101 in combination with tazobactam in dogs after intravenous administration. 49th Annual Interscience Conference on Antimicrobial Agents and Chemotherapy (ICAAC 2009); Sep. 12-15, 2009. Poster F1-2001 (Abstract).

Ge et al., Pharmacokinetics and safety of CXA-101, a new antipseudomonal cephalosporin, in healthy adult male and female subjects receiving single- and multiple-dose intravenous infusions. Antimicrob Agents Chemother. 2010 vol. 54, No. 8, pp. 3427-3431.

Giske et al., Activity of Cephalosporin CXA-101 and Comparators against Extended-spectrum-beta-lactamase—producing Pseudomonas aeruginosa. Journal of Antimicrobial Chemotherapy 2009, vol. 64, No. 2, pp. 430-431.

Giske et al., CXA-101 (CXA) has high activity against clinical isolates of Pseudomonas aeruginosa including ceftazidime-resistant isolates. 49th Annual Interscience Conference on Antimicrobial Agents and Chemotherapy (ICAAC 2009); Sep. 12-15, 2009. Poster F1-1988 (Abstract).

Goncalves-Pereira et al., Antibiotics in Critically Ill Patients: A Systematic Review of the Pharmacokinetics of Beta-lactams. Crit. Care. 2011, vol. 15, No. 5, pp. 1-17.

Guidance for Industry Pharmacokinetics in Patients with Impaired Renal Function—Study Design, Data Analysis, and Impact on Dosing and Labeling. Updated May 1998. Accessed Online Mar. 15, 2016 http://www.fda.gov/downloads/Drugs/GuidanceComplianceRegulatoryInformation/Guidances/ucm072127.pdf.

Halimi et al., Comparative Evaluation of Ceftolozane/tazobactam MIC testing with Etest® and CLSI Broth Microdilution Methods. 23rd Annual Meeting of the European Congress of Clinical Microbiology (ECCMID 2013); Apr. 27-30, 2013; Berlin, Germany. Poster P1606. (Abstract).

(56) References Cited

OTHER PUBLICATIONS

Harrisons Principles of Internal Medicine: Hospital-Acquired (Nosocomial) Pneumonia; ed. Kasper, et al.; 16th ed. New York: McGraw-Hill, Medical Pub. Division. 2005, pp. 1538-1541.

Hatano et al., In vivo Anti-Pseudomonas Aeruginosa Activity of Novel Parenteral Cephalosporin, FR264205. 45th Annual Interscience Conference on Antimicrobial Agents and Chemotherapy (ICAAC 2005); Dec. 16-19, 2005. Oral Presentation F-1165.

Hayakawa et al., Epidemiology and Risk Factors for Isolation of *Escherichia coli* Producing CTX-M-Type Extended-Spectrum Beta-Lactamase in a Large U.S. Medical Center. Antimicrob Agents Chemother. 2013 vol. 57, No. 8, pp. 4010-4018.

Hershberger et al., CXA-101/Tazobactam Probability of Target Attainment Using Population Pharmacokinetic Analysis. Joint Meeting of the European Congress of Clinical Microbiology and Infectious Diseases and International Congress of Chemotherapy (ECCMID-ICC 2011); May 7-12, 2011. Poster 1520; This poster is obtainable at: http://www.poster-submission.com/search/sresult (Abstract).

Hershberger et al., Pharmacokinetics of CXA-101/tazobactam in Subjects with Mild or Moderate Renal Impairment. Joint Meeting of the European Congress of Clinical Microbiology and Infectious Diseases and International Congress of Chemotherapy (ECCMID-ICC 2011); May 7-12, 2011. Poster 1519; This poster is obtainable at: http://www.poster-submission.com (Abstract).

Hong et al., Ceftolozane/tazobactam: a novel antipseudomondal cephalosporin and betalactamase-inhibitor combination, Infection and Drug Resistance, 2013 vol. 29, No. 6, pp. 215-223.

International Preliminary Report on Patentability for PCT/US2012/054191, dated Mar. 12, 2014, 8 pages.

International Search Report and Written Opinion of the International Searching Authority for Application No. PCT/US2014/054757, dated Nov. 13, 2014, 10 pages.

International Search Report for PCT/US2012/054191, dated Feb. 20, 2013, 4 pages.

Jacqueline et al., 50% effective dose determination of CXA-101 alone or in combination with tazobactam for treating experimental peritonitis in mice due to extended-spectrum beta-lactamase-producing *Escherichia coli* strains: comparison with ceftazidime and piperacillin/tazobactam. 49th Annual Interscience Conference on Antimicrobial Agents and Chemotherapy (ICAAC 2009); Sep. 12-15, 2009. Poster F1-2000 (Abstract).

Jacqueline et al., Assessment of the in vivo Activity of CXA-101 in a Murine Model of Pseudomonas aeruginosa Pneumonia: Comparison with Ceftazidime and Piperacillin-Tazobactam. 50th Annual Interscience Conference on Antimicrobial Agents and Chemotherapy (ICAAC 2010); Sep. 12-15, 2010. Poster B-1401 (Abstract).

Jacqueline et al., ED50 Determination of CXA-101 Alone and in Combination with Tazobactam for Treating Experimental Peritonitis in Mice Due to ESBL-Producing Klebsiella pneumoniae strains: Comparison with Ceftazidime and Piperacillinffazobactam. 50th Annual Interscience Conference on Antimicrobial Agents and Chemotherapy (ICAAC 2010); Sep. 12-15, 2010; Boston, MA. Poster B-708. (Abstract).

Jacqueline et al., Efficacy of Ceftolozane in a Murine Model of Pseudomonas aeruginosa acute pneumonia: in vivo Antimicrobial Activity and Impact on Host Inflammatory Response. Journal of Antimicrobial Chemotherapy 2012, vol. 68, No. 1, pp. 1-7.

Jacqueline et al., Efficacy of ceftolozane in a murine model of Pseudomonas aeruginosa acute pneumonia: in vivo antimicrobial activity and impact on host inflammatory response. J Antimicrob Chemother. 2013 vol. 63, No. 1, pp. 177-183.

Jacqueline et al., FIC Index determination of CXA-101/tazobactam in combination with amikacin, aztreonam, meropenem, levofloxacin, and tigecycline against *Escherichia coli*, Klebsiella pneumoniae, and Pseudomonas aeruginosa strains. 49th Animal Interscience Conference on Antimicrobial Agents and Chemotherapy (ICAAC 2009); Sep. 12-15, 2009. Poster F1-1995 (Abstract).

Jacqueline et al., In vitro assessment using time-kill curves of CXA-101/tazobactam against *Escherichia coli*, Klebsiella pneumoniae, and Pseudomonas aeruginosa strains. 49th Annual Interscience Conference on Antimicrobial Agents and Chemotherapy (ICAAC 2009); Sep. 12-15, 2009. Poster F1-1996 (Abstract).

Jacqueline et al., In vivo Activity of CXA-101 against Pseudomonas aeruginosa in a Rabbit Experimental Pneumonia: Comparison with Ceftazidime Piperacillin-Tazobactam and Imipenem. 51st Annual Interscience Conference on Antimicrobial Agents and Chemotherapy (ICAAC 2011); Sep. 17-20, 2011; Chicago, IL. Poster B-590. (Abstract).

Jones et al., Microbial etiologies of hospital-acquired bacterial pneumonia and ventilator-associated bacterial pneumonia; Clin Infect Dis; 2010, Suppl 1, pp. S81-S87.

Joseph et al., Ventilator-associated pneumonia: A Review; EurJ Intern Med; 2010, vol. 21(5), pp. 360-368.

Juan et al., Activity of a new antipseudomonal cephalosporin, CXA-101, against carbapenem-resistant and multidrugresistant Pseudomonas aeruginosa clinical strains. Antimicrob Agents Chemother. 2010, vol. 54, No. 2, pp. 846-851.

Juan et al., Activity of the new cephalosporin CXA-101 against carbapenem-resistant Pseudomonas aeruginosa isolates from a Spanish multicenter study. 49th Annual Interscience Conference on Antimicrobial Agents and Chemotherapy (ICAAC 2009); Sep. 12-15, 2009. Poster F1-1987 (Abstract).

Killian et al., An Equivalency Study of a Sensititre Dried MIC Plate Compared with the CLSI Broth Microdilution Reference Method for CXA-201 and Comparator Antimicrobials. 51st Annual Interscience Conference on Antimicrobial Agents and Chemotherapy (ICAAC 2011); Sep. 17-20, 2011. Poster D-691A (Abstract).

Klevens, et al., Estimating health care-associated infections and deaths in U.S. hospitals, 2002; Public Health Rep, 2007, vol. 122, pp. 160-166.

Knaus et al., APACHE II: A severity of disease classification system; Crit Care Med, 1985, vol. 13, pp. 818-829.

Komuro et al., Inhibition of the renal excretion of tazobactam by piperacillin; J Antimicrob Chemother, 1994, vol. 34, pp. 555-564.

Kurpiel et al., Point Mutations in the inc Antisense RNA Gene Are Associated with Increased Plasmid Copy Number, Expression of BlaCMY-2 and Resistance to Piperacillinffazobactam in *Escherichia coli*. Journal of Antimicrobial Chemotherapy 2012;67:339.

Lister et al., Importance of Beta-Lactamase Inhibitor Pharmacokinetics in the Pharmacodynamics of Inhibitor-Drug Combinations: Studies with Piperacillin-Tazobactam and Piperacillin-sulbactam. Antimicrobial Agents and Chemotherapy 1997;41:721.

Livermore et al., Activity of Cephalosporin CXA-101 against Pseudomonas aeruginosa and Burkholderia cepacia strains and Isolates. International Journal of Antimicrobial Agents 2009, vol. 34, No. 5, pp. 402-406.

Livermore et al., Chequerboard titration of cephalosporin CXA-101 and tazobactam versus beta-lactamase-producing Enterobacteriaceae. J Antimicrob Chemother. 2010 65 1972-4.

Livermore et al., Chequerboard titrations of cephalosporin CXA-101 and tazobactam vs. betalactamase producing Enterobacteriaceae. 49th Annual Interscience Conference on Antimicrobial Agents and Chemotherapy (ICAAC 2009); Sep. 12-15, 2009; San Francisco, CA. Poster F1-1994. (Abstract).

Louie et al., Pharmacodynamics of Beta-Lactamase Inhibition by NXL104 in Combination with Cefaroline: Examining Organisms with Multiple Types of b-Lacramases. Antimicrobial Agents and Chemotherapy. 2012, 56, 258.

Lucasti et al., A Multicenter, Double-Blind, Randomized, Phase 2 Study to Assess the Safety and Efficacy of Ceftolozane/Tazobactam (TOUTAZ) plus Metronidazole (MTZ) Compared to Meropenem (MER) in Adult Patients with Complicated Intra-abdominal Infections (c1A1). 53rd Annual Interscience Conference on Antimicrobial Agents and Chemotherapy (ICAAC 2013); Sep. 10-13, 2013; Denver, CO. Poster K-1709. (Abstract).

Lucasti, A Phase 3, Randomized, Double-Blind Study of Ceftobiprole Medocaril Versus Linezolid Plus Ceftazidime in the Treatment of Nosocomial Pneumonia; Ceftobiprole: Clinical Study Report Synopsis BAP00248/307; Issue Date: Jul. 14, 2010; Document No. EDMS-PSDB-6906024:3.0, (8 pages).

Marier et al., Pharmacokinetics of a novel anti-pseudomonal cephalosporin, CXA-101, and tazobactam in healthy adult subjects.

(56) References Cited

OTHER PUBLICATIONS

50th Annual Interscience Conference on Antimicrobial Agents and Chemotherapy (ICAAC 2010); Sep. 12-15, 2010. Poster A1-1391 (Abstract).

Marier et al., Population PK Analysis of Intravenous CXA-101 in Subjects with Complicated Urinary Tract Infection, Including Pyelonephritis. 112th Annual Meeting of the American Society for Clinical Pharmacology and Therapeutics (ASCPT 2011); Mar. 2-5, 2011. Poster PII-49 (Abstract).

Marunaka et al., Degradation of beta-lactamase inhibitor, (2S,3R,5S)-3-methyl-7-oxo-3-(1H-1,2,3-triazol-1-yl-methyl)-4-thia-1-azabicyclo[3.2.0]heptane-2-carboxylic acid 4,,4-dioxide (YTR-830H), in Aqueous Solutions and Alkaline MEthanol Solution: Pathway and Structural Elucidation of Products; Chem. Pharm. Bull.; 1988, vol. 36, pp. 4478-4487.

Matsushima et al., Degradation of beta-lactamase inhibitor, (2S,3R,5S)-3-methyl-7-oxo-3-(1H-1,2,3-triazol-1-yl-methyl)-4-thia-1-azabicyclo[3.2.0]heptane-2-carboxylic acid 4,,4-dioxide (YTR-830H) in Solid State: Structural Eldcidation; Chem. Pharm. Bull.; 1988, vol. 36, pp. 4593-4596.

Maxipime, (Cefepime Hydrochloride, USP) Approved Jan. 1996, Product Label. Bristol-Myers Squibb Company, Revised Mar. 2009.

McKindley et al., Chapter 41: Drug Use in the Critically Ill Patient with Renal Dysfunction-Application of the DREM System, in Infectious Diseases in Critical Care Medicine (DTX-355). Copyright 1998.

McKindley et al., Drug Use in the Critically III Patient with Renal Dysfunction: Application of the DREM System. Infectious Diseases in Critical Care Medicine. 1998, Ch. 41, pp. 781-801.

Melchers et al., In vitro Activity of Ceftolozane Alone and in Combination With Tazobactam Against Extended Spectrum Beta-lactamase Harbouring Enterobacteriaceae. 52nd Annual Interscience Conference on Antimicrobial Agents and Chemotherapy (ICAAC 2012); Sep. 9-12, 2012; San Francisco, CA. Poster E-198. (Abstract).

Melchers et al., Pharmacodynamics of Ceftolozane Combined with Tazobactam in a Neutropenic Mouse Thigh Model. 53rd Annual Interscience Conference on Antimicrobial Agents and Chemotherapy (ICAAC 2013); Sep. 10-13, 2013; Denver, CO. Poster A1034. (Abstract).

Melchers et al., Pharmacokinetics of Tazobactam and Ceftolozane Alone and in Combination in Mice. 53rd Annual Interscience Conference on Antimicrobial Agents and Chemotherapy (ICAAC 2013); Sep. 10-13, 2013; Denver, CO. Poster A-1033. (Abstract).

Mesaros et al., Pseudomonas aeruginosa: resistance and therapeutic options at the turn of the new millennium; Clin Microbiol Infect, 2007, vol. 13, pp. 560-578.

Miller et al., CXA-201 dose selection based on probability of target attainment and drug exposure in subjects with varying degrees of renal impairment. 51st Annual Interscience Conference on Antimicrobial Agents and Chemotherapy (ICAAC 2011); Sep. 17-20, 2011; Chicago, IL. Oral Presentation A-1099.

Miller et al., Pharmacokinetics and Safety of Intravenous Ceftolozane-Tazobactam in Healthy Adult Subjects following Single and Multiple Ascending Doses. Antimicrobial Agents and Chemotherapy. 2012. vol. 56, No. 6, pp. 3086-3091.

Miller et al., Probability of Target Attainment (PTA) of CXA-201 in Patients with Renal Hyperclearance. 49th Annual Meeting of the Infectious Diseases Society of America (IDSA 2011); Oct. 20-23, 2011. Poster B1-589 (Abstract).

Miller et al., Safety and Pharmacokinetics (PK) of Intravenous Ceftolozane/tazobactam 3 g every 8 Hours and Cumulative Fraction of Response in Plasma and Epithelial Lining Fluid in a Simulated Ventilator Associated Pneumonia Population. 52nd Annual Interscience Conference on Antimicrobia Agents and Chemotherapy (ICAAC 2012); Sep. 9-12, 2012. Poster A-641 (Abstract).

Moulds et al., Impact of characterized resistance mechanisms on the susceptibility of Pseudomonas aeruginosa to CXA-101. 50th Annual Interscience Conference on Antimicrobial Agents and Chemotherapy (ICAAC Sep. 12-15, 2010. Poster C1-1415; This poster is obtainable at: http://www.cubist.com/downloads/Moulds.PP.ICAAC_2010.Impact_ofresis_mech_on_suscep_of_P_aeruginosa_to_CXA_JNS.pdf (Abstract).

Moya et al., Activity of a new cephalosporin, CXA-101 (FR264205), against beta-lactam-resistant Pseudomonas aeruginosa mutants selected in vitro and after antipseudomonal treatment of intensive care unit patients. Antimicrob Agents Chemother. 2010 ;54(3):1213-7.

Moya et al., Activity of CXA-101 against Pseudomonas aeruginosa beta-lactam resistance mechanisms: ampD, ampDh2, ampDh2, dacB, and oprD mutations. 49th Animal Interscience Conference on Antimicrobial Agents and Chemotherapy (ICAAC 2009); Sep. 12-15, 2009; San Francisco, CA. Poster F1-1989. (Abstract).

Moya et al., Affinity of the new cephalosporin CXA-101 to penicillin-binding proteins of Pseudomonas aeruginosa. 49th Annual Interscience Conference on Antimicrobial Agents and Chemotherapy (ICAAC 2009); Sep. 12-15, 2009. Poster F1-1985 (Abstract).

Moya et al., Affinity of the New Cephalosporin CXA-101 to Penicillin-Binding Proteins of Pseudomonas aeruginosa Antimicrob Agents Chemother. 2010; 54: 3933-3937.

Moya et al., Pan-Beta-lactam resistance development in P. aeruginosa clinical strains: molecular mechanisms, PBPs profiles and binding affinities. 51st Annual Interscience Conference on Antimicrobial Agents and Chemotherapy (ICAAC 2011); Sep. 17-20, 2011. Poster C1-619 (Abstract).

Moya et al., Pan-Beta-Lactam Resistance Development in Pseudomonas aeruginosa Clinical Strains: Molecular Mechanisms, Penicillin-Binding Protein Profiles, and Binding Affinities. Antimicrob Agents Chemother. 2012 56 4771-8.

Murano et al., Structural requirements for the stability of novel cephalosporins to AmpC beta-lactamase based on 3-D structure; Bioorg. Med. Chem. Lett.; 2007, vol. 16, pp. 2261-2275.

Mushtaq et al., Activity of cephalosporin CXA-101 (FR264205) vs. Pseudomonas aeruginosa. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-355; This poster is obtainable at: http://www.hpa.org.uk/webdHPAwebFile/HPAweb_C/1225354148015 (Abstract).

Mushtaq et al., Activity of cephalosporin CXA-101 (FR264205) with B-lactamase inhibitors vs. Enterobacteriaceae. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-356; This poster is obtainable at: http://www.hpa.org.uk/webc/HPAwebFile/HPAweb_C/1225354148047 (Abstract).

Mutschler et al., Chapter 2: Pharmacokinetics in Drug Actions: Basic Principles and Therapeutic Aspects. Medpharm Scientific Publishers, Stuttgart, Germany p. 5-47 (DTX-371). Copyright 1995.

Nicasio et al., Pharmacokinetics-Pharmacodynamics of Tazobactam (TAZ) in Combination with Piperacillin (PIP) in an In Vitro Infection Model (IVIM). 53rd Annual Interscience Conference on Antimicrobial Agents and Chemotherapy (ICAAC 2013); Sep. 10-13, 2013; Denver, CO. Oral Presentation.

Noel et al., Pharmacodynamics of Ceftolozane/Tazobactam Against Gram Negative Bacilli. 53rd Annual Interscience Conference on Antimicrobial Agents and Chemotherapy (ICAAC 2013); Sep. 10-13, 2013; Denver, CO. Poster. (Abstract).

Non-Final Office Action issued for U.S. Appl. No. 14/214,234, dated Jul. 7, 2014 (16 pages).

Occhipinti et al., Pharmacokinetics and pharmacodynamics of two multiple-dose piperacillin-tazobactam regimens; Antimicrob Agents Chemother, 1997, vol. 41, pp. 2511-2517.

Office Action of the United States Patent and Trademark Office, U.S. Appl. No. 14/020,212, dated Apr. 6, 2015, 19 pages.

Office Action of the United States Patent and Trademark Office, U.S. Appl. No. 14/211,216, dated Mar. 17, 2015, 14 pages.

Office Action of the United States Patent and Trademark Office, U.S. Appl. No. 14/211,229, dated Jul. 30, 2015, 15 pages.

Office Action of the United States Patent and Trademark Office, U.S. Appl. No. 14/286,392, dated Dec. 29, 2014, 10 pages.

(56) References Cited

OTHER PUBLICATIONS

Pai et al. Identification of CTX-M-14 extended-spectrum β-lactamase in clinical isolates of Shigella sonnei, *Escherichia coli*, and Klebsiella pneumoniae in Korea Journal of clinical microbiology 39.10 (2001), pp. 3747-3749.

Pankey, Tigecycline; J Antimicrob Chemotherapy, 2005, vol. 56, pp. 470-480.

Patent Examination Report No. 1 issued for Australian Application No. 2014233637, dated Apr. 10, 2015 (8 pages).

Pea et al., The antimicrobial therapy puzzle: could pharmacokinetic-pharmacodynamic relationships be helpful in addressing the issue of appropriate pneumonia treatment in critically ill patients?; Clin Infect Dis, 2006, vol. 42, pp, 1764-1771.

Perletti et al., CXA-101—Cephalosporin Antibiotic. Drugs of the Future 2010; 35(12): 977-986.

Reynolds et al., Enterobacteriaceae in the UK and Ireland: Susceptibility to Old and New Agents. 52nd Annual Interscience Conference on Antimicrobial Agents and Chemotherapy (ICAAC 2012); Sep. 9-12, 2012; San Francisco, CA. Poster C2-152. (Abstract).

Reynolds et al., Pseudomonas aeruginosa in the UK and Ireland: Susceptibility to Old and New Agents. 23rd Annual Meeting of the European Congress of Clinical Microbiology (ECCMID 2013); Ap. 27-30, 2013; Berlin, Germany Poster P1519. (Abstract).

Richards et al., Nosocomial infections in medical intensive care units in the United States National Nosocomial Infections Surveillance System; Crit Care Med, 1999, vo. 27(5), pp. 887-892.

Riera et al., Activity of the new cephalosporin CXA-101 against biofilms of relevant P. aurginosa (PA) phenotypes in cystic fibrosis chronic respiratory infection: mucoid and hypermutable strains. 49th Annual Interscience Conference on Antimicrobial Agents and Chemotherapy (ICAAC 2009); Sep. 12-15, 2009. Poster F1-1990 (Abstract).

Riera et al., Anti-biofilm and resistance suppression activities of CXA-101 against chronic respiratory infection phenotypes of Pseudomonas aeruginosa strain PAO1. J Antimicrob Chemother. 2010;65(7):1399-1404.

Rocephin, (Ceftiaxone Sodium) Approved Aug. 1993, Product Label. Roche Laboratories, Copyright 1998.

Rotschafer et al., Therapeutic Update on Glycopeptide and Lipopeptide Antibiotics Pharmacotherapy. 1988, vol. 8, No. 4, pp. 211-219.

Sader et al., Activity of the Novel Antimicrobial Ceftolozane/Tazobactam Tested Against Bacterial Isolates in USA Hospitals from Patients with Pneumonia (2011). IDWeek 2012: A Joint Meeting of IDSA, SHEA, HIVMA, and PIDS; Oct. 17-21, 2012. Poster 846; This poster is obtainable at: http://www.jmilabs.com/data/posters/IDWeek2012/846.Pdf (Abstract).

Sader et al., Activity of the Novel Antimicrobial Ceftolozane/Tazobactam (CXA-201) Tested Against Contemporary Clinical Strains from European Hospitals. 22nd Annual Meeting of the European Congress of Clinical Microbiology (ECCMID 2012); Mar. 31-Apr. 3, 2012. Poster P1446 (Abstract).

Sader et al., Activity of the Novel Antimicrobial Ceftolozanef-fazobactam Tested Against Contemporary Clinical Strains from USA Hospitals (2011). 52nd Annual Interscience Conference on Antimicrobial Agents and Chemotherapy (ICAAC 2012); Sep. 9-12, 2012. Poster E-199 (Abstract).

Sader et al., Activity of the novel cephalosporin CXA-101 tested in combination with tazobactam against cephalosporin-resistant Enterobacteriaceae, P. aeruginosa and B. fragilis. 49th Annual Interscience Conference on Antimicrobial Agents and Chemotherapy (ICAAC 2009); Sep. 12-15, 2009. Poster F1-1992; This poster is obtainable at: http://www.jmilabs.com/data/posters/ICAAC2009/F1-1992.pdf (Abstract).

Sader et al., Antimicrobial activity of ceftolozane/tazobactam and comparator agents tested against Pseudomonas aeruginosa isolates from United States (USA) medical centers (2011-2012). To be presented at the 2nd Annual IDWeek (IDWeek 2013); Oct. 2-6, 2013; San Francisco, CA. Poster #695.

Sader et al., Antimicrobial activity of ceftolozane/tazobactam and comparator agents tested against Pseudomonas aeruginosa strains from 14 European countries and Israel. 23rd Annual Meeting of the European Congress of Clinical Microbiology (ECCMID 2013); Apr. 27-30, 2013; Berlin, Germany. Poster P1630. (Abstract).

Sader et al., Antimicrobial Activity of Ceftolozane/Tazobactam Tested Against Gram-Negative Bacterial Isolates from Hospitalized Patients with Pneumonia in European Hospitals (2011). 23rd Annual Meeting of the European Congress of Clinical Microbiology (ECCMID 2013); Apr. 27-30, 2013; Berlin, Germany. Oral Presentation 0-181.

Sader et al., Antimicrobial Activity of Ceftolozane/Tazobactam Tested Against Gram-negative Bacterial Isolates from Hospitalized Patients with Pneumonia in United States (USA) and European (EU) Hospitals (2012). 53rd Annual Interscience Conference on Antimicrobial Agents and Chemotherapy (ICAAC 2013); Sep. 10-13, 2013; Denver, CO. Poster C2-1633. (Abstract).

Sader et al., Antimicrobial activity of CXA-101, a novel cephalosporin tested in combination with tazobactam against Enterobacteriaceae, Pseudomonas aeruginosa, and Bacteroides fragilis strains having various resistance phenotypes. Agents Chemother. 2011 55(5):2390-4.

Sader et al., Antimicrobial susceptibility of gram-negative bacteria causing urinary tract infections in European and United States hospitals (2009-2011). 23rd Annual Meeting of the European Congress of Clinical Microbiology (ECCMID 2013); Apr. 27-30, 2013; Berlin, Germany. Poster P1516. (Abstract).

Sader et al., Ceftolozane/tazobactam activity tested against aerobic Gram-negative organisms isolated from intraabdominal infections in European and United States hospitals (2012). To be presented at the 2nd Annual IDWeek (IDWeek 2013); Oct. 2-6, 2013; San Francisco, CA. Poster #698. (Abstract).

Sader et al., Frequency of occurrence and antimicrobial susceptibility of Gram-negative organisms isolated from health care associated urinary tract infections: Results from the Program to Assess Ceftolozane/Tazobactam Susceptibility (PACTS). To be presented at the 2nd Annual IDWeek (IDWeek 2013); Oct. 2-6, 2013; San Francisco, CA. Poster 699. (Abstract).

Sader et al., Post Beta-Lactamase Inhibitor Effect of Tazobactam When Associated with Ceftolozane and Tested against ESBL-Producing Strains. 53rd Annual Interscience Conference on Antimicrobial Agents and Chemotherapy (ICAAC 2013); Sep. 10-13, 2013; Denver, CO. Poster A-1030. (Abstract).

Sader et al., Post-Beta-Lactamase-Inhibitor Effect of Tazobactam in Combination with Ceftolozane on Extended-Spectrum-Beta-Lactamase-Producing Strains. Antimicrob Agents Chemother. 2014 vol. 58 No. 4, pp. 2434-243.

Sakagami et al., Synthetic Cephalosporins. VI.: Synthesis and Antibacterial Activity of 7-[(Z)-2-(2-Aminothiazol-4-yl)-2-(1-carboxy-1-methyl)ethoxyiminoacetamido]-3-(3-hydroxy-4-pyridon-1-yl)methyl-3-cephem-4-carboxylic Acid and Related Compounds. Chemical and Pharmaceutical Bulletin. 1990, vol. 38, No. 8, pp. 2271-2273.

Schulgen et al., Estimation of extra hospital stay attributable to nosocomial infections: heterogeneity and timing of events; J Clin Epidemiol; Apr. 2000, vol. 53(4), pp. 409-417.

Search Request Confirmation; Science IP; Dec. 6, 2010, 3 pages.

Seetulsingh et al., Activity of Clavulanate Combinations against TEM-1 b-Lactamase-Producing *Escherichia coli* Isolates Obtained in 1982 and 1989. Journal of Antimicrobial Chemotherapy 1991;27:749.

Singh et al., Short-course empiric antibiotic therapy for patients with pulmonary infiltrates in the intensive care unit. A proposed solution for indiscriminate antibiotic prescription; Am J Respir Crit Care Med, Aug. 2000, vol. 162(2, Pt 1), pp. 505-511.

Snydman et al., Activity of Ceftolozane/Tazobactam (CXA-201) against 270 recent isolates from the bacteroides group. 22nd Annual Meeting of the European Congress of Clinical Microbiology (ECCMID 2012); Mar. 31-Apr. 3, 2012. Poster P1445; This poster is obtainable at: http://www.escmid_orgtescmid_library/online_lecture_library/?search=1&current_page=1&search_term=snydman (Abstract).

Snydman et al., Activity of Ceftolozane/Tazobactam Against a Broad Spectrum of Recent Clinical Anaerobic Isolates. Antimicrob Agents Chemother. 2014 vol. 58, No. 2, pp. 1218-1223.

Soon et al., A Novel Mathematical Modeling Approach to Characterize the Pharmacodynamics of Ceftolozane/Tazobactam, a p-lactam & p-lactannase Inhibitor Combination. 52nd Annual Interscience

(56) References Cited

OTHER PUBLICATIONS

Conference on Antimicrobial and Chemotherapy (ICAAC 2012); Sep. 9-12, 2012. Oral Presentation A-1762.
Soon et al., In vitro Pharmacodynamics of CXA-201 Ceftolozane (TOL)/Tazobactam (TAZ) against Beta-lactamase (BL) Producing *Eschericia coli* (*Ec*). 52nd Annual Interscience Conference on Antimicrobial Agents and Chemotherapy (ICAAC 2012); Sep. 9-12, 2012. Poster E-201 (Abstract).
Steenbergen et al., Potency of CXA-101/Tazobactam for Pathogens from ICU and non-ICU Correlated to Probability of Pharmacokinetic/Pharmacodynamic (PK/PD) Target Attainment. ICAAC 2011. Oral Presentation A-1689.
Strayer et al., Pharmacodynamics of Piperacillin Alone and in Combination with Tazobactam against Piperacillin-Resistant and -Susceptible Organisms in an In Vitro Model of Infection. Antimicrobial Agents and Chemotherapy 1994;38:2351.
Sutcliffe et al., Multidrug-Resistant Gram-Negative Pathogens: New Strategies; Tetraphase Pharmaceuticals. Retrieved online from: http://www.tufts.edu/med/apua/practitioners/resources_23_2817980013.pdf Retrieved Mar. 19, 2014.
Takeda et al., In vitro and in vivo activities of a new cephalosporin, FR264205, against Pseudomonas aeruginosa. Antimicrob Agents Chemother. 2007; 51(3):826-30.
Takeda et al., Stability of FR264205 against AmpC beta-lactamase of Pseudomonas aeruginoas. International Journal Antimicrobial Agents, 2007. vol. 30, No. 5, pp. 443-445.
Teflaro, (Ceftaroline fosamil) Approved Oct. 2010, Product Label. Forest Laboratories, Inc. 2010.
Thomson et al., Beta-Lactamase Production in Members of the Family *Enterobacteriaceae* and Resistance to Beta-Lactam-Enzyme Inhibitor Combinations Antimicrobial Agents and Chemotherapy 1990;34:622.
Titelman et al., Activity of CXA-101 (CXA) plus tazobactam against ESBL-producing *E. coli* and K. pneumoniae. 49th Annual Interscience Conference on Antimicrobial Agents and Chemotherapy (ICAAC 2009); Sep. 12-15, 2009. Poster F1-1993 (Abstract).
Titelman et al., In vitro Activity of CXA-101 Plus Tazobactum against CTX-M-14 and CTX-M-15-producing *Escherichia* and Klebsiella pneumoniae. Diagnostic Microbiology and Infectious Disease. 2011, vol. 70, No. 1, pp. 137-141.
Toda et al., FR264205, A Novel Parenteral Antipseudomonal Cephem: Synthesis and SAR of 3-(2,4-Disubstituted 3-Aminopyrazolio)methyl Cephalosporins. 46th Annual Interscience Conference on Antimicrobial Agents and Chemotherapy (ICAAC 2006); Sep. 27-30, 2006; San Francisco, CA. Oral Presentation F1-0240.
Toda et al., Synthesis and SAR of Novel Parenteral Antipseudomonal cephalosporins: Discovering of FR264205. Med Chem Lett. 2008, vol. 18, No. 17, pp. 4849-4852.
U.S. National Institutes of Health, Safety and Efficacy Study of Ceftolozane/Tazobactam to Treat Ventilated Nosocomial Pneumonia (ASPECT-NP). Sponsored by Cubist Pharmaceuticals. http://www.clinicaltrials.gov/ct2/show/NCT02070757?term=ceftolozane&rank=1 Updated Feb. 21, 2014. ClinicalTrials.gov Identifier: NCT02070757 (Study not yet open for participant recruitment).
U.S. National Institutes of Health, Safety and Efficacy Study of IV CXA-101 and IV Ceftazidime in Patients with Complicated Urinary Tract Infections. Sponsored by Cubist Pharmaceuticals. http://www.clinicaltrials.govict2/show/NCT00921024?term=ceftolozane&rank=4 Updated Aug. 5, 2010. ClinicalTrials.gov Identifier: NCT00921024 (Study has been completed).
U.S. National Institutes of Health, Safety and Efficacy Study to Compare IV CXA 101/Tazobactam and Metronidazole With Meropenem in Complicated Intraabdominal Infections. Sponsored by Cubist Pharmaceuticals. http://www.chnicaltnals.govict2/show/NCT01147640?term=ceftolozane&rank=2 Updated May 5, 2011. ClinicalTrials.gov Identifier: NCT01147640 (Study has been completed).
U.S. National Institutes of Health, Study of Intravenous Ceftolozane/Tazobactam vs. Piperacillin/Tazobactam in Ventilator Associated Pneumonia. Sponsored by Cubist Pharmaceuticals. http ://www.clinicaltrials.gov/ct2/show/NCT01853982?term=ceftolozane&rank=3 Updated Jan. 28, 2014. ClinicalTrials.gov Identifier: NCT01853982 (Study has been terminated).
Udy et al., Augmented renal clearance: implications for antibacterial dosing in the critically ill; Clin Pharmacokinet, 2010, vol. 49(1), pp. 1-16.
Udy et al., How Should We Dose Antibiotics for Pneumonia in the ICU? Current Opinion in Infectious Diseases. 2013, vol. 26, No. 2, pp. 189-195.
Umeh et al., A double-blind, randomized, phase 2 study to compare the safety and efficacy of intravenous CXA-101 and intravenous ceftazidime in complicated urinary tract infection. 50th Annual Interscience Conference on Agents and Chemotherapy (ICAAC 2010); Sep. 12-15, 2010. Poster L1-361a; This poster is obtainable at: http://www.cubist.com/downloads/Umeh_ICAAC2010_08144v2.pdf (Abstract).
Vanscoy et al., Identification of a Translational Relationship Between Tazobactam (TAZ) Exposure in Combination with Ceftolozane (TOL) and Efficacy Against ESBL-Producing Enterobacteriaceae. 53rd Annual Interscience Conference on Antimicrobial Agents and Chemotherapy (ICAAC 2013); Sep. 10-13, 2013; Denver, CO. Poster A-1032. (Abstract).
Vanscoy et al., Pharmacokinetics-Pharmacodynamics (PK-PD) of Tazobactam in Combination with Ceftolozane in an In Vitro Infection Model. 23rd Annual Meeting of the European Congress of Clinical Microbiology (ECCMID 2013); Apr. 27-30, 2013; Berlin, Germany. Poster P900. (Abstract).
Vanscoy et al., Pharmacokinetics-Pharmacodynamics of Tazobactam in Combination with Ceftolozane in an In Vitro Infection Model. Antimicrob Agents Chemother. 2013 vol. 57, No. 6, pp. 2809-2814.
Vanscoy et al., Pharmacological basis of beta-lactamase inhibitor therapeutics: tazobactam in combination with Ceftolozane. Antimicrob Agents Chemother. 2013. vol. 57 No. 12, pp. 5924-5930.
Vanscoy et al., Relationship between Ceftolozane/Tazobactam (TOL/TAZ) Exposure and *E. coli* Resistance Amplification Prevention in a Hollow Fiber Infection Model (HFIM). 53rd Annual Interscience Conference on Antimicrobial Agents and Chemotherapy (ICAAC 2013); Sep. 10-13, 2013; Denver, CO. Poster A-1031. (Abstract).
Vanscoy et al., Relationship between Ceftolozane/Tazobactam Exposure and Drug-Resistance Amplification in a Hollow-Fiber Infection Model. Antimicrob Agents Chemother. Jun. 17, 2013. [Epub ahead of print] PubMed PMID: 23774429.
Vincent et al., Use of the SOFA score to assess the incidence of organ dysfunction/failure in intensive care units: results of a multicenter, prospective study. Working group on sepsis-related problems of the European Society of Intensive Care Medicine; Crit Care Med, 1998, vol. 26(11), pp. 1793-1800.
Walkty et al., In Vitro Activity of Ceftolozane/Tazobactam (CXA-201) versus Pseudomonas aeruginosa Isolates Obtained from Patients in Canadian Hospitals: CANWARD 2011. IDWeek 2012: A Joint Meeting of IDSA, SHEA, HIVMA, and PIDS; Oct. 17-21, 2012. Poster 1616; This poster is obtainable at: https://idsa.confex.com/idsa/2012/webprogam/Hadoutit509/POSTER202_1616.pdf (Abstract).
Walkty et al., In vitro activity of ceftolozane-tazobactam against Pseudomonas aeruginosa isolates obtained from patients in Canadian hospitals in the CAN WARD study, 2007 to 2012. Antimicrob Agents Chemother. 2013, vol. 57, No. 11, pp. 5707-5709.
Wooley et al., Impact of renal function on the pharmacokinetics and safety of ceftolozane-tazobactam. Antimicrob Agents Chemother. 2014 vol. 58, No. 4, pp. 2249-2255.
Wooton et al., BAL 9141, a new borad-spectrum pyrrolidinone cephalosporin: activity against clinically significant anaerobes in comparison with 10 other antimicrobials; Journal of Antimicrobial Chemotherapy; (2002) vol. 49, pp. 535-539.
Written Opinion of the International Searching Authority for PCT/US2012/054191, dated Feb. 20, 2013, 7 pages.
Wunderink et al., Linezolid in methicillin-resistant *Staphylococcus aureus* nosocomial pneumonia: a randomized, controlled study; Clin Infect Dis, 2012, vol. 54(5), pp. 621-629.
Yamana et al., Comparative Stability of Cephalosporins in Aqueous Solution: Kinetics and Mechanisms of Degradation. Journal of Pharmaceutical Sciences 1976, vol. 65, No. 11, pp. 1563-1574.

(56) References Cited

OTHER PUBLICATIONS

Yano et al., Evaluating Pharmacokinetic/Pharmacodynamic Models Using the Posterior Predictive Check. Journal of Pharmacokinetics and Pharmacodynamics. 2001, vol. 28, No. 2, pp. 171-192.

Yoshizawa et al., New broad-spectrum parenteral cephalosporins exhibiting potent activity against both methicilln-resistant *Staphlococcus aureus* (MRSA) and Pseudomonas aeruginosa Part 3: &Beta42-(5-Amino-1,2,4-thiadiazol-3-yl)-2-ethoxfiminoacetamido] cephalosporins bearing 4-[3-(aminoalkyl)-ureido]-1-pyridinium at C3; Bioorg Med Chem Lett; 2004, vol. 12, pp. 4221-4231.

Zamorano et al., Activity of the new cephalosporin CXA-101 against P. aeruginosa (PA) isolates from chronically infected cystic fibrosis patients. 49th Annual Interscience Conference on Antimicrobial Agents and Chemotherapy (ICAAC 2009); Sep. 12-15, 2009. Poster F1-1991 (Abstract).

Zamorano et al., Activity of the new cephalosporin CXA-101 against Pseudomonas aeruginosa isolates from chronically-infected cystic fibrosis patients. Clin Microbiol Infect 2010 16(9):1482-7.

Zhanel et al., Ceftolozane/Tazobactam: A Novel Cephalosporin/β-Lactamase Inhibitor Combination with Activity Against Multidrug-Resistant Gram-Negative Bacillii Drugs. 2014 vol. 74 No 1, pp. 31-51.

Zhanel et al., In Vitro Activity of Ceftolozane/Tazobactam Against 5,715 Gram-Negative and Gram-Positive Pathogens Isolated from Patients in Canadian Hospitals in 2011 and 2012: CANWARD Surveillance Study. 53rd Annual Interscience Conference on Antimicrobial Agents and Chemotherapy (ICAAC 2013); Sep. 10-13, 2013; Denver, CO. Poster E-1689. (Abstract).

Zhanel et al., In Vitro Activity of Ceftolozane/tazobactam Tested Against 1,705 Gram-Negative Pathogens Isolated from Patients in Canadian Hospitals in 2011: CANWARD Surveillance Study. 52nd Annual Interscience Conference on Antimicrobial Agents and Chemotherapy (ICAAC 2012); Sep. 9-12, 2012. Poster E-200 (Abstract).

Zilberberg et al., Epidemiology of healthcare-associated pneumonia (HCAP); Semin Respir Crit Care Med, 2009, vol. 30, pp. 10-15.

Zilberberg et al., Gram-negative resistance and need for ICU among urinary tract infections in the United States. Making a Difference in Infectious Diseases Pharmacotherapy Conference (MAD-ID 2013); May 9-11, 2013; Orlando, FL. Encore Presentation from ISICEM 2013. (Abstract).

Zilberberg et al., Multidrug resistance among P. aeruginosa and Enterobacteriaceae in the US hospitals, 2000-2009. Making a Difference in Infectious Diseases Pharmacotherapy Conference (MAD-ID 2013); May 9-11, 2013; Orlando, FL. Encore Presentation from SCCM 2013. (Abstract).

Zilberberg et al., Multidrug resistant Pseudomonas aeruginosa among hospitalized patients with pneumonia, US 2000-2009. Making a Difference in Infectious Diseases Pharmacotherapy Conference (MAD-ID 2013); May 9-11, 2013; Orlando, FL. Encore Presentation from ISICEM 2013.

Zilberberg et al., Prevalence of antibiotic resistance among P. aeruginosa in US hospitals, 2000-2009. To be presented at the 2nd Annual IDWeek (IDWeek 2013); Oct. 2-6, 2013; San Francisco, CA. Poster #1580. (Abstract).

Zilberberg et al., Prevalence of multidrug-resistant Pseudomonas aeruginosa and carbapenem-resistant Enterobacteriaceae among specimens from hospitalized patients with pneumonia and bloodstream infections in the United States from 2000 to 2009. J Hosp Med. 2013 vol. 8, No. 10, pp. 559-563.

Zilberberg et al., Secular Trends in Gram-Negative Resistance among Urinary Tract Infection Hospitalizations in the United States, 2000-2009. Infect Control Hosp Epidemiol. 2013, vol. 34, No. 9, pp. 940-946.

Zilberberg et al., Secular trends in gram-negative resistance among urinary tract infection hospitalizations in the US, 2000-2009. 23rd Annual Meeting of the European Congress of Clinical Microbiology (ECCMID 2013); Apr. 27-30, 2013; Berlin, Germany. Poster P1517. (Abstract).

Zithromax, (azithromycin injection) Approved Sep. 1994, Product Label. Pfizer Labs, Revised Feb. 2013.

Zosyn®. Prescribing Information. Wyeth Pharmaceuticals, Inc., Philadelphia, PA, USA; http://labeling.pfizer.com/showlabeling.aspx?id=416 (Apr. 23, 2012, date last accessed), 26 pages.

Figure 1A

| Characteristic | Ceftolozane/ Tazobactam (n=398) | Levofloxacin (n=402) |
|---|---|---|
| Sex, male, n (%) | 105 (26.4) | 103 (25.6) |
| Race, white, n (%) | 340 (85.4) | 346 (86.1) |
| Age, yr, mean (SD) | 49.1 (19.7) | 48.1 (20.2) |
| Age ≥65 yr, n (%) | 100 (25.1) | 99 (24.6) |
| Body mass index, kg/m$^2$, mean (SD) | 25.5 (5.8) | 26.1 (5.6) |
| Baseline creatinine clearance, ml/min, n (%) | | |
|    Normal (≥80) | 247 (62.1) | 274 (68.2) |
|    Mild renal impairment (>50–<80) | 116 (29.1) | 100 (24.9) |
|    Moderate renal impairment (≥30–≤50) | 31 (7.8) | 27 (6.7) |
|    Severe renal impairment (<30) | 3 (0.8) | 1 (0.2) |
| Primary diagnosis, n (%) | | |
|    Pyelonephritis | 328 (82.4) | 328 (81.6) |
|    cLUTI | 70 (17.6) | 74 (18.4) |
| Prior antibiotics within 14 days of first dose,* n (%) | 14 (3.5) | 6 (1.5) |
| Urinary catheter,† n (%) | 11 (2.8) | 10 (2.4) |
| Bacteremia, n (%) | 29 (7.3) | 33 (8.2) |
| Diabetes, n (%) | 42 (10.6) | 40 (10.0) |
| Hypertension, n (%) | 125 (31.4) | 119 (29.6) |

Figure 1B

| Pathogen | Ceftolozane/Tazobactam no. pathogens within a specific category/pathogens with a baseline MIC available (%) | | | Levofloxacin no. pathogens within a specific category/pathogens with a baseline MIC available (%) | | |
|---|---|---|---|---|---|---|
| | Susceptible | Intermediate | Resistant | Susceptible | Intermediate | Resistant |
| Gram-negative aerobes | 706/731 (96.6) | 5/731 (0.7) | 20/731 (2.7) | 517/731 (70.7) | 19/731 (2.6) | 195/731 (26.7) |
| Enterobacteriaceae | 694/709 (97.9) | 4/709 (0.6) | 11/709 (1.6) | 509/709 (71.8) | 18/709 (2.5) | 182/709 (25.7) |
| Escherichia coli | 592/594 (99.7) | 0/594 | 2/594 (0.3) | 440/594 (74.1) | 10/594 (1.7) | 144/594 (24.2) |
| Klebsiella pneumonia | 48/55 (87.3) | 1/55 (1.8) | 6/55 (10.9) | 26/55 (47.3) | 5/55 (9.1) | 24/55 (43.6) |
| Proteus mirabilis | 23/23 (100) | 0/23 | 0/23 | 19/23 (82.6) | 2/23 (8.7) | 2/23 (8.7) |
| Enterobacter spp. | 15/19 (78.9) | 2/19 (10.5) | 2/19 (10.5) | 10/19 (52.6) | 1/19 (5.3) | 8/19 (42.1) |
| Other Enterobacteriaceae | 16/18 (88.9) | 1/18 (5.6) | 1/18 (5.6) | 14/18 (77.8) | 0/18 | 4/18 (22.2) |
| Pseudomonas aeruginosa | 12/20 (60.0) | 1/20 (5.0) | 7/20 (35.0) | 7/20 (35.0) | 1/20 (5.0) | 12/20 (60.0) |
| Other | 0/2 | 0/2 | 2/2 (100) | 1/2 (50.0) | 0/2 | 1/2 (50.0) |
| Gram-positive aerobes | 0/45 | 0/45 | 45/45 (100) | 20/45 (44.4) | 2/45 (4.4) | 23/45 (51.1) |
| Enterococcus faecalis | 0/35 | 0/35 | 35/35 (100) | 15/35 (42.9) | 1/35 (2.9) | 19/35 (54.3) |
| Other | 0/10 | 0/10 | 10/10 (100) | 5/10 (50.0) | 1/10 (10.0) | 4/10 (40.0) |

Figure 1E

| Adverse Event | Ceftolozane/tazobactam (N=533) n (%) | Levofloxacin (N=535) n (%) |
|---|---|---|
| Headache | 31 (5.8) | 26 (4.9) |
| Constipation | 21 (3.9) | 17 (3.2) |
| Nausea | 15 (2.8) | 9 (1.7) |
| Diarrhea | 10 (1.9) | 23 (4.3) |
| Upper abdominal pain | 7 (1.3) | 6 (1.1) |
| Vomiting | 6 (1.1) | 6 (1.1) |
| Hypertension | 16 (3.0) | 7 (1.3) |
| Pyrexia | 8 (1.5) | 4 (0.7) |
| Urinary tract infection | 9 (1.7) | 9 (1.7) |
| Insomnia | 7 (1.3) | 14 (2.6) |
| Dizziness | 6 (1.1) | 1 (0.2) |
| Myalgia | 6 (1.1) | 4 (0.7) |
| Arthralgia | 1 (0.2) | 6 (1.1) |
| Alanine aminotransferase increased | 9 (1.7) | 5 (0.9) |
| Aspartate aminotransferase increased | 9 (1.7) | 5 (0.9) |

Figure 1F

| Serious Adverse Event | Ceftolozane/Tazobactam (N=533) n (%) | Levofloxacin (N=535) n (%) |
|---|---|---|
| Any serious adverse event | 15 (2.8) | 18 (3.4) |
| Urinary tract infection | 3 (0.6) | 2 (0.4) |
| Pneumonia | 2 (0.4) | 0 |
| Urosepsis | 2 (0.4) | 0 |
| Abdominal abscess | 1 (0.2) | 0 |
| C. difficile colitis | 1 (0.2) | 0 |
| Diverticulitis | 1 (0.2) | 0 |
| Liver abscess | 1 (0.2) | 0 |
| Pseudomembranous colitis | 1 (0.2) | 0 |
| Pyelonephritis | 0 | 6 (1.1) |
| Emphysematous pyelonephritis | 0 | 1 (0.2) |
| Escherichia sepsis | 0 | 1 (0.2) |
| Pyelonephritis acute | 0 | 1 (0.2) |
| Sepsis | 0 | 1 (0.2) |
| Calculus urinary | 1 (0.2) | 0 |
| Renal colic | 1 (0.2) | 0 |
| Urinary retention | 1 (0.2) | 0 |
| Renal tubular acidosis | 0 | 1 (0.2) |
| Bladder cancer | 2 (0.4) | 0 |
| Diabetic retinopathy | 1 (0.2) | 0 |
| Angina unstable | 0 | 1 (0.2) |
| Cardiac failure congestive | 0 | 1 (0.2) |
| Gastric ulcer | 0 | 1 (0.2) |
| Hernia obstructive | 0 | 1 (0.2) |
| Contrast media allergy | 0 | 1 (0.2) |
| Pneumothorax traumatic | 0 | 1 (0.2) |
| Transient ischemic attack | 0 | 1 (0.2) |
| Chronic obstructive pulmonary disease | 0 | 1 (0.2) |

Figure 2

| Study | Phase | Population | Drug administration and dose |
|---|---|---|---|
| Ge et al. Pharmacokinetics and safety of CXA-101, a new antipseudomonal cephalosporin, in healthy adult male and female subjects receiving single- and multiple-dose intravenous infusions. Antimicrob Agents Chemother. 2010; 54(8):3427-3431. | 1 | Healthy | IV Ceftolozane 250, 500, 1000, 1500, 2000 mg (single and multiple). Sampling up to 24 hours |
| Miller et al. Pharmacokinetics and safety of intravenous ceftolozane-tazobactam in healthy adult subjects following single and multiple ascending doses. Antimicrob Agents Chemother. 2012; 56(6):3086-3091. | 1 | Healthy | IV Ceftolozane/tazobactam 500/250, 1000/500, 1500/750, 2000/1000 mg (single and multiple). Sampling up to 24 hours; 10-day study |
| Chandorkar et al. Intrapulmonary penetration of ceftolozane/tazobactam in healthy adult subjects. J Antimicrob Chemother. 2012; 67(10):2463-2469. | 1 | Healthy | IV Ceftolozane/tazobactam 1000/500 mg (multiple). Sampling up to 8 hours |
| Miller et al. Safety and pharmacokinetics of intravenous ceftolozane/tazobactam 3 g every 8 hours and cumulative fraction of response in plasma and epithelial lining fluid in a simulated ventilator associated pneumonia population. Presented at: 52nd Annual Interscience Conference on Antimicrobial Agents and Chemotherapy (ICAAC 2012); September 9-12, 2012; San Francisco, CA. Poster A-624 | 1 | Healthy | IV Ceftolozane/tazobactam 2000/1000 mg (multiple). Sampling up to 24 hours; 10-day study |
| Wooley et al. Impact of Renal Function on the Pharmacokinetics and Safety of Ceftolozane/Tazobactam. Antimicrob Agents Chemother. 2014. | 1 | Normal, mild and moderate RI | IV Ceftolozane/tazobactam 1000/500 mg (single). Sampling up to 36h |
| Wooley et al. Impact of Renal Function on the Pharmacokinetics and Safety of Ceftolozane/Tazobactam. Antimicrob Agents Chemother. 2014. | 1 | Severe RI | IV Ceftolozane/tazobactam 500/250 mg (single). Sampling up to 48 hours |
| Umeh et al. A double-blind, randomized, phase 2 study to compare the safety and efficacy of intravenous CXA-101 and intravenous ceftazidime in complicated urinary tract infection. Presented at: 50th Annual Interscience Conference on Antimicrobial Agents and Chemotherapy (ICAAC 2010); September 12-15, 2010; Boston, MA. Poster L1-361A. NCT00921024 | 2 | cUTI | IV Ceftolozane 1000 mg (q8h). Sampling up to 6 hours |
| Lucasti et al. A multicenter, double-blind, randomized, phase 2 study to assess the safety and efficacy of ceftolozane/tazobactam (TOL/TAZ) plus metronidazole (MTZ) compared to meropenem (MER) in adult patients with complicated intra-abdominal infections (cIAI). Presented at: 53rd Annual Interscience Conference on Antimicrobial Agents and Chemotherapy (ICAAC 2013); September 10-13, 2013; Denver, CO. Poster K-1709. NCT01147640 | 2 | cIAI | IV Ceftolozane/tazobactam 1000/500 mg (q8h). Sampling up to 7 hours |

Figure 3

| Characteristic | Ceftolozane (n = 376) | | Tazobactam (n = 243) | |
|---|---|---|---|---|
| | Phase 1, No Infection (n = 226) | Phase 2, Infection[a] (n = 150) | Phase 1, No Infection (n = 166) | Phase 2, Infection[b] (n = 77) |
| Men/women, n (%) | 129 (57.1)/97 (42.9) | 83 (55.3)/67 (44.7) | 96 (57.8)/70 (42.2) | 43 (55.8)/34 (44.2) |
| Race, white, n (%) | 187 (82.7) | 145 (96.7) | 136 (81.9) | 76 (98.7) |
| Age, y, mean (range) | 44.7 (18-79) | 53.5 (18-86) | 43.7 (18-79) | 47.0 (18-86) |
| Weight, kg, mean (range) | 73.5 (49-106) | 79.6 (43-173) | 74.1 (49-106) | 78.0 (50-145) |
| BMI, kg/m², mean (range) | 25.8 (19-35) | 27.3 (17-56) | 26.0 (19-35) | 26.6 (18-51) |
| Estimated CrCL, mL/min, mean (range) | 101.0 (19-215) | 97.4 (41-309) | 100.4 (19-238) | 105 (41-309) |
| Renal impairment,[c] n (%) | | | | |
| None (normal) | 186 (82.3) | 69 (46.0) | 137 (82.5) | 48 (62.3) |
| Mild | 28 (12.4) | 78 (52.0) | 17 (10.2) | 26 (33.8) |
| Moderate | 6 (2.7) | 3 (2.0) | 6 (3.6) | 3 (3.9) |
| Severe | 6 (2.7) | 0 (0) | 6 (3.6) | 0 (0) |

Figure 4
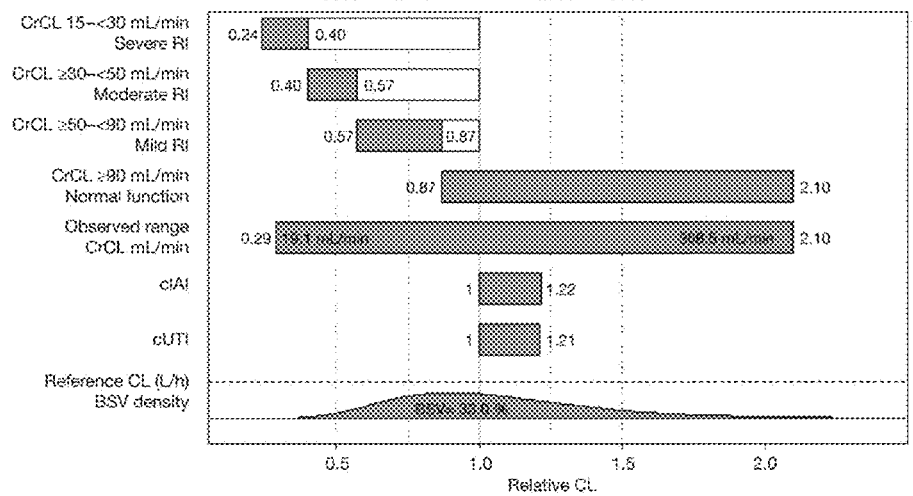
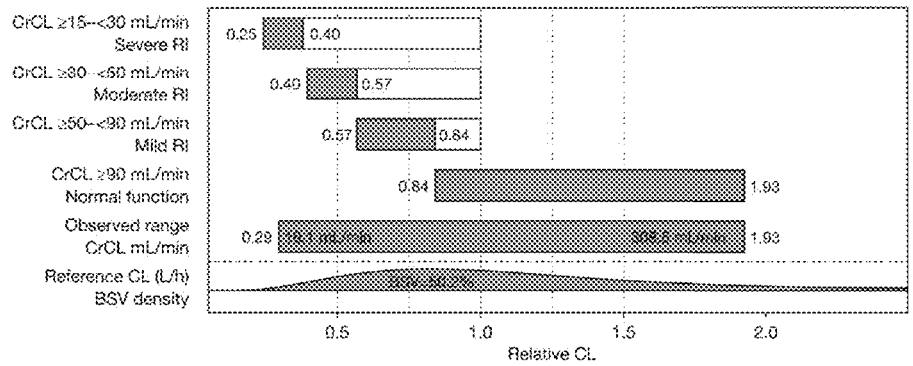

Figure 5

[A] Ceftolozane

| Parameter | | Population estimates (RSE %) | BSV % (RSE %) | Shrinkage (%) |
|---|---|---|---|---|
| CL (L/h) | No infection | $5.11 (2.15)*(CrCl/109)^{0.715 (8.14)}$ | 33.3 (3.94) | 3.5 |
| | With cUTI | x 1.21 (24.6) | | |
| | With cIAI | x 1.22 (22.5) | | |
| Vc (L) | No infection | $11.4 (2.70)*(weight/74)$ | 39.8 (4.50) | 8.3 |
| | With cUTI | $x 1.21 (30.1)*(weight/74)$ | | |
| | With cIAI | x 1.59 (12.3) | | |
| $CL_2$ (L/h) | | 1.19 (2.24) | Fixed at 0 | NA |
| Vp (L) | | 2.88 (fixed) | Fixed at 0 | NA |
| Proportional error (%) | | 16.8 (11.8) | NA | NA |
| Additional error (μg/mL) | | 0.05 (8.07) | NA | NA |

[B] Tazobactam

| Parameter | | Population estimates (RSE %) | BSV % (RSE %) | Shrinkage (%) |
|---|---|---|---|---|
| CL (L/h) | | $18.0 (3.39)*(CrCl/115)^{0.67 (11.1)}$ | 50.2 (4.98) | 4.68 |
| Vc (L) | No infection | 14.2 (4.45) | 52.5 (6.14) | 11.5 |
| Vc (L) | With cIAI | x 1.47 (21.9) | | |
| $CL_2$ (L/h) | | 3.13 (4.59) | Fixed at 0 | NA |
| Vp (L) | | 4.29 (2.61) | Fixed at 0 | NA |
| Proportional error (%) | | 26.0 (1.64) | NA | NA |

Figure 6
[A] Ceftolozane
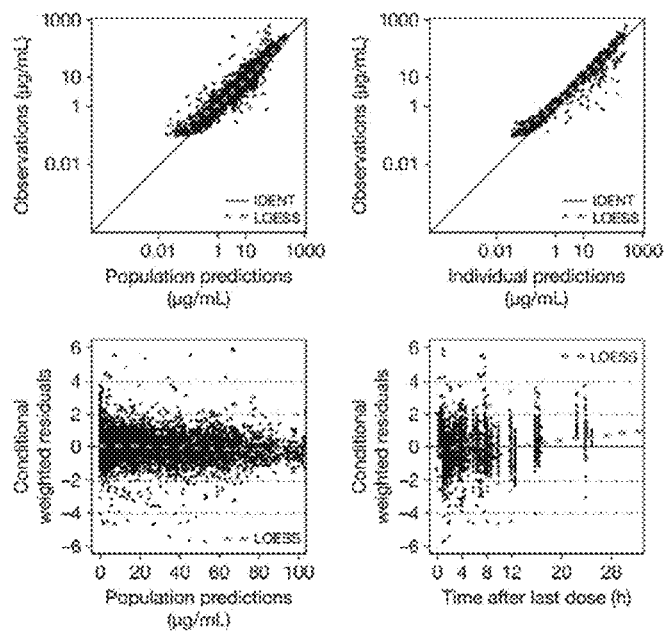
[B] Tazobactam
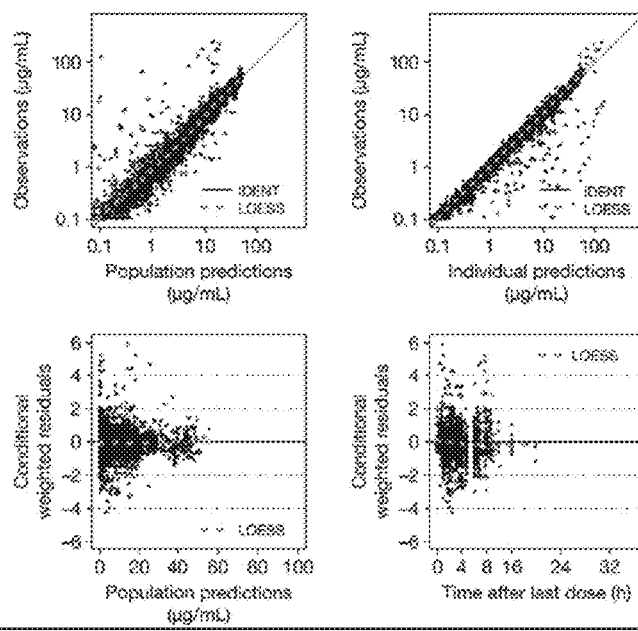

Figure 8

| Characteristic | Normal (n = 11) | Mild RI ($CL_{CR}$,[b] 60 to 89 ml/min) (n = 6) | Moderate RI ($CL_{CR}$, 30 to 59 ml/min) (n = 7) | Severe RI ($CL_{CR}$, 15 to 29 ml/min) (n = 6) | ESRD (n = 6) |
|---|---|---|---|---|---|
| No. (%) of males/females | 5 (45.5)/6 (54.5) | 2 (33.3)/4 (66.7) | 3 (42.9)/4 (57.1) | 1 (16.7)/5 (83.3) | 4 (66.7)/2 (33.3) |
| No. (%) of: | | | | | |
| Whites | 10 (90.9) | 4 (66.7) | 5 (71.4) | 5 (83.3) | 1 (16.7) |
| Blacks or African Americans | 1 (9.1) | 0 | 2 (28.7) | 1 (16.7) | 5 (83.3) |
| Asians | 0 | 2 (33.3) | 0 | 0 | 0 |
| Mean age, yr (SD) | 61.5 (7.1) | 72.3 (7.8) | 65.6 (18.7) | 66.2 (6.7) | 50.0 (11.1) |
| Mean wt, kg (SD) | 84.1 (10.2) | 65.4 (15.4) | 83.9 (22.6) | 65.3 (13.9) | 83.4 (31.9) |
| Mean BMI,[c] kg/m² (SD) | 28.6 (2.7) | 24.9 (12.7) | 29.8 (18.9) | 25.5 (5.8) | 28.9 (7.7) |
| Mean estimated $CL_{CR}$, ml/min (SD) | 118.0 (19.7) | 70.6 (15.1) | 43.6 (14.9) | 21.5 (2.3) | NA[d] |

[a] RI, renal impairment.
[b] $CL_{CR}$ estimated by the Cockcroft-Gault formula.
[c] BMI, body mass index.
[d] NA, not applicable.

Figure 9

| Parameter | Normal (n = 11), 1,000/500 mg C-T[a] | Mild RI (n = 6), 1,000/500 mg C-T | Moderate RI (n = 7), 1,000/500 mg C-T | Severe RI (n = 6), 500/250 mg C-T | ESRD (n = 6) Non-HD (day 1), 500/250 mg C-T | On HD (day 4, over 44 h), 500/250 mg C-T[b] |
|---|---|---|---|---|---|---|
| $t_{1/2}$, h | 3.1 (2.4–3.6) | 3.3 (2.9–3.8) | 5.6 (2.9–10.8) | 11.1 (7.7–14.9) | 40.5 (20.8–58.1) | 43.2 (32.8–56.9)[b] |
| $C_{max}$, µg/ml | 72.8 (42–139) | 93.4 (73.8–141) | 84.5 (64–136) | 47.0 (37.5–76.3) | 44.2 (30.2–60.6) | 41.1 (17.5–56.4) |
| $AUC_{0-\tau}$, µg·h/ml | 230 (160–310) | 313 (255–339) | 585 (305–840) | 498 (403–711) | 903 (572–1233) | 298 (179–437) |
| $AUC_{0-\infty}$, µg·h/ml | 231 (161–311) | 315 (255–342) | 589 (306–980) | 509 (439–762) | 1829 (466–2750) | 574 (287–1024) |
| $CL$, liters/h | 4.3 (3.2–6.2) | 3.2 (2.9–3.9) | 1.7 (1.1–3.3) | 1.0 (0.7–1.2) | 0.3 (0.2–1.1) | 0.9 (0.5–1.7) |
| $CL_R$, liters/h | 3.5 (2.4–4.9) | 2.9 (2.5–3.2) | 1.3 (1.1–2.3) | 0.7 (0.5–1.0)[c] | ND[d] | ND |
| $V_z$, liters | 14.6 (8.9–24.7) | 12.3 (9.2–13) | 13.9 (10.6–18.6) | 12.5 (11.3–20.4) | 17.9 (11.9–31.7) | 54.6 (38.8–77.9) |

[a] C-T, ceftolozane-tazobactam.
[b] The $t_{1/2}$ on HD was calculated from the post-HD terminal elimination phase.
[c] Incomplete urine recovery over 48 h.
[d] ND, not determined. As a majority of the subjects with ESRD were anuric, the $CL_R$ could not be determined.

Figure 10

| Parameter | Normal (n = 11), 1,000/500 mg C-T | Mild RI (n = 6), 1,000/500 mg C-T | Moderate RI (n = 7), 1,000/500 mg C-T | Severe RI (n = 6), 500/250 mg C-T | ESRD (n = 6) Non-HD (day 1), 500/250 mg C-T | ESRD (n = 6) On HD (day 4, over 44 h), 500/250 mg C-T |
|---|---|---|---|---|---|---|
| $t_{1/2}$, h | 1.1 (0.8–1.6)[a] | 1.1 (0.9–1.6) | 1.8 (1.4–2.2) | 2.5 (1.9–3.3) | 4.2 (3.4–9.1) | 5.0 (1.9–8.5)[b] |
| $C_{max}$, µg/ml | 17.0 (14.7–31.4) | 21.9 (18.9–28.3) | 27.1 (23.3–28.7) | 16.3 (10.2–18.3) | 20.2 (15.9–30.3) | 14.9 (7.2–22.9) |
| $AUC_{0-last}$, µg · h/ml | 29.8 (21.6–40.1) | 34.4 (28.9–43.1) | 65.3 (48.9–91.2) | 33.7 (34.2–68.1) | 107 (43.3–169) | 37.1 (19.9–57.8) |
| $AUC_{0-\infty}$, µg · h/ml | 30.1 (21.7–40.4) | 34.7 (29.1–43.4) | 65.9 (49.1–91.9) | 36.5 (35.8–70.9) | 109 (46.0–170) | 40.3 (23.3–58.6) |
| $CL$, liters/h | 16.6 (12.4–23.0) | 14.4 (11.5–17.2) | 7.6 (5.4–10.2) | 4.4 (3.5–7.0) | 2.4 (1.5–5.4) | 6.2 (4.3–10.7) |
| $CL_r$, liters/h | 12.0 (9.2–14.9) | 10.2 (9.4–15.9) | 5.3 (3.2–7.6) | 1.6 (1.2–2.9) | ND | ND |
| $V_{ss}$, liters | 19.9 (13.8–26.1) | 16.0 (12.7–22.0) | 16.8 (13.9–23.1) | 15.7 (12.2–23.5) | 15.2 (11.5–27.1) | 27.4 (15.4–56.7) |

[a] Each value shown is a median (range).
[b] The $t_{1/2}$ on HD was calculated from the post-HD terminal elimination phase.

Figure 13
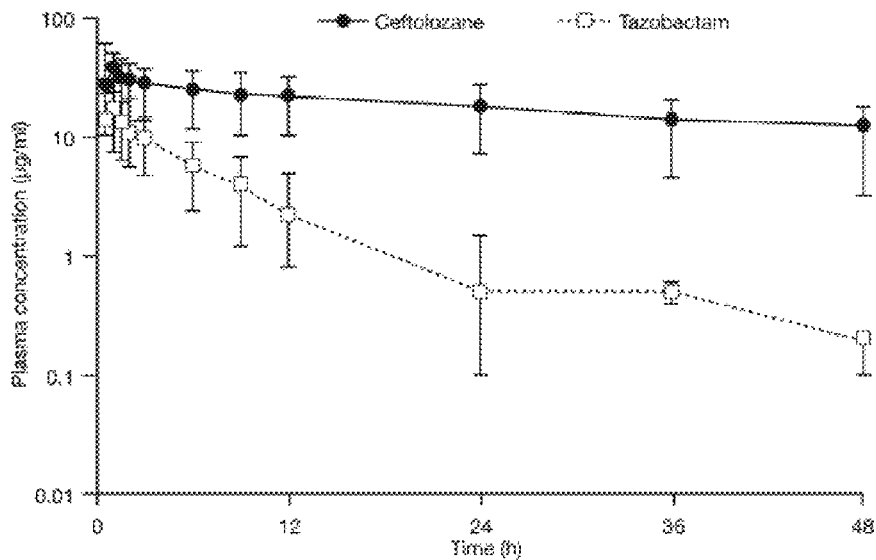
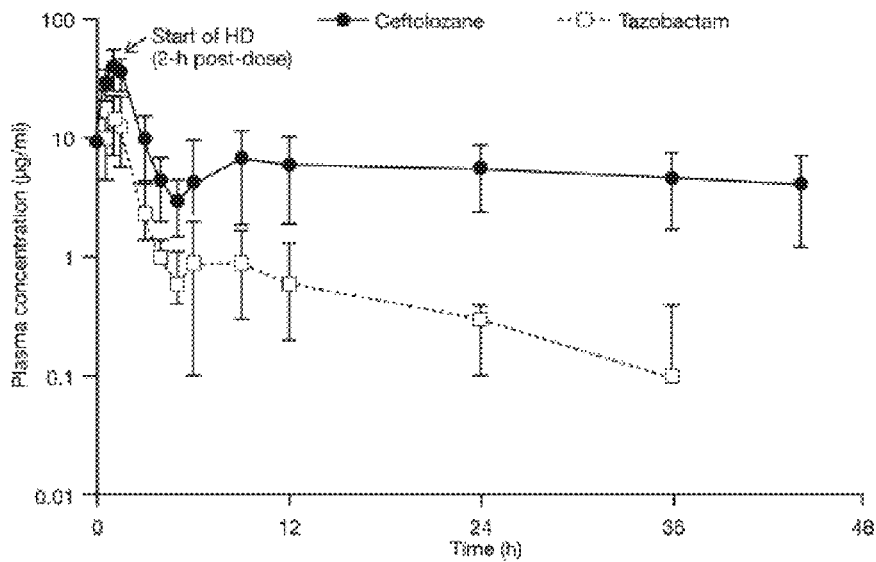

Figure 14A

| Type of Study | Study Identifier | Location of Study Report | Objective(s) of the Study | Study Design and Type of Control | Test Product(s); Dosage Regimen; Route of Administration | Number of Subjects | Healthy Subjects or Diagnosis of Patients | Duration of Treatment | Study Status; Type of Report |
|---|---|---|---|---|---|---|---|---|---|
| Phase 1, renal function | CXA-REN-11-03 | M5.3.3.3 | Safety, tolerability, PK | Open label, prospective, multi-center | Severe renal impairment: single dose of TOL/TAZ 500/250 mg as a 60-minute IV infusion<br><br>ESRD requiring hemodialysis: single dose of TOL/TAZ 500/250 mg as a 60-minute IV infusion | N=6 severe renal function<br>N=6 ESRD | Subjects with severe renal impairment (CLcr <30 mL/min) Subjects with ESRD requiring hemodialysis | 1 day<br><br>2 days (Day 1, immediately after hemodialysis; and Day 4, 2 hours before hemodialysis) | Complete<br><br>Full |

CLcr = Creatinine clearance; TOL = Ceftolozane; TOL/TAZ = Ceftolozane/tazobactam; ESRD = end-stage-renal-disease; PK = pharmacokinetics

Figure 14B (ctd.)

Figure 14B (ctd.)

Figure 14B (ctd.)

Figure 14B (ctd.)

| | | |
|---|---|---|
| 1101-001-0206 | 12 HOURS POST START OF INFUSION | 3.68 |
| 1101-001-0206 | 24 HOURS POST START OF INFUSION | 3.59 |
| 1101-001-0206 | 36 HOURS POST START OF INFUSION | 2.84 |
| 1101-001-0206 | 44 HOURS POST START OF INFUSION | 3.48 |

<LLOQ: Less than lower limit of quantitation
**: Excluded from POP PK analysis

Figure 14C

| Subject ID | Nominal Time (hr) | Concentration (µg/mL) |
|---|---|---|
| 1101-001-0201 | PREDOSE | <LLOQ |
| 1101-001-0201 | 0.5 HOURS POST START OF INFUSION | 15.9 |
| 1101-001-0201 | 1 HOUR POST START OF INFUSION | 30.3 |
| 1101-001-0201 | 1.5 HOUR POST START OF INFUSION | 13.1 |
| 1101-001-0201 | 2 HOURS POST START OF INFUSION | 10.7 |
| 1101-001-0201 | 3 HOURS POST START OF INFUSION | 9.75 |
| 1101-001-0201 | 6 HOURS POST START OF INFUSION | 4.51 |
| 1101-001-0201 | 9 HOURS POST START OF INFUSION | 2.94 |
| 1101-001-0201 | 12 HOURS POST START OF INFUSION | 1.51 |
| 1101-001-0201 | 24 HOURS POST START OF INFUSION | 0.185 |
| 1101-001-0201 | 36 HOURS POST START OF INFUSION | <LLOQ |
| 1101-001-0201 | 48 HOURS POST START OF INFUSION | <LLOQ |
| 1101-001-0201 | PREDOSE | <LLOQ |
| 1101-001-0201 | 0.5 HOURS POST START OF INFUSION (VENOUS) | 9.98 |
| 1101-001-0201 | 1 HOUR POST START OF INFUSION | 16.5 |
| 1101-001-0201 | 1.5 HOUR POST START OF INFUSION | 14.6 |
| 1101-001-0201 | 3 HOURS POST START OF INFUSION (VENOUS) | 4.41 |
| 1101-001-0201 | 4 HOURS POST START OF INFUSION (VENOUS) | 0.906 |
| 1101-001-0201 | 5 HOURS POST START OF INFUSION (VENOUS) | 0.428 |
| 1101-001-0201 | 6 HOURS POST START OF INFUSION (VENOUS) | 1.52 |
| 1101-001-0201 | 9 HOURS POST START OF INFUSION | 0.874 |
| 1101-001-0201 | 12 HOURS POST START OF INFUSION | 0.532 |
| 1101-001-0201 | 24 HOURS POST START OF INFUSION | <LLOQ |
| 1101-001-0201 | 36 HOURS POST START OF INFUSION | <LLOQ |
| 1101-001-0202 | PREDOSE | <LLOQ |

Figure 14C (ctd)

| ID | Timepoint | Value |
|---|---|---|
| 1101-001-0202 | 0.5 HOURS POST START OF INFUSION | 12.3 |
| 1101-001-0202 | 1 HOUR POST START OF INFUSION | 23.7 |
| 1101-001-0202 | 1.5 HOUR POST START OF INFUSION | 19.4 |
| 1101-001-0202 | 2 HOURS POST START OF INFUSION | 21 |
| 1101-001-0202 | 3 HOURS POST START OF INFUSION | 12.7 |
| 1101-001-0202 | 6 HOURS POST START OF INFUSION | 7.78 |
| 1101-001-0202 | 9 HOURS POST START OF INFUSION | 4.92 |
| 1101-001-0202 | 12 HOURS POST START OF INFUSION | 2.97 |
| 1101-001-0202 | 24 HOURS POST START OF INFUSION | 0.485 |
| 1101-001-0202 | 36 HOURS POST START OF INFUSION | <LLOQ |
| 1101-001-0202 | 48 HOURS POST START OF INFUSION | <LLOQ |
| 1101-001-0202 | PREDOSE | <LLOQ |
| 1101-001-0202 | 0.5 HOURS POST START OF INFUSION | 15 |
| 1101-001-0202 | 1 HOUR POST START OF INFUSION | 22.9 |
| 1101-001-0202 | 1.5 HOUR POST START OF INFUSION | 22.5 |
| 1101-001-0202 | 3 HOURS POST START OF INFUSION (VENOUS) | 3.93 |
| 1101-001-0202 | 4 HOURS POST START OF INFUSION (VENOUS) | 1.23 |
| 1101-001-0202 | 5 HOURS POST START OF INFUSION (VENOUS) | 1.09 |
| 1101-001-0202 | 6 HOURS POST START OF INFUSION | 1.97 |
| 1101-001-0202 | 9 HOURS POST START OF INFUSION | 1.34 |
| 1101-001-0202 | 12 HOURS POST START OF INFUSION | 0.771 |
| 1101-001-0202 | 24 HOURS POST START OF INFUSION | 0.125 |
| 1101-001-0202 | 36 HOURS POST START OF INFUSION | <LLOQ |
| 1101-001-0202 | 44 HOURS POST START OF INFUSION | <LLOQ |
| 1101-001-0203 | PREDOSE | <LLOQ |
| 1101-001-0203 | 0.5 HOURS POST START OF INFUSION | 12.4 |
| 1101-001-0203 | 1 HOUR POST START OF INFUSION | 16.9 |
| 1101-001-0203 | 1.5 HOUR POST START OF INFUSION | 13.3 |
| 1101-001-0203 | 2 HOURS POST START OF INFUSION | 11 |
| 1101-001-0203 | 3 HOURS POST START OF INFUSION | 10 |

Figure 14C (ctd)

| | | |
|---|---|---|
| 1101-001-0203 | 6 HOURS POST START OF INFUSION | 7.12 |
| 1101-001-0203 | 9 HOURS POST START OF INFUSION | 4.9 |
| 1101-001-0203 | 12 HOURS POST START OF INFUSION | 4.04 |
| 1101-001-0203 | 24 HOURS POST START OF INFUSION | 1.48 |
| 1101-001-0203 | 36 HOURS POST START OF INFUSION | 0.581 |
| 1101-001-0203 | 48 HOURS POST START OF INFUSION | 0.298 |
| 1101-001-0203 | PREDOSE | <LLOQ |
| 1101-001-0203 | 0.5 HOURS POST START OF INFUSION | 10.7 |
| 1101-001-0203 | 1 HOUR POST START OF INFUSION | 13 |
| 1101-001-0203 | 1.5 HOURS POST START OF INFUSION | 11.8 |
| 1101-001-0203 | 3 HOURS POST START OF INFUSION (VENOUS) | 1.58 |
| 1101-001-0203 | 4 HOURS POST START OF INFUSION (VENOUS) | 0.948 |
| 1101-001-0203 | 5 HOURS POST START OF INFUSION (VENOUS) | 0.564 |
| 1101-001-0203 | 6 HOURS POST START OF INFUSION | <LLOQ |
| 1101-001-0203 | 9 HOURS POST START OF INFUSION | 0.859 |
| 1101-001-0203 | 12 HOURS POST START OF INFUSION | 0.729 |
| 1101-001-0203 | 24 HOURS POST START OF INFUSION | 0.26 |
| 1101-001-0203 | 36 HOURS POST START OF INFUSION | <LLOQ |
| 1101-001-0203 | 44 HOURS POST START OF INFUSION | <LLOQ |
| 1101-001-0204 | PREDOSE | <LLOQ |
| 1101-001-0204 | 0.5 HOURS POST START OF INFUSION | 15.4 |
| 1101-001-0204 | 1 HOUR POST START OF INFUSION | 23 |
| 1101-001-0204 | 1.5 HOUR POST START OF INFUSION | 16.9 |
| 1101-001-0204 | 2 HOURS POST START OF INFUSION | 17.6 |
| 1101-001-0204 | 3 HOURS POST START OF INFUSION | 14.6 |
| 1101-001-0204 | 6 HOURS POST START OF INFUSION | 9.11 |
| 1101-001-0204 | 9 HOURS POST START OF INFUSION | 6.84 |
| 1101-001-0204 | 12 HOURS POST START OF INFUSION | 4.98 |
| 1101-001-0204 | 24 HOURS POST START OF INFUSION | 1.33 |
| 1101-001-0204 | 36 HOURS POST START OF INFUSION | 0.369 |

Figure 14C (ctd)

| | | |
|---|---|---|
| 1101-001-0204 | 48 HOURS POST START OF INFUSION | 0.113 |
| 1101-001-0204 | PREDOSE | <LLOQ |
| 1101-001-0204 | 0.5 HOURS POST START OF INFUSION | 190** |
| 1101-001-0204 | 1 HOUR POST START OF INFUSION | 22.1 |
| 1101-001-0204 | 1.5 HOUR POST START OF INFUSION | 15.4 |
| 1101-001-0204 | 3 HOURS POST START OF INFUSION (VENOUS) | 1.38 |
| 1101-001-0204 | 4 HOURS POST START OF INFUSION (VENOUS) | 0.861 |
| 1101-001-0204 | 5 HOURS POST START OF INFUSION (VENOUS) | 0.493 |
| 1101-001-0204 | 9 HOURS POST START OF INFUSION | 1.74 |
| 1101-001-0204 | 12 HOURS POST START OF INFUSION | 1.3 |
| 1101-001-0204 | 24 HOURS POST START OF INFUSION | 0.401 |
| 1101-001-0204 | 36 HOURS POST START OF INFUSION | 0.101 |
| 1101-001-0204 | 44 HOURS POST START OF INFUSION | <LLOQ |
| 1101-001-0205 | Predose | <LLOQ |
| 1101-001-0205 | 0.5 HOURS POST START OF INFUSION | 7.38 |
| 1101-001-0205 | 1 HOUR POST START OF INFUSION | 15.9 |
| 1101-001-0205 | 1.5 HOUR POST START OF INFUSION | 6.29 |
| 1101-001-0205 | 2 HOURS POST START OF INFUSION | 5.64 |
| 1101-001-0205 | 3 HOURS POST START OF INFUSION | 4.68 |
| 1101-001-0205 | 6 HOURS POST START OF INFUSION | 2.4 |
| 1101-001-0205 | 9 HOURS POST START OF INFUSION | 1.23 |
| 1101-001-0205 | 12 HOURS POST START OF INFUSION | 1.07 |
| 1101-001-0205 | 24 HOURS POST START OF INFUSION | 0.124 |
| 1101-001-0205 | 36 HOURS POST START OF INFUSION | <LLOQ |
| 1101-001-0205 | 48 HOURS POST START OF INFUSION | <LLOQ |
| 1101-001-0205 | PREDOSE | 1.9** |
| 1101-001-0205 | 0.5 HOURS POST START OF INFUSION | 4.49 |
| 1101-001-0205 | 1 HOUR POST START OF INFUSION | 7.19 |
| 1101-001-0205 | 1.5 HOUR POST START OF INFUSION | 5.81 |
| 1101-001-0205 | 3 HOURS POST START OF INFUSION (VENOUS) | 1.88 |

Figure 14C (ctd)

| Subject | Timepoint | Value |
|---|---|---|
| 1101-001-0205 | 4 HOURS POST START OF INFUSION (VENOUS) | 1.14 |
| 1101-001-0205 | 5 HOURS POST START OF INFUSION (VENOUS) | <LLOQ |
| 1101-001-0205 | 6 HOURS POST START OF INFUSION (VENOUS) | 0.335 |
| 1101-001-0205 | 9 HOURS POST START OF INFUSION | 0.612 |
| 1101-001-0205 | 12 HOURS POST START OF INFUSION | 0.426 |
| 1101-001-0205 | 24 HOURS POST START OF INFUSION | <LLOQ |
| 1101-001-0205 | 36 HOURS POST START OF INFUSION | <LLOQ |
| 1101-001-0205 | 44 HOURS POST START OF INFUSION | <LLOQ |
| 1101-001-0206 | PREDOSE | <LLOQ |
| 1101-001-0206 | 0.5 HOURS POST START OF INFUSION | 10.4 |
| 1101-001-0206 | 1 HOUR POST START OF INFUSION | 17.1 |
| 1101-001-0206 | 1.5 HOUR POST START OF INFUSION | 11.1 |
| 1101-001-0206 | 2 HOURS POST START OF INFUSION | 9.08 |
| 1101-001-0206 | 3 HOURS POST START OF INFUSION | 5.47 |
| 1101-001-0206 | 6 HOURS POST START OF INFUSION | 2.69 |
| 1101-001-0206 | 9 HOURS POST START OF INFUSION | 1.4 |
| 1101-001-0206 | 12 HOURS POST START OF INFUSION | 0.786 |
| 1101-001-0206 | 24 HOURS POST START OF INFUSION | <LLOQ |
| 1101-001-0206 | 36 HOURS POST START OF INFUSION | <LLOQ |
| 1101-001-0206 | 48 HOURS POST START OF INFUSION | <LLOQ |
| 1101-001-0206 | PREDOSE | <LLOQ |
| 1101-001-0206 | 0.5 HOURS POST START OF INFUSION | 9.55 |
| 1101-001-0206 | 1 HOUR POST START OF INFUSION | 13.2 |
| 1101-001-0206 | 1.5 HOUR POST START OF INFUSION | 10.6 |
| 1101-001-0206 | 3 HOURS POST START OF INFUSION (VENOUS) | 2.54 |
| 1101-001-0206 | 4 HOURS POST START OF INFUSION (VENOUS) | 1.43 |
| 1101-001-0206 | 5 HOURS POST START OF INFUSION (VENOUS) | 0.572 |
| 1101-001-0206 | 6 HOURS POST START OF INFUSION (VENOUS) | 0.334 |
| 1101-001-0206 | 9 HOURS POST START OF INFUSION | 0.311 |
| 1101-001-0206 | 12 HOURS POST START OF INFUSION | 0.176 |
| 1101-001-0206 | 24 HOURS POST START OF INFUSION | <LLOQ |
| 1101-001-0206 | 36 HOURS POST START OF INFUSION | <LLOQ |
| 1101-001-0206 | 44 HOURS POST START OF INFUSION | <LLOQ |

<LLOQ Less than lower limit of quantitation

Figure 14D

Renal Group = ESRD on HD

| Subject ID Age/Race/ Ethnicity/Sex | Study Visit | Start Time Stop Time | Average Dialysis Flow Rate (mL/min) | Average Blood Flow Rate (mL/min) | Hemodialyzer Make and Model | High Flux Membrane (m²) | Ultra Filtration Coefficient (mL/hr/mmHg) | BUN Collected before Dialysis | | BUN Collected after Dialysis | |
|---|---|---|---|---|---|---|---|---|---|---|---|
| | | | | | | | | Time | Result (mmol/L) | Time | Result (mmol/L) |
| 001-0201 50/B/N/M | BASELINE STUDY DAY 1 | 6:29 8:29 | 800 | 550 | GAMBRO REVACLEAR | 1.4 | 50 | | | | |
| | DAY 4 (HD SUBJECTS) | 9:15 12:15 | 600 | 550 | GAMBRO REVACLEAR | 1.4 | 50 | 7:10 | 30.3 | 14:10 | 10.7 |
| | DAY 6 (HD SUBJECTS) | 8:25 12:25 | 600 | 550 | GAMBRO REVACLEAR | 1.4 | 50 | 8:24 | 29.6 | 11:25 | 7.9 |
| 001-0202 71/B/N/F | BASELINE STUDY DAY 1 | 6:07 9:08 | 600 | 400 | GAMBRO REVACLEAR | 1.4 | 50 | | | | |
| | DAY 4 (HD SUBJECTS) | 9:00 12:00 | 600 | 400 | GAMBRO REVACLEAR | 1.4 | 50 | 6:15 | 17.5 | 12:00 | 3.6 |
| | DAY 6 (HD SUBJECTS) | 6:50 9:54 | 600 | 400 | GAMBRO REVACLEAR | 1.4 | 50 | 5:00 | 11.4 | 9:52 | 2.1 |
| 001-0203 47/B/N/M | BASELINE STUDY DAY 1 | 8:10 12:10 | 600 | 600 | BAXTER CT190G | 1.9 | 36 | | | | |
| | DAY 4 (HD SUBJECTS) | 12:15 16:15 | 800 | 600 | BAXTER CT190G | 1.9 | 36 | 9:55 | 21.1 | 16:15 | 2.8 |
| | DAY 6 (HD SUBJECTS) | 6:20 10:21 | 600 | 600 | BAXTER CT190G | 1.9 | 36 | 6:05 | 14.6 | 10:21 | 3.6 |
| 001-0204 50/B/N/F | BASELINE STUDY DAY 1 | 6:15 9:17 | 600 | 264 | GAMBRO REVACLEAR | 1.4 | 50 | | | | |
| | DAY 4 (HD SUBJECTS) | 9:15 12:15 | 600 | 300 | GAMBRO REVACLEAR | 1.4 | 50 | 6:29 | 23.9 | 12:15 | 7.1 |
| | DAY 6 (HD SUBJECTS) | 7:35 10:35 | 600 | 400 | GAMBRO REVACLEAR | 1.4 | 50 | 9:15 | 21.8 | 10:35 | 5.7 |

Figure 14D Cont.

Renal Group = ESRD on HD

| Subject ID Age/Race/ Ethnicity/Sex | Study Visit | Start Time Stop Time | Average Dialysis Flow Rate (mL/min) | Average Blood Flow Rate (mL/min) | Hemodialyzer Make and Model | High Flux Membrane (m²) | Ultra Filtration Coefficient (mL/hr/mmHg) | BUN Collected before Dialysis Time | Result (mmol/L) | BUN Collected after Dialysis Time | Result (mmol/L) |
|---|---|---|---|---|---|---|---|---|---|---|---|
| 001-0205 40/B/H/M | BASELINE STUDY DAY 1 | 6:15 10:15 | 600 | 550 | GAMBRO REVACLEAR MAX | 1.8 | 60 | | | | |
| | DAY 4 (HD SUBJECTS) | 10:35 14:35 | 600 | 550 | GAMBRO REVACLEAR MAX | 1.8 | 60 | 7:40 | 25.7 | 14:35 | 5.6 |
| | DAY 6 (HD SUBJECTS) | 7:10 11:10 | 600 | 550 | GAMBRO REVACLEAR MAX | 1.8 | 60 | 4:35 | 22.1 | 12:10 | 7.5 |
| 001-0206 40/W/H/M | BASELINE STUDY DAY 1 | 5:55 9:55 | 800 | 583 | GAMBRO REVACLEAR MAX | 1.8 | 60 | | | | |
| | DAY 4 (HD SUBJECTS) | 10:45 14:45 | 800 | 600 | GAMBRO REVACLEAR MAX | 1.8 | 60 | 8:15 | 29.3 | 14:46 | 5.4 |
| | DAY 6 (HD SUBJECTS) | 8:10 12:10 | 800 | 600 | GAMBRO REVACLEAR MAX | 1.8 | 60 | 7:21 | 17.9 | 12:10 | 3.9 |

FIG. 14D Cont.

Renal Group = ESRD on HD

| Subject ID Age/Race/ Ethnicity/Sex | Study Visit | Start Time Stop Time | Average Dialysis Flow Rate (mL/min) | Average Blood Flow Rate (mL/min) | Hemodialyzer Make and Model | High Flux Membrane (m²) | Ultra Filtration Coefficient (mL/hr/mmHg) | BUN Collected before Dialysis Time | Result (mmol/L) | BUN Collected after Dialysis Time | Result (mmol/L) |
|---|---|---|---|---|---|---|---|---|---|---|---|
| 001-0205 42/B/N/M | BASELINE STUDY DAY 1 | 6:15 10:15 | 600 | 550 | GAMBRO REVACLEAR MAX | 1.8 | 60 | | | | |
| | DAY 4 (HD SUBJECTS) | 10:35 14:35 | 650 | 550 | GAMBRO REVACLEAR MAX | 1.8 | 60 | 7:40 | 25.7 | 14:35 | 9.6 |
| | DAY 6 (HD SUBJECTS) | 7:10 11:10 | 650 | 550 | GAMBRO REVACLEAR MAX | 1.8 | 60 | 4:35 | 22.3 | 11:10 | 7.5 |
| 001-0206 40/W/N/M | BASELINE STUDY DAY 1 | 5:55 9:55 | 650 | 580 | GAMBRO REVACLEAR MAX | 1.8 | 60 | | | | |
| | DAY 4 (HD SUBJECTS) | 10:45 14:45 | 650 | 600 | GAMBRO REVACLEAR MAX | 1.8 | 60 | 8:15 | 29.3 | 14:46 | 5.4 |
| | DAY 6 (HD SUBJECTS) | 8:10 12:10 | 850 | 600 | GAMBRO REVACLEAR MAX | 1.8 | 60 | 7:21 | 17.9 | 12:10 | 3.9 |

FIG. 15

Two-compartment PK structure model for Ceftolozane and Tazobactam

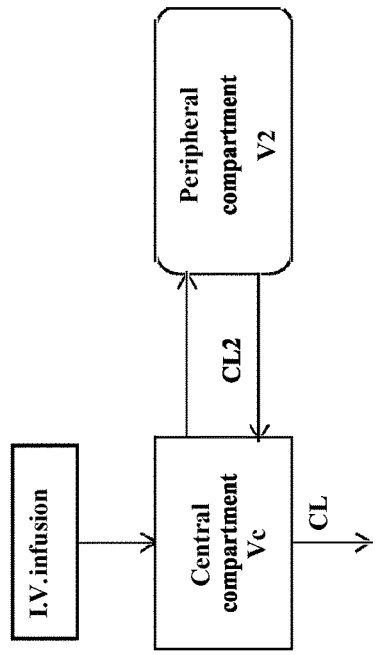

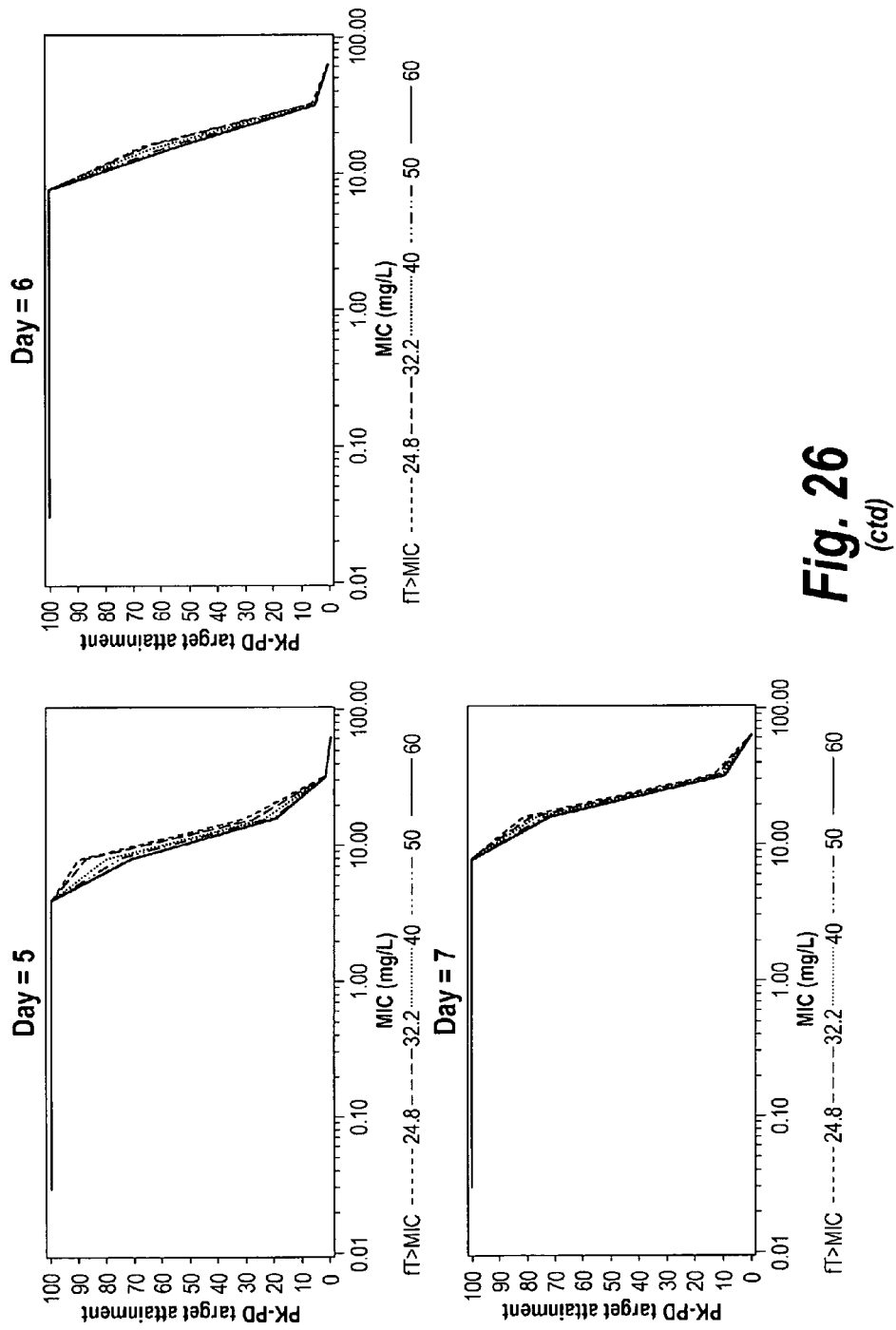
Fig. 26 (ctd)

Figure 27(ctd.)

Figure 28

| Brand Name | Administration | Recommended Dose for Adult Patients | Recommended Dose for Patients on Dialysis | Recommended Dose for Patients with Severe Renal Impairment | % Renal Excretion | % Clearance by Dialysis | Pharmacokinetic Parameters in Normal Patients | Pharmacokinetic Parameters in Patients with Severe Renal Impairment |
|---|---|---|---|---|---|---|---|---|
| DORIBAX® (doripenem)[3] | Intravenous over 1 hour | 500 mg every 8 hours | There is insufficient information to make dose adjustment recommendations in patients on hemodialysis | CrCl 30 to 50 mL/min: 250 mg over 1 hour every 8 hours<br><br>CrCl 10 to 30 mL/min: 250 mg over 1 hour every 12 hours | 70% of dose recovered in unchanged form<br><br>15% of dose is recovered as ring-opened metabolite | 52% of the dose after a 4 hour session | $t_{1/2}$ = 1 hour<br>CL = 15.9 ± 5.3 L/hour | $t_{1/2}$ = 11 to 14 hours<br>CL = Not available |
| INVANZ® (ertapenem)[7] | Intravenous infusion over 30 minutes | 1 g once daily | 500 mg/day within 6 hours prior to hemodialysis, a supplementary dose of 150 mg is recommended following the hemodialysis session | CrCl ≤ 30 mL/min: 500 mg every 24 hours | 38% of dose recovered in unchanged form<br><br>37% of dose is recovered as ring-opened metabolite | 30% of the dose after a 4 hour session | $t_{1/2}$ = 4 hours<br>CL = 1.8 L/hour | $t_{1/2}$ = 11 to 14 hours<br>CL = Not available |
| PRIMAXIN® (imipenem)[8] | Intravenous infusion 125, 250, or 500 mg dose over 20 to 30 minutes. Infuse a 750 mg or 1 g dose over 40 to 60 minutes | 250 mg to 1 g every 6-8 hours for different indications | Continuous renal replacement therapy: 500 mg IV every 6 hours[4] Loading dose 1 g[5]<br><br>Intermittent hemodialysis: 250 to 500 mg IV every 12 hours[5] | CrCl ≤ 30 mL/min: 125 – 500 mg IV every 6-12 hours depending on weight and initial dose | 70% of both cilastatin and imipenem recovered in unchanged form | Not available | $t_{1/2}$ = 1 hour<br>CL = Not available | $t_{1/2}$ = Not available<br>CL = Not available |

Figure 28 (ctd.)

| Brand Name | Administration | Recommended Dose for Adult Patients | Recommended Dose for Patients on Dialysis | Recommended Dose for Patients with Severe Renal Impairment | % Renal Excretion | % Clearance by Dialysis | Pharmacokinetic Parameters in Normal Patients | Pharmacokinetic Parameters in Patients with Severe Renal Impairment |
|---|---|---|---|---|---|---|---|---|
| MERREM® (meropenem)⁸ | Intravenous infusion over 15 to 30 minutes | 500mg to 1 g every 8 hours for different indications | Continuous renal replacement therapy: 1 to 2 g every 12 hours⁴ Intermittent hemodialysis: 500 mg IV every 24 hours administered after the dialysis session⁵ Peritoneal dialysis: recommended dose every 24 hours⁵ | CrCl 10 to 25 mL/min: 250mg to 500 mg every 12 hours for different indications CrCl ≤10 mL/min: 250mg to 500 mg every 24 hours for different indications | 70% of dose recovered in unchanged form 28% of dose is recovered as an inactive metabolite | Not available | t₁/₂ = 1 hour CL = 8.4 to 13.8 L/hour⁵ | t₁/₂ = 3.4 to 20 hours or longer⁵ CL = Not available |
| ANCEF® (cefazolin)⁹ | Intravenous infusion over 30 minutes | 250 mg to 1.5 g every 6 to 12 hours for different indications | Continuous renal replacement therapy: 250 mg to 2 g IV every 12 hours⁶ Loading dose 2 g⁵ Intermittent hemodialysis: 500 mg to 1 g IV every 24 hours administered after dialysis on dialysis days⁵ Peritoneal dialysis: 500 mg IV every 12 hours⁴ | CrCl 11 to 34 mL/min: 125 mg to 500 mg every 12 hours for different indications CrCl ≤10 mL/min: 125 mg to 500 mg every 18 to 24 hours for different indications | 80% to 80% of dose recovered in unchanged form | 60% of the dose⁵ | t₁/₂ = 1.8 hours CL = 4.03 ± 0.68 L/hour⁸ | t₁/₂ = Not available CL = Not available |

Figure 28 (ctd.)

| Brand Name | Administration | Recommended Dose for Adult Patients | Recommended Dose for Patients on Dialysis | Recommended Dose for Patients with Severe Renal Impairment | % Renal Excretion | % Clearance by Dialysis | Pharmacokinetic Parameters in Normal Patients | Pharmacokinetic Parameters in Patients with Severe Renal Impairment |
|---|---|---|---|---|---|---|---|---|
| CEPOTAN® (cefotetan) | Intravenous | 500 mg to 3 g every 12 hours for different indications | 25% of the usual recommended dose should be given every 24 hours on days between dialysis and 50% of the usual recommended dose on the day of dialysis | CrCl 10 to 30 mL/min: 500 mg to 3 g every 24 hours; CrCl ≤ 10 mL/min: 500 mg to 3 g every 48 hours | 51% to 81% of dose recovered in unchanged form | Not available | $t_{1/2}$ = 3 to 4.6 hours; CL = 1.8 ± 0.3 L/hour | $t_{1/2}$ = 10 hours (moderate impairment); CL = Not available |
| FORTAZ® (ceftazidime) | Intravenous | 250 mg to 1 g every 8 to 12 hours for different indications | Continuous renal replacement therapy: 1 to 2 g every 12 hours; Loading dose 2 g; Intermittent hemodialysis: Loading dose of 1 g, followed by 1 g after each hemodialysis period; Peritoneal dialysis: Loading dose of 1 g, followed by 500 mg every 24 hours | CrCl 16 to 30 mL/min: 1 g every 24 hours; CrCl 6 to 15 mL/min: 500 mg every 24 hours; CrCl ≤ 5 mL/min: 500 mg every 48 hours | 80% to 90% of dose recovered in unchanged form | Not available | $t_{1/2}$ = 1.9 hours; CL = 6 L/hour | $t_{1/2}$ = Not available; CL = Not available |

Figure 28 (ctd.)

| Brand Name | Administration | Recommended Dose for Adult Patients | Recommended Dose for Patients on Dialysis | Recommended Dose for Patients with Severe Renal Impairment | % Renal Excretion | % Clearance by Dialysis | Pharmacokinetic Parameters in Normal Patients | Pharmacokinetic Parameters in Patients with Severe Renal Impairment |
|---|---|---|---|---|---|---|---|---|
| MAXIPIME® (cefepime)[12] | Intravenous infusion over 30 minutes | 500 mg to 2 g every 12 hours for different indications | Continuous renal replacement therapy: 1 to 2 g every 12 hours[4] Loading dose 2g[4] Intermittent hemodialysis: 1 g on Day 1 followed by 500 mg every 24 hours | CrCl 11 to 29 mL/min: 500 mg to 2g every 24 hours for different indications CrCl ≤ 10 mL/min: 250 mg to 1 g every 24 hours for different indications | 85% of dose recovered in unchanged form | 68% of the dose | $t_{1/2}$ = 2.1 ± 0.3 hours CL = 7.2 ± 0.48 L/hour | $t_{1/2}$ = 13.5 ± 2.7 hours (hemodialysis) $t_{1/2}$ = 19 ± 2 hours (peritoneal dialysis) CL = Decreases proportionally with creatinine clearance |
| TEFLARO™ (ceftaroline)[13] | Intravenous infusion over 1 hour | 600 mg every 12 hours | 200 mg every 12 hours following hemodialysis | CrCl 15 to 30 mL/min: 300 mg every 12 hours | 88% of dose recovered in unchanged form | 21.6% of the dose | $t_{1/2}$ = 2.66 ± 0.4 hours CL = 9.6 ± 1.4 L/hour | $t_{1/2}$ = Not available CL = Not available |
| UNASYN® (ampicillin/ sulbactam)[14] | Intravenous infusion over 10 to 15 minutes | 1.5 g to 3 g every 6 hours for different indications | Continuous renal replacement therapy: Loading dose of 3 g, followed by 1.5 g to 3 g every 8 hours[5] Intermittent hemodialysis: 1.5 to 3 g IV every 12 to 24 hours[5] | CrCl 15 to 29 mL/min: 1.5 to 3 g every 12 hours CrCl 5 to 14 mL/min: 1.5 to 3 g every 24 hours | 75% to 85% of both ampicillin and sulbactam recovered in unchanged form | Not available | $t_{1/2}$ = 1 hour CL = Not available | $t_{1/2}$ = 5 to 9 hours CL = Not available |

Figure 28 (ctd.)

| Brand Name | Administration | Recommended Dose for Adult Patients | Recommended Dose for Patients on Dialysis | Recommended Dose for Patients with Severe Renal Impairment | % Renal Excretion | % Clearance by Dialysis | Pharmacokinetic Parameters in Normal Patients | Pharmacokinetic Parameters in Patients with Severe Renal Impairment |
|---|---|---|---|---|---|---|---|---|
| AUGMENTIN® (amoxicillin/ clavulanate)[25] | Oral | 250 mg to 2 g every 8 to 12 hours for different indications | 250 mg to 500 mg every 24 hours and an additional dose both during and after each hemodialysis session | CrCl 10 to 30 mL/min: 250 mg to 500 mg every 12 hours<br>CrCl ≤10 mL/min: 250 mg to 500 mg every 24 hours | 50% to 70% of amoxicillin and 25% to 40% of clavulanic acid recovered in unchanged form | Amoxicillin:47% Clavulanic acid: 34% | Amoxicillin $t_{1/2}$ = 1.4 ± 0.3 hours CL = 8.9 ± 0.4 L/h/kg<br>Clavulanic acid: $t_{1/2}$ = 1.1 ± 0.3 hours CL = 1.1 ± 1.1 L/h/kg | $t_{1/2}$ = 1.3 hours CL = Not available |
| TIMENTIN® (ticarcillin/ clavulanate)[25] | Intravenous infusion over 30 minutes | 3.1 g every 4 to 6 h loading dose, followed by 200 to 300 mg/kg/day in divided doses every 4 to 6 h for different indications and weight | Hemodialysis: 2 g every 12 hours supplemented with 3 g IV after each dialysis<br>Peritoneal dialysis: 3 g every 12 hours | CrCl 10 to 30 mL/min: 2 g every 8 hours<br>CrCl ≤10 mL/min: 2 g every 12 hours | 60% to 70% of ticarcillin and 35% to 45% of clavulanic acid recovered in unchanged form | Not available | Ticarcillin $t_{1/2}$ = 1.1 hours[25] CL = 6.96 L/hour[25]<br>Clavulanic acid: $t_{1/2}$ = 1.1 hours[25] CL = 14.46 L/hour[25] | $t_{1/2}$ = 13 hours CL = Not available |

Figure 28 (ctd.)

| Brand Name | Administration | Recommended Dose for Adult Patients | Recommended Dose for Patients on Dialysis | Recommended Dose for Patients with Severe Renal Impairment | % Renal Excretion | % Clearance by Dialysis | Pharmacokinetic parameters in Normal Patients | Pharmacokinetic Parameters in Patients with Severe Renal Impairment |
|---|---|---|---|---|---|---|---|---|
| ZOSYN® (piperacillin/ tazobactam)[a] | Intravenous infusion over 30 minutes | For all indications except nosocomial pneumonia: 3.375 g every 6 hours. Nosocomial pneumonia: 4.5 g every 6 hours | For all indications except nosocomial pneumonia: 2.25 g every 12 hours; 0.75 g after each session. Nosocomial pneumonia: 2.25 g every 6 hours; 0.75 g after each session | For all indications except nosocomial pneumonia: CrCl 20 to 40 mL/min: 2.25 g every 6 hours. CrCl ≤20 mL/min: 2.25 g every 8 hours. Nosocomial pneumonia: CrCl 20 to 40 mL/min: 3.375 g every 6 hours. CrCl ≤20 mL/min: 2.25 g every 6 hours | 68% of piperacillin recovered in unchanged form. 80% of tazobactam recovered in unchanged form | Hemodialysis: 30% to 40% of piperacillin/ tazobactam dose. Peritoneal dialysis: 6% and 21% of piperacillin/ tazobactam dose | Piperacillin: t½ = 0.79 to 0.84 hours. CL = 9.4 L/hour. Tazobactam: t½ = 0.77 to 0.82 hours. CL = 9.96 L/hour | Piperacillin: t½ = 1.92 ± 1.5 hours[a]. CL = 85 ± 10 L/hour[a]. Tazobactam: t½ = 3.98 ± 46.5 hours. CL = 49.5 ± 8.1 L/hour[a] |

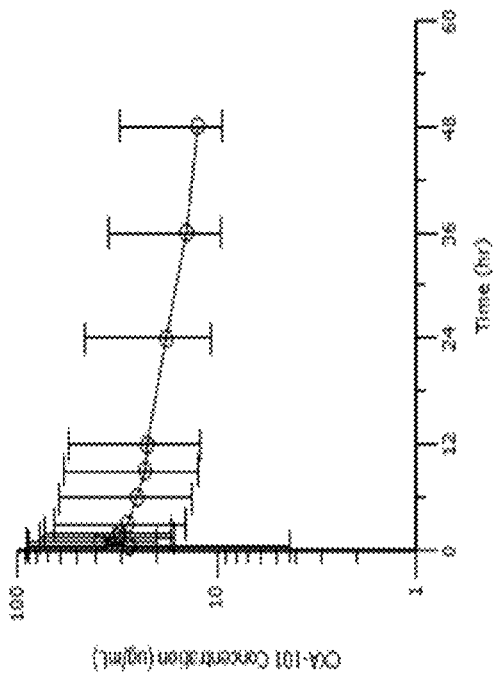
Figure 36: Plasma Concentration (Median and Range) versus Time Profile for Ceftolozane During Non-Hemodialysis in Subjects with ESRD (Study Day 1)

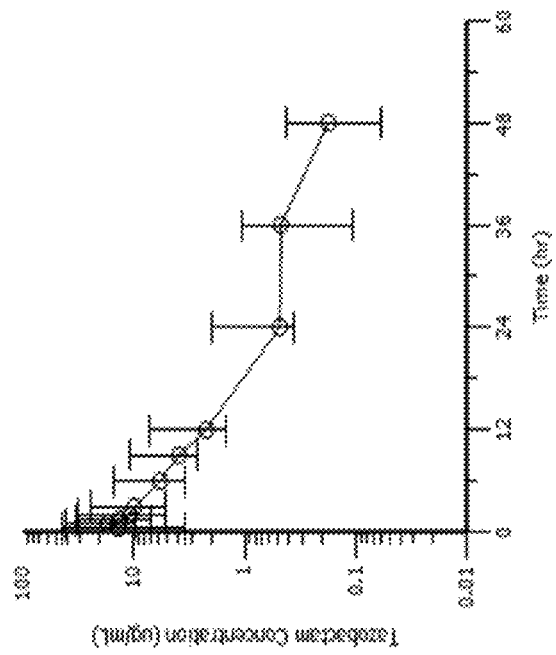
Figure 37: Plasma Concentration (Median and Range) versus Time Profile for Tazobactam During Non-Hemodialysis in Subjects with ESRD (Study Day 1)

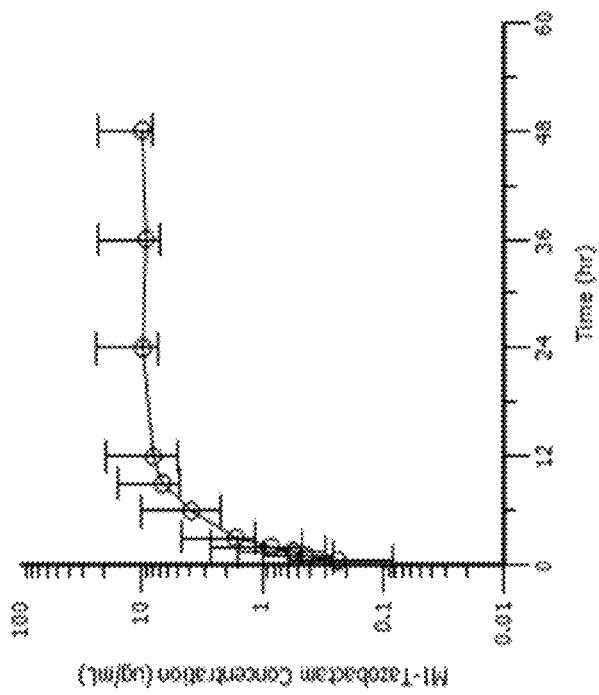
Figure 38: Plasma Concentration (Median and Range) versus Time Profile for the M-1 Metabolite of Tazobactam During Non-Hemodialysis in Subjects with ESRD (Study Day 1)

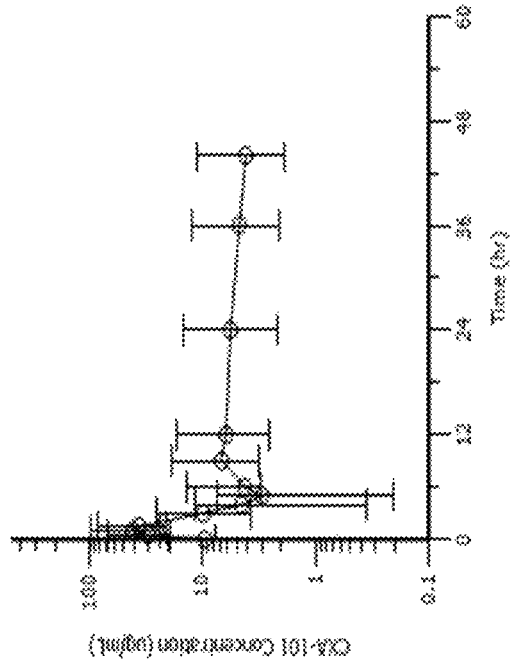
Figure 39: Plasma Concentration (Median and Range) versus Time Profile for Ceftolozane in Subjects with ESRD During HD (Study Day 4)

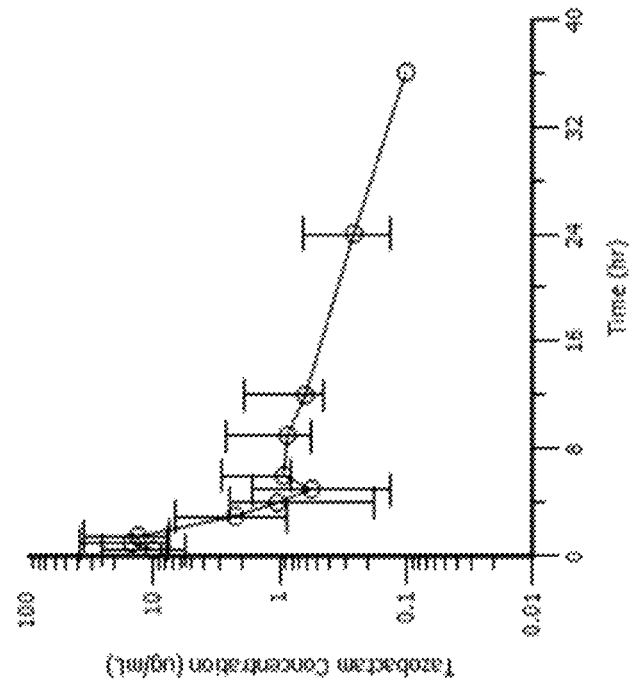
Figure 40: Plasma Concentration (Median and Range) versus Time Profile for Tazobactam in Subjects with ESRD During HD (Study Day 4)

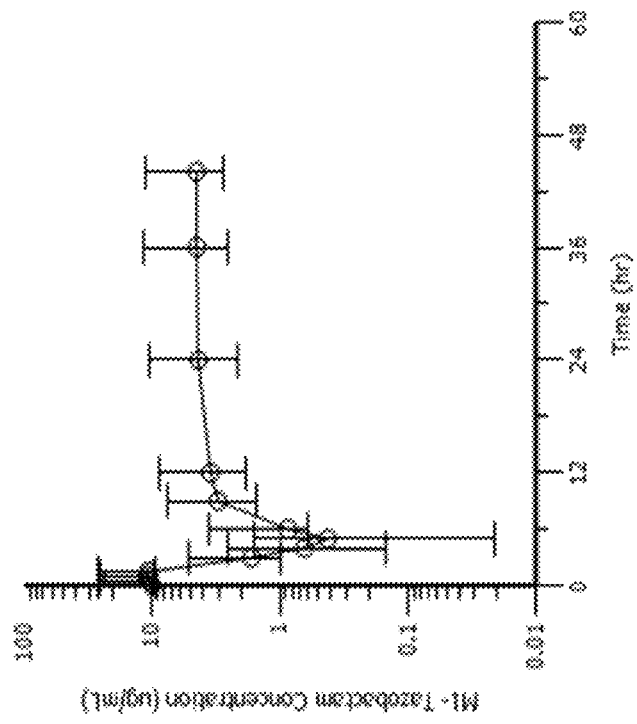
Figure 41: Plasma Concentration (Median and Range) versus Time Profile for the M-1 Metabolite of Tazobactam in Subjects with ESRD During HD (Study Day 4)

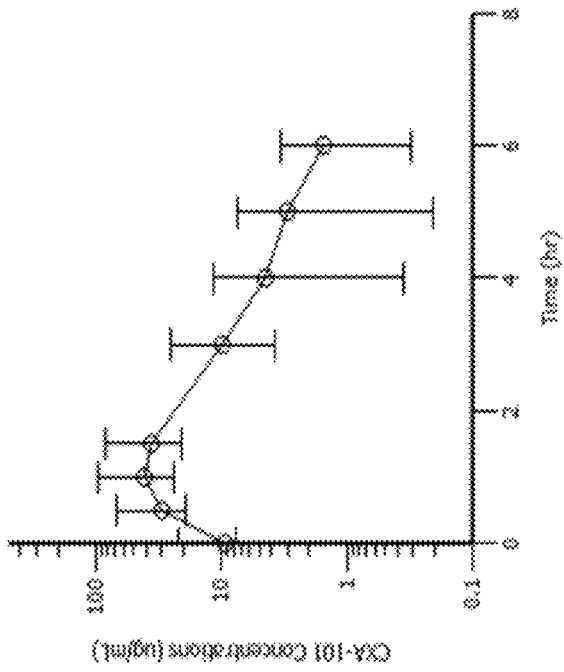
Figure 42: Plasma Concentration (Median and Range) versus Time Profile for Ceftolozane in Subjects with ESRD (Start of Dosing to End of Dialysis)

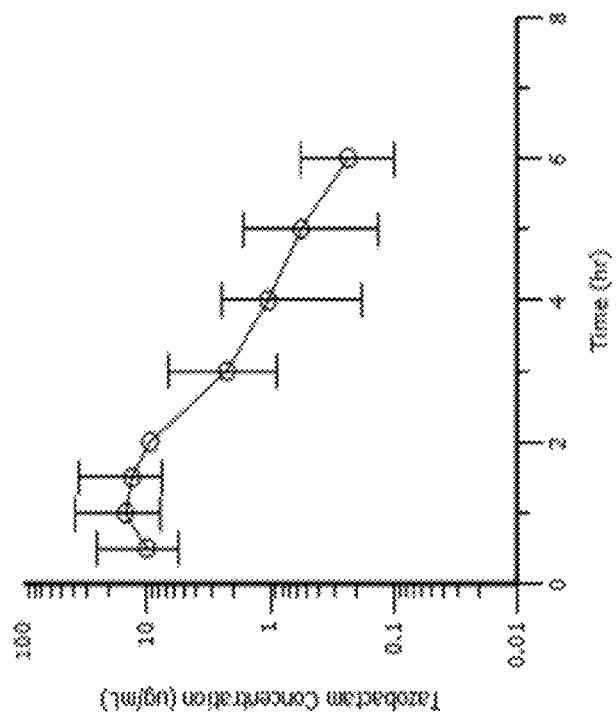
Figure 43: Plasma Concentration (Median and Range) versus Time Profile for Tazobactam in Subjects with ESRD (Start of Dosing to End of Dialysis)

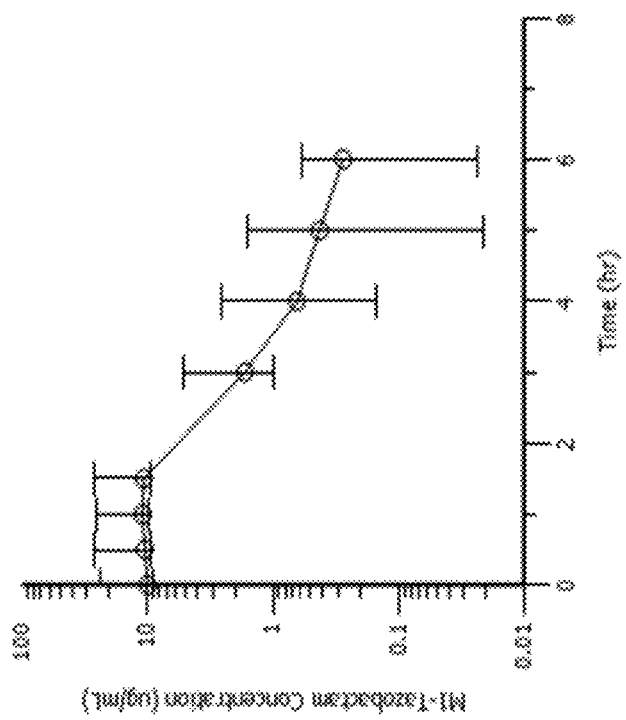
Figure 44: Plasma Concentration (Median and Range) versus Time Profile for the M-1 Metabolite of Tazobactam in Subjects with ESRD (Start of Dosing to End of Dialysis)

TREATING INFECTIONS WITH CEFTOLOZANE/TAZOBACTAM IN SUBJECTS HAVING IMPAIRED RENAL FUNCTION

RELATED APPLICATIONS

This application is a continuation of U.S. patent application Ser. No. 14/481,496, filed Sep. 9, 2014, now U.S. Pat. No. 10,376,496, which claims the benefit of U.S. Provisional Patent Applications 62/046,417 (filed Sep. 5, 2014), 62/002,457 (filed May 23, 2014), 61/875,358 (filed Sep. 9, 2013), 61/883,579 (filed Sep. 27, 2013), and 61/984,299 (filed Apr. 25, 2014), and 61/988,085 (filed May 2, 2014), each of which is incorporated herein by reference in its entirety.

TECHNICAL FIELD

This disclosure relates to the administration of ceftolozane/tazobactam to human patients with impaired renal function.

BACKGROUND

The cephalosporin (6R,7R)-3-[(5-amino-4-{[(2-aminoethyl)carbamoyl]amino}-1-methyl-1H-pyrazol-2-ium-2-yl)methyl]-7-({(2Z)-2-(5-amino-1,2,4-thiadiazol-3-yl)-2-[(1-carboxy-1-methylethoxy)imino]acetyl}amino)-8-oxo-5-thia-1-azabicyclo[4.2.0]oct-2-ene-2-carboxylate (also referred to as "ceftolozane") is an antibacterial agent. The antibacterial activity of ceftolozane is believed to result from its interaction with penicillin binding proteins (PBPs) to inhibit the biosynthesis of the bacterial cell wall which acts to stop bacterial replication.

Ceftolozane can be combined (e.g., mixed) with a β-lactamase inhibitor ("BLI"), such as tazobactam. Tazobactam is a BLI against Class A and some Class C β-lactamases, with well-established in vitro and in vivo efficacy in combination with active β-lactam antibiotics. The combination of ceftolozane, or a pharmaceutically acceptable salt thereof and tazobactam or a pharmaceutically acceptable salt thereof in an amount providing a 2:1 weight ratio between the amount of ceftolozane active and tazobactam active is an antibiotic pharmaceutical composition ("CXA-201") formulated for parenteral administration. CXA-201 displays potent antibacterial activity in vitro against common Gram-negative and selected Gram-positive organisms that cause complicated intra-abdominal infections or complicated urinary tract infections. Moreover, CXA-201 has demonstrated efficacy in clinical trials against these infections (See, e.g., Examples 3-5), and the recommended dosage for patients with normal kidney function [creatinine clearance (CrCL)>50 mL/min] is 1.5 grams of CXA-201 (1 g ceftolozane active/500 mg tazobactam active) administered intravenously over one hour every eight hours (See Table 1 below).

TABLE 1

Dosage of CXA-201 by Infection in Patients with Creatinine Clearance (CrCL) > 50 mL/min

| Infection | Dose CXA-201 | Frequency | Infusion Time (hours) | Duration of Treatment |
|---|---|---|---|---|
| Complicated Intra-Abdominal Infections | 1.5 g | Every 8 Hours | 1 | 4-14 days |
| Complicated Urinary Tract Infections, including Pyelonephritis | 1.5 g | Every 8 Hours | 1 | 7 days |

The intravenous formulation of CXA-201 can be prepared by reconstituting a fixed dose combination mixture of two active components (ceftolozane and tazobactam), and intravenously administering the reconstituted pharmaceutical composition. The pharmacokinetic (PK) profile of ceftolozane/tazobactam has been studied in several preclinical and clinical studies. In healthy volunteers the PK of ceftolozane/tazobactam is dose-proportional and linear across a wide range of doses (up to 3000 mg/1500 mg as a single dose) with a terminal elimination half-life ($t_{1/2\beta}$) of approximately 2.5 hours for ceftolozane and 1 hour for tazobactam. Both ceftolozane and tazobactam are primarily excreted in the urine; ceftolozane almost completely in the urine as unchanged parent drug suggesting minimal metabolism, and tazobactam with 80% as the unchanged parent drug and the remaining as inactive M1 metabolite that is formed via hydrolysis of tazobactam (See, e.g., Miller B, Hershberger E, Benziger D, Trinh M, Friedland I., "Pharmacokinetics and safety of intravenous ceftolozane-tazobactam in healthy adult subjects following single and multiple ascending doses," Antimicrob Agents Chemother. 2012; 56(6):3086-3091).

Ceftolozane is eliminated through the kidney. Example 7 provides the pharmacokinetics of ceftolozane/tazobactam in healthy volunteers. In healthy volunteers the PK of ceftolozane/tazobactam is dose-proportional and linear across a wide range of doses (up to 3000 mg/1500 mg as a single dose) with a terminal elimination half-life ($t_{1/2\beta}$) of approximately 2.5 hours for ceftolozane and 1 hour for tazobactam. Both ceftolozane and tazobactam are primarily excreted in the urine; ceftolozane almost completely in the urine as unchanged parent drug suggesting minimal metabolism, and tazobactam with 80% as the unchanged parent drug and the remaining as inactive M1 metabolite that is formed via hydrolysis of tazobactam. There is no drug-drug interaction between ceftolozane and tazobactam when co-administered.

However, impaired kidney function can result in slower drug clearance of ceftolozane and in increased plasma drug levels. Accordingly, the dosing of CXA-201 in Table 1 is not appropriate for certain patients with advanced renal impairment (including, for example, patients with creatinine clearance less than about 50 mL/minute, such as patients with moderate to severe renal disease or patients in end stage renal disease who are undergoing hemodialysis). Therefore, there remains a medical need for determining appropriate dosing adjustments for safely and effectively administering a CXA-201 product to a patient at various stages of renal function impairment, including treatment of patients with end stage renal disease (ESRD) (e.g., patients having a creatinine clearance of less than 15 mL/min).

Adjustments in methods of administering other parenteral anti-infective therapies to patients with impaired renal function do not adequately address the unmet medical need for determining safe and effective methods of administering ceftolozane/tazobactam to patients with renal impairment. Modifications in the manner of administering parenteral anti-infective therapies to treat patients with impaired renal function include changes in the dose amount and/or dose interval (including products disclosed, e.g., in FIG. 28). For example, modifications in the parenteral administration of a pharmaceutical composition to patients with impaired renal function can include (1) decreasing the individual dose and increasing the time between doses (e.g., administering 2.25 g of piperacillin/tazobactam every 8 or 12 hours with an additional 0.75 g following dialysis, instead of 3.375 g administered every 6 hours, for treating indicated infections other than nosocomial pneumonia), (2) increasing the time between doses (e.g., administering 1 g of cefepime hydrochloride on day 1 followed by 500 mg every 24 hours thereafter, instead of 0.5-1 or 2 g administered every 12 hours, for urinary tract or intra-abdominal infections), (3) decreasing the amount of individual doses without changing the time between doses (e.g., administering 200 mg of ceftaroline fasamil every 12 hours, instead of 600 mg administered every 12 hours, for certain skin infections or pneumonia), and (4) not changing the dose amount or time between doses (e.g., when administering intravenous linezolid or ceftriaxone sodium to a patient with renal impairment).

There remains a need for safe and effective methods of administering a CXA-201 anti-infective product to patients having various levels of renal impairment as characterized by reduced creatinine clearance (CrCl).

SUMMARY

Dosage adjustment of ceftolozane/tazobactam pharmaceutical compositions is required in patients with moderate (CrCL 30 to 50 mL/min) or severe (CrCL 15 to 29 mL/min) renal impairment and in patients with end stage renal disease on hemodialysis (ESRD on HD).

In one embodiment, methods of administering ceftolozane and tazobactam in one or more pharmaceutical compositions for treating a patient in need thereof can comprise administering a dose of ceftolozane and tazobactam, with or without a loading dose, in amounts and at a dosing interval effective to provide at least an unbound concentration of ceftolozane of at least 8 micrograms/mL for at least 30% of the time between successive treatment days and unbound tazobactam of about 1 microgram/mL for at least 20% of the time and about 0.5 microgram/mL for about or higher than 50% of the time. Preferably, the ceftolozane and tazobactam are administered in a 2:1 weight ratio between the amount of ceftolozane active and the amount of tazobactam active.

In another embodiment, use of a therapeutically effective amount of a pharmaceutical composition comprising ceftolozane active and tazobactam active in a 2:1 weight ratio, is disclosed for treating an infection in a patient. The therapeutically effective amount can be selected to provide a dose of the pharmaceutical composition, with or without a loading dose, in amounts and at a dosing interval therapeutically effective to provide at least an unbound concentration of ceftolozane of at least 8 micrograms/mL in the patient for at least 30% of the time between successive treatment days and unbound tazobactam of about 1 microgram/mL for at least 20% of the time and about 0.5 microgram/mL for about or higher than 50% of the time during the duration of treatment. Examples of preferred embodiments include: (1) the use of 750 mg of a pharmaceutical composition comprising ceftolozane active and tazobactam active in a 2:1 weight ratio for the treatment of an infection in a patient having a creatinine clearance rate of about 20-50 mL/min; (2) the use of 375 mg of a pharmaceutical composition comprising ceftolozane active and tazobactam active in a 2:1 weight ratio for the treatment of an infection in a patient having a creatinine clearance rate of about 15-29 mL/min; and (3) the use of a single loading dose of 750 mg followed by use of a 150 mg maintenance dose of a pharmaceutical composition comprising ceftolozane active and tazobactam active in a 2:1 weight ratio administered IV every 8 hours for the remainder of the treatment period (on hemodialysis days, the dose should be administered at the earliest possible time following completion of dialysis).

In an embodiment, a pharmaceutical composition comprising ceftolozane active and tazobactam active in a 2:1 weight ratio is administered to a patient with impaired renal function in accordance with Table 2A below:

TABLE 2A

Dosage of CXA-201 in Patients with Impaired Renal Function

| Estimated CrCL (mL/min) | Recommended Dosage Regimen for CXA-201 |
|---|---|
| 30 to 50 | 750 mg IV every 8 hours |
| 15 to 29 | 375 mg IV every 8 hours |
| End stage Renal Disease (ESRD) on hemodialysis (HD) | A single loading dose of 750 mg followed by a 150 mg maintenance dose administered IV every 8 hours for the remainder of the treatment period (on hemodialysis days, the dose should be administered at the earliest possible time following completion of dialysis) |

In a preferred embodiment, the invention provides for the use of 500 mg ceftolozane active and 250 mg tazobactam active administered intravenously every 8 hours to a patient having a creatinine clearance (CrCl) of 30 to 50 ml/min. In a preferred embodiment, the invention provides for the use of 250 mg ceftolozane active and 125 mg tazobactam active administered intravenously every 8 hours to a patient having a creatinine clearance (CrCl) of 15 to 29 ml/min. In a preferred embodiment, the invention provides for the use of 500 mg ceftolozane active and 250 mg tazobactam active administered intravenously to a patient with End Stage Renal Disease (ESRD) undergoing hemodialysis (HD) followed by use of a maintenance dose of 100 mg ceftolozane active and 50 mg tazobactam active administered intravenously every 8 hours for the remainder of the treatment period.

In other embodiments, one or more doses can be administered at the same or different durations of 1-4 hours each. In other embodiments, one or more doses are administered 1-4 times per day at the same or different intervals between doses.

In other embodiments, the doses are selected from the group consisting of:
 a) a loading dose of 600 mg ceftolozane active and 300 mg tazobactam active, and a maintenance dose of 300 mg ceftolozane active and 150 mg tazobactam active;
 b) a loading dose of 500 mg ceftolozane active and 250 mg tazobactam active, and a maintenance dose of 300 mg ceftolozane active and 150 mg tazobactam active;
 c) a loading dose of 500 mg ceftolozane active and 250 mg tazobactam active, and a maintenance dose of 100 mg ceftolozane active and 50 mg tazobactam active;
 d) a loading dose of 400 mg ceftolozane active and 200 mg tazobactam active, and a maintenance dose of 100 mg ceftolozane active and 50 mg tazobactam active;

e) 300 mg ceftolozane active and 150 mg tazobactam active; and
f) 100 mg ceftolozane active and 50 mg tazobactam active.

In certain embodiments, each dose is administered in a 1-hour intravenous infusion.

In other embodiments, the doses are selected from the group consisting of:
a) a loading dose of 600 mg ceftolozane active and 300 mg tazobactam active, and a maintenance dose of 300 mg ceftolozane active and 150 mg tazobactam active, all 1-hour intravenous infusion;
b) a loading dose of 500 mg ceftolozane active and 250 mg tazobactam active, and a maintenance dose of 300 mg ceftolozane active and 150 mg tazobactam active, all 1-hour intravenous infusion;
c) a loading dose of 500 mg ceftolozane active and 250 mg tazobactam active, and a maintenance dose of 100 mg ceftolozane active and 50 mg tazobactam active, all 1-hour intravenous infusion;
d) a loading dose of 400 mg ceftolozane active and 200 mg tazobactam active, and a maintenance dose of 100 mg ceftolozane active and 50 mg tazobactam active;
e) 300 mg ceftolozane active and 150 mg tazobactam active, 1-hour intravenous infusion;
f) 100 mg ceftolozane active and 50 mg tazobactam active, 1-hour intravenous infusion; and
g) 300 mg ceftolozane active and 150 mg tazobactam active, 4-hour intravenous infusion.

In another embodiment, the use of a ceftolozane and tazobactam in one or more pharmaceutical compositions for treating a patient in need thereof wherein the amount of the ceftolozane/tazobactam composition dose is doubled.

In another embodiment, the use of a ceftolozane and tazobactam in one or more pharmaceutical compositions for treating a patient in need thereof comprises administering an additional dose of ceftolozane and tazobactam immediately after the patient receives each hemodialysis.

In another embodiment, the use of a ceftolozane and tazobactam in one or more pharmaceutical compositions for treating a patient in need thereof comprises doubling the dose administered after the patient receives each hemodialysis.

As disclosed herein, methods and uses for safely and effectively administering ceftolozane in a pharmaceutical composition (such as a CXA-201 pharmaceutical composition) can include administering a loading dose of ceftolozane followed by a maintenance dose of the ceftolzoane in amounts and at a dosing interval effective to provide a ceftolozane concentration of at least 8 micrograms/mL in the blood for at least 30% of the time between successive treatment days.

In one embodiment, a method for reducing the concentration of ceftolozane in the blood of a subject is disclosed comprising subjecting the blood of the patient to hemodialysis for a period of 3-4 hours to reduce the exposure of ceftolozane in the blood of the subject by 66%.

In another preferred embodiment, ceftolozane and tazobactam can be administered in a 2:1 fixed dose combination of ceftolozane active to tazobactam active ("CXA-201") for treating a patient having a creatinine clearance of less than 15 mL/minute (e.g., a patient with end stage renal disease on hemodialysis) by parenterally administering to the patient a single loading dose of 750 mg of a CXA-201 pharmaceutical composition (i.e., an amount providing 500 mg of ceftolozane active and 250 mg of tazobactam active), followed by a 150 mg maintenance dose of the CXA-201 pharmaceutical composition (i.e., an amount providing 100 mg of ceftolozane active and 50 mg of tazobactam active) administered every 8 hours for the remainder of the treatment period, where the duration of therapy is guided by the severity and site of infection and the patient's clinical and bacteriological progress (Table 2B).

TABLE 2B

Dosage of CXA-201 by Infection in ESRD Patients Undergoing Hemodialysis

| Infection | Dose | Frequency | Infusion Time (hours) | Duration of Treatment |
|---|---|---|---|---|
| Complicated Intra-Abdominal Infections | A single loading dose of 750 mg (500 mg ceftolozane active/250 mg tazobactam active) followed by a 150 mg (100 mg ceftolozane active/50 mg tazobactam active) maintenance dose administered every 8 hours for the remainder of the treatment period (on hemodialysis days, the dose should be administered at the earliest possible time following completion of dialysis) | Every 8 Hours | 1 | 4-14 days |
| Complicated Urinary Tract Infections, including Pyelonephritis | A single loading dose of 750 mg (500 mg ceftolozane active/250 mg tazobactam active) followed by a 150 mg maintenance dose administered every 8 hours for the remainder of the treatment period (on hemodialysis days, the dose should be administered at the earliest possible time following completion of dialysis) | Every 8 Hours | 1 | 7 days |

In one embodiment, the loading dose is administered intravenously over one hour. In another aspect, each maintenance dose is administered intravenously over one hour. In another aspect, the maintenance dose is administered every 8 hours. In another aspect, each maintenance dose is administered intravenously over one hour every eight hours. In yet another aspect, the loading dose is administered intravenously over one hour and each maintenance dose is administered intravenously over one hour every 8 hours.

Typically, the duration of treatment (including loading dose and maintenance dose) for complicated intra-abdominal infections is 4-14 days; and the duration of treatment (including loading dose and maintenance dose) for complicated urinary tract infections is 7 days.

In an embodiment, the invention provides for the use of ceftolozane and tazobactam for treating a complicated intra-abdominal infection or a complicated urinary tract infection in a human patient having a creatinine clearance of less than 15 mL/minute, comprising intravenously administering to the patient 500 mg of ceftolozane active and 250 mg tazobactam active, followed by administering one or more additional doses of 100 mg ceftolozane active and 50 mg of tazobactam active to the patient every 8 hours for the duration of a treatment period.

In one embodiment, the 500 mg of ceftolozane active is co-administered with the 250 mg tazobactam in a single pharmaceutical composition.

In one embodiment, the 100 mg of ceftolozane active is co-administered with the 50 mg tazobactam in a single pharmaceutical composition.

In one embodiment, the infection is a complicated intra-abdominal infection.

In one embodiment, the use of ceftolozane and tazobactam for treating a complicated intra-abdominal infection or a complicated urinary tract infection in a human patient having a creatinine clearance of less than 15 mL/minute further comprises administering to the patient a therapeutically effective amount of metronidazole.

In another embodiment, the complicated intra-abdominal infection is caused by a microorganism selected from the group consisting of: *Enterobacter cloacae, Escherichia coli* (including CTX-M-14/15 extended spectrum beta-lactamase (ESBL)-producing strains), *Klebsiella oxytoca, Klebsiella pneumoniae* (including CTX-M-15 ESBL-producing strains), *Proteus mirabilis, Pseudomonas aeruginosa, Bacteroides fragilis, Bacteroides ovatus, Bacteroides thetaiotaomicron, Bacteroides vulgatus, Streptococcus anginosus, Streptococcus constellatus,* and *Streptococcus salivarius.*

In one embodiment, the complicated urinary tract infection is caused by one of the following Gram-negative microorganisms: *Escherichia coli* (including levofloxacin resistant and/or CTX-M-14/15 ESBL-producing strains), *Klebsiella pneumoniae* (including levofloxacin resistant and/or CTX-M-15-ESBL producing strains), *Proteus mirabilis,* and *Pseudomonas aeruginosa.*

In one embodiment, the ceftolozane active is provided as ceftolozane sulfate and the tazobactam active is provided as tazobactam sodium.

In one embodiment, the pharmaceutical composition is obtained by reconstituting a mixture comprising a total of 1000 mg ceftolozane active and 500 mg tazobactam active with sterile water for injection or 0.9% Sodium Chloride for injection, USP to form a reconstituted solution and withdrawing a portion of the reconstituted solution and adding it to an infusion bag containing 0.9% Sodium Chloride for Injection, USP or 5% Dextrose Injection, USP.

In one embodiment, the ceftolozane active is provided as ceftolozane sulfate and the tazobactam is provided as tazobactam sodium.

In one embodiment, the pharmaceutical composition is administered intravenously over one hour.

In one embodiment, provided herein is the use of ceftolozane and tazobactam for treating a complicated intra-abdominal infection or a complicated urinary tract infection, wherein
 a. the 500 mg of ceftolozane active is co-administered with the 250 mg tazobactam in a first single pharmaceutical composition;
 b. the 100 mg of ceftolozane active is co-administered with the 50 mg tazobactam in a second single pharmaceutical composition;
 c. the ceftolozane active is provided as ceftolozane sulfate and the tazobactam active is provided as tazobactam sodium;
 d. the first pharmaceutical composition is obtained by reconstituting a mixture comprising ceftolozane sulfate and tazobactam sodium with sterile water for injection or 0.9% Sodium Chloride for injection, USP to form a reconstituted solution and withdrawing at least a portion of the reconstituted solution and adding it to an infusion bag containing 0.9% Sodium Chloride for Injection, USP or 5% Dextrose Injection, USP;
 e. the first pharmaceutical composition and the second pharmaceutical compositions are each separately administered intravenously over one hour;
 f. the complicated intra-abdominal infection is caused by a microorganism selected from the group consisting of: *Enterobacter cloacae, Escherichia coli* (including CTX-M-14/15 extended spectrum beta-lactamase (ESBL)-producing strains), *Klebsiella oxytoca, Klebsiella pneumoniae* (including CTX-M-15 ESBL-producing strains), *Proteus mirabilis, Pseudomonas aeruginosa, Bacteroides fragilis, Bacteroides ovatus, Bacteroides thetaiotaomicron, Bacteroides vulgatus, Streptococcus anginosus, Streptococcus constellatus,* and *Streptococcus salivarius;* or
 g. the complicated urinary tract infection is caused by one of the following Gram-negative microorganisms: *Escherichia coli* (including levofloxacin resistant and/or CTX-M-14/15 ESBL-producing strains), *Klebsiella pneumoniae* (including levofloxacin resistant and/or CTX-M-15-ESBL producing strains), *Proteus mirabilis,* and *Pseudomonas aeruginosa.*

In another embodiment, the invention provides for the use of ceftolozane and tazobactam for treating a complicated intra-abdominal infection or a complicated urinary tract infection in a human patient with end stage renal disease with a ceftolozane/tazobactam composition that includes ceftolozane or a pharmaceutically acceptable salt thereof combined in a fixed dose ratio with tazobactam or a pharmaceutically acceptable salt thereof in an amount providing a 2:1 weight ratio between the amount of ceftolozane active and the amount of tazobactam active in the ceftolozane/tazobactam composition, where the method comprises intravenously administering to the human patient a single loading dose comprising 750 mg of the ceftolozane/tazobactam composition followed by a maintenance dose of the antibiotic composition comprising 150 mg of the ceftolozane/tazobactam composition.

In one embodiment, the infection is a complicated urinary tract infection and the method further comprises repeatedly administering the 150 mg maintenance dose of the ceftolozane/tazobactam composition every 8 hours for up to a total of 7 days.

In one embodiment, the infection is a complicated intra-abdominal infection and the method further comprises repeatedly administering the 150 mg maintenance dose of the ceftolozane/tazobactam composition every 8 hours for a total of 4-14 days.

In one embodiment, the use of ceftolozane and tazobactam for treating a complicated intra-abdominal infection or a complicated urinary tract infection further comprises administering to the patient a therapeutically effective amount of metronidazole to the human patient separately from the ceftolozane and tazobactam.

In one embodiment, the ceftolozane active is provided as ceftolozane sulfate and the tazobactam is provided as tazobactam sodium.

In another embodiment, the invention provides for the use of ceftolozane and tazobactam for treating a complicated intra-abdominal infection or a complicated urinary tract infection in a human patient, wherein
   a. the ceftolozane active is provided as ceftolozane sulfate and the tazobactam active is provided as tazobactam sodium;
   b. the loading dose is obtained by reconstituting a mixture comprising ceftolozane sulfate and tazobactam sodium with sterile water for injection or 0.9% Sodium Chloride for injection, USP to form a reconstituted solution and withdrawing at least a portion of the reconstituted solution and adding it to an infusion bag containing 100 mL of 0.9% Sodium Chloride for Injection, USP or 5% Dextrose Injection, USP;
   c. the loading dose and each maintenance dose are each separately administered intravenously over one hour;
   d. the complicated intra-abdominal infection is caused by a microorganism selected from the group consisting of: *Citrobacter freundii, Enterobacter cloacae, Escherichia coli, Escherichia coli* CTX-M-14 extended spectrum beta-lactamase producing strains, *Escherichia coli* CTX-M-15 extended spectrum beta-lactamase producing strains, *Klebsiella oxytoca, Klebsiella pneumonia, Klebsiella pneumoniae* CTX-M-15 extended spectrum beta-lactamase producing strains, *Proteus mirabilis, Pseudomonas aeruginosa, Bacteroides fragilis, Bacteroides ovatus, Bacteroides thetaiotaomicron, Bacteroides vulgatus, Streptococcus anginosus, Streptococcus constellatus,* and *Streptococcus salivarius*; or
   e. the complicated urinary tract infection is caused by one of the following Gram-negative microorganisms: *Escherichia coli, Escherichia coli* levofloxacin resistant strains, *Escherichia coli* CTX-M-14 extended spectrum beta-lactamase producing strains, *Escherichia coli* CTX-M-15 extended spectrum beta-lactamase producing strains, *Klebsiella pneumoniae, Klebsiella pneumonia* levofloxacin resistant strains, *Klebsiella pneumonia* CTX-M-15 extended spectrum beta-lactamase producing strains, *Proteus mirabilis* or *Pseudomonas aeruginosa.*

On hemodialysis days, the dose can be administered at the earliest possible time following completion of hemodialysis. For example, the loading dose can be followed immediately after completion of hemodialysis (e.g., within 3 hours, 2 hours, 1 hour, 0.5 hours, 0.25 hours following completion of hemodialysis) by a maintenance dose comprising 100 mg of ceftolozane active and 50 mg tazobactam active. CXA-201 can be administered as a fixed dose ratio of ceftolozane and tazobactam to these patients according to the methods of treatment disclosed herein. These methods of treating ESRD patients undergoing hemodialysis can be used to treat patients having a complicated intra-abdominal infection and/or a complicated urinary tract infection as disclosed herein.

The invention is based in part on the discovery that, following administration of a single 1.5 g intravenous dose of CXA-201 to healthy male adults, greater than 95% of ceftolozane was excreted in the urine as unchanged parent drug. More than 80% of tazobactam was excreted as the parent compound with the remainder excreted as the tazobactam M1 metabolite. After a single dose of CXA-201, renal clearance of ceftolozane (3.41-6.69 L/h) was similar to plasma CL (4.10 to 6.73 L/h) and similar to the glomerular filtration rate for the unbound fraction, suggesting that ceftolozane is eliminated by the kidney via glomerular filtration. Furthermore, the probability of target attainment (PTA) exceeded 90% for a minimum inhibitory concentration (MIC) up to 8 µg/mL for ceftolozane across all the tested scenarios in Example 9. Out of all the tested scenarios, the 500 mg/250 mg C/T single loading dose followed by 100 mg/50 mg every 8 hours maintenance dose via 1-hr infusion achieved a >99% PTA against all targets up to an MIC of 8 µg/mL on day 1 and >97% PTA on all other days without HD. The PTA for bactericidal activity on post HD days was 89%.

BRIEF DESCRIPTION OF THE DRAWINGS

FIG. 1A shows the demographic and baseline patient characteristics of the mMITT population. No antibiotics were permitted within 48 hours prior to obtaining the baseline urine culture. Urinary catheter was removed before end of treatment in all but three patients in the ceftolozane/tazobactam group and one patient in the levofloxacin group. cLUTI denotes complicated lower urinary tract infections, mMITT microbiological modified intent-to-treat.

FIG. 1B shows the susceptibility of baseline uropathogens to ceftolozane/tazobactam and levofloxacin (mMITT, microbiologically modified intent-to-treat). Notes: Percentages are calculated as 100×(n/N). If fewer than 10 patients reported an isolate overall, the isolate was reported alongside other isolates of the same genus which meet the same criteria. Not all isolates were received at the central microbiology laboratory for susceptibility testing. For ceftolozane/tazobactam, Susceptible/Indeterminate/Resistant breakpoints were defined as MIC≤8 mg/l; MIC=16 mg/l; and MIC≥32 mg/l, respectively.

FIG. 1E shows a summary of Adverse Events Occurring in ≥1% of Patients in Either Treatment Group (Safety Population).

FIG. 1F shows a summary of serious adverse events by system organ class (safety population).

FIG. 2 shows summary of published clinical studies of ceftolozane and/or ceftolozane/tazobactam. The following abbreviations apply: cIAI, complicated intra-abdominal infections; cUTI, complicated urinary tract infections; ESRD, end-stage renal disease; IV, intravenous; q8h, every 8 hours; and RI, renal impairment.

FIG. 3 shows the baseline characteristics of subjects included in the population PK model. The following abbreviations apply: BMI, body mass index; CrCL, creatinine clearance; RI, renal impairment; a includes patients with cUTIs or cIAIs, b includes patients with cIAIs; c CrCL ranges for normal, mild, moderate and severe renal impairment were ≥90 mL/min, ≥50-<90 mL/min, ≥30-<50 mL/min and ≥15-<30 mL/min, respectively. CrCL estimated by the Cockcroft-Gault formula.

FIG. 4 shows a Tornado plot showing the effect of infection, renal impairment (based on CrCl categories over a standardized range) and BSV on the relative CL of [A] ceftolozane and [B] tazobactam. Numbers represent the CL range. The following abbreviations apply: BSV, between subject variability; CL, clearance; CrCL, creatinine clearance.

FIG. 5 shows final population-pharmacokinetic models derived for [A] ceftolozane and [B] tazobactam. The following abbreviations apply: BSV, between-subject variability; CL, clearance; CL2, peripheral clearance; CrCl, creatinine clearance; IAI, intra-abdominal infection; NA, not applicable; RSE, relative standard error; UTI, urinary tract infection; Vc, central volume of distribution; Vp, peripheral volume of distribution.

FIG. 6 shows population and individual predicted versus observed plasma concentrations of [A] ceftolozane and [B] tazobactam for the final PK model (Goodness of fit plot). The following abbreviations apply: IDENT: Identity line; LOESS: Locally weighted scatter smoothing.

FIG. 8 shows the baseline characteristics of subjects. a RI, renal impairment. b CrCl estimated by the Cockcroft-Gault formula. c BMI, body mass index. d NA, not applicable.

FIG. 9 shows the median pharmacokinetic values for ceftolozane following single-dose administration of intravenous ceftolozane/tazobactam. a C/T, ceftolozane/tazobactam. b The $t_{1/2}$ on HD was calculated from the terminal elimination phase post HD. c Incomplete urine recovery over 48 h. d ND, not determined. As a majority of the subjects with ESRD were anuric, $CL_r$ could not be determined.

FIG. 10 shows the median pharmacokinetic values for tazobactam following single-dose administration of intravenous ceftolozane/tazobactam. a The $t_{1/2}$ on HD was calculated from the terminal elimination phase post HD.

FIG. 13 shows the median (range) plasma concentration-time profiles of ceftolozane and tazobactam following administration of intravenous ceftolozane/tazobactam (500 mg/250 mg) in subjects with ESRD on [A] day 1 (post-HD) and [B] day 4 (on HD) (semi-log plot).

FIG. 14A shows an overview of the clinical study included in this analysis.

FIG. 14C shows the individual plasma concentrations of tazobactam included for population PK analysis.

FIG. 14D shows the characteristics of the dialysis criteria in the safety population. Unless otherwise indicated herein, clinical data disclosed herein obtained in patients on hemodialysis (HD) with end stage renal disease (ESRD) subjects, including BUN collected before and after dialysis, was obtained using HD dialysis parameters provided in FIG. 14. Note: A=Asian; B=Black or African American; P=Native Hawaiian or Other Pacific islander; I=American Indian or Alaska Native; O=Other; W=White; H=Hispanic or Latino; N=Not Hispanic or Latino; M=Male; F=Female. Unless otherwise indicated herein, subjects underwent HD for 3 to 4 hours using a high-flux membrane (either 1.4, 1.8, or 1.9 m2) on Days 1, 4, and 6 as scheduled. Average blood flow rate was 264 to 600 mL/min and average dialysis flow rate was either 600 or 800 mL/min for all subjects with ESRD.

FIG. 15 shows the two-compartment PK structure model for ceftolozane and tazobactam.

In FIG. 21, DV stands for measured concentrations; PRED stands for model-predicted population concentrations; IPRED stands for model-predicted individual concentrations; CWRES stands for conditional weighted residuals.

In FIG. 22, the gray, yellow and gray bands represent the model-predicted 5th-95th confidence interval of the model-predicted (green) and observed (red) $5^{th}$ (dashed line), 50th (solid line) and 95th (dashed line) percentile, respectively.

In FIG. 23, symbols stand for measured concentrations; lines stand for model-predicted concentrations; IVAR stand for time since first dose; IPRED and DV stand for model-predicted and measured individual concentrations, respectively; i, Cobs stand for the $i^{th}$ individual patient number.

In FIG. 24, the solid line represents median concentrations and the dashed line represents the lower 10th percentile of the simulated concentrations; the gray area represents the 5th-95th percentiles. All BSVs were set at log-scale 50% (variance of 0.25) except for hemodialysis.

In FIG. 25, the solid line represents median concentrations and the dashed line represents the lower 10th percentile of the simulated concentrations; the gray area represents the 5th-95th percentiles. All BSVs were set at 50% (variance of 0.25) except for hemodialysis.

FIG. 36 is a graph showing the plasma concentration (Median and Range) versus time profile for ceftolozane during non-hemodialysis in subjects with ESRD (Study Day 1).

FIG. 37 is a graph showing the plasma Concentration (Median and Range) versus time profile for tazobactam during non-hemodialysis in subjects with ESRD (Study Day 1).

FIG. 38 is graph showing the plasma Concentration (Median and Range) versus time profile for the M-1 metabolite of tazobactam during non-hemodialysis in Subjects with ESRD (Study Day 1).

FIG. 39 is a graph showing the plasma concentration (Median and Range) versus time profile for ceftolozane in subjects with ESRD during HD (Study Day 4).

FIG. 40 is a graph of the plasma Concentration (Median and Range) versus time profile for tazobactam in subjects with ESRD during HD (Study Day 4).

FIG. 41 is a graph showing the plasma Concentration (Median and Range) versus time profile for the M-1 metabolite of tazobactam in subjects with ESRD during HD (Study Day 4).

FIG. 42 is a graph showing the plasma Concentration (Median and Range) versus time profile for ceftolozane in subjects with ESRD (Start of Dosing to End of Dialysis).

FIG. 43 is a graph showing plasma Concentration (Median and Range) versus time profile for tazobactam in subjects with ESRD (Start of Dosing to End of Dialysis)

FIG. 44 is a graph showing the plasma Concentration (Median and Range) versus time profile for the M-1 Metabolite of tazobactam in subjects with ESRD (Start of Dosing to End of Dialysis).

DETAILED DESCRIPTION

Figure 1C:
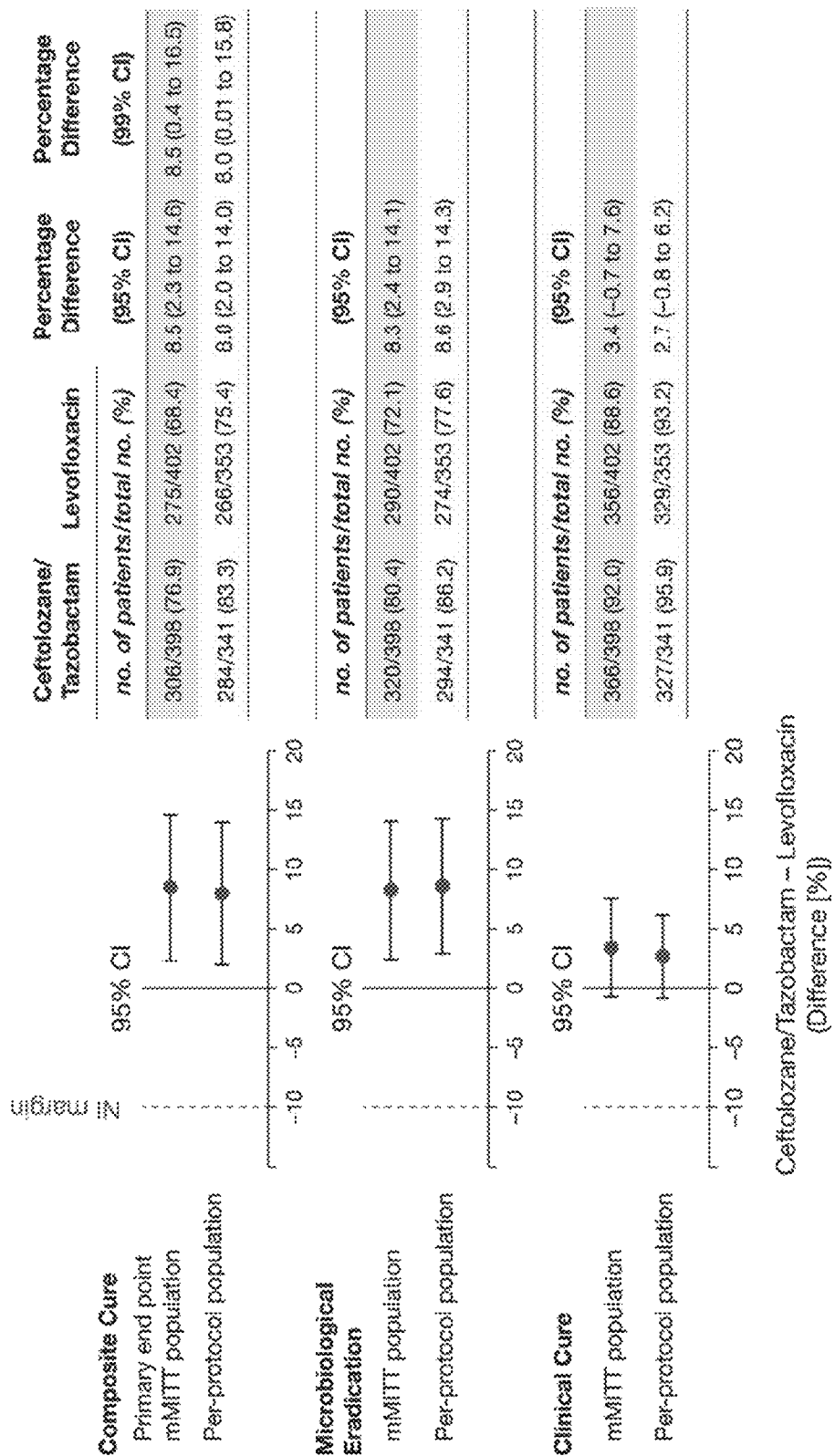
FIG. 1C shows the primary and secondary analysis end points at the Test-of-Cure visit (mMITT and per-protocol populations).

Ceftolozane (formula (I) below) is a cephalosporin antibacterial agent, also referred to as CXA-101, FR264205, or by chemical names such as (6R,7R)-3-[(5-amino-4-{[(2-aminoethyl)carbamoyl]amino}-1-methyl-1H-pyrazol-2-ium-2-yl)methyl]-7-({(2Z)-2-(5-amino-1,2,4-thiadiazol-3-yl)-2-[(1-carboxy-1-methylethoxy)imino]acetyl}amino)-8-oxo-5-thia-1-azabicyclo[4.2.0]oct-2-ene-2-carboxylate, and 7β-[(Z)-2-(5-amino-1,2,4-thiadiazol-3-yl)-2-(1-carboxy-1-methylethoxyimino)acetamido]-3-{3-amino-4-[3-(2-amino-ethyl)ureido]-2-methyl-1-pyrazolio}methyl-3-cephem-4-carboxylate. The antibacterial activity of ceftolozane is believed to result from its interaction with penicillin binding proteins (PBPs) to inhibit the biosynthesis of the bacterial cell wall which acts to stop bacterial replication.

Commonly used tazobactam salts include the sodium salt or arginine salt. Tazobactam can also be a hydrate or solvate. "Tazobactam active" refers to the active portion of a salt form of tazobactam, i.e., tazobactam free acid. For example, "500 mg of tazobactam as tazobactam active" refers to an amount of the salt form of tazobactam (e.g., tazobactam sodium or tazobactam arginine) effective to provide 500 mg of tazobactam active. As used herein, "TAZ" can refer to tazobactam or a pharmaceutically acceptable salt thereof.

A CXA-201 composition includes ceftolozane (e.g., as a pharmaceutically acceptable ceftolozane salt) and tazobactam (e.g., as a pharmaceutically acceptable tazobactam

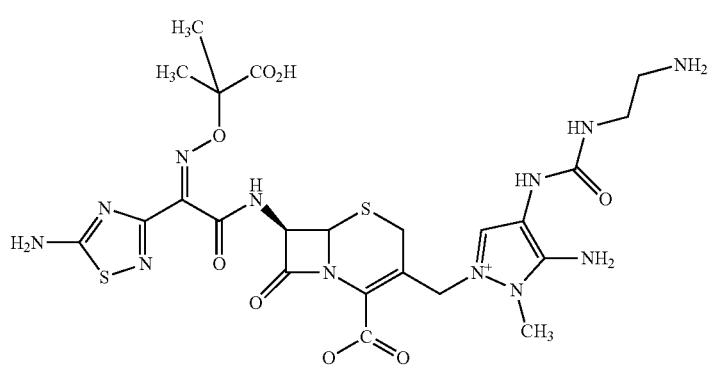

(I)

salt) in amounts that provide a 2:1 ratio between the amount of ceftolozane active and the amount of the tazobactam active. A preferred antibiotic composition used in the disclosed methods contains 2:1 w/w of ceftolozane active/tazobactam active formulated for parenteral administration. In one aspect, the antibiotic composition is referred to as "CXA-201" and comprises ceftolozane sulfate and tazobactam sodium in sufficient quantities to provide 2:1 w/w of ceftolozane active/tazobactam active. In another aspect, CXA-201 is formulated for parenteral administration. As used herein, "TOL/TAZ" refers to a CXA-201 composition.

CXA-201 can be provided as a lyophilized powder of ceftolozane sulfate and tazobactam sodium ready for reconstitution. In one aspect, the unit dosage form of CXA-201 is provided in a vial ready for reconstitution. The pharmaceutical composition can be obtained by combining the ceftolozane composition with a (second) tazobactam composition (e.g., preferably, but not necessarily, prepared in the absence of ceftolozane) by forming a second solution comprising tazobactam. The tazobactam can be included in an amount providing about 5 mg of tazobactam active per 10 mg ceftolozane active (i.e., a 1:2 weight ratio of tazobactam active to ceftolozane active). Tazobactam is a beta-lactamase inhibitor in its free acid form. Unless otherwise indicated, tazobactam can be a free acid, a sodium salt, an arginine salt, or a hydrate or solvate thereof. In one embodiment, the tazobactam in the (second) tazobactam composition is tazobactam acid and the second composition further comprises sodium bicarbonate or sodium hydroxide. Lyophilizing tazobactam in the presence of sodium bicarbonate or sodium hydroxide forms a lyophilized tazobactam sodium, which can then be further blended with the (first) lyophilized ceftolozane composition.

Unless otherwise indicated herein, the term "ceftolozane" refers to pharmaceutically acceptable salts of ceftolozane as well as ceftolozane free base. Ceftolozane sulfate is an example of a pharmaceutically acceptable ceftolozane salt of the compound of formula (I) that can be formulated for intravenous administration or infusion. As used herein, unless otherwise indicated, the term "ceftolozane active" refers to the active portion of a salt form of ceftolozane (e.g., ceftolozane sulfate), i.e., the free base form of ceftolozane. As used herein, unless otherwise indicated, the phrase "1,000 mg of ceftolozane as ceftolozane active" refers to an amount of ceftolozane in any form, including a ceftolozane salt (e.g., ceftolozane sulfate), in an amount that provides 1,000 mg of the ceftolozane active moiety. As used herein, "TOL" can refer to ceftolozane or a pharmaceutically acceptable salt thereof.

Ceftolozane can be combined with the β-lactamase inhibitor ("BLI") tazobactam to form an antibiotic pharmaceutical composition suitable for intravenous administration. Tazobactam is a BLI against Class A and some Class C β-lactamases, with in vitro and in vivo efficacy in combination with active beta-lactam antibiotics. The term "tazobactam" refers to the free acid tazobactam form of formula (II), as well as pharmaceutically acceptable salts of the compound of formula (II)).

Pharmaceutical compositions can be obtained by lyophilization. Specific methods of lyophilization are described in Remington's Pharmaceutical Sciences, Chapter 84, page 1565, Eighteenth Edition, A. R. Gennaro, (Mack Publishing Co., Easton, Pa., 1990).

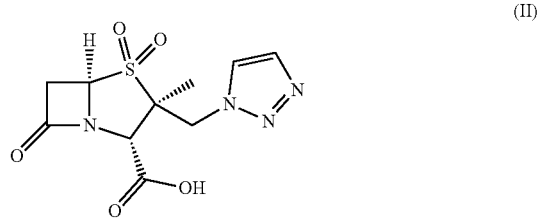 [SMILES: C[C@]1(Cn2ccnn2)[C@H](C(=O)O)N2C(=O)C[C@H]2S1(=O)=O]

(II)

Pharmaceutical compositions comprising ceftolozane and tazobactam can be formulated to treat infections by parenteral administration (including subcutaneous, intramuscular, and intravenous) administration. Pharmaceutical compositions may additionally comprise excipients, stabilizers, pH adjusting additives (e.g., buffers) and the like. Non-limiting examples of these additives include sodium chloride, citric acid and L-arginine. For example, the use of sodium chloride results in greater stability; L-arginine is used to adjust pH and to increase the solubility of ceftolozane; and citric acid is used to prevent discoloration of the product, due to its ability to chelate metal ions. In one particular embodiment, the pharmaceutical compositions described herein are formulated for administration by intravenous injection or infusion.

The pharmaceutical antibiotic compositions can be provided in a unit dosage form container (e.g., in a vial or bag, or the like). The unit dosage form can be dissolved with a pharmaceutically acceptable carrier, and then intravenously administered. The unit dosage form comprises ceftolozane active and tazobactam active, typically 1000 mg ceftolozane active as ceftolozane sulfate and 500 mg of tazobactam active as tazobactam sodium. The unit dosage forms are commonly stored in vials.

In one aspect, provided herein is a unit dosage form container (e.g., a bag, vial or the like) containing a unit dosage form of a pharmaceutical composition formulated for parenteral administration for the treatment of complicated intra-abdominal infections, the pharmaceutical composition comprising a therapeutically effective amount of ceftolozane sulfate and tazobactam in a ratio of 1,000 mg ceftolozane active per 500 mg of tazobactam active, the pharmaceutical composition obtained by a process comprising the steps of:

a. lyophilizing a first aqueous solution in the absence of tazobactam, the first aqueous solution comprising ceftolozane sulfate, about 487 mg of sodium chloride per 1,000 mg of ceftolozane active, L-arginine and/or citric acid in an amount effective to adjust the pH of the first aqueous solution to 5-7 (e.g., 6-7) prior to lyophilization to obtain a first lyophilized ceftolozane composition, b. lyophilizing a second solution in the absence of ceftolozane, the second solution comprising tazobactam being lyophilized to form a second lyophilized tazobactam composition; and c. blending the first lyophilized ceftolozane composition and the second lyophilized tazobactam composition to obtain a blended pharmaceutical composition in the unit dosage form.

In one embodiment of the unit dosage form container, the tazobactam in the second solution is tazobactam acid, and wherein the tazobactam acid in the second solution is lyophilized in the presence of sodium bicarbonate or sodium hydroxide, thereby forming lyophilized tazobactam sodium in the second lyophilized tazobactam solution.

The pharmaceutical compositions provided herein comprising ceftolozane sulfate and tazobactam in a ratio of 1,000 mg ceftolozane active per 500 mg of tazobactam active, can be obtained by a process comprising the steps of:

a. lyophilizing a first aqueous solution in the absence of tazobactam, the first aqueous solution comprising ceftolozane sulfate at a pH of 5-7 (e.g., 6-7) prior to lyophilization to obtain a first lyophilized ceftolozane composition, b. blending the first lyophilized ceftolozane composition with tazobactam to obtain an antibacterial composition.

As provided herein, ceftolozane can be stabilized in a pharmaceutical composition comprising ceftolozane and a stabilizing effective amount of a stabilizing agent selected from the group consisting of: sodium chloride, or a non-reducing sugar such as trehalose and/or sucrose. The pharmaceutical compositions provided herein are based in part on the surprising discovery that ceftolozane pharmaceutical compositions comprising these stabilizing agents demonstrate improved ceftolozane residual rates (e.g., % ceftolozane remaining after 3 days at 70 degrees C. as measured by HPLC) and/or chemical stability (e.g., lower reduction in ceftolozane purity measured by HPLC after 7 days at 60 degrees C. in a stability test) compared control samples comprising ceftolozane without a stabilizing agent.

Accordingly, preferred pharmaceutical antibiotic compositions can include ceftolozane sulfate and a stabilizing agent (e.g., 300 to 500 mg of a stabilizing agent per 1,000 mg ceftolozane active) in a lyophilized unit dosage form (e.g., powder in a container). The unit dosage form can be dissolved with a pharmaceutically acceptable carrier (e.g., 0.9% sodium chloride aqueous isotonic saline and/or water for injection), and then intravenously administered. In certain ceftolozane compositions, the stabilizing agent can be selected from the group consisting of: sodium chloride, lactose, maltose and dextran 40, and/or selected from the group consisting of: sodium chloride, trehalose and sucrose.

An exemplary unit dosage form is described in Example 2, a white to yellow sterile powder consisting of ceftolozane sulfate (1147 mg/vial) and tazobactam sodium (537 mg/vial) packaged in glass vials. The product contains sodium chloride (487 mg/vial) as a stabilizing agent, citric acid (21 mg/vial), and L-arginine (approximately 600 g/vial) as excipients. The vial with the unit dosage form is constituted with 10 mL of sterile water for injection or 0.9% Sodium Chloride for injection, USP (normal saline) and gently shaken to dissolve. In another aspect, 10 mL of 5% Dextrose Injection, USP is used. The final volume is approximately 11.4 mL. The resultant concentration is approximately 132 mg/mL. For preparation of a 1.5 g dose, the entire contents (approximately 11.4 mL) of the reconstituted vial is removed, for example, by using a syringe, and added to an infusion bag containing 100 mL of 0.9% Sodium Chloride for Injection, USP (normal saline) or 5% Dextrose Injection, USP. In another aspect, 100 mL of sterile water for injection can be used. For preparation of the 750 mg dose, approximately 5.7 mL of the contents of the reconstituted vial is withdrawn and added it to an infusion bag containing 100 mL of 0.9% Sodium Chloride for Injection, USP (normal saline) or 5% Dextrose Injection, USP. In another aspect, 100 mL of sterile water for injection is used. For preparation of the 375 mg dose, approximately 2.9 mL of the contents of the reconstituted vial is withdrawn and added to an infusion bag containing 100 mL of 0.9% Sodium Chloride for Injection, USP (normal saline) or 5% Dextrose Injection, USP. In another aspect, 100 mL of sterile water for injection is used. For preparation of the 150 mg dose, approximately 1.2 mL of the contents of the reconstituted vial is withdrawn and added it to an infusion bag containing 100 mL of 0.9% Sodium Chloride for Injection, USP (normal saline) or 5% Dextrose Injection, USP. In another aspect, 100 mL of sterile water for injection is used.

Preferably, the ceftolozane/tazobactam pharmaceutical product does not contain a bacteriostatic preservative. Aseptic technique is preferably followed in preparing the infusion solution.

A therapeutically effective amount of metronidazole or a pharmaceutically acceptable salt thereof can be administered to a patient receiving the ceftolozane/tazobactam pharmaceutical composition for treatment of an intra-abdominal infection, including a complicated intra-abdominal infection. Metronidazole is a synthetic nitroimidazole antibacterial agent 2-methyl-5-nitro-1Himidazole-1-ethanol. Metronidazole hydrochloride (formula III) is a pharmaceutically acceptable salt of metronidazole that can be intravenously administered.

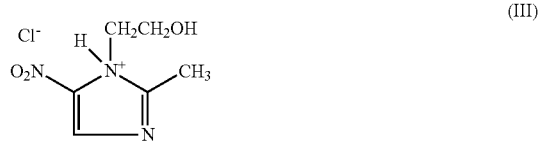

(III)

An effective amount of metronidazole is administered in the treatment methods described herein. Metronidazole is preferably administered intravenously using a dosage regimen of 15 mg/kg loading dose (1 gram for a 70 kg adult) followed six hours later by 7.5 mg/kg (500 mg for a 70 kg adult) maintenance dose. Maintenance doses of 7.5 mg/kg are given intravenously every six hours. The usual duration of therapy for treating the intra-abdominal infection can be 4-14 days, possibly 7-10 days. Metronidazole is preferably administered separately from the ceftolozane/tazobactam.

Preferably, the metronidazole is separately intravenously administered to a patient having, for example, an intra-abdominal infection. Metronidazole is an antibiotic that can be administered to patients having intra-abdominal infections, including peritonitis, intra-abdominal abscess, and liver abscess, caused by *Bacteroides* species including the *B. fragilis* group (*B. fragilis, B. distasonis, B. ovatus, B. thetaiotaomicron, B. vulgatus*), *Clostridium* species, *Eubacterium* species, *Peptococcus* species, and *Peptostreptococcus* species.

Preferably, the metronidazole is intravenously administered as a pharmaceutically composition of metronidazole hydrochloride for injection in a sterile 500 mg parenteral unit dosage form of the synthetic nitroimidazole antibacterial agent 2-methyl-5-nitro-1Himidazole-1-ethanol. The unit dosage form of metronidazole can be obtained by reconstituting a single-dose vial of lyophilized metronidazole hydrochloride (e.g., sold under the brand name FLAGYL I.V.) containing sterile, nonpyrogenic metronidazole hydrochloride, equivalent to 500 mg metronidazole, and 415 mg mannitol.

CXA-201 refers to pharmaceutical compositions comprising ceftolozane active and tazobactam active in a 2:1 weight ratio. CXA-201 can be provided in a single vessel (e.g., a bag, vial or blended composition) or in multiple vessels (e.g., a first container containing ceftolozane active without tazobactam active, and a second container containing tazobactam active without ceftolozane active). The ceftolozane active and tazobactam acid in CXA-201 can be combined prior to intravenous administration, or separately intravenously administered. Accordingly, a 1.5 g dose of CXA-201 comprises a total of 1 g of ceftolozane active and a total of 0.5 g of tazobactam active. Similarly, a 750 mg dose of CXA-201 comprises a total of 500 mg ceftolozane active and a total of 250 mg of tazobactam active. A 150 mg dose of CXA-201 comprises a total of 100 mg ceftolozane active and a total of 50 mg of tazobactam active.

A preferred CXA-201 pharmaceutical composition is the ceftolozane/tazobactam composition in Example 2. The $C_{max}$ and AUC of this preferred CXA-201 composition increases in proportion to dose. Plasma levels of this preferred CXA-201 do not increase appreciably following multiple IV infusions of up to 3.0 g administered every 8 hours for up to 10 days in healthy adults with normal renal function. The elimination half-life ($t_{1/2}$) of ceftolozane is independent of dose. The binding of ceftolozane and tazobactam to human plasma proteins is approximately 16% to 21% and 30%, respectively. The mean (CV %) steady-state volume of distribution of the CXA-201 composition of Example 2 in healthy adult males (n=51) following a single 1.5 g IV dose of the CXA-201 composition of Example 2 was 13.5 L (21%) and 18.2 L (25%) for ceftolozane and tazobactam, respectively, similar to extracellular fluid volume.

Ceftolozane is eliminated in the urine as unchanged parent drug and thus does not appear to be metabolized to any appreciable extent. The beta-lactam ring of tazobactam is hydrolyzed to form the pharmacologically inactive, tazobactam metabolite M1.

The CXA-201 composition of Example 2 and the tazobactam metabolite M1 are eliminated by the kidneys. Following administration of a single 1.5 g IV dose of the CXA-201 composition of Example 2 to healthy male adults greater than 95% of ceftolozane was excreted in the urine as unchanged parent drug. More than 80% of tazobactam was excreted as the parent compound with the remainder excreted as the tazobactam M1 metabolite. After a single dose of the CXA-201 composition of Example 2, renal clearance of ceftolozane (3.41-6.69 L/h) was similar to plasma CL (4.10 to 6.73 L/h) and similar to the glomerular filtration rate for the unbound fraction, suggesting that ceftolozane is eliminated by the kidney via glomerular filtration.

The CXA-201 composition of Example 2 and the tazobactam metabolite M1 are eliminated by the kidneys. The ceftolozane dose normalized geometric mean AUC increased up to 1.26-fold, 2.5-fold, and 5-fold in subjects with mild, moderate, and severe renal impairment, respectively, compared to healthy subjects with normal renal function. The respective tazobactam dose normalized geometric mean AUC increased approximately up to 1.3-fold, 2-fold, and 4-fold. To maintain similar systemic exposures to those with normal renal function, dosage adjustment is required.

In subjects with ESRD on HD, approximately two-thirds of the administered CXA-201 composition of Example 2 is removed by HD. The recommended dose in subjects with ESRD on HD is a single loading dose of 750 mg of the CXA-201 composition of Example 2 followed by a 150 mg maintenance dose of the CXA-201 composition of Example 2 administered every 8 hours for the remainder of the treatment period. On HD days, the dose should be administered at the earliest possible time following completion of HD.

CXA-201 is useful for the treatment of complicated intra-abdominal infections caused by one of the following Gram-negative and Gram-positive microorganisms: *Citrobacter freundii, Enterobacter cloacae, Escherichia coli, Escherichia coli* CTX-M-14 extended spectrum beta-lactamase producing strains, *Escherichia coli* CTX-M-15 extended spectrum beta-lactamase producing strains, *Klebsiella oxytoca, Klebsiella pneumonia, Klebsiella pneumoniae* CTX-M-15 extended spectrum beta-lactamase producing strains, *Proteus mirabilis, Pseudomonas aeruginosa, Bacteroides fragilis, Bacteroides ovatus, Bacteroides thetaiotaomicron, Bacteroides vulgatus, Streptococcus anginosus, Streptococcus constellatus,* and *Streptococcus salivarius.*

CXA-201 is also useful for the treatment of complicated urinary tract infection, including where the complicated urinary tract infection is pyelonephritis, with or without concurrent bacteremia, or is caused by one of the following Gram-negative microorganisms: *Escherichia coli*, *Escherichia coli* levofloxacin resistant strains, *Escherichia coli* CTX-M-14 extended spectrum beta-lactamase producing strains, *Escherichia coli* CTX-M-15 extended spectrum beta-lactamase producing strains, *Klebsiella pneumoniae*, *Klebsiella pneumonia* levofloxacin resistant strains, *Klebsiella pneumonia* CTX-M-15 extended spectrum beta-lactamase producing strains, *Proteus mirabilis* or *Pseudomonas aeruginosa*.

CXA-201 can also be used to treat infections caused by the following bacteria: Gram-negative bacteria—*Acinetobacter baumannii*, *Burkholderia cepacii*, *Citrobacter freundii*, *Citrobacter koseri*, *Enterobacter aerogenes*, *Enterobacter cloacae*, *Haemophilus influenza*, *Moraxella catarrhalis*, *Morganella morganii*, *Pantoea agglomerans*, *Proteus vulgaris*, *Providencia rettgeri*, *Providencia stuartii*, *Serratia liquefacians* and *Serratia marcescens*; Gram-positive aerobic bacteria—*Streptococcus agalactiae*, *Streptococcus intermedius*, *Streptococcus pyogenes* and *Streptococcus pneumonia*; Anaerobic microorganisms such as *Fusobacterium* spp, and *Prevotella* spp.

In an embodiment, a pharmaceutical composition comprising ceftolozane active and tazobactam active in a 2:1 weight ratio is administered to a patient with impaired renal function in accordance with the Tables below:

Dosage of CXA-201 in Patients with Renal Impairment

| Estimated CrCL (mL/min)* | Recommended Dosage Regimen for CXA-201** |
|---|---|
| 30 to 50 | 750 mg intravenously every 8 hours |
| 15 to 29 | 375 mg intravenously every 8 hours |
| End stage renal disease (ESRD) on hemodialysis (HD) | A single loading dose of 750 mg followed by a 150 mg maintenance dose administered every 8 hours for the remainder of the treatment period (on hemodialysis days, the dose should be administered at the earliest possible time following completion of dialysis) |

*CrCL estimated using Cockcroft-Gault formula
**All doses of CXA-201 are administered over 1 hour Dosage of Ceftolozane/Tazobactam in Patients with Renal Impairment

| Estimated CrCL (mL/min)* | Recommended Dosage Regimen** |
|---|---|
| 30 to 50 | 500 mg ceftolozane active and 250 mg tazobactam active intravenously administered in a single or separate pharmaceutical compositions every 8 hours |
| 15 to 29 | 250 mg ceftolozane active and 125 mg tazobactam active administered in a single or separate pharmaceutical compositions intravenously every 8 hours |
| End stage renal disease (ESRD) on hemodialysis (HD) | A single loading dose of 500 mg ceftolozane active and 250 mg tazobactam active administered in a single or separate pharmaceutical compositions; followed by a 100 mg ceftolozane active and 50 mg tazobactam active maintenance dose administered in a single or separate pharmaceutical compositions every 8 hours for the remainder of the treatment period (on hemodialysis days, the dose should be administered at the earliest possible time following completion of dialysis) |

*CrCL estimated using Cockcroft-Gault formula
**All doses of CXA-201 are administered over 1 hour
The invention is illustrated by the following non-limiting examples.

In one embodiment, use of a ceftolozane and tazobactam in one or more pharmaceutical compositions for treating a patient in need thereof is disclosed, comprising administering a dose of ceftolozane and tazobactam of the ceftolzoane and tazobactam, with or without a loading dose, in amounts and at a dosing interval effective to provide at least an unbound concentration of ceftolozane of at least 8 micrograms/mL for at least 30% of the time between successive treatment days and unbound tazobactam of about 1 microgram/mL for at least 20% of the time and about 0.5 microgram/mL for about or higher than 50% of the time.

In another embodiment, use of a pharmaceutical composition comprising ceftolozane active and tazobactam active in a 2:1 weight ratio, for treating an infection in a patient is disclosed, comprising administering to the patient a dose of the pharmaceutical composition, with or without a loading dose, in therapeutically effective amounts and at a dosing interval therapeutically effective to provide at least an unbound concentration of ceftolozane of at least 8 micrograms/mL in the patient for at least 30% of the time between successive treatment days and unbound tazobactam of about 1 microgram/mL for at least 20% of the time and about 0.5 microgram/mL for about or higher than 50% of the time during the duration of treatment.

EXAMPLES

Example 1: Manufacturing of Combination Product (Tazobactam and Ceftolozane) by Blending CXA-201 compositions can be obtained by uniformly blending lyophilized ceftolozane or pharmaceutically acceptable salt thereof with lyophilized tazobactam in amounts providing a 2:1 weight ratio between the amount of ceftolozane active and tazobactam active in the blended CXA-201 composition. The ceftolozane can be ceftolozane sulfate lyophilized with one or more excipients without tazobactam. The tazobactam can be lyophilized with one or more excipients (e.g., sodium bicarbonate) without ceftolozane.

Example 2: Components of a Representative CXA-201 Composition

An example of a batch formulae for the RSD for each of ceftolozane and tazobactam content assay was no greater than 2% and the RSD for the ratio of ceftolozane/tazobactam was no greater than 2.2%.

Ceftolozane composition (compounding of ceftolozane substance with excipients such as citric acid, sodium chloride, and L-arginine followed by sterile lyophilization) is found below in Table 5.

TABLE 5

Batch Formula for Ceftolozane Composition

| Component | Target Composition mg/g | Amount per Batch (kg) 1 | 2 |
|---|---|---|---|
| Ceftolozane Sulfate[1] | 172.1 | 114.0 | 202.6 |
| Citric Acid, Anhydrous, USP | 3.2 | 2.1 | 3.7 |
| Sodium Chloride, USP | 73.1 | 48.3 | 86.0 |
| L-Arginine, USP | ~90 QS to achieve target pH[2] | 59.7 | 106.0 |
| Water for Injection, USP | QS to 1000 | QS | QS |
| Total Batch Size | | 660 | 1175 |

[1]Ceftolozane sulfate was charged based on its measured potency to obtain 150 mg free base/g solution.
[2]L-arginine was added as needed to obtain pH 6.5 ± 0.5 in the bulk solution; 90 mg per gram solution was considered a representative amount.

An example of a batch formula for the ceftolozane/tazobactam drug product is presented in Table 6 below.

TABLE 6

Batch Formula Ceftolozane/Tazobactam Drug Product

| Component | Amount per container, mg | Amount per Batch, kg |
|---|---|---|
| Ceftolozane composition1) | 2255 | 112.8 |
| Tazobactam2) | 537 | 26.9 |
| Nitrogen, NF3) | — | — |
| Total | 2792 | 139.7 |
| Total Batch Size, kg | | 139.7 |
| Total container Quantity | | 50,000 |

The target fill for ceftolozane was 1000 mg free base, added to the container as the composition. The amount 2255 mg was based on 100% theoretical potency of the composition. Actual weight will vary based on composition measured potency. The target fill for tazobactam is 500 mg free acid, added to the container as its sodium salt form. The amount 537 mg was based on 100% theoretical potency. Nitrogen was used as a processing aid to blanket containers after powder filling and prior to insertion of stopper. The unit composition of a dosage for reconstitution is described in Table 7.

TABLE 7

Unit Compositions of Ceftolozane/Tazobactam for Injection, 1000 mg/500 mg

| Component | | Function | Nominal Composition mg per container |
|---|---|---|---|
| Ceftolozane composition[1] | Ceftolozane Sulfate | Active | 1147 |
| | Citric Acid, Anhydrous | Chelating Agent | 21 |
| | Sodium Chloride | Stabilizing Agent | 487 |

TABLE 7-continued

Unit Compositions of Ceftolozane/Tazobactam for Injection, 1000 mg/500 mg

| Component | | Function | Nominal Composition mg per container |
|---|---|---|---|
| | L-Arginine | Alkalizing Agent | 600[2] Q.S. for pH adjustment |
| Tazobactam Sodium[3] | | Active | 537 |
| Nitrogen | | Processing Aid[a] | Q.S. |
| | | Total Weight | 2792 |

[1]Actual amount of ceftolozane composition will vary based on the measured potency. Ceftolozane sulfate, 1147 mg, corresponds to 1000 mg ceftolozane free base.
[2]L-arginine was added as needed to achieve pH 6.5 ± 0.5; 600 mg per container was considered a representative total amount.
[3]Actual weight of tazobactam sodium will vary based on the measured potency. Tazobactam sodium 537 mg, corresponds to 500 mg tazobactam free acid.
[4]Nitrogen blanket was applied after powders are dispensed to the container and prior to insertion of stopper.

Example 3: Summary of CXA-201 in Phase 3 Comparator-Controlled Clinical Trials of Complicated Intra-Abdominal Infections and Complicated Urinary Tract Infections The CXA-201 of Example 2 was evaluated in Phase 3 comparator-controlled clinical trials of complicated intra-abdominal infections and complicated urinary tract infections, which included a total of 1015 patients treated with CXA-201 and 1032 patients treated with comparator (levofloxacin or meropenem) for up to 14 days. The most common adverse reactions (≥5% in either indication) occurring in patients receiving CXA-201 were nausea, headache and diarrhea. Table 3 lists adverse reactions occurring in ≥1.0% of patients receiving CXA-201 in Phase 3 clinical trials.

TABLE 3

Adverse Reactions Occurring in ≥1.0% of Patients Receiving CXA-201 in Phase 3 Clinical Trials

| | Complicated Intra-abdominal Infections | | Complicated Urinary Tract Infections, Including Pyelonephritis | |
|---|---|---|---|---|
| Preferred Term | CXA-201 (N = 482) | Meropenem (N = 497) | CXA-201 (N = 533) | Levofloxacin (N = 535) |
| Nausea | 38 (7.9) | 29 (5.8) | 15 (2.8) | 9 (1.7) |
| Headache | 12 (2.5) | 9 (1.8) | 31 (5.8) | 26 (4.9) |
| Diarrhea | 30 (6.2) | 25 (5.0) | 10 (1.9) | 23 (4.3) |
| Constipation | 9 (1.9) | 6 (1.2) | 21 (3.9) | 17 (3.2) |
| Vomiting | 16 (3.3) | 20 (4.0) | 6 (1.1) | 6 (1.1) |
| ALT increased | 7 (1.5) | 5 (1.0) | 9 (1.7) | 5 (0.9) |
| AST increased | 5 (1.0) | 3 (0.6) | 9 (1.7) | 5 (0.9) |
| Abdominal pain | 6 (1.2) | 2 (0.4) | 4 (0.8) | 2 (0.4) |

[a]The CXA-201 dose was 1.5 g IV every 8 hours, adjusted to match renal function where appropriate. In the complicated intra-abdominal infection studies CXA-201 was given in conjunction with metronidazole.

Treatment discontinuation due to adverse events occurred in 2.0% (20/1015) of patients receiving CXA-201 and 1.9% (20/1032) of patients receiving comparator drugs. Renal impairment (including the terms renal impairment, renal failure, and renal failure acute) was the only adverse event that led to discontinuation of treatment in >1 subject receiving CXA-201.

Overdosage

In the event of overdose, CXA-201 should be discontinued and general supportive treatment given. CXA-201 can be removed by hemodialysis. Approximately 66% of ceftolozane, 56% of tazobactam, and 51% of the tazobactam metabolite M1 were removed by dialysis. However, no information is available on the use of hemodialysis to treat overdosage. The highest single dose of CXA-201 received in clinical trials was 4.5 g (comprised of 3.0 g of ceftolozane and 1.5 g of tazobactam); at this dosage no adverse pharmacological effects or increased safety risks have been observed.

Pharmacokinetics

The mean pharmacokinetic parameters of CXA-201 in healthy adults with normal renal function after single and multiple 1-hour IV infusions of 1.5 g CXA-201 administered every 8 hours are summarized in Table 4. Pharmacokinetic parameters were similar for single and multiple dose administration.

TABLE 4

Mean (CV %) Plasma Pharmacokinetic Parameters of CXA-201 After Single and Multiple 1.5 g Intravenous 1-hour Infusions of CXA-201 Every 8 Hours in Healthy Adults

| | Ceftolozane/Tazobactam (1.5 g every 8 hours) | | | |
|---|---|---|---|---|
| | Ceftolozane | | Tazobactam | |
| PK parameters | Day 1 (n = 9)$^a$ | Day 10 (n = 10) | Day 1 (n = 9)$^a$ | Day 10 (n = 10) |
| $C_{max}$ (μg/mL) | 69.1 (11) | 74.4 (14) | 18.4 (16) | 18.0 (8) |
| $t_{max}$ (h)$^b$ | 1.02 (1.01, 1.1) | 1.07 (1.0, 1.1) | 1.02 (0.99, 1.03) | 1.01 (1.0, 1.1) |
| AUC (μg · h/mL)$^c$ | 172 (14) | 182 (15) | 24.4 (18) | 25.0 (15) |
| $t_{1/2}$ (h) | 2.77 (30) | 3.12 (22) | 0.91 (26)$^d$ | 1.03 (19) |

$^a$N = 9, one outlier subject excluded from descriptive statistics
$^b$Median (minimum, maximum) presented
$^c$AUC for Day 1 = $AUC_{last}$ and AUC for Day 10 = steady state AUC ($AUC_{\tau,ss}$)
$^d$N = 8, one subject excluded from descriptive statistics as the concentration-time profile did not exhibit a terminal log-linear phase and $t_{1/2}$ could not be calculated The $C_{max}$ and AUC of CXA-201 increase in proportion to dose. Plasma levels of CXA-201 do not increase appreciably following multiple IV infusions of up to 3.0 g administered every 8 hours for up to 10 days in healthy adults with normal renal function. The elimination half-life ($t_{1/2}$) of ceftolozane is independent of dose.

Distribution

The binding of ceftolozane and tazobactam to human plasma proteins is approximately 16% to 21% and 30%, respectively. The mean (CV %) steady-state volume of distribution of CXA-201 in healthy adult males (n=51) following a single 1.5 g IV dose of CXA-201 was 13.5 L (21%) and 18.2 L (25%) for ceftolozane and tazobactam, respectively, similar to extracellular fluid volume.

Metabolism

Ceftolozane is eliminated in the urine as unchanged parent drug and thus does not appear to be metabolized to any appreciable extent. The beta-lactam ring of tazobactam is hydrolyzed to form the pharmacologically inactive, tazobactam metabolite M1.

Excretion

CXA-201 and the tazobactam metabolite M1 are eliminated by the kidneys. Following administration of a single 1.5 g IV dose of CXA-201 to healthy male adults greater than 95% of ceftolozane was excreted in the urine as unchanged parent drug. More than 80% of tazobactam was excreted as the parent compound with the remainder excreted as the tazobactam M1 metabolite. After a single dose of CXA-201, renal clearance of ceftolozane (3.41-6.69 L/h) was similar to plasma CL (4.10 to 6.73 L/h) and similar to the glomerular filtration rate for the unbound fraction, suggesting that ceftolozane is eliminated by the kidney via glomerular filtration.

Specific Populations

Renal Impairment

Because CXA-201 and the tazobactam metabolite M1 are eliminated primarily by the kidneys, a dosage adjustment is required for patients whose creatinine clearance is <50 mL/min.

The ceftolozane dose normalized geometric mean AUC increased up to 1.26-fold, 2.5-fold, and 5-fold in subjects with mild, moderate, and severe renal impairment, respectively, compared to healthy subjects with normal renal function. The respective tazobactam dose normalized geometric mean AUC increased approximately up to 1.3-fold, 2-fold, and 4-fold. To maintain similar systemic exposures to those with normal renal function, dosage adjustment is required.

In subjects with ESRD on HD, approximately two-thirds of the administered CXA-201 dose is removed by HD. The recommended dose in subjects with ESRD on HD is a single loading dose of 750 mg CXA-201 followed by a 150 mg maintenance dose of CXA-201 administered every 8 hours for the remainder of the treatment period. On HD days, the dose should be administered at the earliest possible time following completion of HD, as summarized in the Table below:

Dosage of CXA-201 in Patients with Renal Impairment

| Estimated CrCL (mL/min)* | Recommended Dosage Regimen for CXA-201** |
|---|---|
| 30 to 50 | 750 mg intravenously every 8 hours |
| 15 to 29 | 375 mg intravenously every 8 hours |
| End stage renal disease (ESRD) on hemodialysis (HD) | A single loading dose of 750 mg followed by a 150 mg maintenance dose administered every 8 hours for the remainder of the treatment period (on hemodialysis days, the dose should be administered at the earliest possible time following completion of dialysis) |

*CrCL estimated using Cockcroft-Gault formula
**All doses of CXA-201 are administered over 1 hour Example 4: Clinical Trials of CXA-201 in Patients with Complicated Intra-Abdominal Infections A total of 979 adults hospitalized with complicated intra-abdominal infections were randomized and received study medications in a multinational, double-blind study comparing CXA-201 (1.5 g IV every 8 hours) plus metronidazole (500 mg IV every 8 hours) to meropenem (1 g IV every 8 hours) for 4 to 14 days of therapy. Complicated intra-abdominal infections included appendicitis, cholecystitis, diverticulitis, gastric/duodenal perforation, perforation of the intestine, and other causes of intra-abdominal abscesses and peritonitis. The primary efficacy endpoint was clinical response at the test-of-cure (TOC) visit in the microbiological intent-to-treat (MITT) population, which included all patients who had at least 1 baseline intra-abdominal pathogen. The key secondary efficacy endpoint was clinical response at the TOC visit in the microbiologically evaluable (ME) population, which included all protocol-adherent MITT patients.

The MITT population consisted of 806 patients; the median age was 52 years and 57.8% were male. Diffuse peritonitis at baseline, a marker of severity, was present in 34.2% of patients. Laparotomy was the initial intra-abdominal intervention in 67.7% of patients, and ESBL-producing Enterobacteriaceae were identified in 58 (7.2%) patients at baseline.

CXA-201 plus metronidazole showed non-inferiority to meropenem with regard to clinical cure rates at the TOC visit in both the MITT and ME populations. Clinical cure rates at the TOC visit are displayed by patient population in Table 8. Clinical cure rates at the TOC visit by pathogen in the ME population are presented in Table 9.

TABLE 8

Clinical Cure Rates in a Phase 3 Study of Complicated Intra-Abdominal Infections

| Analysis Population | CXA-201 plus metronidazole[a] n/N (%) | Meropenem[b] n/N (%) | Percentage Difference (95% CI)[c] |
|---|---|---|---|
| MITT | 323/389 (83.0) | 364/417 (87.3) | -4.2 (-8.91, 0.54) |
| ME | 259/275 (94.2) | 304/321 (94.7) | -1.0 (-4.52, 2.59) |

[a]CXA-201 1.5 g IV every 8 hours + metronidazole 500 mg IV every 8 hours.
[b]1 g IV every 8 hours.
[c]The 95% CI was calculated using the Newcombe method with minimum risk weights

TABLE 9

Per Pathogen Clinical Cure Rates in a Phase 3 Study of Complicated Intra-abdominal Infections (ME Population)

| Pathogen Category Baseline Intra-abdominal Pathogen | CXA-201 plus metronidazole n/N (%) | Meropenem n/N (%) |
|---|---|---|
| Aerobic Gram-negative | 238/252 (94.4) | 273/291 (93.8) |
| Escherichia coli | 197/208 (94.7) | 216/231 (93.5) |
| Escherichia coli (EBSL-producing) | 14/14 (100) | 18/20 (90.0) |
| Escherichia coli (CTX-M-14/15 ESBL-producing) | 9/9 (100) | 7/9 (77.8) |
| Klebsiella pneumonia | 28/30 (93.3) | 22/25 (88.0) |
| Klebsiella pneumoniae (ESBL-producing) | 7/8 (87.5) | 3/4 (75.0) |
| Klebsiella pneumoniae (CTX-M-15 ESBL-producing) | 5/5 (100) | 0/1 (0) |
| Pseudomonas aeruginosa | 26/26 (100) | 27/29 (93.1) |
| Enterobacter cloacae | 19/22 (86.4) | 22/22 (100) |
| Klebsiella oxytoca | 12/12 (100) | 21/22 (95.5) |
| Proteus mirabilis | 10/11 (90.9) | 9/10 (90.0) |

TABLE 9-continued

Per Pathogen Clinical Cure Rates in a Phase 3 Study of Complicated Intra-abdominal Infections (ME Population)

| Pathogen Category Baseline Intra-abdominal Pathogen | CXA-201 plus metronidazole n/N (%) | Meropenem n/N (%) |
|---|---|---|
| Aerobic Gram-positive | 153/168 (91.1) | 170/185 (91.9) |
| Streptococcus anginosus | 25/30 (83.3) | 23/23 (100) |
| Streptococcus constellatus | 17/18 (94.4) | 20/23 (87.0) |
| Streptococcus salivarius | 9/10 (90.0) | 8/8 (100) |
| Anaerobic Gram-negative | 104/109 (95.4) | 132/137 (96.4) |
| Bacteroides fragilis | 39/41 (95.1) | 56/57 (98.2) |
| Bacteroides ovatus | 36/37 (97.3) | 42/42 (100) |
| Bacteroides thetaiotaomicron | 20/20 (100) | 40/43 (93.0) |
| Bacteroides vulgatus | 12/13 (92.3) | 21/22 (95.5) |

Example 5 Clinical Trials with CXA-201 in Patients with Complicated Urinary Tract Infections, Including Pyelonephritis A total of 1068 adults hospitalized with complicated urinary tract infections (including pyelonephritis) were randomized and received study medications in a multinational, double-blind study comparing CXA-201 (1.5 g IV every 8 hours) to levofloxacin (750 mg IV once daily) for 7 days of therapy. The primary efficacy endpoint was the composite microbiological and clinical cure response at the test-of-cure (TOC) visit in the microbiologically modified intent-to-treat (mMITT) population, which included all patients who received study medication and had at least 1 baseline uropathogen. The key secondary efficacy endpoint was the composite microbiological and clinical cure response at the TOC visit in the microbiologically evaluable (ME) population, which included protocol-adherent mMITT patients with a urine culture at the TOC visit.

The mMITT population consisted of 800 patients with cUTI, including 656 (82%) with pyelonephritis, 34.3% had mild or moderate renal impairment, and 24.9% were aged≥65 years. The median age in this population was 50.5 years and 74% were female (FIG. 1A).

Most patients in the mMITT population had a monomicrobial infection (97.0%), most commonly due to *E. coli* (78.6%). Other baseline uropathogens included *Klebsiella pneumoniae* (7.3%), *Proteus mirabilis* (3.0%), and *P. aeruginosa* (2.9%). In the mMITT population, 26.5% (212/800) of patients had levofloxacin-resistant uropathogens and 14.8% (118/800) had ESBL-producing Enterobacteriaceae organisms isolated from the baseline urine culture.

The results of baseline susceptibility testing to both study drugs are provided in FIG. 1B. In the mMITT population, 96.6% of all gram-negative pathogens isolated at baseline were susceptible to ceftolozane/tazobactam (using a breakpoint of ≤8 mg/l) compared with 70.7% susceptible to levofloxacin using CLSI (Clinical and Laboratory Standards Institute) criteria. 11 Of note, 99.7% of *E. coli* isolates were susceptible to ceftolozane/tazobactam, regardless of ESBL phenotype (minimum inhibitory concentration required to inhibit the growth of 50%/90% of organisms [MIC50/90] 0.25/0.5 mg/l) compared with 74.1% for levofloxacin (MIC50/90 0.03/>4 mg/l).

CXA-201 was superior to levofloxacin with regard to the composite microbiological and clinical cure rates at the TOC visit in both the mMITT and ME populations (Table 10 and FIG. 1C).

Microbiological eradication rates at the TOC visit by pathogen in the ME population are presented in Table 11A.

In patients with levofloxacin-resistant pathogens at baseline, CXA-201 was superior to levofloxacin with regards to composite cure rates in the mMITT population, 60/100 (60%) in the CXA-201 treatment arm and 44/112 (39.3) in the levofloxacin treatment arm (95% CI: 20.7) (Table 11B).

TABLE 10

Composite Microbiological and Clinical Cure Rates in a Phase 3 Study of Complicated Urinary Tract Infections

| Analysis Population | CXA-201[a] n/N (%) | Levofloxacin[b] n/N (%) | Treatment Difference (99% CI)[c] |
|---|---|---|---|
| mMITT | 306/398 (76.9) | 275/402 (68.4) | 8.5 (0.36, 16.46) |
| ME | 284/341 (83.3) | 266/353 (75.4) | 8.0 (0.01, 15.84) |

[a]1.5 g IV every 8 hours.
[b]750 mg IV once daily.
[c]The 99% CI was based on the stratified Newcombe method.

TABLE 11A

Per Pathogen Microbiological Eradication Rates in a Phase 3 Study of Complicated Urinary Tract Infections (ME Population)

| Organism Group Pathogen | CXA-201 n/N (%) | Levofloxacin n/N (%) |
|---|---|---|
| Aerobic Gram-negative | 287/323 (88.9) | 263/340 (77.4) |
| Escherichia coli | 237/262 (90.5) | 226/284 (79.6) |
| Escherichia coli (ESBL-producing) | 27/36 (75) | 18/36 (50) |
| Escherichia coli (CTX-M-14/15 ESBL producing) | 20/27 (74.1) | 13/25 (52.0) |
| Klebsiella pneumoniae | 21/25 (84.0) | 14/23 (60.9) |
| Klebsiella pneumoniae (ESBL-producing) | 7/10 (70) | 2/7 (29) |
| Klebsiella pneumoniae (CTX-M-15 ESBL producing) | 5/8 (62.5) | 1/4 (25.0) |
| Proteus mirabilis | 10/10 (100) | 8/11 (72.7) |
| Pseudomonas aeruginosa | 6/7 (85.7) | 7/12 (58.3) |

TABLE 11B

Per Pathogen Microbiological Eradication Rates vs Levofloxacin in the mMITT and ME Populations

| Outcomes in the Levofloxacin-resistant Population at TOC | Population | Ceftolozane/ tazobactam % (n/N) | Levofloxacin % (n/N) | Difference % (95% CI) |
|---|---|---|---|---|
| Composite Cure Rate | mMITT | 60.0 (60/100) | 39.3 (44/112) | 20.7 (7.23 to 33.17) |
|  | ME | 64.0 (57/89) | 43.4 (43/99) | 20.6 (6.33 to 33.72) |
| Per-pathogen Microbiological Eradication Rate | ME |  |  |  |
| Enterobacteriaceae |  | 71.4 (55/77) | 45.2 (38/84) | 26.2 (10.96 to 39.72) |
| Escherichia coli |  | 72.9 (43/59) | 44.1 (30/68) | 28.8 (11.59 to 43.55) |
| Klebsiella pneumoniae |  | 81.8 (9/11) | 30.0 (3/10) | 51.8 (9.50 to 75.05) |
| Pseudomonas aeruginosa |  | 100.0 (3/3) | 37.5 (3/8) | 62.5 (−2.09 to 86.32) |

Figure 1D:
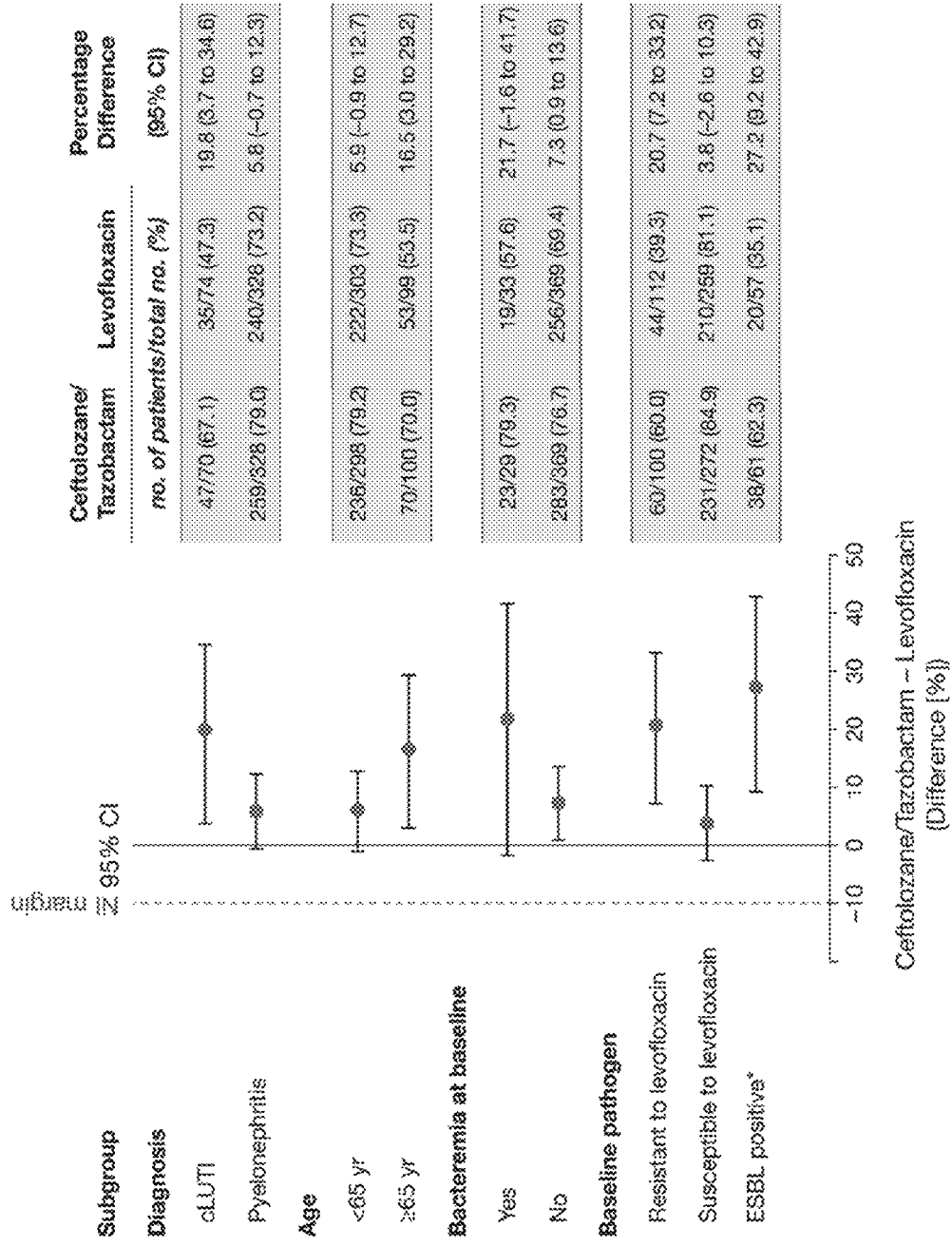
FIG. 1D shows the composite cure at the Test-of-Cure visit, according to subgroups (mMITT population). ESBL (extended-spectrum β-lactamase) positive includes isolates of *E. coli, K. pneumoniae, P. mirabilis, E. cloacae, Enterobacter aerogenes,* and *Serratia marcescens.* cLUTI denotes complicated lower urinary tract infection, mMITT microbiological modified intent-to-treat.

In the mMITT population, composite cure rates in patients with concurrent bacteremia were 23/29 (79.3%) for CXA-201 and 19/33 (57.6%) for levofloxacin (FIG. 1D).

The incidence of adverse events, including serious adverse events, was low and comparable in both treatment groups (FIGS. 1E and 1F). Adverse events occurred in 34.7% (185/533) and 34.4% (184/535) of patients in the ceftolozane/tazobactam and levofloxacin groups, respectively. The most common adverse events were headache (5.8% and 4.9%) and gastrointestinal symptoms (11.8% and 11.4%) for ceftolozane/tazobactam and levofloxacin, respectively. The majority of adverse events were mild to moderate in severity, and the incidence of treatment-limiting adverse events was <2% in both treatment groups. Epidemiology and susceptibility of organisms isolated from patients with cUTI.

Methods 764 isolates of Gram-negative aerobic organisms were isolated from 800 patients in the microbiological modified intent-to-treat population (enrolled in 20 countries in Eastern Europe, North America, South America and 5 countries outside of these regions). Susceptibility (S) testing was performed with ceftolozane/tazobactam at a fixed 4 µg/mL of tazobactam and 10 antibiotic comparators using CLSI broth microdilution methods. ESBL enzymes were identified by PCR.

Results

The activity of ceftolozane/tazobactam was similar across geographic regions with the exception of decreased activity against a subset of P. aeruginosa isolates from E. Europe possessing carbapenemases. Potent activity was observed against isolates of Enterobacteriaceae and P. aeruginosa, with limited Enterococcus spp. activity. E. coli was the most common pathogen (78.6%) and ceftolozane/tazobactam was the most active beta-lactam tested against E. coli (99.7% inhibited at ≤8 µg/mL), including CTX-M-14/15+ isolates (MIC90, 1 µg/mL). The majority (60.0%) of P. aeruginosa isolates were inhibited at ceftolozane/tazobactam concentrations≤8 µg/mL while these isolates exhibited moderate susceptibility to imipenem (IMI, 45.0%), ceftazidime (CAZ; 40.0%), cefepime (FEP, 50.0%), piperacillin/tazobactam (P/T; 40.0%), levofloxacin (LVX; 35.0%), and amikacin (AMI; 55.0%). Against Klebsiella pneumoniae (KPN), ceftolozane/tazobactam activity was improved relative to that of CAZ (87.3% vs 58.2% inhibited at ≤8 µg/mL respectively) including CTX-M-15+ isolates of KPN (73.3% inhibited at ≤8 µg/mL) while the activity of comparators except colistin and IMI was greatly reduced.

Example 6: ESBL-Producing Strains of Gram-Negative Pathogens in the Phase 3 Clinical Trials The clinical response rates of CXA-201 and comparators against E. coli and K. pneumoniae strains producing CTX-M-14/15 ESBLs in the Phase 3 clinical trials are shown in Table 12.

TABLE 12

Clinical Cure Rates by ESBL Status from the Phase 3 Clinical Trials (ME Population)

| Pathogen | CXA-201[a] n/N (%) | All Comparative[b] n/N (%) |
|---|---|---|
| Escherichia coli | 452/470 (96.2) | 483/515 (93.8) |
| Escherichia coli (ESBL-producing) | 49/50 (98.0) | 48/56 (87.5) |
| Escherichia coli (CTX-M-14/15 ESBL-producing) | 35/36 (97.2) | 28/34 (82.4) |
| Klebsiella pneumoniae | 51/55 (92.7) | 41/48 (85.4) |
| Klebsiella pneumonia (ESBL-producing) | 17/18 (94.4) | 8/11 (72.7) |
| Klebsiella pneumoniae (CTX-M-15 ESBL-producing) | 13/13 (100) | 2/5 (40.0) |

[a]The CXA-201 dose received was 1.5 g IV every 8 hours. In the complicated intra-abdominal infection studies CXA-201 was combined with metronidazole.
[b]Comparators included meropenem 1 g IV every 8 hours in the Phase 3 complicated intra-abdominal infection trial and levofloxacin 750 mg IV every 24 hours in the Phase 3 complicated urinary tract infection trials.

Example 7: Population Pharmacokinetics of Ceftolozane/Tazobactam (as CXA-201) in Healthy Volunteers, Subjects with Varying Degrees of Renal Function and Patients with Bacterial Infections Ceftolozane/tazobactam is a novel anti-pseudomonal cephalosporin with a well-established β-lactamase inhibitor. In vitro studies have demonstrated potent activity against *Pseudomonas aeruginosa*, including drug-resistant strains, and other Gram-negative pathogens including most common extended-spectrum β-lactamase (ESBL)-producing Enterobacteriaceae. Ceftolozane exerts its bactericidal activity by inhibition of essential penicillin-binding proteins (PBPs). Tazobactam is an inhibitor of most common class A β-lactamases and some class C β-lactamases that, by binding to the active site of these enzymes, protects ceftolozane from hydrolysis and broadens coverage to include most ESBL-producing Enterobacteriaceae. In addition, ceftolozane/tazobactam has the most potent anti-pseudomonal activity among currently available cephalosporins and is minimally affected by AmpC overexpression, increases in efflux mechanisms, and porin deficiencies. Ceftolozane/tazobactam is currently in clinical development for the treatment of complicated urinary tract infections (cUTIs), complicated intra-abdominal infections (cIAIs), and nosocomial pneumonia.

The pharmacokinetic (PK) profile of ceftolozane/tazobactam has been studied in several preclinical and clinical studies. In healthy volunteers the PK of ceftolozane/tazobactam is dose-proportional and linear across a wide range of doses (up to 3000 mg/1500 mg as a single dose) with a terminal elimination half-life ($t_{1/2\beta}$) of approximately 2.5 hours for ceftolozane and 1 hour for tazobactam. Both ceftolozane and tazobactam are primarily excreted in the urine; ceftolozane almost completely in the urine as unchanged parent drug suggesting minimal metabolism, and tazobactam with 80% as the unchanged parent drug and the remaining as inactive M1 metabolite that is formed via hydrolysis of tazobactam. There is no drug-drug interaction between ceftolozane and tazobactam when co-administered.

PK/pharmacodynamic (PD) models are of particular importance for describing the efficacy and safety of antibacterials and for identifying patient covariates that need to be taken into account for determining optimal dose strategies and evaluating exposure-response relationships. The aims of this analysis were: (1) to develop a population PK model for ceftolozane/tazobactam in healthy subjects and in target populations such as patients with renal impairment and complicated bacterial infections; (2) to identify intrinsic and extrinsic determinants of variability (covariates) in the PK of ceftolozane and tazobactam. The analysis was performed using published guidance from the US Food and Drug Administration (FDA) and European Medicines Agency (EMA).

Materials and Methods

A population-PK analysis was performed on plasma ceftolozane and tazobactam concentration-time data from adult subjects enrolled in 10 studies. Subjects were included from multiple sites and all studies were performed in accordance with the International Conference on Harmonization guidelines on good clinical practice and the Declaration of Helsinki. An investigational review board approved the study protocols at each site.

Serum concentration data were analyzed from 5 studies in healthy volunteers (n=184), 3 studies in subjects with varying degrees of renal impairment (n=42), and 2 phase 2 studies in patients with bacterial infections (cUTIs [n=73] and cIAIs [n=77]). In all studies, ceftolozane was administered as a 1-hour intravenous infusion either alone or in combination with tazobactam at a fixed 2:1 ratio (ceftolozane:tazobactam). Healthy volunteers received single or multiple (every 8 hours [q8h] or every 12 hours [q12h]) doses of ceftolozane alone (250, 500, 1000, 1500, 2000 mg or ceftolozane/tazobactam (500/250, 1000/500, 1500/750, 2000/1000, 3000/1500) (See Example 13) with sampling periods up to 24 hours following infusion (FIG. 2). Subjects with mild (creatinine clearance [CrCL] of ≥50 to <90 mL/min) or moderate (CrCL of ≥30 to <50 mL/min) renal impairment received a single dose of ceftolozane/tazobactam 1000/500 mg, with sampling up to 36 hours. Subjects with severe renal impairment (CrCL of ≥15 to <30 mL/min) received a single dose of ceftolozane/tazobactam 500/250 mg, with sampling up to 48 hours. In the phase 2 trials, cUTI patients received ceftolozane alone 1000 mg (q8h) and cIAI patients received ceftolozane/tazobactam 1000/500 mg (q8h).

All subjects who received at least 1 dose of study medication and had at least 1 measurement of ceftolozane or tazobactam were included (N=376). Plasma concentrations of ceftolozane and tazobactam were determined by a validated liquid-chromatography-tandem mass spectrometry assay (MicroConstants, Inc., San Diego, Calif.) described previously. Concentrations below the limit of quantitation (BLQ), as defined previously, were considered as missing. No substitutions were made to account for these missing data points.

Population Pharmacokinetic Analysis

Base model development. The model was developed in 2 stages: a preliminary PK model was developed based on datasets from 3 studies. In the current analysis, the structural model was refined using the PK data from 10 studies (including patients with cUTI or cIAI) and the covariate analysis repeated. The results based on this revised model are presented here. A nonlinear mixed-effects model was developed with Phoenix® NLME™ software, version 1.2, 2012 (Certara L. P. Pharsight, St. Louis, Mo.) using first-order maximum likelihood estimation, and a 2-compartment structure model was fitted to the plasma concentration time data. The First Order Conditional Estimation-Extended Least Squares (FOCE-ELS) engine was used for model fitting. The software R (R Foundation for Statistical Computing, Vienna, Austria, 2013) was used to generate tables of post hoc PK parameters and descriptive statistics.

Models had the form:

$$C_{P_{ij}} = C(D_i, t_j, \theta_i) + \varepsilon_{ij}$$

$$\theta_i = \theta_{i1}, \ldots, \theta_{im})$$

where $C_{P_{ij}}$ is the concentration at $j^{th}$ time for subject i, $D_i$ represents dosing history for subject i, $\theta_i$ is the vector of m model parameters for subject i, and $\varepsilon_{ij}$ is random error associated with a concentration at the $j^{th}$ time ($t_j$) for subject i.

A variance component, which assumed a log-normal distribution of PK parameters, was used to characterize the between subject variability (BSV) and between occasion variability (BOV) in model parameters using the following equation:

$$\theta_{in} = \theta_{TVn} \exp(\eta_{in})$$

$$(\eta_1 \ldots \eta_m) \sim MVN(0, \Omega)$$

Where $\theta_{TVn}$ is the population typical value for the $n^{th}$ PK parameter (e.g., clearance), and $\eta_{in}$ is the individual random effect ($\eta$ is referred to as ETA hereafter) and occasion random effect on the $n^{th}$ parameter for subject i that jointly follow a multivariate normal distribution (MVN) with mean zero and variance Q.

Residual unexplained variability was modelled using additive±proportional error models, including:

$$y_{ij} = y\hat{}_{ij} * (1 + \varepsilon_{1ij}) + \varepsilon_{2ij}$$

where $y_{ij}$ (observed) and $y\hat{}_{ij}$ (predicted) represent the $j^{th}$ plasma drug concentration for the $i^{th}$ subject, and $\varepsilon$ is the random residual variability. Each $\varepsilon$ ($\varepsilon_1$ and $\varepsilon_2$) is normally distributed with mean 0 and variance $\sigma^2$.

Sources of Variability and Covariate Analysis

Sources of variability, that may affect drug exposure, were identified using correlation plots of individual random effects (ETA with mean 0 and estimated variance $\omega^2$) of parameters such as systemic clearance (CL) and central volume of distribution (Vc) versus covariates. Extrinsic covariates analyzed included dose levels, drug-drug interactions between ceftolozane and tazobactam, and disease status (bacterial infections). Intrinsic covariates analyzed included body weight, age, sex, ethnicity, and baseline calculated CrCL). The CrCL was estimated using the Cockcroft-Gault formula:

$$CrCL = \{[(140 - Age) \times WT]/S_{Cr}\}$$

where CrCL is creatinine clearance (ml/min), age is in years, WT is actual body weight (kg), and $S_{Cr}$ is serum creatinine (mg/dl); for female subjects the value was multiplied by a factor of 0.85. Renal impairment was categorized as normal (CrCL≥90 mL/min), mild (CrCL≥50-<90 mL/min), moderate (CrCL≥30-<50 mL/min), and severe (CrCL≥15-<30 mL/min).

Scatter plots were used to examine the effect of continuous variables and box plots were used for categorical variables. The resulting graphs were screened using visual inspection, and the most statistically relevant covariates were retained and evaluated in the population PK model using an automatic stepwise forward additive-backward elimination approach to identify individual covariates that had a sufficient threshold effect based on the specified criteria (P<0.01 for forward approach and P<0.001 for backward approach). Covariates were introduced in a multiplicative order using a power model standardized by the median for continuous covariates and a linear model with an exponentiated factor relative to the reference for categorical covariates.

Final population PK model: evaluation and performance. The final population-PK models for ceftolozane and tazobactam were evaluated using standard diagnostics, goodness-of-fit criteria, nonparametric bootstrap resampling, and visual predictive check (VPC). Final model selection was based on goodness-of-fit criteria evaluated using the log-likelihood difference between models, pertinent graphical representations of plasma concentrations (fitted, observed [individual dependent variable], population-predicted [PRED], and individual-predicted [IPRED]) versus time plots with assumption of log-normal distribution of PK parameters for BSV and BOV. Sensitivity of outliers was measured using conditional weighted residuals (CWRES) versus time or time after dose (for FOCE) plots. Shrinkage of individual random effects (ETA) toward the population mean was computed to assess whether the final model provided reliable estimates of individual PK parameters: Shrinkage=1-(SD(ETA)/$\omega$). SD(ETA) is the standard deviation of the post hoc or empirical Bayesian estimates of ETA and $\omega$ is the population model estimate of the SD of ETA. Smaller shrinkage≤0.2 indicates good individual estimates. A VPC was performed to allow for comparisons of simulated and original data. The plasma concentration-time profiles of ceftolozane and tazobactam were simulated using 1000 replicates of the subject, and the median 90% prediction intervals (PI) were computed and compared with observed data. In addition, the robustness of the final population PK model was confirmed using non-parametric bootstrap resampling. The final model was fitted to a 1000 bootstrap dataset to obtain the median value of each PK parameter, along with the fixed-effect and random-effect parameters (inter-individual variability and residual error). The nonparametric bootstrap values (median) for each parameter were compared with the original parameter estimates to examine bias and predictive error and were evaluated using 95% confidence intervals (CIs).

Results

Data Sets

The population-PK model included evaluable data from 376 adults who received ceftolozane and 243 who also received tazobactam, with 5048 observations for ceftolozane and 4249 observations for tazobactam. Demographic data stratified by presence or absence of infection are summarized in FIG. 3. Approximately, 39.9% (150/376) of subjects included in the PK model had an infection (cUTI or cIAI) and 32.2% (121/376) were renally impaired. Baseline CrCL was used to describe renal function since serum creatinine was stable across the short treatment duration, with a median value of the actual changes (increase or decrease) of approximately 5% and a median value of the absolute changes of <15%; all changes were judged as not clinically meaningful. The age range of subjects was from 18 to 86 years.

Population Pharmacokinetic Model and Covariate Analysis of Ceftolozane

A 2-compartmental structural model with a diagonal variance (omega) of CL, Vc, peripheral volume of distribution (Vp), and peripheral clearance ($CL_2$) fixed to a value of 0 provided the best data fit. The residual variability was found to be composite (both proportional and additive). Covariate analysis showed that both CL and Vc increased with body weight. A small negative trend between age and CL was also observed but it was not clinically meaningful. Both CL and Vc were significantly different for patients with an infection compared with healthy volunteers, and ceftolozane CL decreased as baseline CrCL decreased. Other covariates such as race, sex, dose level, and drug-drug interaction did not significantly affect CL or Vc of ceftolozane. The stepwise approach to identify significant covariates showed that the greatest improvement in the model included the effect of infection on both CL (<0.001) and Vc (<0 0.001), body weight on Vc (<0.001), and CrCL on CL (<0.001), with a significant difference between the minimum objective function value for the tested and base models [ΔMOF2] of −329.81; P<0.001). The effects of renal impairment and infection status on ceftolozane CL are presented in a tornado plot (FIG. 4a). The plot shows that between-subject variability (BSV 33.0%) had more impact on relative CL than the effect of infection (cIAI or cUTI). Furthermore, severe renal impairment and moderate renal impairment (based on CrCL categories over a standardized range of 19.1-308.5 mL/min) resulted in lower CL compared with normal and mild renal impairment.

The final model was further refined with infection status divided into cUTI and cIAI. Overall, the refined final model for ceftolozane was a 2-compartment model with linear elimination including the effect of baseline CrCL on CL and body weight on Vc, and the effect of cUTI and cIAI infection on both CL and Vc. The population PK estimates, relative standard error (RSE), and BSV of the model are shown in FIG. 5a. In the final refined model, the Vc changed proportionally (linearly) with body weight in subjects without cIAI. However, in cIAI patients, there was no significant correlation between Vc and body weight given the large observed variability. In addition, CL was similar in patients with cUTI and cIAI (6.18 vs 6.23 L/h at CrCL=109 mL/min), both about 20% higher than that in healthy subjects. Vc was about 30% different between these 2 patient groups (13.8 L at 74 kg body weight for cUTI vs 18.2 L for cIAI). The inter-compartment clearance (CL2) was about 1 L/h while volume of distribution in the peripheral compartment was about 3 L. The parameter estimates of the final model were reliable with all standard error of measurement (SEM %) less than 50%, and the residual variability (i.e., the sum of all variability that is not explained by the final model) was low, 16.8% for proportional error and 0.05 μg/mL for additive error. For a fitted ceftolozane concentration of 100 μg/mL, the total residual error would be 16.85 μg/mL.

Diagnostic plots showed a good fit of the final model to ceftolozane plasma concentrations (FIG. 6a). Individual observed and PRED plasma concentrations were symmetrically distributed, and CWRES versus PRED were homogenously distributed around 0 with 25 PK samples from 20 subjects displaying CWRES>4, suggesting no bias in predictions relating to low or high ceftolozane concentrations. Outliers (CWRES>4) were not excluded from the analysis, as they did not have a significant effect on PK parameters (difference range: −0.2% to 6.7%) and the changes in BSV of CL and Vc were less than 31%. VPC simulations were within the 90% PI of the predicted median across all doses. Similarly, differences in PK parameters and covariate effects between the final model and bootstrap runs were <5%.

Population PK Model and Covariate Analysis of Tazobactam

The best-fit model for tazobactam was structurally similar to that for ceftolozane, a 2-compartmental structural model with a diagonal variance (BSV) for CL and Vc and a proportional model for unexplained residual variability. Similar to ceftolozane, in the covariate analysis differences in both CL and Vc were observed between subjects with and without infection, and there was a strong correlation between tazobactam CL and renal impairment category (i.e., decrease in CL with decreasing baseline CrCL). The stepwise approach to identify significant covariates showed that the greatest improvement in the model included the effect of cIAI infection on Vc (note there were no tazobactam data from cUTI patients) and of CrCL on CL (ΔMOF2: −92.84; P<0.001). The ΔMOF2 was −103.02 (P=0.001) when the effect of cIAI infection was included in the model and −109.73 (P=0.01) when weight was included on Vc. No trends were noted between other covariates tested and tazobactam PK.

The final model was confirmed to be a 2-compartmental model with linear elimination that included the effect of baseline CrCL on CL showing a power function of 0.67 (i.e., $[CrCL/115]^{0.67}$) and the effect of infection on Vc. In this model, the population estimates (RSE %) derived for tazobactam were 18.0 L/h (3.39) for CL, 14.2 L (4.45) for Vc in subjects without infection, 3.13 L/h (4.59) for $CL_2$ (inter-compartment clearance), and 4.29 L (2.61) for Vp (FIG. 5b). The parameter estimates of the final model were reliable with all SEM % less than 50%, and a proportional unexplained error of 26.0% (1.64), although the BSV was higher (50.2% for CL and 52.5% for Vc). The tornado plot shows that, similar to ceftolozane, severe and moderate renal impairment resulted in lower CL of tazobactam compared with normal and mild renal impairment (FIG. 4b).

The model was robust showing a good fit to plasma concentrations of tazobactam (FIG. 6b) and CWRES versus PRED were homogenously distributed around 0 with 17 PK samples from 13 subjects displaying CWRES>4 and non-exclusion of outliers (difference range: −2.8% to 7.7%). However, when outliers were excluded the BSV of CL and Vc decreased by 42.5 and 32.5%, respectively. VPC simulations were within 90% PIs of predicted medians and differences in bootstrap resampling analysis were <4% compared with the final model.

Conclusion

In summary, this analysis conducted by combining PK data across a range of subjects provided a comprehensive, stable, and interpretable model explaining the determinants of variability in the disposition of ceftolozane/tazobactam. The final PK models adequately described the plasma concentrations of ceftolozane and tazobactam and form the basis for evaluation of the probability of target attainment in a diverse population with varying demographics and degrees of renal impairment. For both ceftolozane and tazobactam that are primarily renally eliminated, clearance was influenced by renal function. Other covariates tested, such as age, body weight, sex, ethnicity and presence of infection, had no clinically relevant effects on clearance. The model can be utilized to further support optimal dosing scenarios to maximize efficacy and safety of ceftolozane/tazobactam for treatment of serious bacterial infections in subjects with varying degrees of renal impairment. Monte Carlo simulations derived with the population PK/PD model can also be utilized to further guide dosing recommendations for ceftolozane/tazobactam in various populations, for different pathogens of interest, and for other indications such as nosocomial pneumonia infection.

Example 8 Single Dose Pharmacokinetics of Ceftolozane/Tazobactam (as CXA-201) in Subjects with Severe Renal Impairment and End Stage Renal Disease on Hemodialysis Methods for reducing the concentration of ceftolozane in the blood of a subject can include maintaining the subject on hemodialysis for a period of 4 hours to remove about 66% of the ceftolozane in the blood of the subject. This method is useful, for example, in treating a patient after an overdose of ceftolozane, and is based in part on the discovery that about 66% of ceftolozane was removed from patients during dialysis (e.g., Example 8).

Study Design and Objectives

This was a Phase 1, multicenter, prospective, open-label study of 750 mg ceftolozane/tazobactam (as CXA-201) administered IV in male and female adult subjects with severe renal impairment (estimated $CL_{CR}$<30 mL/min) and subjects with end-stage renal disease (ESRD) on hemodialysis (HD). The primary objective of the study was to determine the PK profile of ceftolozane/tazobactam in subjects with severe renal impairment and subjects with ESRD on HD and to determine the effect of HD on the clearance of ceftolozane/tazobactam.

Subjects with severe renal impairment received a single IV 1-hour infusion of 750 mg ceftolozane/tazobactam on Day 1. Subjects with ESRD had a minimum of 3 months of HD prior to enrollment. Subjects in this cohort received an IV dose of 750 mg ceftolozane/tazobactam as a 1 hour infusion immediately after their first HD session on Day 1 (post dialysis, approximately 72 hours prior to the next HD session) and a second dose of ceftolozane/tazobactam approximately 2 hours before their second HD session on Day 4 of the study. Infusion of ceftolozane/tazobactam was completed approximately 1 hour before the start of HD.

Subjects in both cohorts had urine (if not anuric) and plasma samples collected for determination of levels of ceftolozane, tazobactam and the M1 metabolite of tazobactam; subjects in the ESRD on HD cohort also had dialysate fluid samples collected for PK assessment. Plasma, urine, and dialysate levels of ceftolozane, tazobactam and its metabolite M1 collected over a prespecified interval were determined by LC/MS/MS assay.

Results

A total of 12 subjects received 750 mg ceftolozane/tazobactam: 6 subjects with severe renal impairment received a single dose and 6 subjects with ESRD received a dose prior to and following HD; all 12 subjects completed the study. A total of 5 males and 7 females ranging in age from 40 to 76 years were enrolled.

Figure 14B:
FIG. 14B shows the individual plasma concentrations of ceftolozane included for population PK analysis.
Figure 14B:
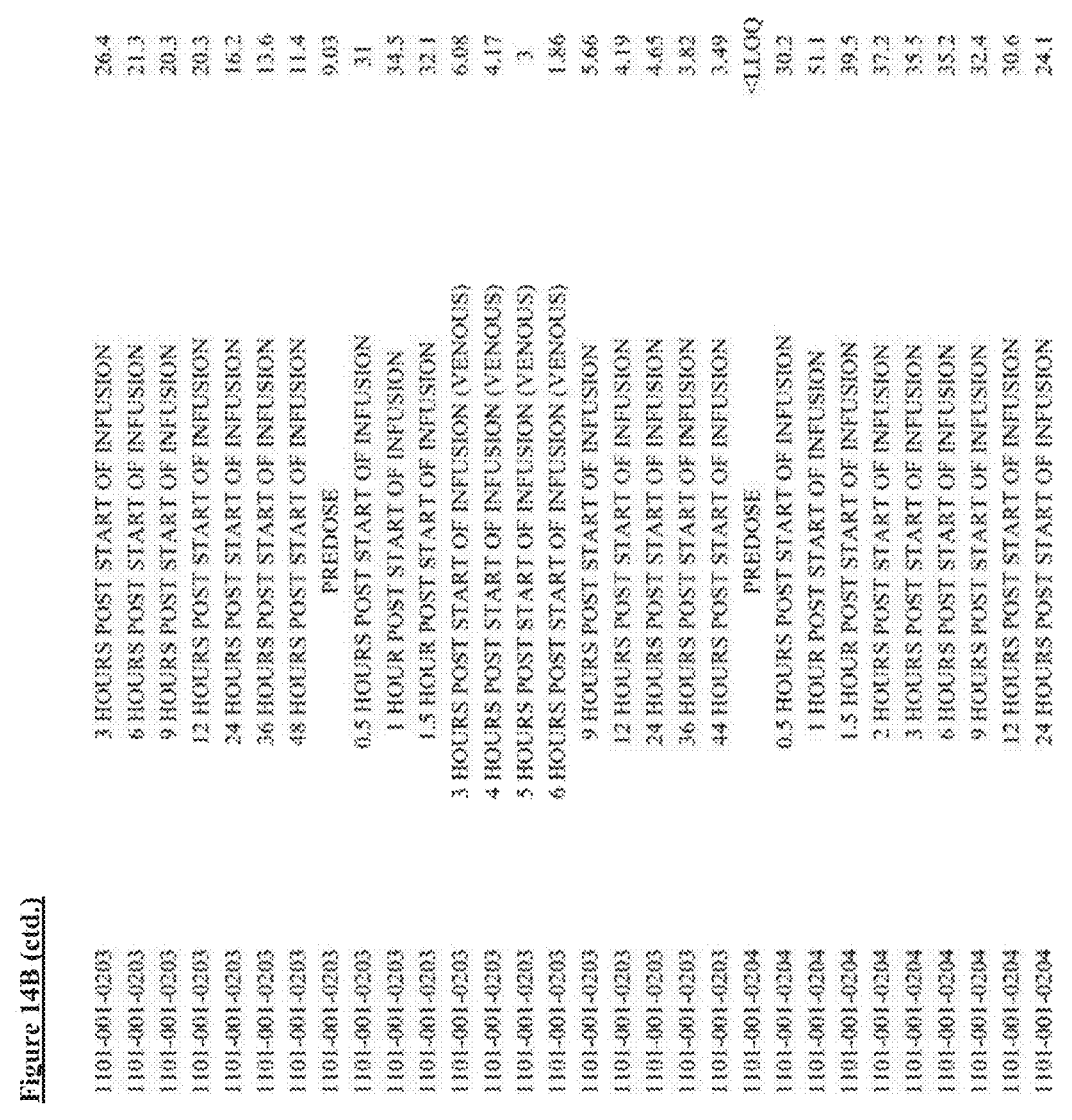

Details regarding the HD procedures for ESRD subjects, including BUN collected before and after dialysis, are provided in FIG. 14. All subjects underwent hemodialysis for 3 to 4 hours using a high-flux membrane (either 1.4, 1.8, or 1.9 m²) on Days 1, 4, and 6 as scheduled. Average blood flow rate was 264 to 600 mL/min and average dialysis flow rate was either 600 or 800 mL/min for all subjects with ESRD.

The PK parameters of ceftolozane, tazobactam, and the M1 metabolite of tazobactam were consistently higher in subjects with severe renal impairment (Table 13) when compared with healthy subjects or subjects with mild or moderate renal impairment from previous studies.

TABLE 13

Plasma Pharmacokinetic Parameters for Ceftolozane, Tazobactam, and Tazobactam M1 Metabolite in Subjects with Severe Renal Impairment After a Single IV 1-hour Infusion of 750 mg Ceftolozane/Tazobactam

| Pharmacokinetic Parameter | Mean (CV %) | | |
|---|---|---|---|
| | Ceftolozane (N = 6) | Tazobactam (n = 6) | M1 Metabolite (n = 6) |
| $C_{max}$ (µg/mL) | 49.9 (28) | 15.2 (22) | 2.2 (20) |
| $AUC_{last}$ (µg · h/mL) | 511 (22) | 50.3 (26) | 53.7 (25) |
| $AUC_\infty$ (µg · h/mL) | 537 (23) | 52.4 (27) | 60.3 (30) |
| $t_{1/2}$ (h) | 11.1 (24) | 2.6 (22) | 12.0 (29) |
| $V_{ss}$ (L) | 13.8 (25) | 16.5 (27) | ND |
| CL (L/h) | 1.0 (20) | 5.1 (29) | ND |

$AUC_\infty$ = area under the plasma concentration-time curve from time zero to infinity;
$AUC_{last}$ = area under the plasma concentration-time curve from time zero to the last measurable concentration (plasma samples were obtained through 48 hours for subjects with severe renal impairment);
CL = total body clearance from plasma;
$C_{max}$ = maximum (peak) plasma drug concentration;
CV = coefficient of variation;
ND = not determined;
$t_{1/2}$ = half-life;
$V_{ss}$ = apparent volume of distribution at steady state after intravenous administration Due to relative increase in exposure, a 4-fold dose reduction to 750 mg ceftolozane/tazobactam every 8 hours and 375 mg ceftolozane/tazobactam every 8 hours is recommended in subjects with moderate and severe renal impairment, respectively, compared to 1.5 g ceftolozane/tazobactam dose in subjects with normal renal function.

The PK parameters for ceftolozane, tazobactam, and the M1 metabolite of tazobactam in subjects with ESRD not being dialyzed (dosed following HD) are summarized in Table 14. The plasma concentrations of the M1 metabolite increased and did not appear to decline over the 12 to 24 hour sampling interval. Therefore, $AUC_\infty$ and $t_{1/2}$ for the M1 metabolite could not be calculated.

TABLE 14

Plasma Pharmacokinetics Parameters for Ceftolozane, Tazobactam, and Tazobactam M1 Metabolite in Subjects with ESRD on HD after the Day 1 Intravenous Infusion (During Non-hemodialysis Phase) of 750 mg Ceftolozane/Tazobactam

| Pharmacokinetic Parameter | Mean (CV %) | | |
|---|---|---|---|
| | Ceftolozane (N = 6) | Tazobactam (n = 6) | M1 Metabolite (n = 6) |
| $C_{max}$ (µg/mL) | 44.5 (25) | 21.2 (26) | 10.0 (40) |
| $AUC_{last}$ (µg · h/mL) | 910 (33%) | 103 (48) | 367 (42) |
| $AUC_\infty$ (µg · h/mL) | 1678 (44) | 105 (47) | ND |
| $t_{1/2}$ (h) | 39.8 (33) | 5.23 (42) | ND |
| $V_{ss}$ (L) | 19.2 (36) | 17.0 (35) | ND |
| CL (L/h) | 0.4 (82) | 3.0 (55) | ND |

$AUC_\infty$ = area under the plasma concentration-time curve from time zero to infinity;
$AUC_{last}$ = area under the plasma concentration-time curve from time zero to the last measurable concentration (plasma samples were obtained through 48 hours for subjects with ESRD on HD following Dose 1);
CL = total body clearance from plasma;
$C_{max}$ = maximum (peak) plasma drug concentration;
CV = coefficient of variation;
ND = not determined;
$t_{1/2}$ = elimination half-life;
$V_{ss}$ = apparent volume of distribution at steady state after intravenous administration The PK parameters for ceftolozane, tazobactam, and the M1 metabolite of tazobactam in subjects dosed approximately 2 hours prior to initiation of their 3 to 4 hour HD session are summarized in Table 15. The concentrations of all 3 analytes increased following the start of the infusion but declined rapidly at the start of dialysis. The concentrations continued to decline during HD and rebounded slightly at the end of HD followed by a slow decline over the remainder of the sampling interval.

TABLE 15

Plasma Pharmacokinetics Parameters for Ceftolozane, Tazobactam, and the M1 Metabolite of Tazobactam in Subjects with ESRD on HD after the Second Intravenous Infusion of 750 mg Ceftolozane/Tazobactam on Day 4 (During HD)

| Pharmacokinetic Parameter | Mean (CV %) | | |
|---|---|---|---|
|  | Ceftolozane (N = 6) | Tazobactam (n = 6) | M1 Metabolite (n = 6) |
| $C_{max}$ (µg/mL) | 40.9 (35) | 15.6 (37) | 10.8 (46) |
| $t_{max}$ (h)$^{(a)}$ | 1.0 (1.0, 1.0) | 1.0 (1.0, 1.0) | 1.5 (0.5, 24.0) |
| $AUC_{last}$ (µg · h/mL) | 304 (35) | 38.4 (37) | 176 (40) |
| $t_{1/2}$ (h) | 43.5 (19) | 5.2 (44) | ** |

$AUC_{last}$ = area under the plasma concentration-time curve from time zero to the last measurable concentration (plasma samples were obtained through 44 hours for subjects with ESRD on HD following Dose 2);
$C_{max}$ = maximum (peak) plasma drug concentration;
CV = coefficient of variation;
ESRD = end-stage renal disease;
HD = hemodialysis;
$t_{1/2}$ = elimination half-life;
$t_{max}$ = time to reach maximum (peak) plasma concentration following drug administration.
Median (minimum, maximum) presented.
** N = 1; one subject showed a slow decline.

A separate analysis was conducted to determine the PK parameters of ceftolozane, tazobactam, and the M1 metabolite of tazobactam in subjects on HD following second dose of CXA-201 on Study Day 4 from the start of the infusion to the end of dialysis. This analysis was conducted in order to determine the PK parameters from the start of infusion to the end of dialysis; results are summarized in Table 16.

TABLE 16

Plasma Pharmacokinetics Parameters for Ceftolozane, Tazobactam, and the M1 Metabolite of Tazobactam in Subjects with ESRD on HD After the Second Intravenous Infusion of 750 mg Ceftolozane/Tazobactam on Day 4 (Start of Infusion to End of Dialysis)

| Pharmacokinetic Parameter | Mean (CV %) | | |
|---|---|---|---|
|  | Ceftolozane (N = 6) | Tazobactam (n = 6) | M1 Metabolite (n = 6) |
| $C_{max}$ (µg/mL) | 40.9 (35) | 15.7 (37) | 10.6 (49) |
| $t_{max}$ (h)$^{(a)}$ | 1.0 (1.0, 1.0) | 1.0 (1.0, 1.0) | 1.5 (0.5, 1.5) |
| $AUC_{last}$ (µg · h/mL) | 87.5 (30) | 28.8 (34) | 23.8 (44) |
| $t_{1/2}$ (h) | 1.25 (30) | 0.98 (32) | 1.54 (48) |

$AUC_{last}$ = area under the plasma concentration-time curve for approximately 6 hours from time of start of infusion to the end of dialysis for subjects with ESRD on HD following Dose 2;
$C_{max}$ = maximum (peak) plasma drug concentration;
CV = coefficient of variation;
ESRD = end-stage renal disease;
HD = hemodialysis;
$t_{1/2}$ = elimination half-life;
$t_{max}$ = time to reach maximum (peak) plasma concentration following drug administration.
Median (minimum, maximum) presented Concentrations of ceftolozane, tazobactam, and the M1 metabolite declined rapidly following the start of HD. The median exposure of ceftolozane/tazobactam ($AUC_{48h}$) during and after dialysis is shown in Table 17. The data shows that a dosing adjustment that replaces the fraction of ceftolozane/tazobactam, removed due to dialysis, is recommended in subjects undergoing intermittent dialysis.

TABLE 17

Exposure (AUC48h) of Ceftolozane, Tazobactam, and the M1 Metabolite of Tazobactam in Subjects with ESRD During and After Hemodialysis (HD)

| Analyte | Median (Range) (µg · h/mL) | | | |
|---|---|---|---|---|
|  | After HD (Day 1) | During HD (Day 3) | Ratio (Day 3:1) | Percent Removed |
| Ceftolozane | 903 (372-1233) | 298 (179-437) | 0.34 (0.26-0.48) | 66 (52-74) |
| Tazobactam | 107 (45.3-169) | 37.1 (199-57.8) | 0.44 (0.26-0.53) | 56 (47-74) |
| M1 Tazobactam metabolite | 389 (99.8-538) | 182 (78-255) | 0.49 (0.38-0.78) | 51 (22-63) |

Based on the results of this study, it is recommended that ceftolozane/tazobactam be dosed following HD, and in the event of an overdose, a standard 3 to 4 hour HD session with a high flux membrane could lower plasma concentrations of ceftolozane, tazobactam, and the M1 metabolite substantially. As a result, a dosing adjustment that replaces the fraction of ceftolozane/tazobactam removed due to dialysis is recommended in subjects undergoing intermittent dialysis.

The recommended dose in subjects undergoing dialysis is a single loading dose of 750 mg ceftolozane/tazobactam (500/250 mg) administered every 8 hours by IV infusion followed after 8 hours by a 150 mg every 8 hours maintenance dose of ceftolozane/tazobactam (100/50 mg) for the remainder of the treatment period. On HD days, the dose should be administered at the earliest possible time following completion of dialysis. These doses are predicted to provide total daily exposures of ceftolozane/tazobactam that are comparable to exposures in subjects with normal renal function.

Pharmacokinetic Conclusions

The PK parameters of ceftolozane, tazobactam, and the M1 metabolite of tazobactam were influenced substantially in subjects with severe renal impairment as well as in subjects with ESRD on HD warranting dose adjustment.

Example 9A Ceftolozane/Tazobactam (as CXA-201) Dose Optimization in Patients with End Stage Renal Disease (ESRD) Requiring Hemodialysis (HD) Using Population Pharmacokinetics (pPK) and Monte Carlo Simulations (MCS)

Objectives

This analysis was performed to characterize a) the PK parameters for ceftolozane and tazobactam in subjects with end stage renal disease (ESRD) on hemodialysis and b) assess probability of target attainment (PTA) based on Monte Carlo simulations and c) recommend optimal dosing regimens for clinical use.

Data

Altogether per protocol, 156 plasma samples were collected from 6 subjects with ESRD/hemodialysis. Out of the 156 plasma samples, there were 141 valid ceftolozane plasma concentrations and 115 valid tazobactam plasma concentrations included for analysis. The high level information about the study design is summarized in FIG. 14A. The key demographics of the 6 subjects are summarized in Table 18 below.

TABLE 18

Demographics of the Subjects with ESRD/Hemodialysis

| Demographics | Values (n = 6) |
|---|---|
| Sex, n (%) | |
| Male | 2 (33.3) |
| Female | 4 (66.7) |
| Race, n (%) | |
| White | 1 (16.7) |
| Black or African American | 5 (83.3) |
| Age (years) | |
| Mean (SD) | 50.0 (11.08) |
| Median (minimum, maximum) | 48.5 (40, 71) |
| BMI (Kg/m$^2$) | |
| Mean (SD) | 28.9 (7.74) |
| Median (minimum, maximum) | 27.2 (21.4, 39.8) |

Below the lower limit of quantification (BLLOQ) and missing samples, if any, were not included for analysis, except the first pre-dose sample. The individual plasma concentrations of ceftolozane and tazobactam are listed in FIGS. 14B and C, respectively. One ceftolozane concentration and 2 tazobactam concentrations were excluded from analysis, as were done in the clinical study report (CSR), because of their abnormal values.

Details regarding the HD procedures for ESRD subjects, including BUN collected before and after dialysis, are provided in FIG. 14D. All subjects underwent hemodialysis for 3 to 4 hours using a high-flux membrane (either 1.4, 1.8, or 1.9 m$^2$) on Days 1, 4, and 6 as scheduled. Average blood flow rate was 264 to 600 mL/min and average dialysis flow rate was either 600 or 800 mL/min for all subjects with ESRD.

Methods
Software

Phoenix™ Non Linear Mixed Effects (NLME) version 1.2 (Pharsight Corporation, Certara USA, Inc., 9666 Olive Blvd., Suite 425, St. Louis, Mo. 63132 USA) with the extended least squares first order conditional estimation (FOCE-ELS) was used for population PK modeling and SAS® 9.3 (SAS Institute Inc., 100 SAS Campus Drive, Cary, N.C. 27513-2414, USA) with finite element method (FEM) was used for Monte Carlo simulation. R (2.15.0) and SAS® 9.3 were used for data management, statistical summaries and table/figures generation.

The previously developed two-compartment disposition model, as illustrated in FIG. 15, was used to fit the ceftolozane or tazobactam plasma concentration-time data without hemodialysis and to test the between subject variabilities (BSV) and the residual variabilities. No other structural model was further tested unless necessary. Ceftolozane or tazobactam plasma concentration-time data with hemodialysis were then included and hemodialysis was tested as a covariate effect on both clearance and volume of distribution for the central compartment. The final model was selected based on the stability of the model, reliability and interpretability of the parameter estimates and the goodness-of-fit plots.

Where CL and Vc are clearance and volume of distribution for the central compartment; CL2 is the inter-compartment clearance and V2 is the volume of distribution for the peripheral compartment.

Monte Carlo Simulations

The above obtained population PK model was then used to simulate the ceftolozane/tazobactam concentration-time profiles in patients with ESRD/hemodialysis. 5000 patients were simulated to each of the following scenarios:

| Scenario | Loading Dose (TOL/TAZ in mg/mg) | Maintenance Dose (TOL/TAZ in mg/mg) | Regimen |
|---|---|---|---|
| 1 | 500/250 | 300/150 | 1-hr infusion, every 24 hours |
| 2 | — | 300/150 | 1-hr infusion, every 24 hours |
| 3 | 600/300 | 300/150 | 1-hr infusion, every 24 hours |
| 4 | — | 100/50 | 1-hr infusion, every 8 hours |
| 5 | — | 300/150 | 4-hr infusion, every 24 hours |
| 6 | 400/200 | 100/50 | 1-hr infusion, every 8 hours |
| 7 | 500/250 | 100/50 | 1-hr infusion, every 8 hours |

TOL: Ceftolozane;
TAZ: Tazobactam

Simulations with inflated between subject variabilities were also conducted for the purpose of sensitivity analysis and risk assessment. A finite element method with a time step of 0.001 hour was used to simulate the plasma concentrations directly from the mass balance differential equations as demonstrated in equations 1-3 below.

Mass Balance Differential Equations:

$$\frac{dA1}{dt} = -K12 \text{ initial condition: } A1 = \text{dose at } t = 0; \qquad (1)$$

$$\frac{dA2}{dt} = K12 + K32 \times A3 - \qquad (2)$$
$$(K20 + K23) \times A2 \text{ initial condition: } A2 = 0 \text{ at } t = 0$$

$$\frac{dA3}{dt} = K23 \times A2 - K32 \times A3 \text{ initial condition: } A3 = 0 \text{ at } t = 0; \qquad (3)$$

Where A1-A3 are the mass of ceftolozane or tazobactam at time t in the infusion device, central compartment and peripheral compartment, respectively; Kij represents the mass transport rate constant from compartment i to compartment j, noting that K12=Dose/infdur represents the infusion rate during infusion and 0 post the end of infusion with infdur standing for infusion duration.

The solution to the above mass balance differential equations using FEM at any given time t can be expressed as below:

$$A1 = A10 - K12 \times \Delta t \quad (4)$$

$$A2 = A20 + [K12 + K32 \times A30 - (K20 + K23) \times A20] \times \Delta t \quad (5)$$

$$A3 = A30 + (K23 \times A20 - K32 \times A30) \times \Delta t \quad (6)$$

Where $\Delta t$ represents a small time step (e.g. 0.001 hour); A10, A20 and A30 are the masses in the infusion device, central compartment and peripheral compartment at time $t-\Delta t$, respectively. A1-A10, A2-A20 and A3-A30 represent the change of mass during the small time step of $\Delta t$ in the infusion device, central compartment and peripheral compartment, respectively. Thus, the plasma concentration Cp at any given time t can be calculated as:

$$Cp = \frac{A2}{V2} \quad (7)$$

Where V2 is the volume of distribution for the central compartment.

For ceftolozane, T>MIC and Probability of target attainment (PTA) were based on a range of MIC from 0.03 to 128 μg/mL.

For tazobactam, there is no MIC value since tazobactam itself does not kill bacteria. However, it is believed that there is somewhat threshold of tazobactam concentration that is needed to inhibit beta-lactamase from hydrolyzing antibiotics (VanScoy B, Mendes R E, et al. Pharmacological Basis of 13-Lactamase Inhibitor Therapeutics: Tazobactam in Combination with Ceftolozane. Antimicrobial Agents and Chemotherapy. 2013; 57(12):5924). Therefore, similar to the minimum inhibitory concentration (MIC) concept for antibiotic ceftolozane, a term of the minimum efficacious concentration (MEC) is used for tazobactam, representing the minimum concentration that is needed to effectively inhibit resistance development of bacteria. Thus in simulation, within each time step $\Delta t$, if Cp*fu is higher than MIC (or MEC), the time step is accumulated into free time above MIC (or MEC) for each patient against microorganisms with this MIC (or MEC). Fu of 0.79 and 0.70 was used for the unbound fraction of ceftolozane and tazobactam, respectively.

Results and Discussion
Data Characteristics

Figure 16:
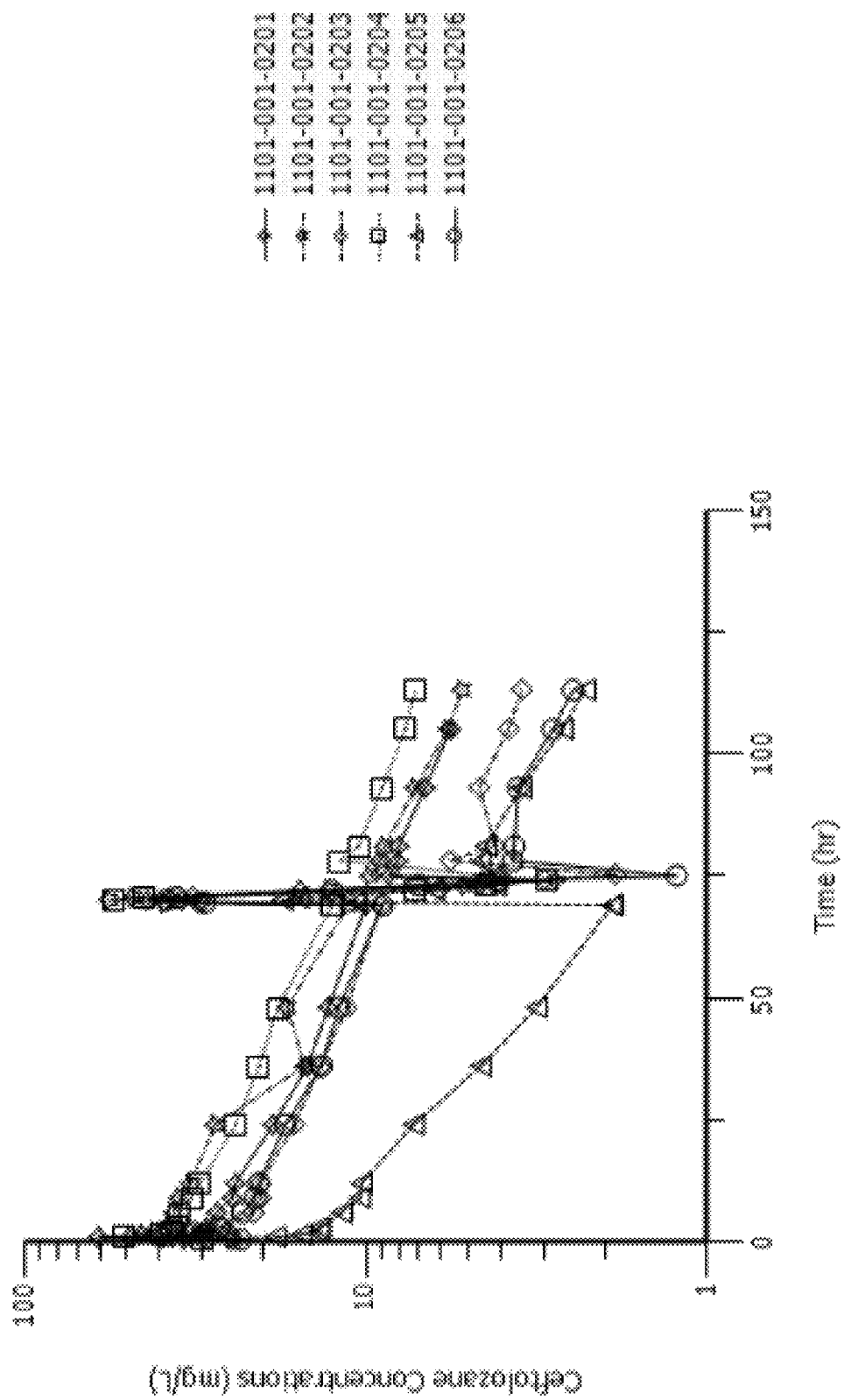
FIG. 16 shows the observed individual plasma concentration-time profiles of ceftolozane in six subjects with ESRD/hemodialysis.
Figure 17:
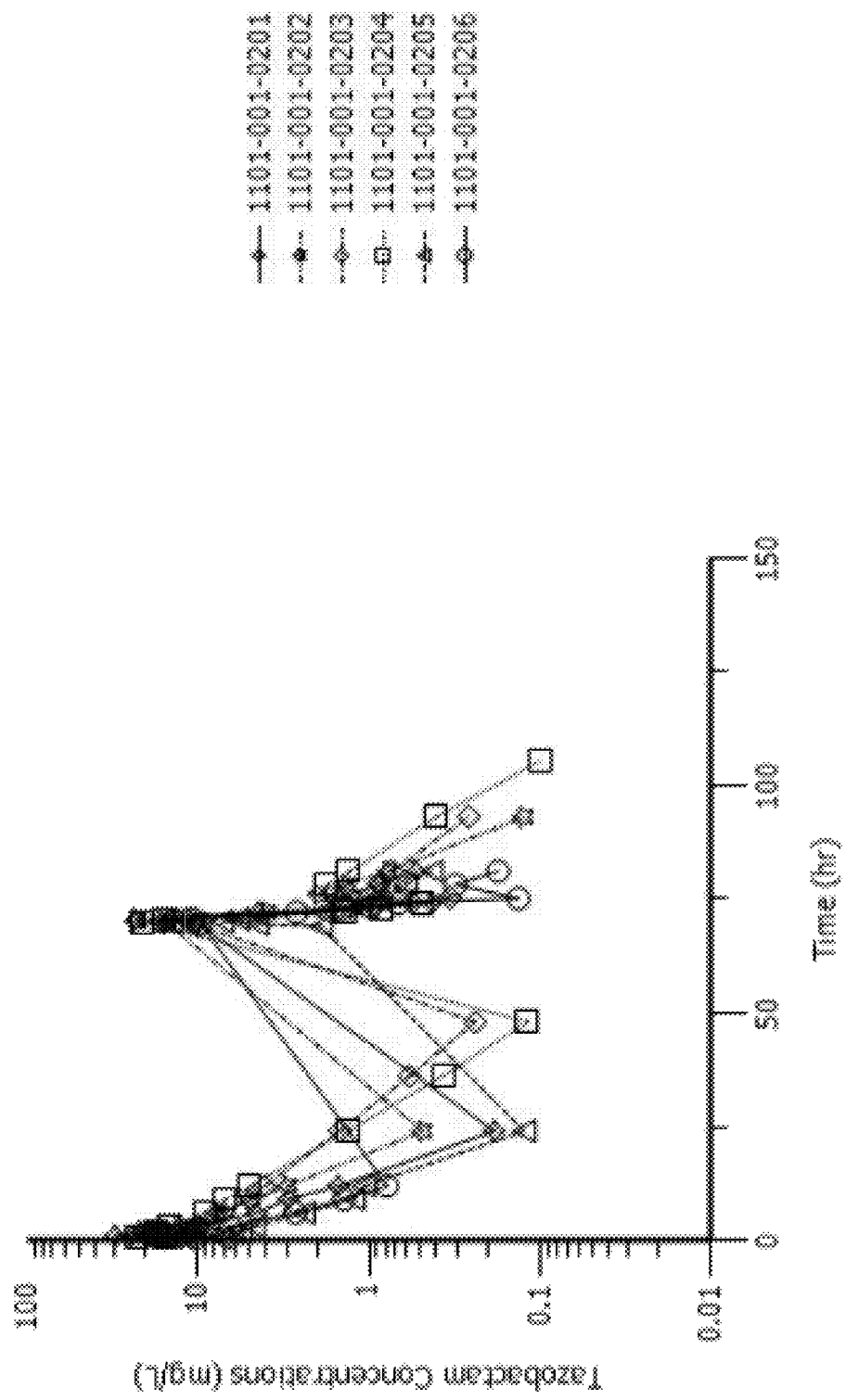
FIG. 17 shows the observed individual plasma concentration-time profiles of tazobactam in six subjects with ESRD/Hemodialysis.

FIG. 16 and FIG. 17 illustrate the plasma concentration-time profiles for ceftolozane and tazobactam, respectively, with or without hemodialysis for 6 subjects (designated 1101-001-201 to 1101-001-0206). Both ceftolozane and tazobactam concentrations post the end of infusion declined in a bi-exponential manner but only ceftolozane had a long half-life in these subjects with ESRD/hemodialysis as compared to those subjects with normal renal function. Both ceftolozane and tazobactam concentrations were rapidly reduced during hemodialysis, followed by a modest rebound post the end of hemodialysis likely because of the redistribution of the drug from peripheral compartment (tissue/organ) to the central compartment (plasma). There was a large overall variability in the concentration-time profiles across the six subjects as shown in FIG. 16 and FIG. 17.

Ceftolozane Population PK Model in Subjects with ESRD

The population PK model for ceftolozane was developed via a 2-step process. First, the ceftolozane plasma concentrations without hemodialysis (first dose) were modeled and best described with a 2-compartment disposition model (FIG. 15) plus a proportional residual error model. The between-subject variability was reliably estimable on all four PK parameters CL, Vc, CL2 and V2. When the ceftolozane plasma concentrations following the second dose with hemodialysis were included, the above model, with the addition of a dichotomous covariate and a between-subject variability for the effect of hemodialysis, was the best to fit the combined data.

The final model was:

$$CL = 0.340 \ast \exp\{[4.09 + N(0, 0.696^2)] \ast HD + N(0, 0.522^2)\} \quad (8)$$

$$Vc = 6 \ast \exp\{[1.54 + N(0, 0.400^2)] \ast HD\} \quad (9)$$

$$CL2 = 19.2 \ast \exp\{N(0, 0.359^2)\} \quad (10)$$

$$V2 = 11.8 \ast \exp\{N(0, 0.484^2)\} \quad (11)$$

$$Cp\_obs = Cp\_ipred \ast [1 + N(0, 0.139^2)] \quad (12)$$

Where CL and Vc are the clearance and volume of distribution for the central compartment; CL2 is inter-compartmental clearance and V2 is volume of distribution for the peripheral compartment; HD stands for hemodialysis (=1 during hemodialysis and =0 otherwise); Cp_obs and Cp_ipred represent the observed and model-predicted individual concentrations, respectively; and $N(0, s^2)$ stands for a normal distribution centering at 0 with a standard error of s (variance of $s^2$). Exp( ) represents an exponential function on the natural base. The detailed parameter estimates and their standard errors are listed in Table 19.

TABLE 19

Parameter Estimates of the Population PK Model for Ceftolozane

| Parameters | Mean Estimate | RSE % | 95% CI | BSV % (RSE %) |
|---|---|---|---|---|
| Vc, volume of distribution for central compartment | 6 FIXED | NA | NA | not estimable |
| V2, Volume of distribution for peripheral compartment | 11.8 | 20.2 | (7.1, 16.5) | 48.4 (29.9) |
| CL, terminal clearance | 0.340 | 21.5 | (0.2, 0.5) | 52.2 (29.2) |
| CL2, inter-compartmental clearance | 19.2 | 19.1 | (12, 26.4) | 35.9 (41.9) |

TABLE 19-continued

Parameter Estimates of the Population PK Model for Ceftolozane

| Parameters | Mean Estimate | RSE % | 95% CI | BSV % (RSE %) |
|---|---|---|---|---|
| Log-scale coefficient of hemodialysis on Vc | 1.54 | 11.8 | (1.2, 1.9) | 40.0 (34.7) |
| Log-scale coefficient of hemodialysis on CL | 4.09 | 7.1 | (3.5, 4.7) | 69.6 (29.8) |
| Residual variability (%) | 13.9 | 6.5 | | NA |

Note:
RSE stands for relative standard error over mean;
CI stands for confidence interval of the mean estimate;
BSV stands for between-subject-variability in percentage;
NA stands for not applicable.

Figure 18:
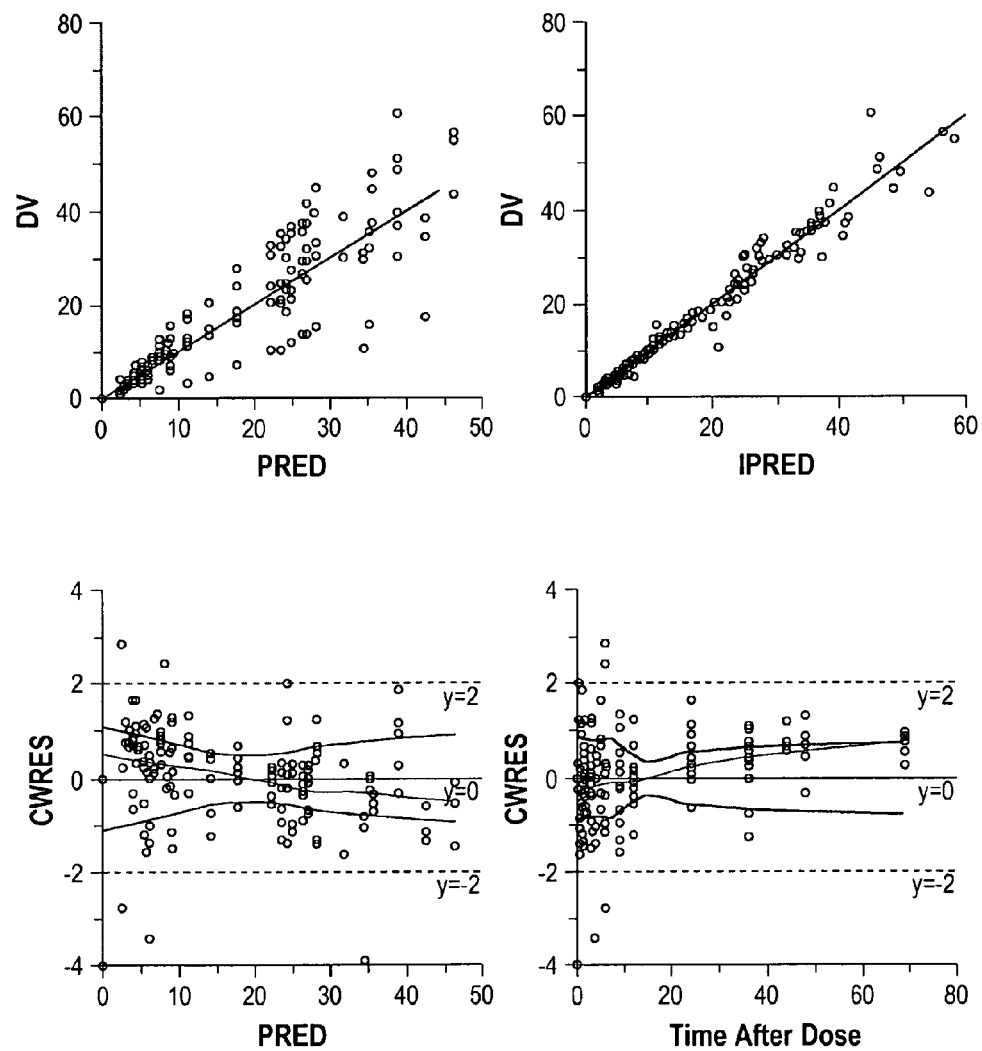
FIG. 18 shows the goodness-of-fit of the population PK model for ceftolozane. Note: DV stands for measured concentrations; PRED stands for model-predicted population concentrations; IPRED stands for model-predicted individual concentrations; CWRES stands for conditional weighted residuals.
Figure 19:
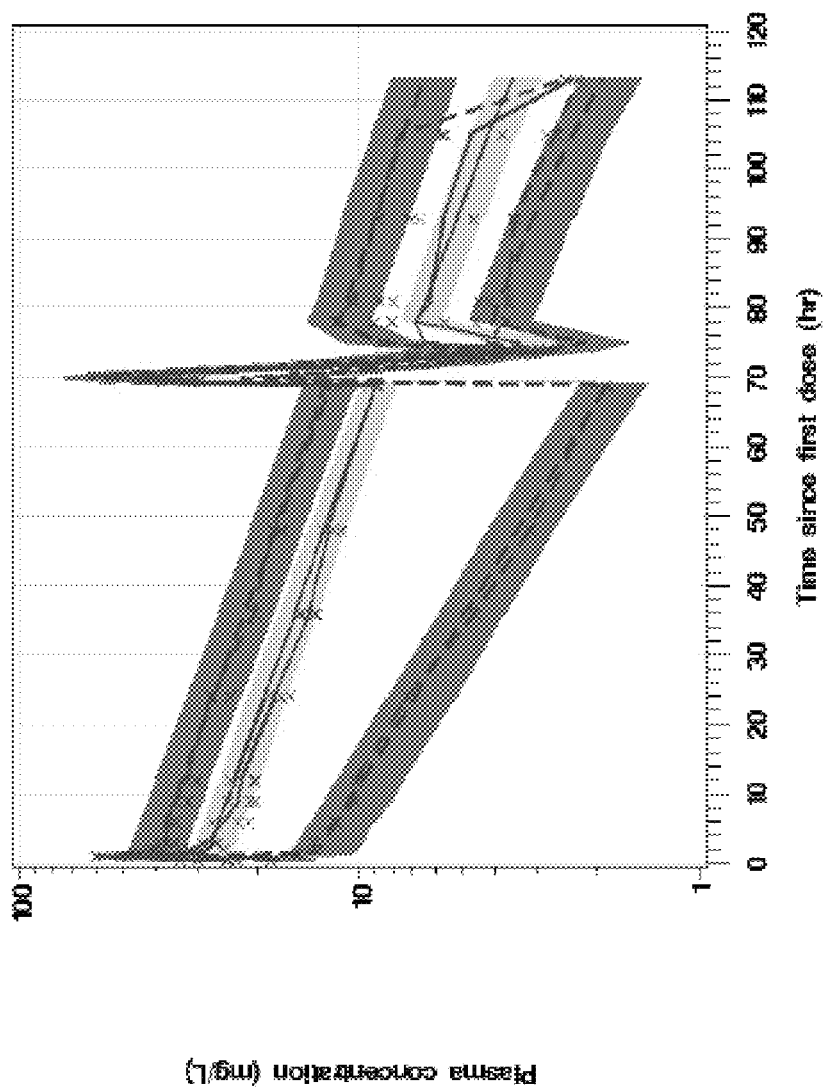
FIG. 19 shows the Visual Predictive Check (VPC) of the population PK model for ceftolozane. Note: gray, yellow and gray bands represent the model-predicted 5th-95th confidence interval of the model-predicted (green) and observed (red) $5^{th}$ (dashed line), 50th (solid line) and 95th (dashed line) percentile, respectively.
Figure 20:
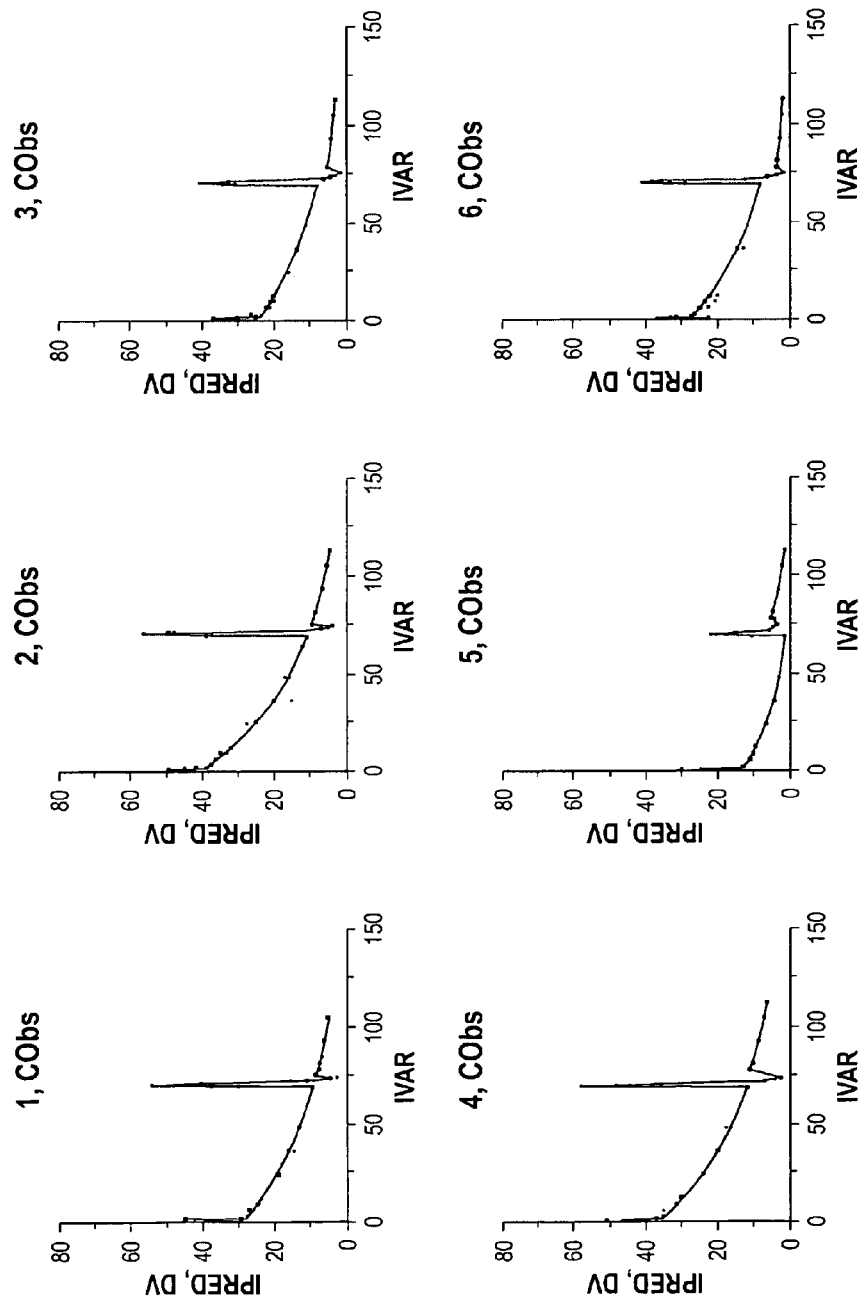
FIG. 20 shows the individual fitting of the ceftolozane PK model. Note: symbols stand for measured concentrations; lines stand for model-predicted concentrations; IVAR stand for time since first dose; IPRED and DV stand for model-predicted and measured individual concentrations, respectively; i, Cobs stand for the $i^{th}$ individual patient number.

When the ceftolozane concentrations with and without hemodialysis were all combined together, the volume of distribution for the central compartment (Vc) was not reliably estimable and was therefore fixed at the value of 6, which was the estimate of the model when only the concentrations following the first dose (without hemodialysis) were included. Otherwise, the model was stable, all converged to the same set of the final estimates with different sets of initial estimates, and the parameter estimates were all reliable and interpretable. The overall fitting was reasonably good, as illustrated by the goodness-of-fit plots in FIG. 18, the visual predictive check (VPC) in FIG. 19, and the individual fitting plots in FIG. 20. As described by the model, the terminal clearance is about 0.34 L/hr, with an apparent terminal half-life of about 40 hours in subjects with ESRD as compared to about 2 hours in subjects with normal renal function. Hemodialysis removes ceftolozane at a clearance of about 20 L/hr. In addition, hemodialysis also increased the apparent volume of distribution for the central compartment from about 6 L to about 28 L. The relatively large inter-compartment clearance of about 19 L/hr suggests an almost instant equilibrium of ceftolozane concentration between the peripheral compartment and the central compartment.

Tazobactam Population PK Model in Subjects with ESRD

Similar to ceftolozane, tazobactam plasma concentrations without hemodialysis (first dose) were first modeled and well described with a 2-compartment disposition model (FIG. 15) plus a proportional residual error model. The between-subject variability was reliably estimable on all four PK parameters CL, Vc, CL2 and V2. When the tazobactam plasma concentrations following the second dose were included, the model with hemodialysis evaluated as a dichotomous covariate with a between-subject variability was the best to fit all the combined data. The final model was:

$$CL = 3.07 * \exp\{[1.89 + N(0, 0.293^2)] * HD + N(0, 1.42^2)\} \quad (13)$$

$$Vc = 11.0 * \exp\{0.434 * HD + N(0, 3.89^2)\} \quad (14)$$

$$CL2 = 3.81 \quad (15)$$

$$V2 = 6.55 * \exp\{N(0, 0.243^2)\} \quad (16)$$

$$Cp\_obs = Cp\_ipred * [1 + N(0, 0.208^2)] \quad (17)$$

Where CL and Vc are the clearance and volume of distribution for the central compartment; CL2 is inter-compartmental clearance and V2 is volume of distribution for the peripheral compartment; HD stands for hemodialysis (=1 during hemodialysis and =0 otherwise); Cp_obs and Cp_ipred represent the observed and model-predicted individual concentrations, respectively; N(0, s2) stands for a normal distribution centering at 0 with a standard error of s (variance of s2). Exp( ) stands for an exponential function on the natural base.

Figure 21:
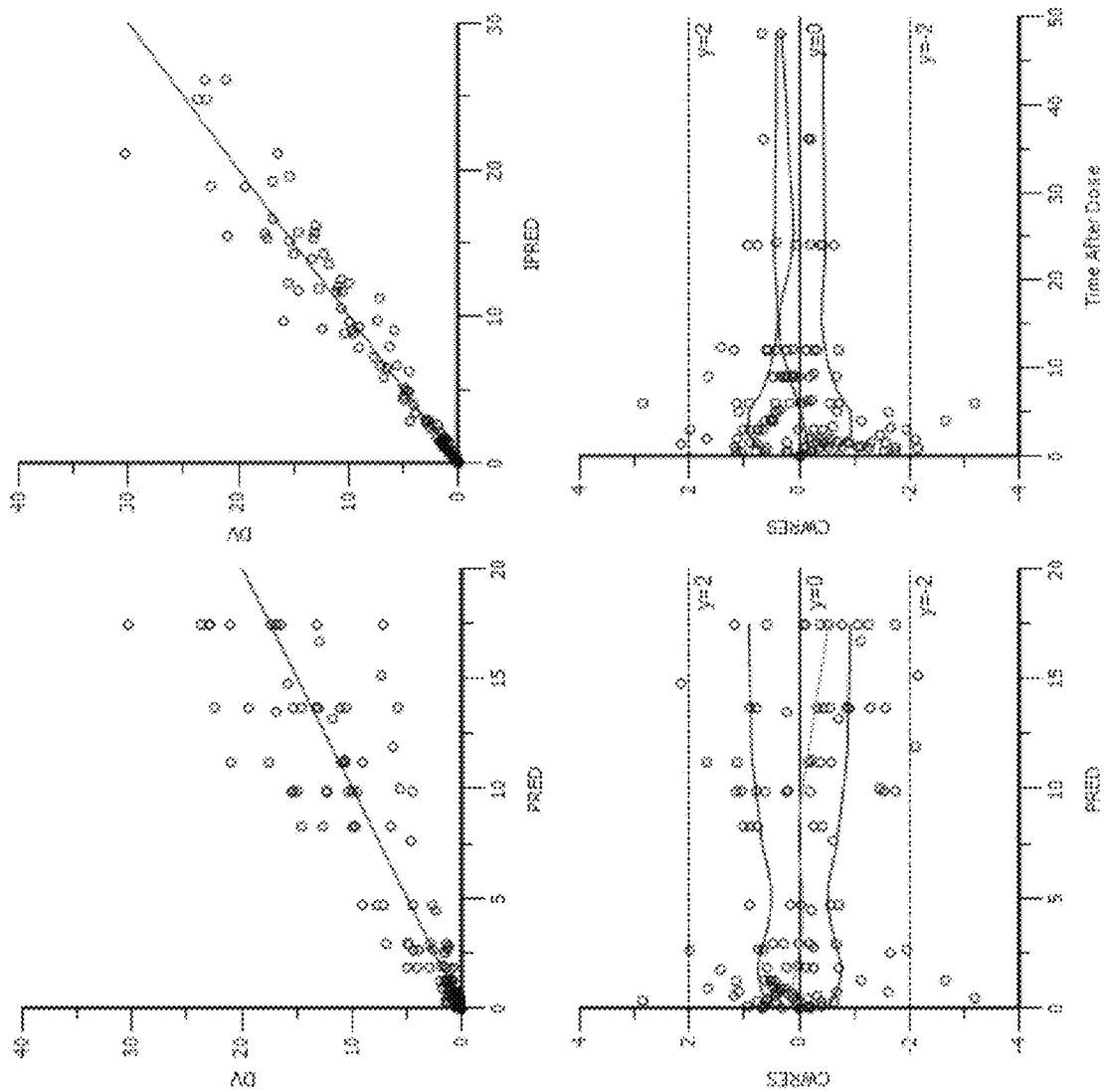
FIG. 21 shows the goodness-of-fit of the population PK model for tazobactam.
Figure 22:
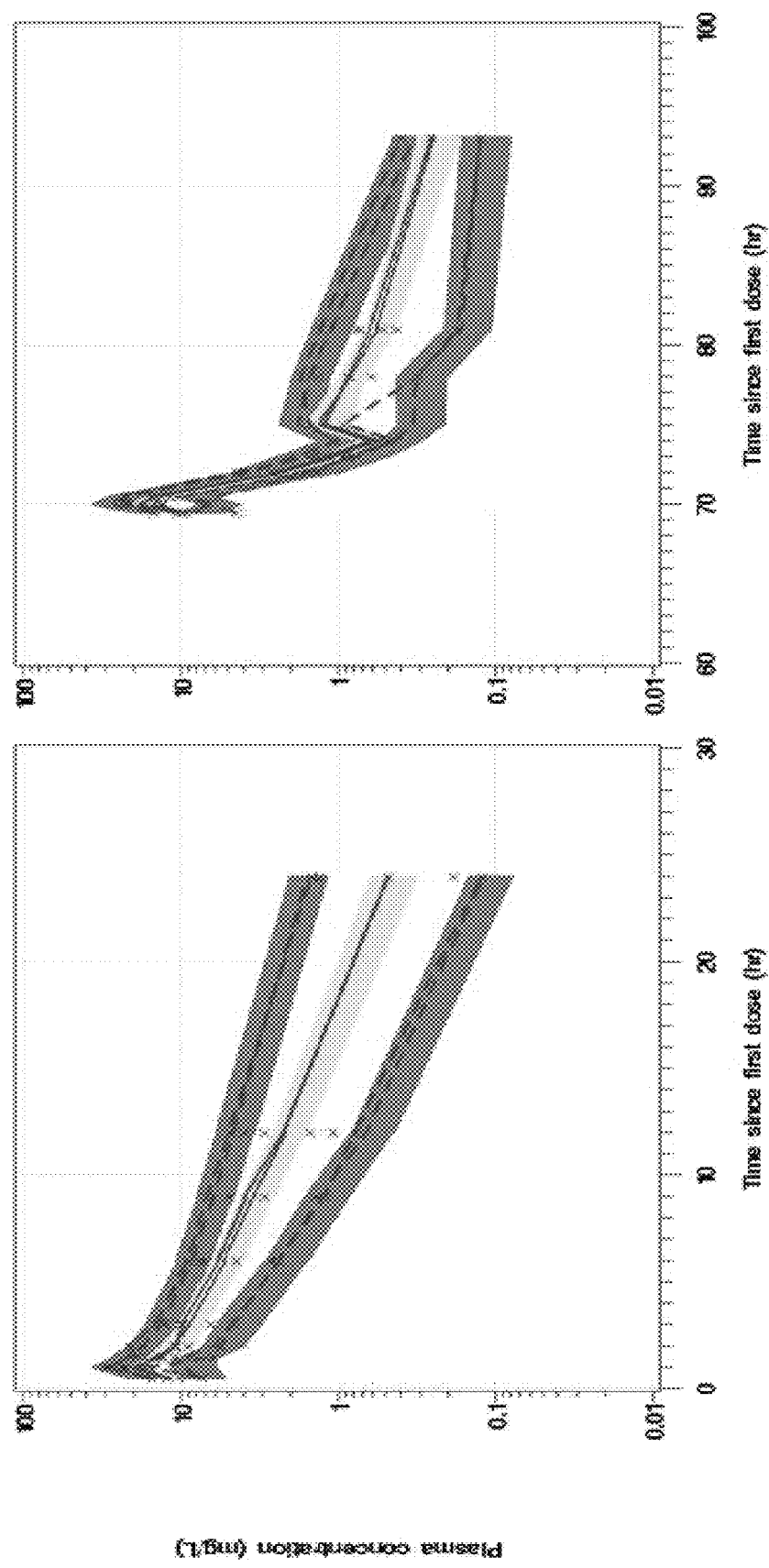
FIG. 22 shows the Visual Predictive Check (VPC) of the population PK model for tazobactam.
Figure 23:
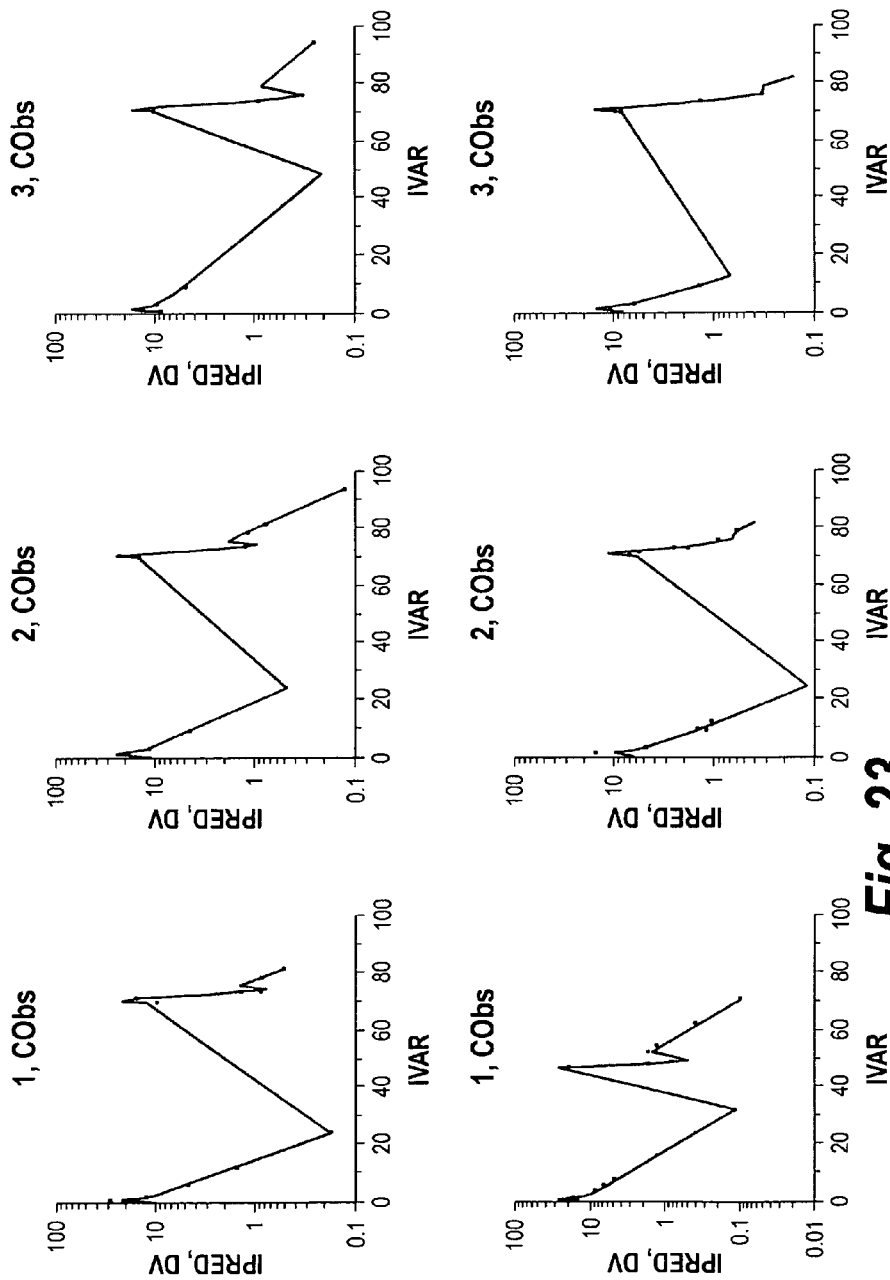
FIG. 23 shows the individual fitting of the ceftolozane PK model.

The detailed parameter estimates and their standard errors are listed in Table 20. The parameters were reliably estimated, with SEM values less than 50%. Additional testing with different sets of initial estimates confirmed that the model was stable—all converged to the same set of final parameter estimates. The overall quality of fitting was good as illustrated by the goodness-of-fit plots in FIG. 21 and the VPC plot in FIG. 22. The individual fitting was also reasonably good as illustrated in FIG. 23.

As described by the model, the terminal clearance was about 3 L/hr for tazobactam in subjects with ESRD, much larger than ceftolozane due to its metabolic elimination path. The apparent half-life was about 4 hours in subjects with ESRD as compared to about 1 hour in subjects with normal renal function. Hemodialysis increased the terminal clearance of tazobactam from about 3 L/hr to about 20 L/hr and the apparent volume of distribution for the central compartment from about 11 L to about 16 L. The estimated BSV was very large in both clearance and volume of distribution, partially reflecting the observed variability in this type of subjects with ESRD and the fact of the small number of subjects.

TABLE 20

Parameter Estimates of the Population PK Model for Tazobactam

| Parameters | Mean Estimate | RSE % | 95% CI | BSV % (RSE %) |
|---|---|---|---|---|
| Vc, volume of distribution for central compartment | 11.0 | 16.4 | (7.4, 14.5) | 398 (34.3) |
| V2, Volume of distribution for peripheral compartment | 6.55 | 16.0 | (4.5, 8.6) | 24.3 (39.8) |
| CL, terminal clearance | 3.07 | 19.0 | (1.9, 4.2) | 142 (29.3) |
| CL2, inter-compartmental clearance | 3.81 | 23.1 | (2.1, 5.5) | not estimable |
| Log-scale coefficient of hemodialysis on Vc | 0.434 | 47.7 | (0, 0.8) | not estimable |

TABLE 20-continued

Parameter Estimates of the Population PK Model for Tazobactam

| Parameters | Mean Estimate | RSE % | 95% CI | BSV % (RSE %) |
|---|---|---|---|---|
| Log-scale coefficient of hemodialysis on CL | 1.89 | 11.7 | (1.5, 2.3) | 29 (31.4) |
| Residual variability (%) | 20.8 | 7.7 | | not applicable |

Note:
RSE stands for relative standard error over mean;
CI stands for confidence interval of the mean estimate;
BSV stands for between-subject-variability in percentage.

Monte Carlo Simulations

Based on the above population PK model for ceftolozane and tazobactam, a Monte Carlo simulation of 5000 subjects with end stage renal disease was performed for each of the following scenarios:

| Scenario | Loading Dose (TOL/TAZ in mg/mg) | Maintenance Dose (TOL/TAZ in mg/mg) | Regimen |
|---|---|---|---|
| 1 | 500/250 | 300/150 | 1-hr infusion, every 24 hours |
| 2 | — | 300/150 | 1-hr infusion, every 24 hours |
| 3 | 600/300 | 300/150 | 1-hr infusion, every 24 hours |
| 4 | — | 100/50 | 1-hr infusion, every 8 hours |
| 5 | — | 300/150 | 4-hr infusion, every 24 hours |
| 6 | 400/200 | 100/50 | 1-hr infusion, every 8 hours |
| 7 | 500/250 | 100/50 | 1-hr infusion, every 8 hours |

The simulated treatment duration was set for 14 days. A pre-dose 4-hour hemodialysis session was assumed on Monday, Wednesday and Friday (or the last 4 hours of the previous dosing day). Considering that only 6 subjects were used to estimate BSV values, which might not be representative, a typical 50% BSV (i.e., a variance of 0.25) in log-scale was actually set in simulations for all PK parameters except hemodialysis. For sensitivity analysis and risk assessment, three additional situations were also simulated for each of the above scenarios:

a) The BSV values as the model estimated;
b) the BSV was inflated to 63% (or 0.40 for variance) in log-scale for the parameters with lower model-estimated BSV, except for hemodialysis which was considered to be machine related;
c) the BSV was inflated to 63% (or 0.40 for variance) in log-scale if the model-estimate was lower and deflated to 63% if the model-estimate was higher, except for hemodialysis which was considered to be machine related.

The simulated results indicated that hemodialysis reduced the residual accumulation, if any, from the previous dosing regimens to a minimal level. In addition, for ceftolozane alone, of which the terminal half-life was significantly extended in subjects with ESRD as compared to the subjects with normal renal function, all scenarios above were similar and covered the same level of MIC of 8 μg/mL with PTA>90%. The changes in BSV values as described above did not change this conclusion although some specific numbers might slightly change depending on the specific situations. Obviously, the 1-hr once daily infusion is practically the simplest and preferred dosing regimen for ceftolozane alone.

However, the extension of the terminal half-life of tazobactam in subjects with ESRD was not significant enough to optimally justify a once-daily dosing regimen if its efficacy is primarily driven by AUC and/or MEC, rather than Cmax.

In this case, a more frequent dosing regimen is preferred. The simulated results suggested that at the same total daily dose, a Q8h dosing regimen may potentially move the coverage of MEC (analogy to MIC) up for 2 dilutions as compared to the Q24h dosing regimen and a change in BSV may impact the coverage.

Therefore, with the considerations of maximizing ceftolozane efficacy but limiting its daily AUC to be around/within 1100 μg·hr/mL that has previously been shown to be safe and tolerable in humans (note, the maximum tolerable dose—MTD—has never been reached), maximizing tazobactam efficacy in terms of MEC coverage, maximizing the drug exposure on the first day to maximally and rapidly kill bacterial and avoid/inhibit resistance development, and the fixed ceftolozane/tazobactam (TOL/TAZ) dose ratio of 2, an optimal dosing regimen for clinical use in subjects with ESRD/hemodialysis was suggested: a loading dose of 500 mg ceftolozane/250 mg Tazobactam, followed by maintenance doses of 100 mg ceftolozane/50 mg Tazobactam, all for 1-hr infusion, three times a day.

With this dosing regimen, the potential coverage of 8 mg/L MIC for ceftolozane and about 1 mg/L MEC for tazobactam, will result in a 90% target attainment on the first day. The simulated results of this dosing regimen are described below.

Figure 24:
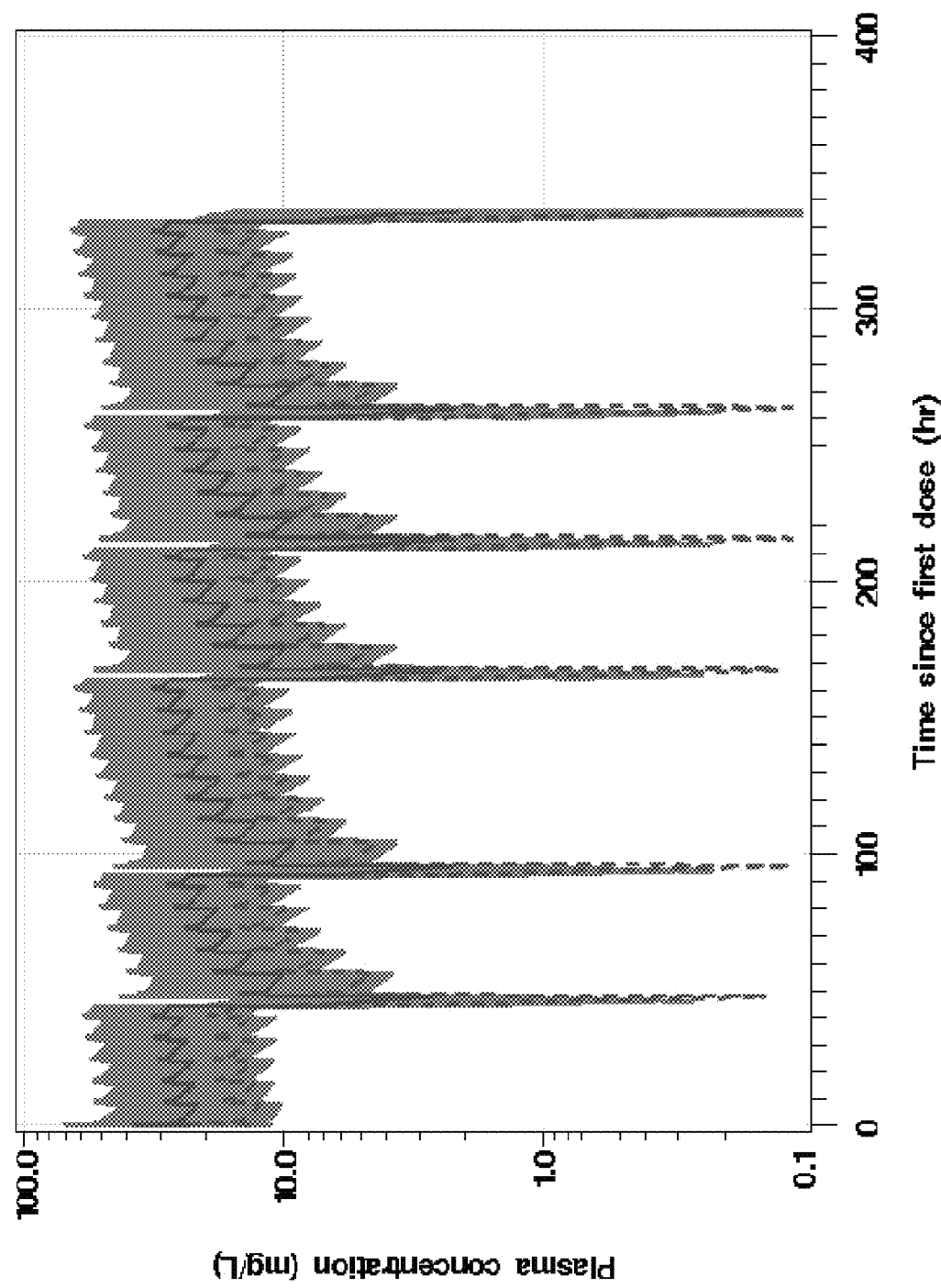
FIG. 24 shows the simulated total ceftolozane plasma concentration-time profiles in subjects with ESRD for the dosing regimen: a Loading Dose of 500 mg ceftolozane/250 mg tazobactam+maintenance doses of 100 mg ceftolozane/50 mg tazobactam, all for 1-hr infusion every 8 hours. (BSV=50% in log scale and N=5000).
Figure 25:
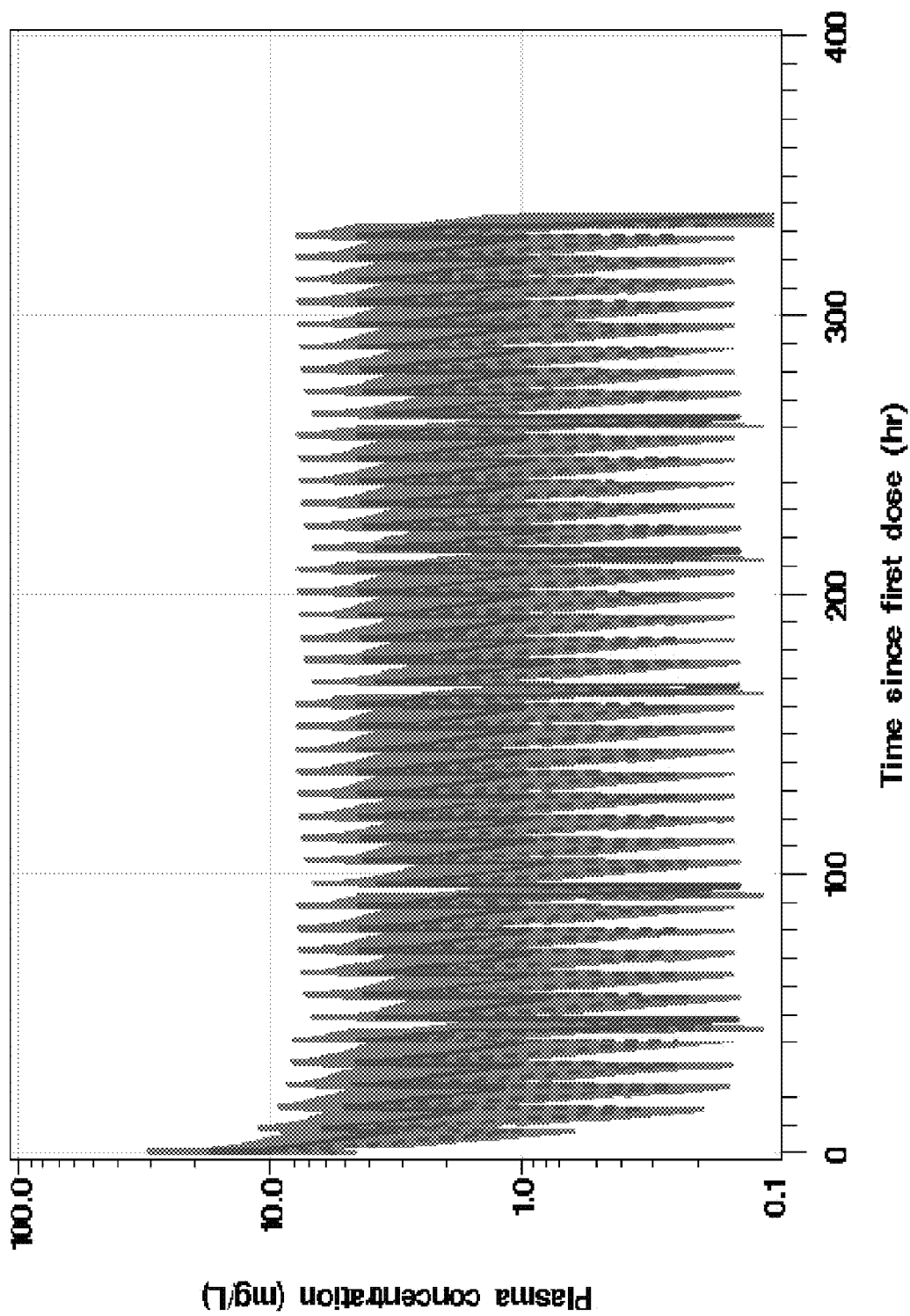
FIG. 25 shows the simulated total tazobactam plasma concentration-time profiles in subjects with ESRD for the dosing regimen: a loading dose of 500 mg ceftolozane/250 mg tazobactam+maintenance doses of 100 mg ceftolozane/50 mg tazobactam, all for 1-hr infusion every 8 hours. (BSV=50% in log scale and N=5000).
Figure 26:
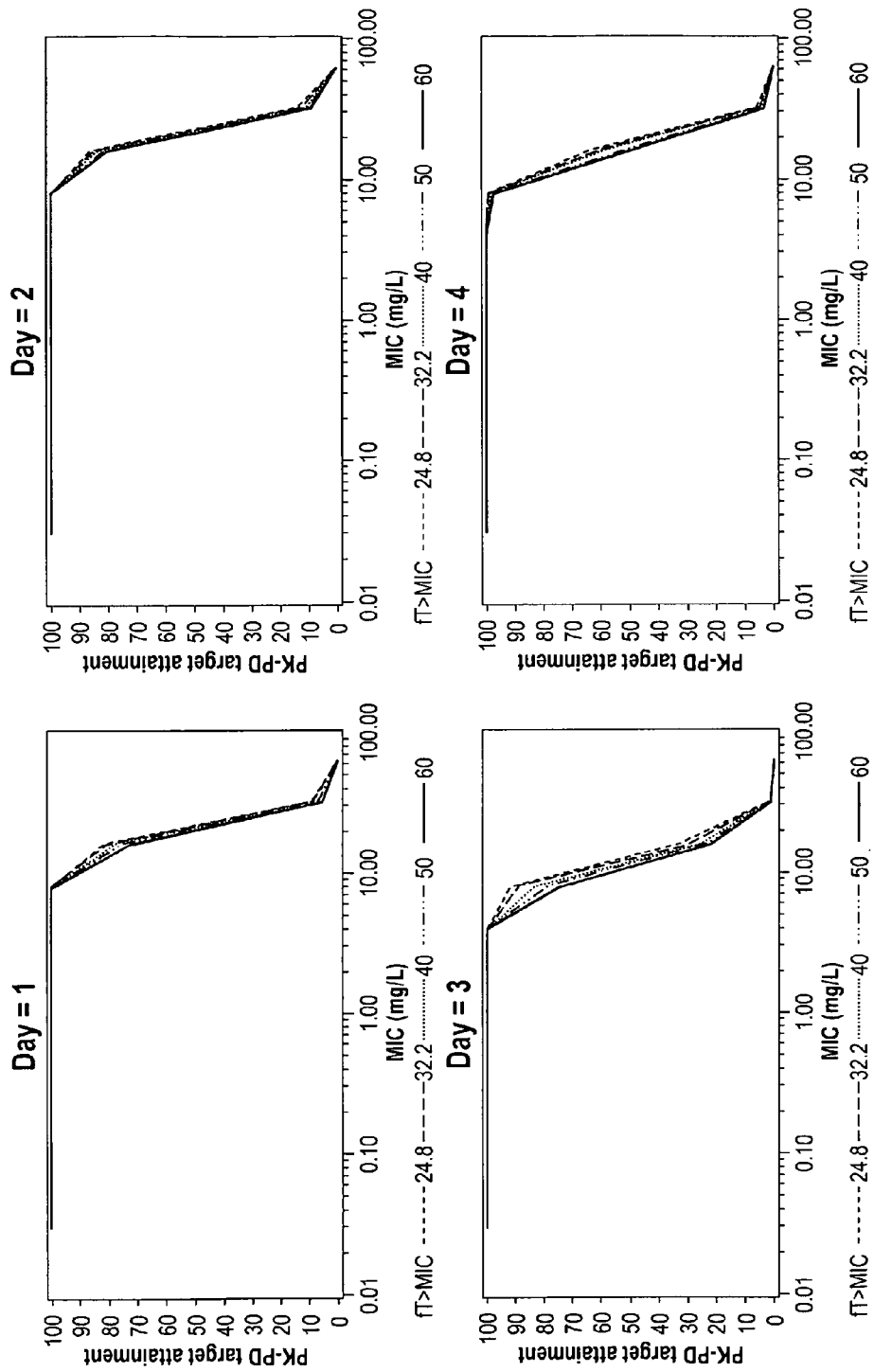
FIG. 26 shows the simulated daily free-ceftolozane % T>MIC targets by MIC values in patients with ESRD for the dosing regimen: a loading dose of 500 mg ceftolozane/250 mg tazobactam+maintenance doses of 100 mg ceftolozane/50 mg tazobactam, all for 1-hr infusion every 8 hours. (BSV=50% in log scale and n=5000). Note: fT>MIC stands for free-drug percentage of time above MIC.
Figure 27:
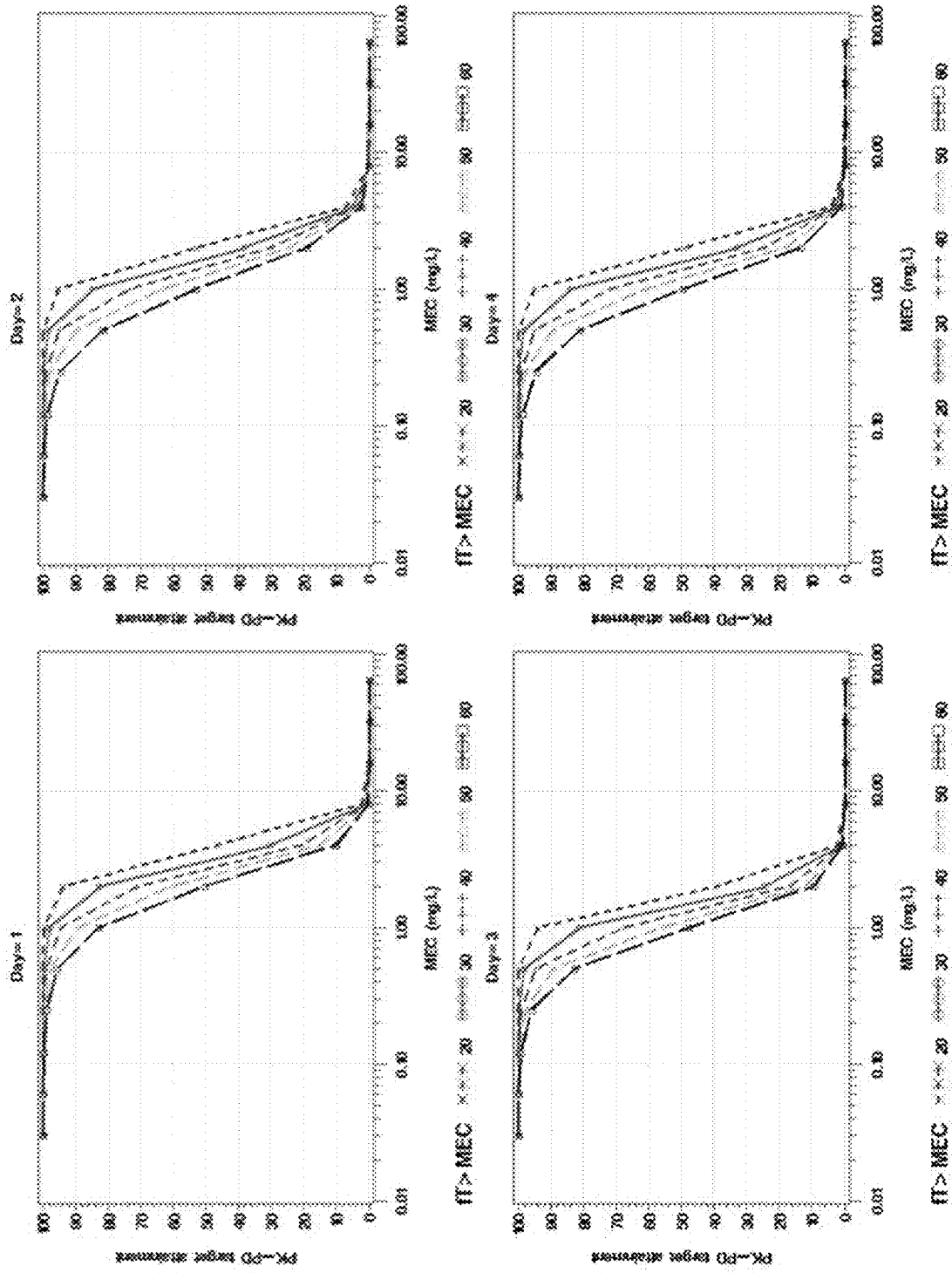
FIG. 27 shows the simulated daily free-tazobactam % T>MEC targets by MEC values in patients with ESRD for the dosing regimen: a loading dose of 500 mg ceftolozane/250 mg tazobactam+maintenance doses of 100 mg ceftolozane/50 mg tazobactam, all for 1-hr infusion every 8 hours. (BSV=50% in log scale and N=5000). Note: ft>MEC represents free-drug % time above a minimum efficacious concentration.
Figure 28:
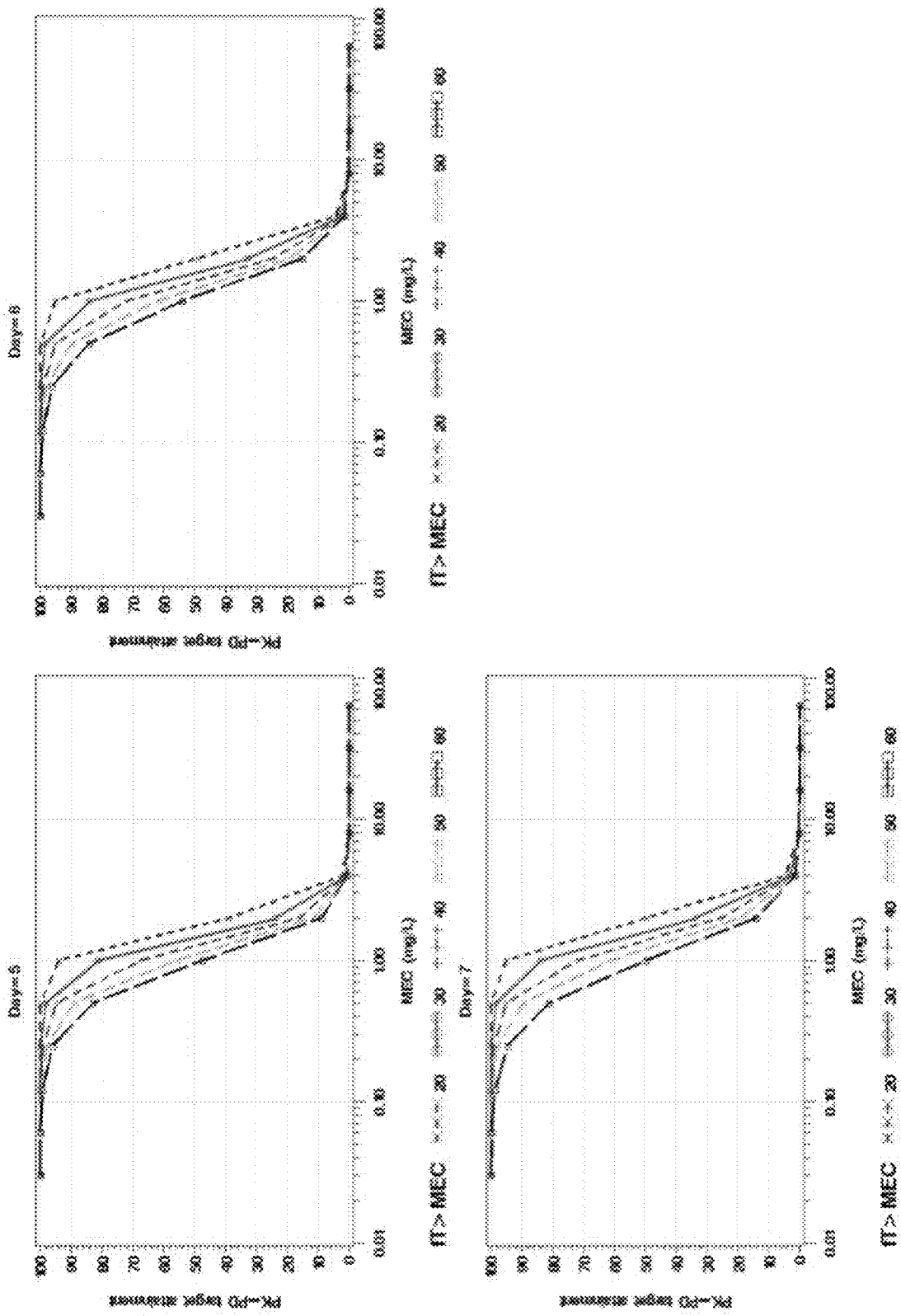
FIG. 28 shows a dosing table for commonly prescribed antibiotics.

For efficacy, FIG. 24 and FIG. 25 illustrate the simulated total plasma concentration-time profiles for ceftolozane and tazobactam, respectively. The simulated ceftolozane and tazobactam plasma concentrations in subjects with ESRD were comparable to those at the recommended clinical dose in patients with normal renal function or other renal impairments FIG. 26 and FIG. 27 illustrate their daily target attainment. The achievable target attainments for the above recommended dosing regimen in subjects with ESRD were also comparable to those at the clinical dose in patients with normal renal function. The detailed daily targeted attainment values for ceftolozane and tazobactam are also tabulated in FIGS. 28 and 29, respectively. For safety, Table 21 and Table 22 list the simulated daily Cmax and AUC for ceftolozane and tazobactam, respectively. The 95th percentile of the simulated daily AUC of ceftolozane for the recommended dosing regimen was within the limit of 1100 μg*hr/mL. Even in the worst case of the above tested BSV situations, the maximum 95th percentile of the simulated daily AUC values were within 15% of 1100 μg*hr/mL and were limited on days 6-7 and 13-14 only—The 95th percentile of the simulated daily Cmax and AUC for tazobactam for the recommended dosing regimen were about 30 μg/mL and 194

μg*hr/mL, respectively, on day 1 and down to about 8 μg/mL and 100 μg*hr/mL thereafter. These values were in the safe range typically observed in clinical use (Halstenson C E, Wong M O, Johnson C A, Zimmerman S W, Onorato J J, Keane W F, et al. Pharmacokinetics of tazobactam M1 metabolite after administration of Cmax 1994; 34(12): 1208-17). In the worst case where the model-estimated abnormally large BSV values were used for CL and Vc while the BSV values for CL2 and V2 were inflated to 50% in log-scale, the potential 95th percentile of daily Cmax and AUC for tazobactam were 74 μg/mL and 418 μg*hr/mL, respectively, on day 1 and down to about 23 μg/mL and 340 μg*hr/mL thereafter. These values were in the range that other recommended clinical dosing regimens would have reached for tazobactam e.g. in Zosyn® (see Halstenson (1994) cited above).

In summary, the dosing regimen of 500/250 (ceftolozane/Tazobactam in mg/mg) loading dose, followed by a 100/50 maintenance dose for 1-hr infusion, three times a day is optimal and therefore recommended for clinical use.

TABLE 21

Simulated Median (5th, 95th percentile) Daily Cmax and AUC of Total Ceftolozane for the Dosing Regimen: a Loading Dose of 500 mg ceftolozane/250 mg Tazobactam + Maintenance Doses of 100 mg ceftolozane/50 mg Tazobactam, All for 1-hr Infusion Every 8 Hours. (log-scale 50% BSV, N = 5000)

| Day | Daily Cmax Median ($5^{th}$, $95^{th}$ percentile) | Daily AUC Median ($5^{th}$, $95^{th}$ percentile) |
|---|---|---|
| 1 | 38.4 (23.2, 63) | 610 (362.1, 1008) |
| 2 | 33.5 (20.6, 54) | 583.3 (334.1, 969) |
| 3 | 21.7 (12.6, 52) | 339.4 (180.4, 754) |
| 4 | 28 (16.7, 47) | 455.3 (253, 841) |
| 5 | 21 (12.3, 54) | 323.9 (173.5, 784) |
| 6 | 27.7 (16.5, 48) | 520.7 (290.4, 981) |
| 7 | 32.1 (18.5, 55) | 550.1 (294.8, 1010) |
| 8 | 21.5 (12.5, 62) | 337.2 (177.8, 871) |
| 9 | 28.2 (16.7, 50) | 456.2 (251.2, 916) |
| 10 | 21 (123, 59) | 324 (173.7, 834) |
| 11 | 27.8 (16.5, 50) | 448.2 (248.3, 892) |
| 12 | 20.9 (12.3, 58) | 322.2 (173, 827) |
| 13 | 27.7 (16.5, 49) | 520.6 (290.3, 1016) |
| 14 | 32.1 (18.5, 56) | 550.3 (294.8, 1045) |

TABLE 22

Simulated Median (5th, 95th percentile) Daily Cmax and AUC of Total Tazobactam for the Dosing Regimen: a Loading Dose of 500 mg ceftolozane/250 mg Tazobactam + Maintenance Doses of 100 mg ceftolozane/50 mg Tazobactam, All for 1-hr Infusion Every 8 Hours. (log-scale 50% BSV, N = 5000)

| Day | Daily Cmax Median ($5^{th}$, $95^{th}$ percentile) | Daily AUC Median ($5^{th}$, $95^{th}$ percentile) |
|---|---|---|
| 1 | 17.1 (8.6, 30) | 103.1 (48.7, 194) |
| 2 | 4.7 (2.6, 8) | 47 (20.5, 115) |
| 3 | 4.3 (2.5, 8) | 44.2 (20.7, 93) |
| 4 | 4.4 (2.5, 8) | 45 (20.3, 100) |
| 5 | 4.3 (2.5, 7) | 44.1 (20.7, 91) |
| 6 | 4.4 (2.5, 8) | 48.5 (21.5, 108) |
| 7 | 4.4 (2.5, 8) | 45.2 (20.3, 103) |
| 8 | 4.3 (2.5, 7) | 44.1 (20.7, 92) |
| 9 | 4.4 (2.5, 8) | 44.9 (20.3, 99) |
| 10 | 4.3 (2.5, 7) | 44.1 (20.7, 91) |
| 11 | 4.4 (2.5, 8) | 44.9 (20.3, 99) |
| 12 | 4.3 (2.5, 7) | 44.1 (20.7, 91) |
| 13 | 4.4 (2.5, 8) | 48.5 (21.5, 108) |
| 14 | 4.4 (2.5, 8) | 45.2 (20.3, 103) |

Conclusions

Ceftolozane/tazobactam plasma concentrations following ceftolozane/Tazobactam infusion in subjects with ESRD and hemodialysis can be best described with a 2-compartment disposition model plus a covariate effect of hemodialysis on both clearance and volume of distribution of the central compartment.

The residual accumulation, if any, from previous doses prior to each hemodialysis is manageable.

Ceftolozane terminal half-life is significantly extended such that a daily or Q 8 hr dosing regimen in subjects with ESRD are equally adequate in achieving PTA of >90% for an MIC of up to 8 μg/mL.

Tazobactam terminal half-life is modestly extended but not long enough to justify changing the Q 8 hr dosing regimen to a daily dosing regimen, With consideration of maximizing tazobactam efficacy and limiting ceftolozane daily AUC around or within 1100 μg/mL, an optimal dosing regimen is recommended for clinical use in subjects with ESRD: a single loading dose of 500 mg ceftolozane/250 mg tazobactam via 1-hr IV infusion, followed in 8 hr by a maintenance dose of 100 mg ceftolozane/50 mg tazobactam via 1-hr infusion every 8 hours. A maintenance dose is suggested to be given at the earliest possible time post the end of each hemodialysis session.

Example 9B: Ceftolozane/Tazobactam Dose Optimization in Patients with End-Stage Renal Disease Requiring Hemodialysis Using Population Pharmacokinetics and Monte Carlo Simulations Abstract Background Ceftolozane/tazobactam (TOL/TAZ) is being developed for treatment of complicated urinary tract infection and intra-abdominal infection. The objective of this study was to characterize the population pharmacokinetics (pPK) of TOL/TAZ, determine the probability of target attainment (PTA) of various dosing regimens, and identify the optimal clinical dose in subjects with end-stage renal disease (ESRD) on hemodialysis (HD).

Methods:

Ceftolozane/tazobactam plasma concentrations from 6 subjects with ESRD following a single dose without HD and a second dose with HD were used to develop a pPK model (Phoenix NLME). Monte Carlo stimulation was performed (SAS 9.3) to predict individual Ceftolozane/tazobactam concentrations in 5000 subjects to assess the PTA for different dosing regimens and test a range of free-drug time above minimum inhibitory concentration (MIC) (fT>MIC) targets, including 24.8% for bacteriostasis, 32.2% for bactericidal activity (1–log kill) as well as higher thresholds for bactericidal effects up to 60% fT>MIC. Monte Carlo simulations used ceftolozane MIC determined with 4 mg/L tazobactam.

Figure 30A:
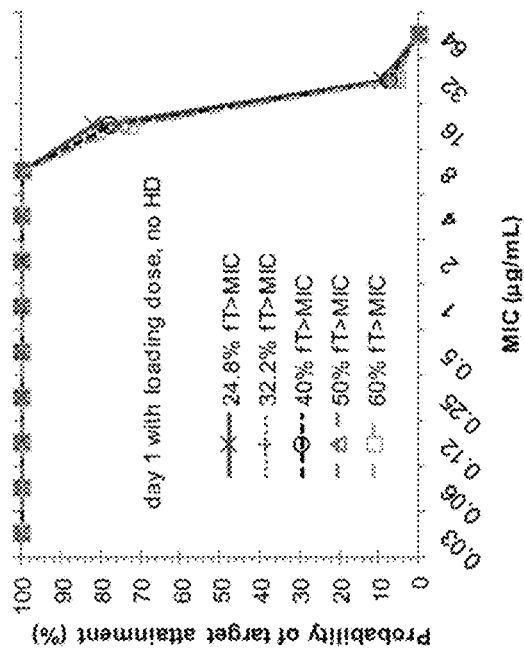
FIGS. 30A and 30B show that the 500 mg/250 mg C/T single loading dose followed by 100 mg/50 mg every 8 hours maintenance dose via 1-hr infusion achieved a >99% PTA against all targets up to an MIC of 8 µg/mL on day 1 (FIG. 30A) and >97% PTA on all other days without HD. The PTA for bactericidal activity on post HD days was 89% (FIG. 30B).
Figure 30B:
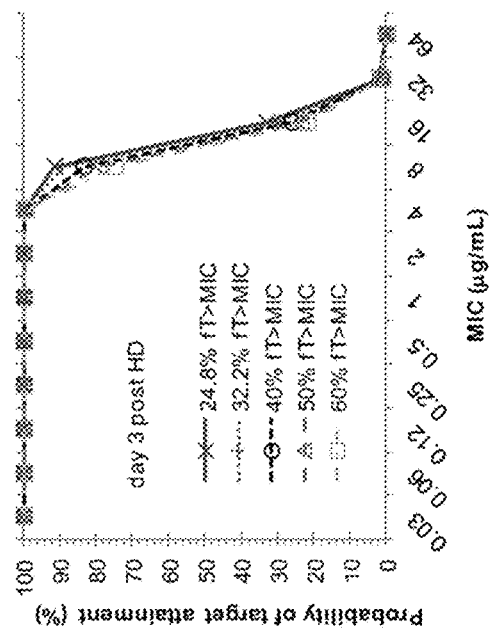

Results:

A 2-compartment disposition model plus a covariate effect of HD best described the observed Ceftolozane/tazobactam plasma concentrations. The key parameter estimates for the final pPK model were: for ceftolozane, terminal clearance (CL) and central volume of distribution ($V_c$) of 0.34 L/h and 6 L, respectively, with HD increasing CL and $V_c$ by 60- and 4.7-fold, respectively; for tazobactam, CL and Vc of 3.07 L/h and 11 L, respectively, with HD increasing CL and $V_c$ by 6.6- and 1.5-fold, respectively. PTA exceeded 90% for an MIC up to 8 mg/L for ceftolozane across all the tested scenarios. Out of all the tested scenarios, the 500 mg/250 mg Ceftolozane/tazobactam single loading dose followed by 100 mg/50 mg every 8 hours maintenance dose via 1-hour infusion achieved a >99% PTA against all targets up to an MIC of 8 mg/L on day 1 (FIG. 30A) and >97% PTA on all other days without HD. The PTA for bactericidal activity on post HD days was 89% (FIG. 30B).

Conclusion

Plasma concentrations following Ceftolozane/tazobactam infusion in subjects with ESRD on HD can be best described with a 2-compartment disposition model plus a covariate effect of HD on both CL and $V_c$. In patients with ESRD on HD, a single loading dose of 500 mg/250 mg Ceftolozane/tazobactam infused over 1 hour, followed by 100 mg/50 mg every 8 hours infused over 1 hour, preferably at the earliest possible time following completion of each dialysis, achieved a high PTA and was identified as the optimal dose.

Introduction

Ceftolozane/tazobactam is a novel antibacterial with activity against *Pseudomonas aeruginosa*, including drug-resistant strains, and other common Gram-negative pathogens, including most extended-spectrum β-lactamase (ESBL)-producing Enterobacteriaceae. Ceftolozane/tazobactam is primarily eliminated by the kidneys, and its clearance would be expected to be reduced in those with impaired renal function. Data from the 2 renal impairment studies suggested that a decrease in the dose, frequency of administration, or both is necessary for those patients with moderate or severe renal impairment or end-stage renal disease (ESRD).

The objectives of this analysis were to characterize the pharmacokinetic (PK) parameters for ceftolozane and tazobactam in subjects with ESRD on hemodialysis, determine the probability of target attainment (PTA) of various dosing regimens and identify the optimal dose in patients with ESRD on hemodialysis.

Methods

Phoenix™ NLME version 1.2 (Pharsight Corporation, Certara USA, Inc.; St. Louis, Mo.) with the extended least squares first order conditional estimation was used for population PK modeling and SAS® 9.3 (SAS Institute Inc., Cary, N.C.) was used for the Monte Carlo simulation.

Population PK Modeling

Ceftolozane/tazobactam plasma concentrations collected from 6 patients with ESRD following a single dose without hemodialysis and a second dose with hemodialysis were used to develop a population PK model (Phoenix™ Non Linear Mixed Effects [NLME]).

A 2-compartment disposition model was used to fit the ceftolozane or tazobactam plasma concentration-time data without hemodialysis and to test the between-subject variability and residual variability. Ceftolozane or tazobactam plasma concentration-time data with hemodialysis were then included and hemodialysis was tested as a covariate effect on both clearance and volume of distribution for the central compartment.

The final model was selected based on the stability of the model, reliability and interpretability of the parameter estimates, and the goodness-of-fit plots.

Monte Carlo Simulations

The population PK model was used to simulate the ceftolozane/tazobactam concentration-time profiles in patients with ESRD/hemodialysis.

Monte Carlo simulations were performed to predict individual ceftolozane/tazobactam concentrations in 5000 patients to assess the PTA for each of 7 different dosing regimens (Table 23), narrowed down stepwise from many potential scenarios that might meet the criteria on free-drug time above minimum inhibitory concentration (fT>MIC), maximum concentration ($C_{max}$), and daily area under the curve (AUC) that assure both efficacy and safety. A range of fT>MIC targets were tested, including 24.8% for bacteriostasis, 32.2% for bactericidal activity (1–log kill), which were the targets for ceftolozane/tazobactam efficacy as previously determined in a murine-thigh infection model,[4] as well as higher thresholds for bactericidal effects up to 60% fT>MIC.

TABLE 23

Monte Carlo Simulation Dosing Regimens

| Scenario | Loading Dose (TOL/TAZ in mg/mg) | Maintenance Dose (TOL/TAZ in mg/mg) | Regimen | MIC < 8 with > 25% fT > MIC at 90% PTA for TOL? | MEC < 0.5 > with > 40% fT > MEC at 90% PTA for TAZ? | Daily AUC > 1100 mg/L · hr for TOL? | Outcome[a] |
|---|---|---|---|---|---|---|---|
| 1 | — | 100/50 | 1-h infusion, every 8 h | Y | N | Y | F |
| 2 | — | 300/150 | 1-h infusion, every 24 h | Y | Y | Y | F |
| 3 | — | 300/150 | 4-h infusion, every 24 h | Y | Y | N | F |
| 4 | 400/200 | 100/50 | 1-h infusion, every 8 h | Y | N | Y | F |
| 5 | 600/300 | 300/150 | 1-h infusion, every 24 h | N | Y | Y | F |
| 6 | 500/250 | 300/150 | 1-h infusion, every 24 h | N | Y | Y | F |
| 7 | 500/250 | 100/50 | 1-h infusion, every 8 h | N | N | N | S |

[a]A simulation is a success if the response to the 3 questions is no.
AUC = area under the curve;
F = failure;
fT > MIC = free-drug time above minimum inhibitory concentration;
MEC = minimum efficacious concentration;
N = No;
PTA = probability of target attainment;
S = success;
TAZ = tazobactam;
TOL = ceftolozane;
Y = Yes.

Monte Carlo simulations used ceftolozane MIC determined with 4 mg/L tazobactam.

The final dosing regimen was selected based on:
Maximizing ceftolozane efficacy but limiting its daily AUC to be within 1100 mg·h/L, which has previously been shown to be safe and tolerable in humans (note, the maximum tolerable dose has never been reached),
Maximizing tazobactam efficacy in terms of minimum efficacious concentration (MEC) coverage,
Maximizing the drug exposure on the first day to maximally and rapidly kill bacterial and avoid/inhibit resistance development, and
A fixed ceftolozane/tazobactam dose ratio of 2:1.

Results
Data Characteristics 156 plasma samples were collected from 6 patients with ESRD on hemodialysis; 66.7% were female, 83.3% were black or African American, the mean (SD) age was 50.0 (11.1) and the mean (SD) body mass index was 28.9 kg/m2 (7.7).

Both ceftolozane and tazobactam concentrations declined in a bi-exponential manner (FIG. 29) following the end of infusion, but only ceftolozane had a long half-life compared with patients with normal renal function.3

Figure 29:
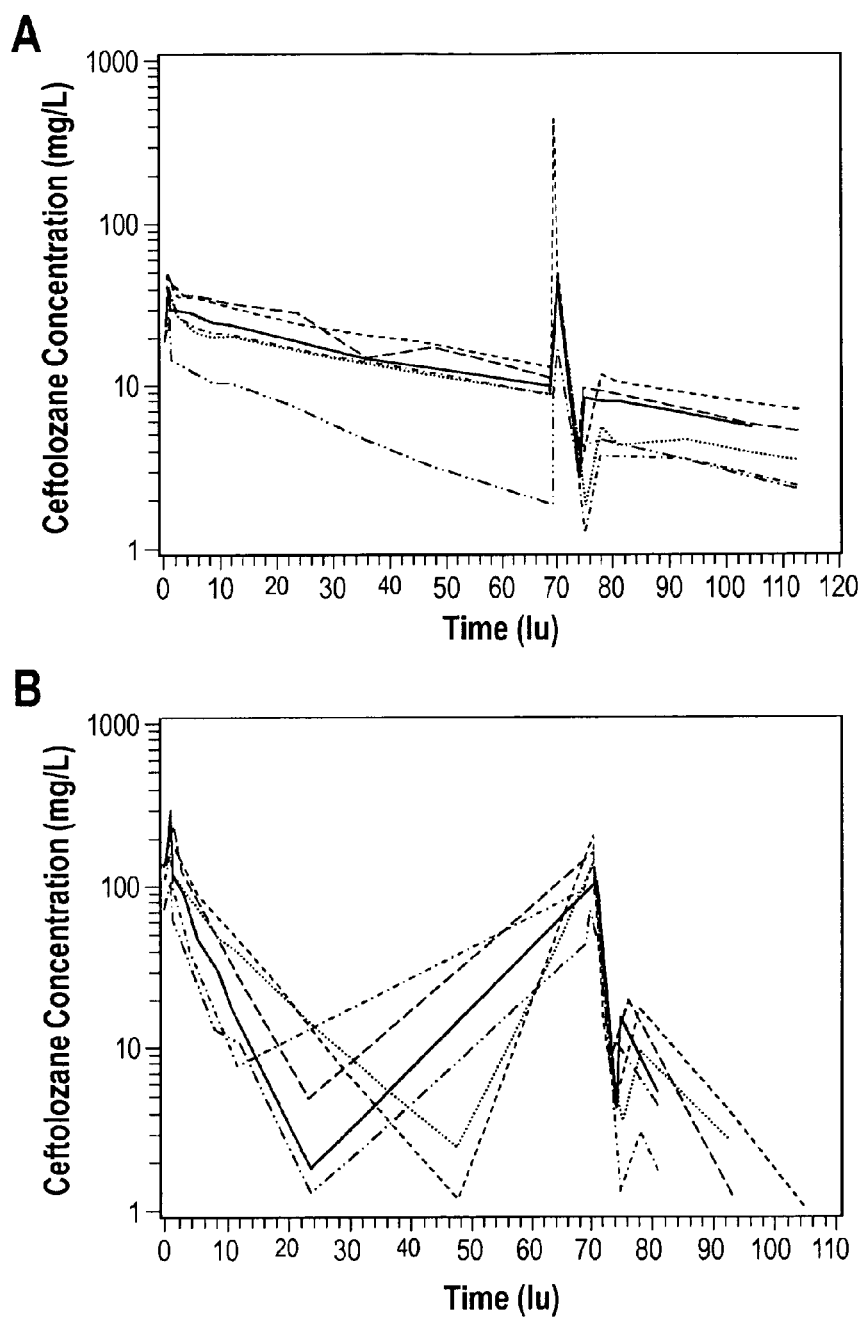
FIG. 29 shows the observed individual plasma concentration-time profiles of ceftolozane (A) and tazobactam (B) in 6 patients with ESRD/hemodialysis.

Both ceftolozane and tazobactam concentrations were rapidly reduced during hemodialysis, followed by a modest rebound following the end of hemodialysis likely due to the redistribution of the drug from the peripheral compartment to the central compartment (FIG. 29). There was a large variability in the concentration-time profiles across the 6 patients.

Population PK Model in Patients with ESRD

A 2-compartment disposition model plus a covariate effect of hemodialysis best described the observed ceftolozane/tazobactam plasma concentrations.

The key parameter estimates for the final population PK model are set forth in Table 24.

4.7-fold, respectively. For tazobactam, CL and $V_c$ were 3.07 L/h and 11 L, respectively, with HD increasing CL and $V_c$ by 6.6- and 1.5-fold, respectively.

Monte Carlo Simulations

PTA exceeded 90% for an MIC up to 8 mg/L for ceftolozane across all the tested scenarios (data not shown).

Out of all the tested scenarios, the optimal dosing regimen of ceftolozane/tazobactam for clinical use in patients with ESRD/hemodialysis is a single loading dose of 500 mg/250 mg ceftolozane/tazobactam, followed by a maintenance dose of 100 mg/50 mg every 8 hours, all as 1-hour infusions (Table 23).

Figure 7A:
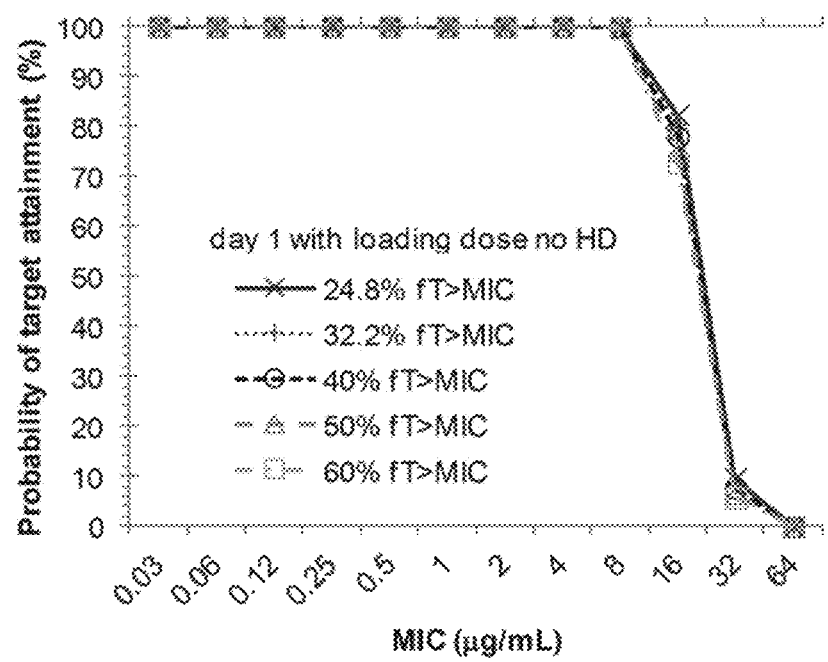
FIGS. 7A and 7B show two graphs of the simulated probability of target attainment on day 1 (top, with loading dose) and day 3 (bottom, post HD) in patients with ESRD on HD (n=5000) after administration of a loading dose of 500 mg/250 mg C/T, followed in 8 hr by 100 mg/50 mg C/T, 1-hr IV infusion every 8 hours.
Figure 7B:
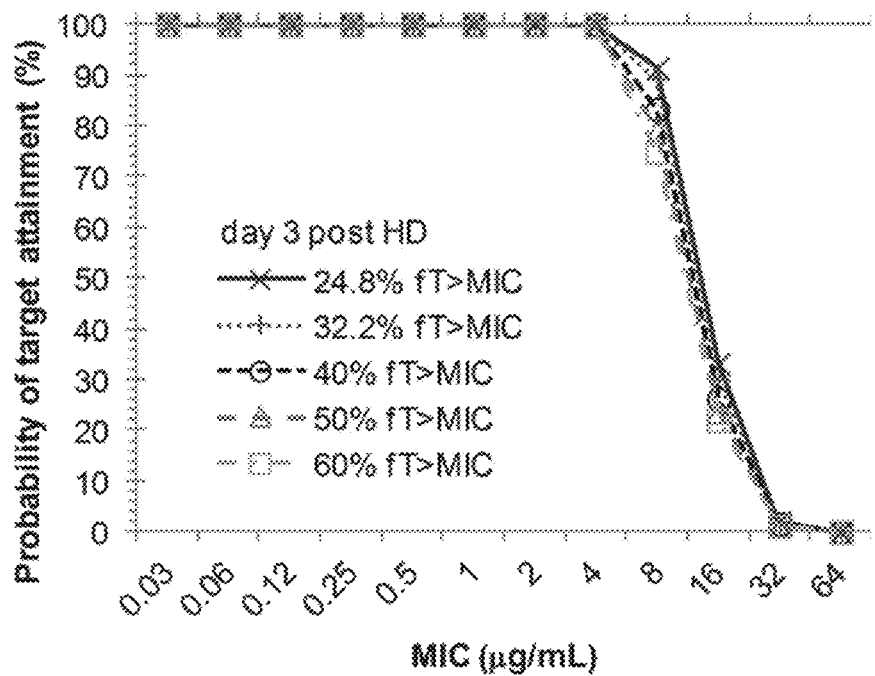

For ceftolozane, this dosing regimen achieved a >99% PTA against all targets up to an MIC of 8 mg/L on day 1 (FIG. 7A) and >97% PTA on all other days without HD. The PTA for bactericidal activity on post HD days was 89% (FIG. 7B).

Figure 30C:
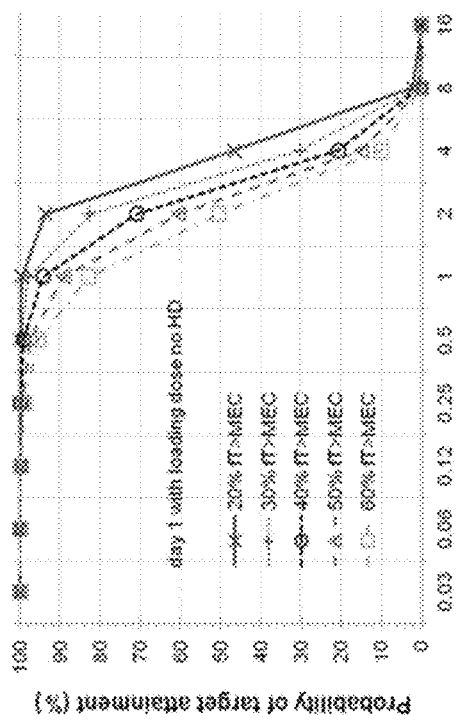
FIGS. 30C and 30D show the simulated daily free-tazobactam % T>MEC targets by MIC values in patients with ESRD on day 1, no hemodialysis (FIG. 30C) and day 3, post hemodialysis (FIG. 30D). Dosing regimen: a loading dose of 500 mg/250 mg ceftolozane/tazobactam+maintenance doses of 100 mg/50 mg, all for 1-h infusion every 8 hours (BSV=50% in log scale and N=5000).
Figure 30D:
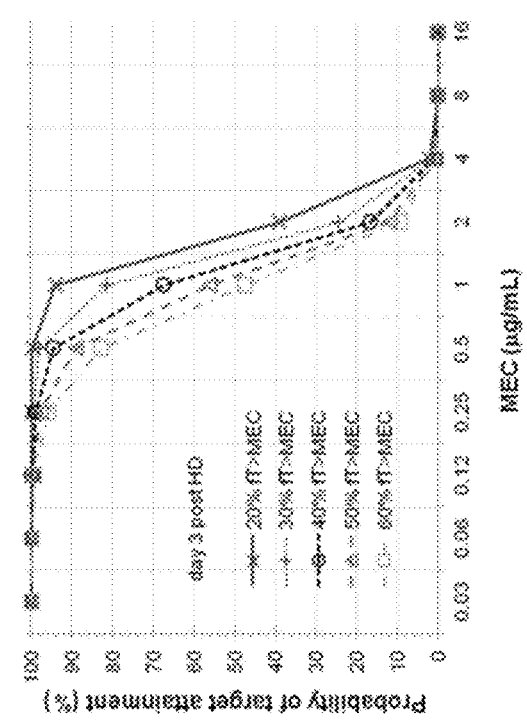

For tazobactam, the optimal dosing regimen achieved a >94% PTA against a target up to an MEC of 1 mg/L on day 1 (FIG. 30C) and >94% PTA on day 3 (FIG. 30D) and all other days without hemodialysis.

Table 25 lists the simulated daily $C_{max}$ and AUC for ceftolozane and tazobactam.

The 95th percentile of the simulated daily AUC of ceftolozane for the recommended dosing regimen was within the limit of 1100 mg·h/L, the highest daily exposure achieved in clinical trials that was proved to be safe. For comparison, the median daily steady-state AUC values in subjects with normal renal is observed to be 690 mg·h/L (Wooley M, et al. *Antimicrob Agents Chemother.* 2014; 58: 2249-2255).

The 95th percentile of the simulated daily AUC for tazobactam for the recommended dosing regimen was approximately 194 mg·h/L, respectively on day 1 and down to approximately 100 mg·h/L thereafter. These values were

TABLE 24

Population PK Parameter Estimates for Ceftolozane and Tazobactam

| Parameters | Ceftolozane | | | | Tazobactam | | | |
|---|---|---|---|---|---|---|---|---|
| | Mean Estimate | RSE % | 95% CI | BSV % (RSE %) | Mean Estimate | RSE % | 95% CI | BSV % (RSE %) |
| $V_c$, volume of distribution for central compartment | 6 FIXED | NA | NA | not estimable | 11.0 | 16.4 | (7.4-14.5) | 398 (34.3) |
| $V_2$, Volume of distribution for peripheral compartment | 11.8 | 20.2 | (7.1-16.5) | 48.4 (29.9) | 6.55 | 16.0 | (4.5-8.6) | 24.3 (39.8) |
| CL, terminal clearance | 0.34 | 21.5 | (0.2-0.5) | 52.2 (29.2) | 3.1 | 19.0 | (1.9-4.2) | 142 (29.3) |
| $CL_2$, inter-compartmental clearance | 19.2 | 19.1 | (12-26.4) | 35.9 (41.9) | 3.8 | 23.1 | (2.1-5.5) | Not estimable |
| Log-scale coefficient of hemodialysis on $V_c$ | 1.5 | 11.8 | (1.2-1.9) | 40.0 (34.7) | 0.43 | 47.7 | (0-0.8) | Not estimable |
| Log-scale coefficient of hemodialysis on CL | 4.1 | 7.1 | (3.5-4.7) | 69.6 (29.8) | 1.9 | 11.7 | (1.5-2.3) | 29 (31.4) |
| Residual variability (%) | 13.9 | 6.5 | | NA | 20.8 | 7.7 | | NA |

BSV = between-subject variability in percentage;
CI = confidence interval of the mean estimate;
NA = not applicable;
RSE = relative standard error over mean.

For ceftolozane, terminal clearance (CL) and central volume of distribution ($V_c$) were 0.34 L/h and 6 L, respectively, with hemodialysis increasing CL and $V_c$ by 60- and in the safe range typically observed in clinical studies with the median steady-state AUC value in normal renal subjects estimated to be 89.4 mg·h/L, respectively.

TABLE 25

Simulated Median (5th, 95th percentile) Daily Cmax and AUC of Total Ceftolozane and Tazobactam

| Day | Ceftolozane | | Tazobactam | |
|---|---|---|---|---|
| | Daily $C_{max}$ Median (5th, 95th Percentile) | Daily AUC Median (5th, 95th Percentile) | Daily $C_{max}$ Median (5th, 95th Percentile) | Daily AUC Median (5th, 95th Percentile) |
| 1 | 38.4 (23.2, 63) | 610 (362.1, 1008) | 17.1 (8.6, 30) | 103.1 (48.7, 194) |
| 2 | 33.5 (20.6, 54) | 583.3 (334.1, 969) | 4.7 (2.6, 8) | 47 (20.5, 115) |
| 3 | 21.7 (12.6, 52) | 339.4 (180.4, 754) | 4.3 (2.5, 8) | 44.2 (20.7, 93) |
| 4 | 28 (16.7, 47) | 455.3 (253, 841) | 4.4 (2.5, 8) | 45 (20.3, 100) |
| 5 | 21 (12.3, 54) | 323.9 (173.5, 784) | 4.3 (2.5, 7) | 44.1 (20.7, 91) |
| 6 | 27.7 (16.5, 48) | 520.7 (290.4, 981) | 4.4 (2.5, 8) | 48.5 (21.5, 108) |
| 7 | 32.1 (18.5, 55) | 550.1 (294.8, 1010) | 4.4 (2.5, 8) | 45.2 (20.3, 103) |
| 8 | 21.5 (12.5, 62) | 337.2 (177.8, 871) | 4.3 (2.5, 7) | 44.1 (20.7, 92) |
| 9 | 28.2 (16.7, 50) | 456.2 (251.2, 916) | 4.4 (2.5, 8) | 44.9 (20.3, 99) |
| 10 | 21 (12.3, 59) | 324 (173.7, 834) | 4.3 (2.5, 7) | 44.1 (20.7, 91) |
| 11 | 27.8 (16.5, 50) | 448.2 (248.3, 892) | 4.4 (2.5, 8) | 44.9 (20.3, 99) |
| 12 | 20.9 (12.3, 58) | 322.2 (173, 827) | 4.3 (2.5, 7) | 44.1 (20.7, 91) |
| 13 | 27.7 (16.5, 49) | 520.6 (290.3, 1016) | 4.4 (2.5, 8) | 48.5 (21.5, 108) |
| 14 | 32.1 (18.5, 56) | 550.3 (294.8, 1045) | 4.4 (2.5, 8) | 45.2 (20.3, 103) |

Dosing regimen: a loading dose of 500 mg/250 mg ceftolozane/tazobactam + maintenance doses of 100 mg/50 mg, all for 1-h infusion every 8 hours (log-scale 50% BSV, N = 5000)
AUC = area under the curve;
$C_{max}$ = maximum concentration.

Conclusions

Plasma concentrations following ceftolozane/tazobactam infusion in patients with ESRD on hemodialysis can be best described with a 2-compartment disposition model plus a covariate effect of hemodialysis on both CL and $V_c$.

In patients with ESRD on hemodialysis, a single loading dose of 500 mg/250 mg ceftolozane/tazobactam infused over 1 hour, followed by 100 mg/50 mg every 8 hours infused over 1 hour, achieved a high PTA and was identified as the optimal dose.

Example 10 Pharmacodynamic Target Attainment Analyses Supporting the Selection of In Vitro Susceptibility Test Interpretive Criteria for Ceftolozane/Tazobactam (as CXA-201) Against *Pseudomonas aeruginosa*

Modeling is used to show that the dosages recommend for the different renal types is appropriate to hit the PK/PD targets of % T>MIC The human phase 1 and 2 PK data was used in a Monte Carlo model to predict the curves at the dosing regimens and the probability that the drug levels would be high enough at the corresponding MIC values.

Monte Carlo Simulation

Using SAS 9.2 [SAS 9.2 for Windows [computer program]. Cary, N.C.: SAS Institute Inc. 2010] Version Monte Carlo simulation was conducted to generate 5,000 patients, with 1,000 in each of five renal function categories. These categories (and corresponding creatinine clearance (CLcr) ranges) were as follows:
High normal renal function (150< to ≤200 mL/min);
Normal renal function (90< to ≤150 mL/min);
Mild renal impairment (50< to ≤90 mL/min);
Moderate renal impairment (29≤ to ≤50 mL/min); and
Severe renal impairment (15≤ to <29 mL/min).

Using the fixed and random effects parameter estimates and variance-covariance matrix from a previously-developed population PK model for ceftolozane, plasma concentration-time profiles for ceftolozane were generated for simulated patients in each renal function category following selected CXA-201 dosing regimens.

CXA-201 dosing regimens administered over 1 hr every 8 hrs. (q8h) by renal function category included 1000 mg and 2000 mg ceftolozane adjusted for renal function categories as follows:

1000 mg ceftolozane regimens:
1000/500 mg CXA-201 in patients with high normal and normal renal function and patients with mild renal impairment;
500/250 mg CXA-201 in patients with moderate renal impairment; and
250/125 mg CXA-201 in patients with severe renal impairment.

2000 mg ceftolozane regimens:
2000/1000 mg CXA-201 in patients with high normal and normal renal function and patients with mild renal impairment;
1000/500 mg CXA-201 in patients with moderate renal impairment; and
500/250 mg CXA-201 in patients with severe renal impairment.

As the activity of ceftolozane is not enhanced significantly by Tazobactam due to lack of inhibition of AmpC beta-lactamase [SAS 9.2 for Windows [computer program]. Cary, N.C.: SAS Institute Inc. 2010], only ceftolozane exposures were considered in these analyses.

PK-PK Target Attainment Analyses

Using non-clinical PK-PD targets, PK-PD TA by MIC was assessed for simulated patients in each renal function category in the context of MIC distributions for CXA-201 against *P. aeruginosa* based on surveillance data from the United States (US) and the European Union (EU).

Non-clinical PK-PD targets were based on the results from a neutropenic murine-thigh infection model in which *P. aeruginosa* was evaluated JMI Laboratories. Surveillance of ceftolozane/tazobactam antimicrobial activity when tested against Gram-negative organisms and streptococci isolated in the USA (2012). Final Report. February 2013; Craig W A, Andes D R. Antimicrob Agents Chemother. 2013; 57:1577-82]

The percentage of the dosing interval that concentrations are above the MIC (% T>MIC) was the PK-PD driver most associated with efficacy for ceftolozane.

For the PK-PD analyses carried out, free-drug (f) % T>MIC targets of 24.8 and 32.2, which were associated with net bacterial stasis and a 1–log$_{10}$ colony forming units (CFU) reduction from baseline, respectively, and f % T>MIC targets of 40, 50, and 60 were assessed.

The percentage of simulated patients that attained these targets during the dosing interval at steady-state for MIC values ranging from 0.03 to ≥32.2 mg/L was determined for each ceftolozane dosing regimen evaluated within each renal function category.

For patients severe renal impairment administered CXA-201 250/125 mg q8h a PK-PD MIC cut-off value of 8 mg/L was identified (which is similar to the cutoff predicted for the 1.5 g dose for normal renal function).

The PK-PD MIC cutoff values for CXA-201 1000 and 2000 mg q8h dosing regimens against *P. aeruginosa* by renal function category is shown in Table 26.

TABLE 26

PK-PD MIC Cutoff Values for CXA-201 Dosing Regimens Against *P. aeruginosa* by Renal Function Category

| Renal function category$^A$ | CXA-201 dosing regimen (mg)$^B$ | MIC (mg/L)$^C$ | % simulated patients achieving free-drug fT>MIC targets 24.8/≥32.2$^D$ |
|---|---|---|---|
| High normal | 1000/500 | 4 | 99.5/96.1 |
| | 2000/1000 | 8 | 99.5/96.1 |
| Normal | 1000/500 | 8 | 99.1/94.7 |
| | 2000/1000 | 16 | 99.1/94.7 |
| Mild | 1000/500 | 8 | 100/99.8 |
| | 2000/1000 | 16 | 100/99.8 |
| Moderate | 500/250 | 8 | 99.9/99.5 |
| | 1000/500 | 16 | 99.9/99.5 |
| Severe | 250/125 | 8 | 98.4/96.1 |
| | 500/250 | 16 | 98.4/96.1 |

$^A$Renal function categories were defined as follows: High normal function = CLcr (mL/min) <150-≤200; Normal renal function = CLcr (mL/min) <90-≤150; Mild renal impairment = CLcr (mL/min) <50-≤90; Moderate renal impairment = CLcr (mL/min) <29-≤50; Severe renal impairment = CLcr (mL/min) <15-≤29.
$^B$CXA-201 administration via 1 h intravenous infusion Q8 h.
$^C$Represents the highest MIC associated with ≥90% PK-PDTA.

Example 11: Impact of Renal Function on the Pharmacokinetics and Safety of Ceftolozane/Tazobactam The pharmacokinetics (PK) of ceftolozane/tazobactam in patients with normal renal function are linear across a wide range of doses (up to 3,000 mg/1,500 mg as a single dose). Terminal elimination half-lives ($t_{1/2}$) are approximately 2.5 h for ceftolozane and 1 h for tazobactam. Both compounds exhibit low protein binding (approximately 20% for ceftolozane and 30% for tazobactam) and are primarily excreted in the urine; ceftolozane as unchanged parent drug suggesting minimal metabolism, and tazobactam with 80% as the unchanged parent drug and the remaining as inactive M1 metabolite. In the present studies, the PK and safety of ceftolozane/tazobactam were investigated in subjects with varying degrees of renal function, including subjects with end-stage renal disease (ESRD) on hemodialysis (HD).

Materials and Methods
Study Populations

Male and female subjects, aged 18 to 79 years, with varying degrees of renal function were enrolled in two, prospective, open-label, phase I studies of intravenous ceftolozane/tazobactam. A total of 36 subjects were enrolled into cohorts based on degree of renal function: normal (n=11), mild impairment (n=6), moderate impairment (n=7), severe impairment (n=6), and ESRD on HD (n=6). To ensure subjects with ESRD were receiving effective HD, a target adequacy of HD calculated from the pre- and post-blood urea nitrogen ratios (Kt/V) of at least 1.2 for a minimum of 3 months prior to enrollment was required. Renal impairment groups were classified according to the 2010 U.S. Food and Drug Administration draft guidance using creatinine clearance (CrCl) estimated by the Cockcroft-Gault formula (normal impairment, >90 ml/min; mild impairment, 60 to 89 ml/min; moderate impairment, 30 to 59 ml/min; and severe impairment, 15 to 29 ml/min, ESRD<15 ml/min).

Dosing/Design

All cohorts received ceftolozane/tazobactam as an intravenous infusion over 1 h. The normal, mild, and moderate renal impairment cohorts received a single dose of ceftolozane/tazobactam 1,000 mg/500 mg; the severe renal impairment cohort received a single dose of ceftolozane/tazobactam 500 mg/250 mg; the ESRD cohort received a dose of ceftolozane/tazobactam 500 mg/250 mg initiated at the end of HD on day 1 and another dose initiated 2 h before HD on day 4. Subjects with ESRD underwent HD for 3 to 4 h using a high-flux membrane as scheduled; average dialysis flow rate was 600 to 800 ml/min. Revaclear hemodialyzers (Gambro, Stockholm, Sweden) were used in 5 subjects (ultrafiltration coefficient 50 to 60 ml/h/mmHg, high flux membrane of 1.4 to 1.8 m$^2$) and a CT 190G hemodialyzers (Baxter Healthcare, McGaw Park, Ill.) was used in 1 subject (ultrafiltration coefficient 36 ml/h/mmHg, high flux membrane of 1.9 m$^2$). The average blood flow rate was 400 to 600 ml/min with the exception of one subject with rates between 264 and 400 ml/min.

Pharmacokinetic Evaluations

Plasma concentrations of ceftolozane and tazobactam were measured prior to, during, and following administration of ceftolozane/tazobactam. Blood samples were collected 30 min prior to administration, at the end of administration and at 5, 15, and 30 min and 1, 2, 3, 5, 7, 9, 11, 15, 25, and 35 h after completion of ceftolozane/tazobactam administration in the normal, mild, and moderate renal impairment cohorts. Severe renal impairment and ESRD cohorts off HD had samples taken 30 min prior to administration and at 0.5, 1, 1.5, 2, 3, 6, 9, 12, 24, 36, and 48 h after the start of administration. On the day of and following HD, the subjects with ESRD had samples taken 30 min prior to administration and at 0.5, 1, 1.5, 2, 3, 4, 5, 6, 9, 12, 24, 36, and 44 h after the start of the administration. The entire dialysate was collected at each of the following intervals: 0 to 1, 1 to 2, 2 to 3, and 3 h to the end of dialysis. Urine for PK analysis was obtained in the normal, mild, and moderate cohorts at 0 to 2, 2 to 4, 4 to 8, 8 to 12, 12 to 24, and 24 to 36 h after the start of ceftolozane/tazobactam administration. In the ESRD and severe renal impairment cohorts, urine was collected during the confinement period pre-dose, 0 to 24 h, and 24 to 48 h after the start of the administration, unless the subject was anuric. A validated LC/MS/MS method was utilized to analyze all plasma, urine, and dialysate samples for ceftolozane and tazobactam (MicroConstants Inc., San Diego, Calif.) (4). The lower limit of quantification (LLOQ) in plasma was 0.25 µg/ml for ceftolozane and 0.1 µg/ml for tazobactam. The assay was linear between 0.25 and 150 µg/ml for ceftolozane and between 0.1 and 50 µg/ml for tazobactam. The precision of the assay for ceftolozane and tazobactam ranged between 3.13 and 7.97% while the accuracy was ±1 and ±6.25%, respectively. The LLOQ in dialysate for both ceftolozane and tazobactam was 1 ng/ml and the assay was linear between 1 and 500 ng/ml. The precision of the assay in dialysate samples for ceftolozane and tazobactam ranged between 1.28 and 9.18% while the accuracy for ceftolozane and tazobactam was ±8.3 and ±9.67%, respectively. The LLOQ for ceftolozane and tazobactam in urine was 5 and 10 µg/ml, respectively, and the assay was linear between 5 and 5,000 µg/ml for ceftolozane and between 10 and 10,000 µg/ml for tazobactam. The precision of the assay for ceftolozane and tazobactam ranged between 3.71 and 9.06% while the accuracy was ±9.20 and 7.33%, respectively.

Pre-dose values below the LLOQ values were set to zero and all missing values below the LLOQ obtained after the first quantifiable concentration were designated as missing and not included in the analysis. The maximum plasma concentration ($C_{max}$) and plasma concentration when the last quantifiable concentration was observed relative to the end of infusion ($C_{last}$) were taken directly from concentration-time data. Terminal elimination $t_{1/2}$ was calculated as 0.693/$\lambda_z$ where $\lambda_z$ is the terminal elimination rate constant, estimated by regression of the terminal log-linear phase of the plasma concentration versus time curve. Area under the plasma concentration time curve (AUC) from time zero to the last measurable concentration ($AUC_{0-t}$) was calculated using the linear trapezoidal rule. The AUC extrapolated to infinity ($AUC_{0-\infty}$) was estimated using the formula $AUC_{0-last}+(C_{last}/\lambda_z)$ using the linear trapezoidal rule. Total body clearance from plasma (CL) was calculated as dose/$AUC_{0-\infty}$. Volume of distribution at steady-state ($V_{ss}$) was calculated as mean residence time*CL. Renal clearance ($CL_r$) in subjects that provided urine samples was calculated from the equation $CL_r=A_c/AUC_{0-\infty}$ where $A_c$ is the cumulative amount of drug recovered in the urine during the sampling period. Dialysis clearance was calculated as the amount of ceftolozane or tazobactam recovered in dialysate divided by AUC from the time of the second dose to the end of HD ($AUC_{(t0-t1)}$). The rate of decrease in plasma concentration (RDHD) was calculated from the difference between the concentration at the end of dialysis ($C_2$) and the concentration at the beginning of HD ($C_1$). The percent reduction was calculated using the equation $RDHD=100*(C_1-C_2)/C_1$. Extraction ratio was calculated as $100*(C_A-C_V)/C_A$ where $C_A$ and $C_V$ are pre- and post-dialyzer paired drug concentrations at the arterial and venous sites. Total effective removal was calculated with individual $AUC_{0-\infty}$ values as $(AUC_{off-HD}-AUC_{on-HD})$ divided by $AUC_{off-HD}$ (6). Dialysis clearance ($CL_D$) was calculated as amount of drug in dialysate divided by $AUC_{(t0-t1)}$.

The PK parameters were calculated by non-compartmental analysis using Phoenix WinNonlin version 6.1 (Pharsight Corporation, Mountain View, Calif.).

Safety Monitoring

Safety was assessed by monitoring for adverse events (AEs) from the first dose of drug through the last study evaluation, and by review of vital signs, physical examinations, 12-lead electrocardiograms, and clinical laboratory evaluations.

Results

Demographics and Disposition

A total of 36 subjects received ceftolozane/tazobactam. No subjects withdrew consent or discontinued due to an AE, and all subjects were included in the PK and safety analyses. The demographic characteristics of the subjects are presented in FIG. 8. The majority were white, except in the ESRD cohort in whom five of the six subjects were black or African American. Subjects ranged in age from 40 to 79 years with a median age of 62 years.

Pharmacokinetic Summary

Normal Renal Function and Mild, Moderate, and Severe Renal Impairment

Figure 11:
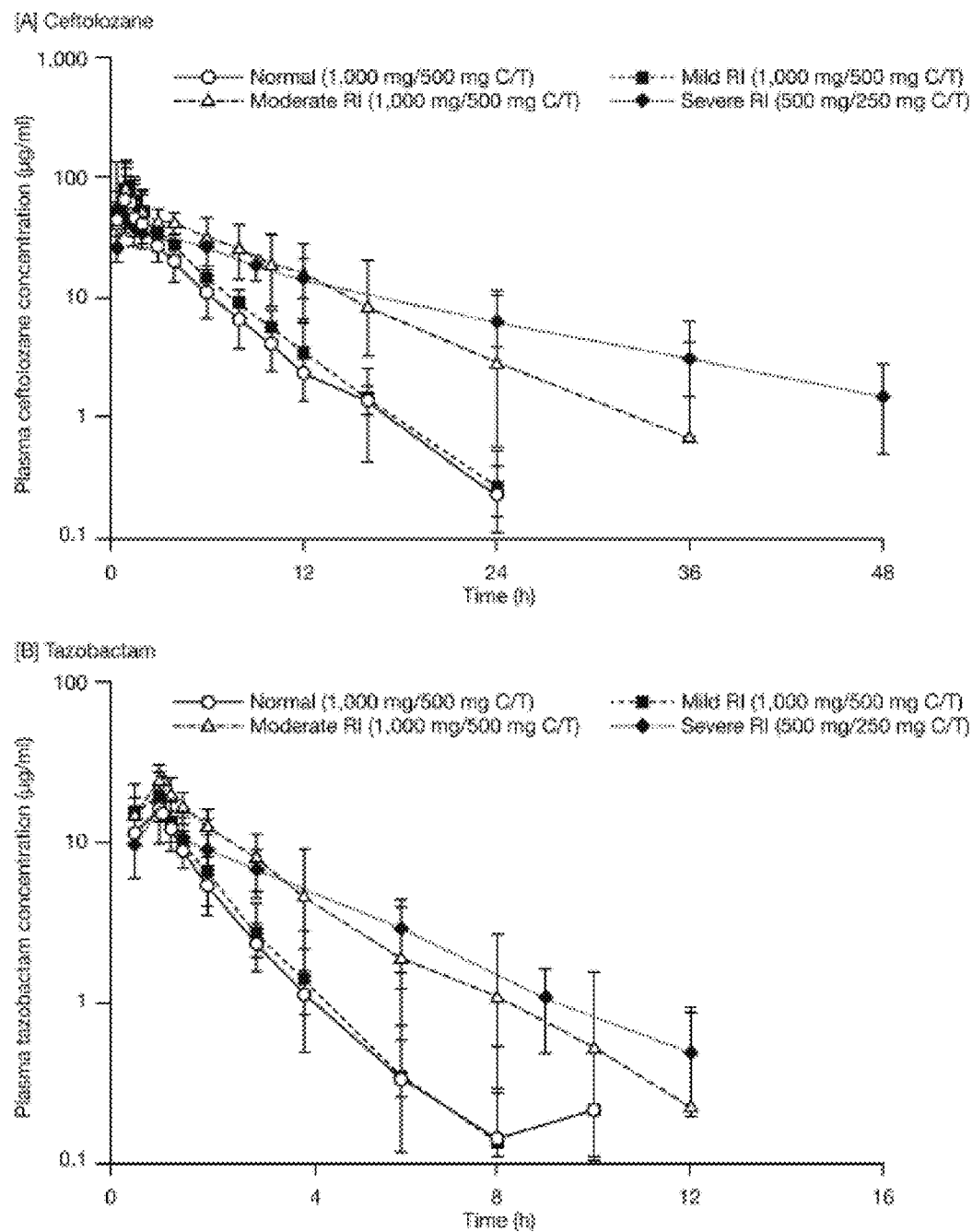
FIG. 11 shows the median (range) plasma concentration-time profiles of [A] ceftolozane and [B] tazobactam following single-dose administration of intravenous ceftolozane/tazobactam (semi-log plot). a C/T, ceftolozane/tazobactam. b RI, renal impairment.
Figure 12:
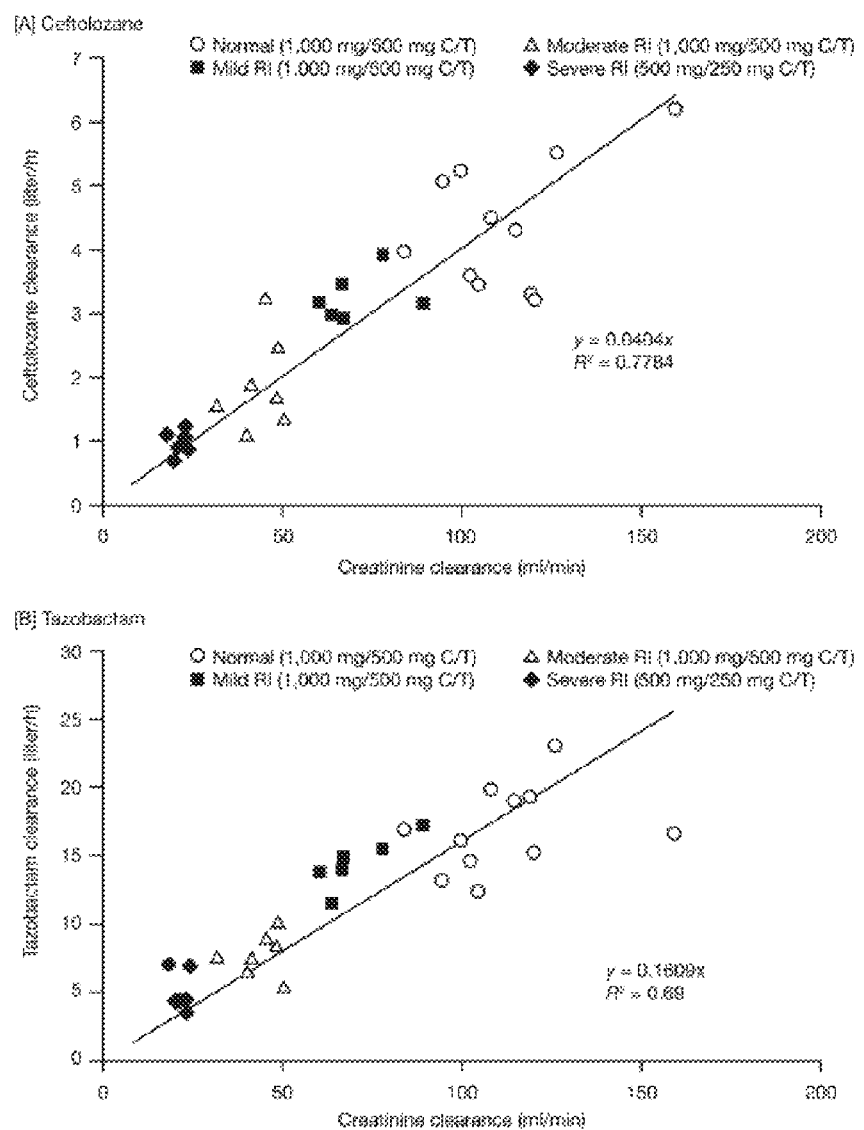
FIG. 12 shows regression plots of [A] ceftolozane and [B] tazobactam plasma clearance versus CrCl following single-dose administration of intravenous ceftolozane/tazobactam. a C/T, ceftolozane/tazobactam. b RI, renal impairment.

Compared with subjects with normal renal function, the concentration-time profiles of ceftolozane/tazobactam were increasingly altered in subjects with increasingly impaired renal function (FIGS. 11A and 11B). Pharmacokinetic parameters are summarized in FIGS. 9 and 10 for ceftolozane and tazobactam, respectively. Ceftolozane and tazobactam plasma clearance by CrCl are provided in FIGS. 12A and 12B, respectively. Exposure ($AUC_{0-\infty}$ and $C_{max}$) was similar in subjects with normal renal function and mild renal impairment following a single ceftolozane/tazobactam 1,000 mg/500 mg dose as was $t_{1/2}$. In subjects with moderate renal impairment, decreases in clearance led to increased ceftolozane and tazobactam exposure compared with subjects with normal renal function with median $AUC_{0-\infty}$ and $C_{max}$ increased for ceftolozane (2.5- and 1.2-fold, respectively) and tazobactam (2.2- and 1.6-fold, respectively). In subjects with severe renal impairment, the median $AUC_{0-\infty}$ and $C_{max}$ increased 4.4- and 1.3-fold for ceftolozane and 3.8- and 1.9-fold for tazobactam, respectively, compared with the dose-normalized exposure in the normal renal function group.

End-Stage Renal Disease on Hemodialysis

Median concentration-time profiles for ceftolozane and tazobactam in subjects with ESRD post-HD and on HD are shown in FIGS. 13A and 13B, respectively. The PK parameters of ceftolozane and tazobactam differed substantially in subjects with ESRD compared with the other renal impairment groups. Pharmacokinetic parameters are summarized in FIGS. 9 and 10 for ceftolozane and tazobactam, respectively. The median elimination $t_{1/2}$ of ceftolozane and tazobactam in subjects with ESRD during non-HD was prolonged and the median $C_{max}$ in plasma was 1.2- and 2.4-fold higher compared with subjects with normal renal function when dose normalized. The $t_{1/2}$ during the HD period for ceftolozane and tazobactam were 1.13 and 0.91 h, respectively. The extraction ratios at 1 h and 2 h after the start of HD and at end of HD for ceftolozane and tazobactam were 42, 48, and 47% and 48, 54, and 55%, respectively. The average extraction ratio during HD was 46% (±16) for ceftolozane and 53% (±22) for tazobactam. Ceftolozane and tazobactam concentrations declined rapidly following the start of HD with approximately 66 and 56% reductions in overall exposure to ceftolozane and tazobactam, respectively, based on the $AUC_{0-\infty}$ on and off HD. The median RDHD for ceftolozane and tazobactam was 92 and 95%, respectively, indicating significant removal by HD; however, in the period following HD, plasma concentrations rebounded and peaked at approximately 17 and 6% of the original $C_{max}$ of ceftolozane and tazobactam, respectively. The median $CL_D$ for ceftolozane and tazobactam was 5.75 and 4.39 liter/h, respectively.

Safety

Overall, seven of the 36 subjects experienced a total of 12 AEs. The most common AE reported was headache in three subjects. All events reported were mild in severity with the exception of one event of moderate headache in a subject with normal renal function. Two subjects with normal renal function and one subject with mild renal impairment reported the AE of headache. Diarrhea, infusion-site hemorrhage, and injection-site hemorrhage were reported in one subject each in the mild impairment group. Flatulence, glossodynia, myalgia, and vulvovaginal pain were reported in one subject each in the ESRD on HD group. No AEs were reported in the moderate or severe renal impairment groups. One serious AE of thrombosis of an arteriovenous fistula was reported in a subject with ESRD on HD 7 days after the last dose of the study drug. No subjects withdrew due to AEs. Review of clinical laboratory values, physical examination, and vital signs showed no meaningful changes from baseline.

In summary, the exposure to ceftolozane/tazobactam in subjects with mild renal impairment was increased relative to that in normal controls, but the increase was small and not clinically meaningful, suggesting that no dose adjustment is necessary in this population. However, data from these phase I studies suggest that a decrease in dose or frequency of administration, or both, is necessary in those with moderate or severe renal impairment, or with ESRD.

Example 12: Ceftolozane/Tazobactam Dosing

Out of the 7 tested dosing regimens listed below (Table 27), all failed except the last one (scenario 7) which was recommended for clinical use. The failure was defined if not meeting:

1). PTA≥90% and fT>MIC≥32.2% (1−log kill) on day 1 and 2 or >=24.8% on any of the other later days for CXA at MIC=8 mg/L; and 2). Daily AUC is about or less than 1100 mg/L*hr every day; and 3). PTA≥90% at about 50% fT>MEC for MEC=0.5 mg/L for Taz.

TABLE 27

Tested dosing regimens

| Scenario | Loading Dose (TOL/TAZ in mg/mg) | Maintenance Dose (TOL/TAZ in mg/mg) | Regimen |
|---|---|---|---|
| 1 | 500/250 | 300/150 | 1-hr infusion, every 24 hours |
| 2 | — | 300/150 | 1-hr infusion, every 24 hours |
| 3 | 600/300 | 300/150 | 1-hr infusion, every 24 hours |
| 4 | — | 100/50 | 1-hr infusion, every 8 hours |
| 5 | — | 300/150 | 4-hr infusion, every 24 hours |
| 6 | 400/200 | 100/50 | 1-hr infusion, every 8 hours |
| 7 | 500/250 | 100/50 | 1-hr infusion, every 8 hours |

Example 13: Cardiac Safety Study: Single Dose Pharmacokinetics and Effects on the QT/QTc Interval of Ceftolozane/Tazobactam Study Design and Objectives:

This TQT study was a single-center, prospective, randomized, double-blind, double-dummy, placebo and active controlled, 4-way crossover study that evaluated a single therapeutic 1.5 g and a single supratherapeutic 4.5 g dose of ceftolozane/tazobactam compared with placebo. Moxifloxacin 400 mg, given orally, was used as a positive control. All subjects received study drug on 4 dosing days (Day 1, Day 5, Day 9, and Day 13) in a crossover fashion with a 3-day wash-out period between doses. Healthy men and women were randomized on a 1:1:1:1 basis to 1 of 4 dosing sequences.

The primary objectives of the study were to evaluate the effect of a single IV supratherapeutic dose of ceftolozane/tazobactam on ventricular repolarization as measured by QTc interval in healthy subjects compared to baseline-adjusted, time-matched placebo and to evaluate the change from the period-specific predose baseline of QT/QTc interval corrected by QTcI (individual QT correction subject-specific formula) across all dose groups. Pharmacokinetics of ceftolozane/tazobactam was a secondary objective of this study.

Electrocardiograms were recorded (triplicate measurements) over 24 hours on Day 1, Day 5, Day 9, and Day 13 using a 12-lead Holter monitor. Blood samples for determination of ceftolozane, tazobactam, and the M1 metabolite of tazobactam levels were obtained at prespecified time intervals prior to and following each electrocardiogram (ECG) reading on dosing days. Plasma levels of ceftolozane, tazobactam, and its metabolite M1 were determined by LC/MS/MS assay.

Results:

A total of 52 healthy volunteers were randomized into the study, including 13 in each dosing sequence. Two subjects withdrew prematurely, including 1 subject who withdrew after receiving both the therapeutic and supratherapeutic doses of ceftolozane/tazobactam and 1 who withdrew after receiving only moxifloxacin. The latter subject was not included in the PK analyses. The 51 subjects in the PK analyses included 28 males and 23 females who ranged in age from 18 to 45 years.

A single dose of ceftolozane/tazobactam 1.5 g or 4.5 g did not increase QTc intervals. The largest mean difference from placebo for changes from predose in QTcI (ΔΔQTcI) was 4.16 msec observed 1 hour following dosing with ceftolozane/tazobactam 4.5 g, and the largest one-sided 95% upper confidence bound was 6.25 msec. The 95% lower confidence bounds on the differences from baseline for QTcI between moxifloxacin and placebo was above 5 ms. These data indicate the study's sensitivity to demonstrate a sufficiently small QTc change.

Figure 31:
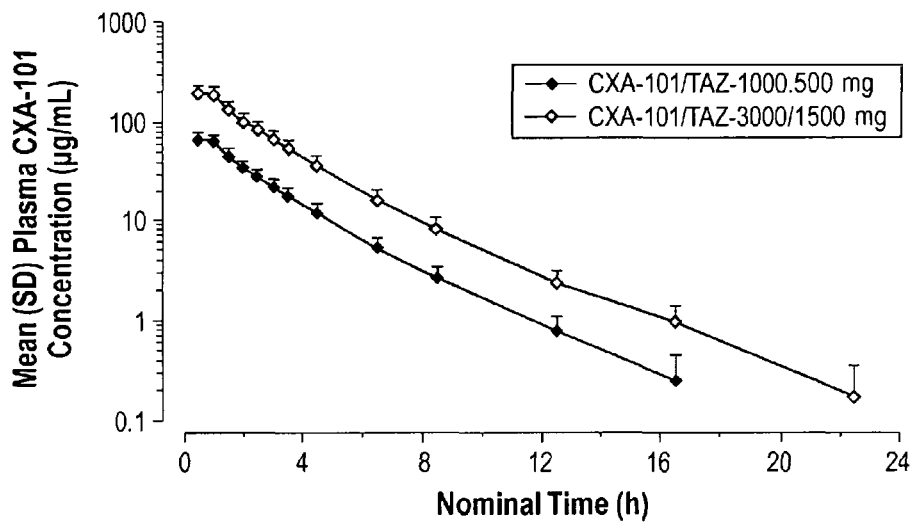
FIG. 31 shows the mean (SD) ceftolozane plasma concentrations over time after therapeutic (1.5 g) and suprtherapeutic (4.5 g) intravenous 1-hour infusions of Ceftolozane/Tazobactam (Tables 28-29). CXA-101/TAZ=ceftolozane/tazobactam; SD=standard deviation.

Following dosing with both therapeutic and supratherapeutic doses of ceftolozane/tazobactam, mean ceftolozane $C_{max}$, $AUC_{last}$ and $AUC_\infty$ appeared to increase in a dose-proportional manner (Table 28). Ceftolozane plasma $t_{1/2}$, CL, and $V_{ss}$ were comparable for therapeutic and supratherapeutic doses. Further, results of the ANOVA confirmed dose proportionality between the therapeutic and supratherapeutic doses as the ratio of least square (LS) means and 90% CIs of ceftolozane PK parameters were all within the 80% to 125% range. The ceftolozane plasma concentration-time profile is shown in FIG. 31.

Figure 32:
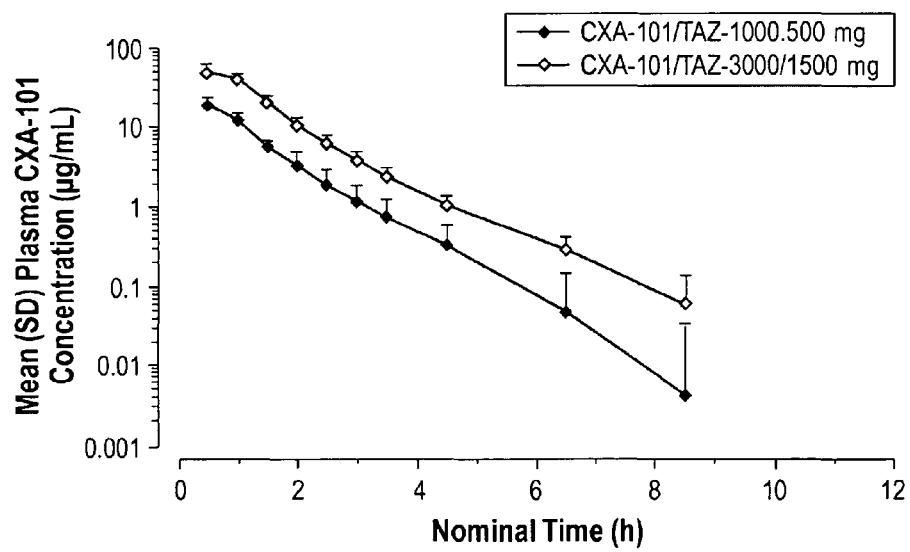
FIG. 32 shows the mean (SD) tazobactam plasma concentrations over time after therapeutic (1.5 g) and suprtherapeutic (4.5 g) intravenous 1-hour infusions of ceftolozane/tazobactam (Tables 28-29). CXA-101/TAZ=ceftolozane/tazobactam; SD=standard deviation.

Similar to ceftolozane, mean $C_{max}$, $AUC_{last}$ and $AUC_\infty$ of tazobactam and its M1 metabolite appeared to increase in a dose-proportional manner when the tazobactam dose was increased from 500 mg to 1.5 g. Tazobactam mean plasma $t_{1/2}$, CL, and $V_{ss}$ were comparable for therapeutic and supratherapeutic doses (Table 29). The tazobactam plasma concentration-time profile is shown in FIG. 32. Median $t_{max}$ of the M1 metabolite of tazobactam was 3.7 hours, which was longer than the median $t_{max}$ for ceftolozane or tazobactam. Mean plasma $t_{1/2}$ of metabolite M1 was 3.6 hours for the supratherapeutic dose and was similar to that observed for the therapeutic dose (3.2 hours). Results of the ANOVA confirmed dose proportionality between the therapeutic and supratherapeutic doses as the ratio of LS means and 90% CIs of both tazobactam and metabolite M1 AUC and $C_{max}$ were all within the 80% to 125% range (Table 28).

TABLE 28

Ceftolozane Plasma Pharmacokinetic Parameters after Administration of Therapeutic (1.5 g) and Supratherapeutic (4.5 g) Intravenous 1-hour Infusions of Ceftolozane/Tazobactam

| Ceftolozane PK Parameter | Mean (CV %) | |
| --- | --- | --- |
| | Ceftolozane/Tazobactam Therapeutic Dose 1000/500 mg (n = 51) | Ceftolozane/Tazobactam Supratherapeutic Dose 3000/1500 mg (n = 51) |
| $C_{max}$ (µg/mL) | 66.5 (19) | 199 (19) |
| $t_{max}$ (h)a | 0.667 (0.667, 1.17) | 0.667 (0.667, 1.18) |
| $AUC_{last}$ (µg · h/mL) | 184 (18) | 560 (18) |
| $AUC_\infty$ (µg · h/mL) | 186 (18) | 562 (17) |
| $t_{1/2}$ (h) | 2.29 (15) | 2.72 (21) |
| $V_{ss}$ (L) | 13.5 (21) | 13.7 (20) |
| CL (L/h) | 5.57 (18) | 5.50 (17) |

$AUC_\infty$ = area under the plasma concentration-time curve from time zero to infinity;
$AUC_{last}$ = area under the plasma concentration-time curve from time zero to the last measureable concentration (plasma samples were obtained through 22.5 hours);
CL = total body clearance from plasma;
$C_{max}$ = maximum (peak) plasma drug concentration;
CV = coefficient of variation;
PK = pharmacokinetic;
$t_{1/2}$ = elimination half-life;
tmax = time to reach maximum (peak) plasma concentration following drug administration;
$V_{ss}$ = apparent volume of distribution at steady state after intravenous administration
aMedian (minimum, maximum) presented

TABLE 29

Tazobactam Plasma Pharmacokinetic Parameters after Administration of Therapeutic (1.5 g) and Supratherapeutic (4.5 g) Intravenous 1-hour Infusions of Ceftolozane/Tazobactam

| Tazobactam PK Parameter | Mean (CV %) | |
| --- | --- | --- |
| | Ceftolozane/Tazobactam 1000/500 mg (n = 51) | Ceftolozane/Tazobactam 3000/1500 mg (n = 51) |
| $C_{max}$ (µg/mL) | 18.6 (23) | 51.2 (21) |
| $t_{max}$ (h)a | 0.667 (0.667-1.17) | 0.667 (0.667, 1.17) |
| $AUC_{last}$ (µg · h/mL) | 23.5 (24) | 73.1 (19) |
| $AUC_\infty$ (µg · h/mL) | 23.8 (24) | 73.4 (19) |
| $t_{1/2}$ (h) | 0.870 (18) | 1.05 (17) |
| $V_{ss}$ (L) | 18.2 (25) | 19.3 (22) |
| CL (L/h) | 22.1 (21) | 21.2 (19) |

Figure 33:
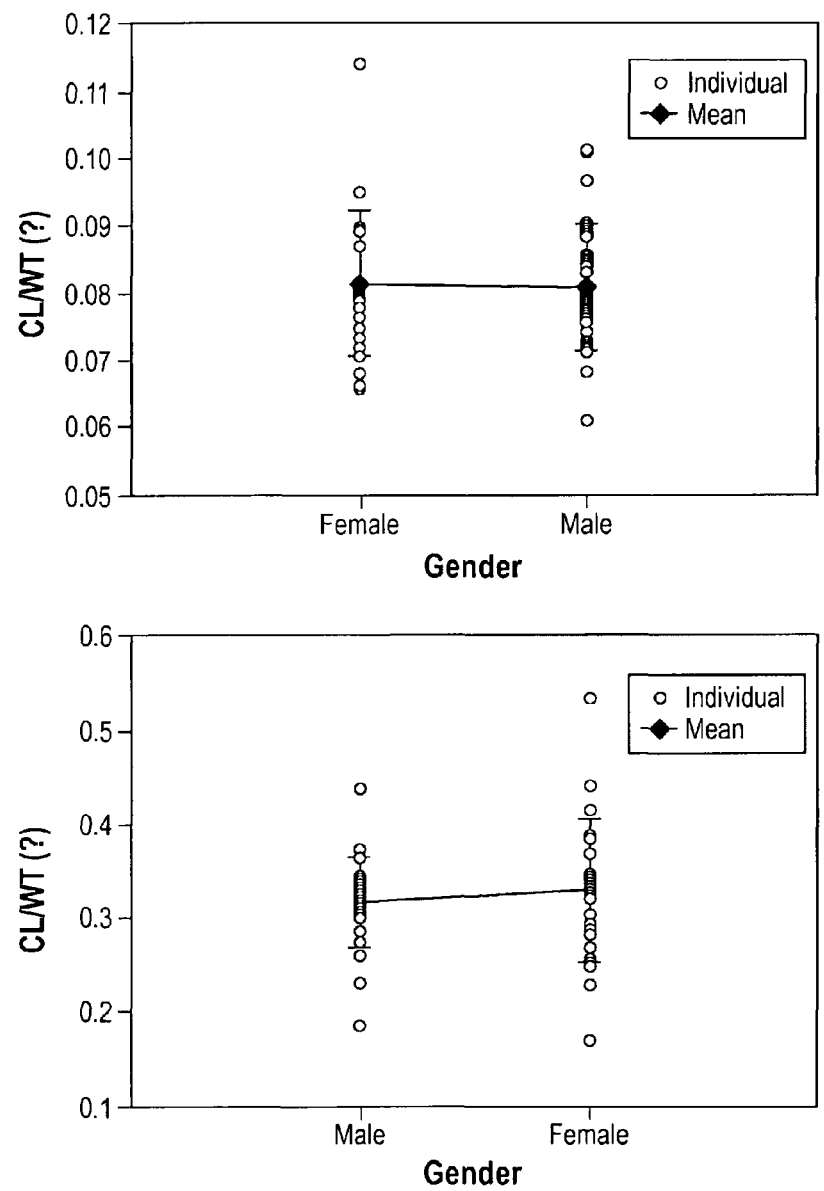
FIG. 33 shows the individual and mean (SD) PK parameters (CL/WT) of ceftolozane (Top Panel) and tazobactam (Bottom Panel) by gender after a therapeutic (1.5 g) intravenous 1-hour infusion of ceftolozane/tazobactam (Tables 28-29). CL/WT=total body clearance from plasma adjusted for weight; SD=standard deviation.
Figure 34A:
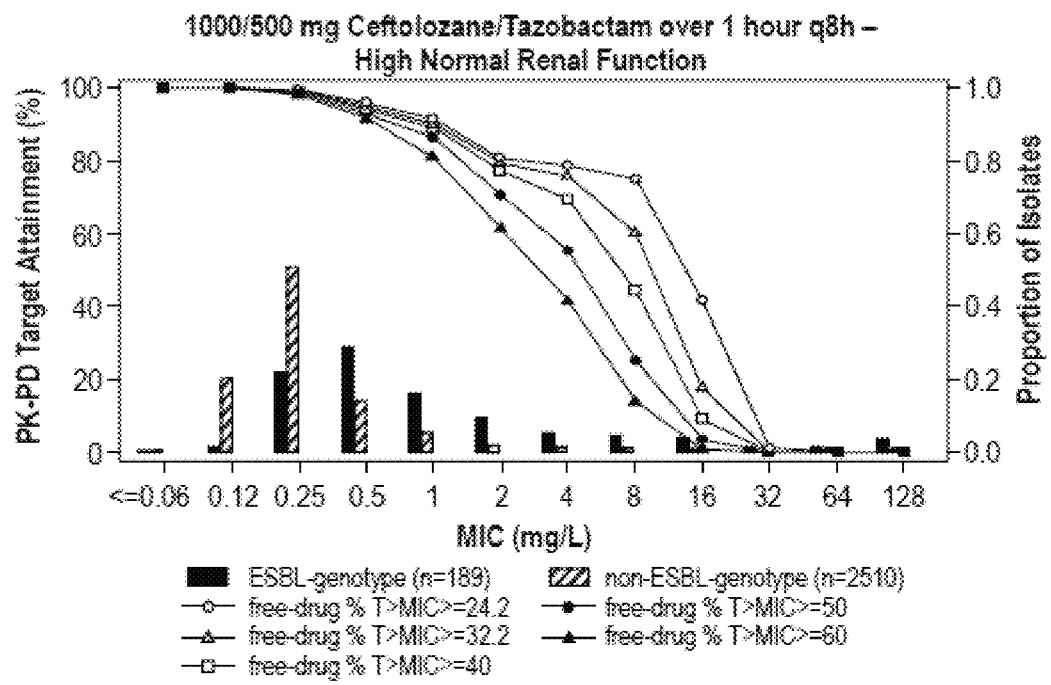
FIGS. 34A-E show the percentage of simulated patients achieving free-drug % T>MIC targets for Enterobacteriaceae by MIC at steady-state following administration of [A] 1000/500 mg Ceftolozane/Tazobactam over 1 hour q8h (High Normal Renal Function), [B] 1000/500 mg Ceftolozane/Tazobactam over 1 hour q8h (Normal Renal Function), [C] 1000/500 mg Ceftolozane/Tazobactam over 1 hour q8h (Mild Renal Impairment), [D] 500/250 mg Ceftolozane/Tazobactam over 1 hour q8h (Moderate Renal Impairment) and [E] 250/125 mg Ceftolozane/Tazobactam over 1 hour q8h (Severe Renal Impairment) dosing regimens overlaid on histograms showing the clinical trial program MIC distributions for TOL/TAZ against Enterobacteriaceae.
Figure 34B:
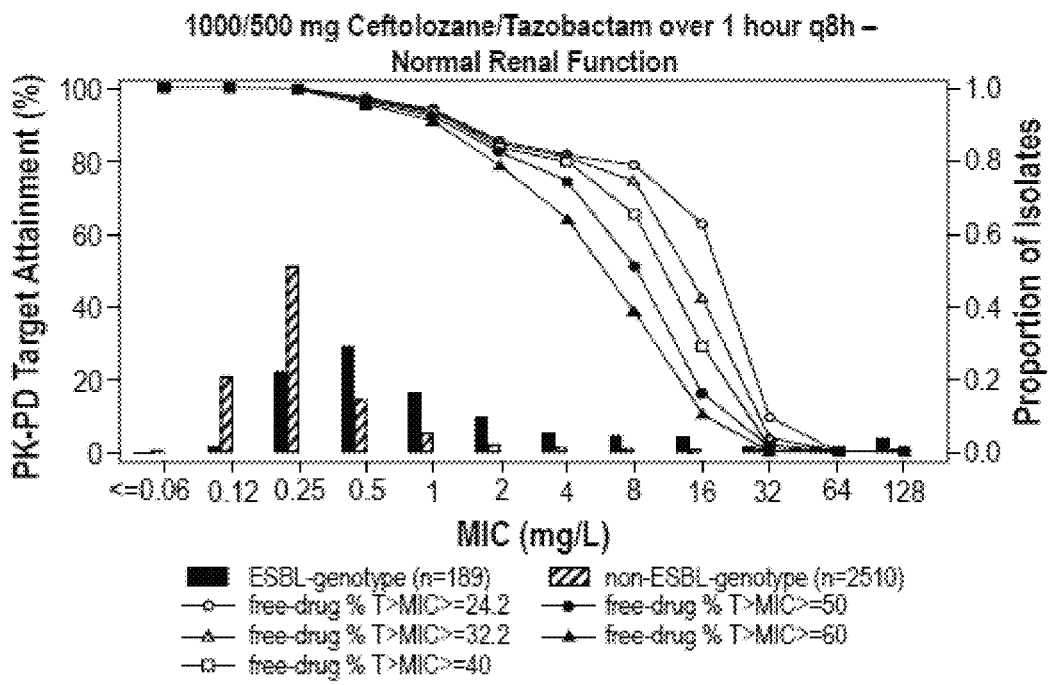
Figure 34C:
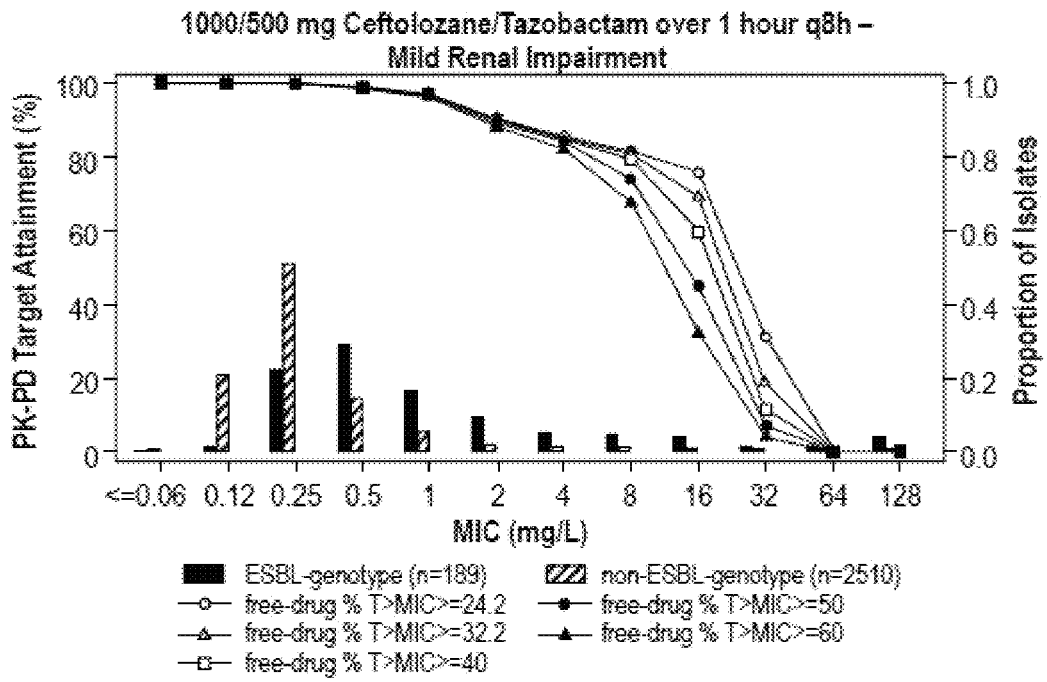
Figure 34D:
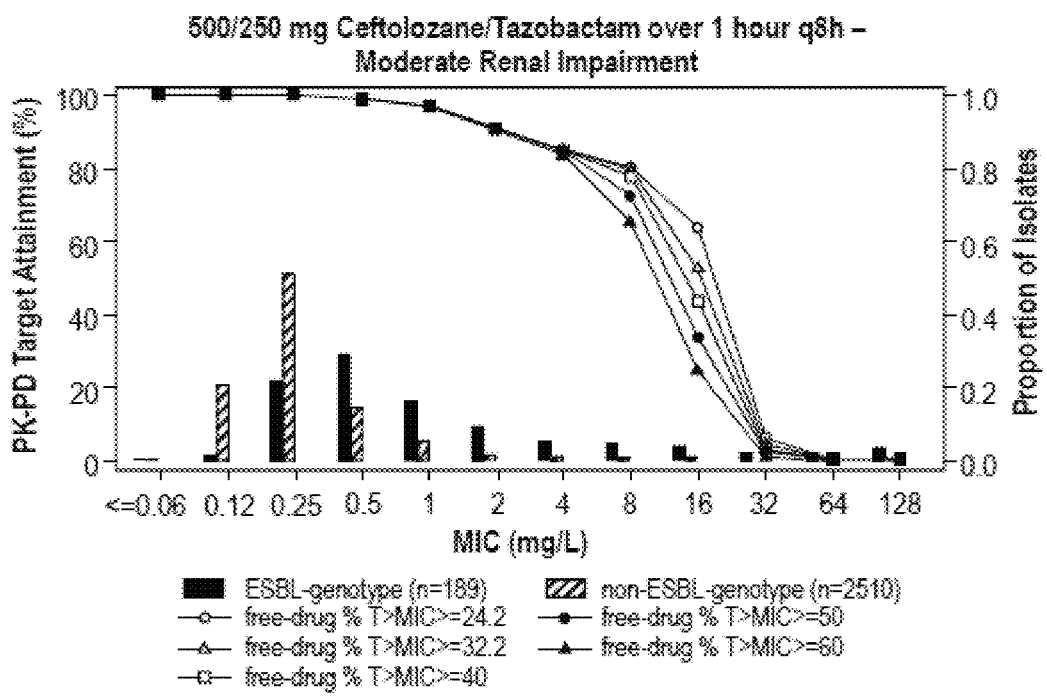
Figure 34E:
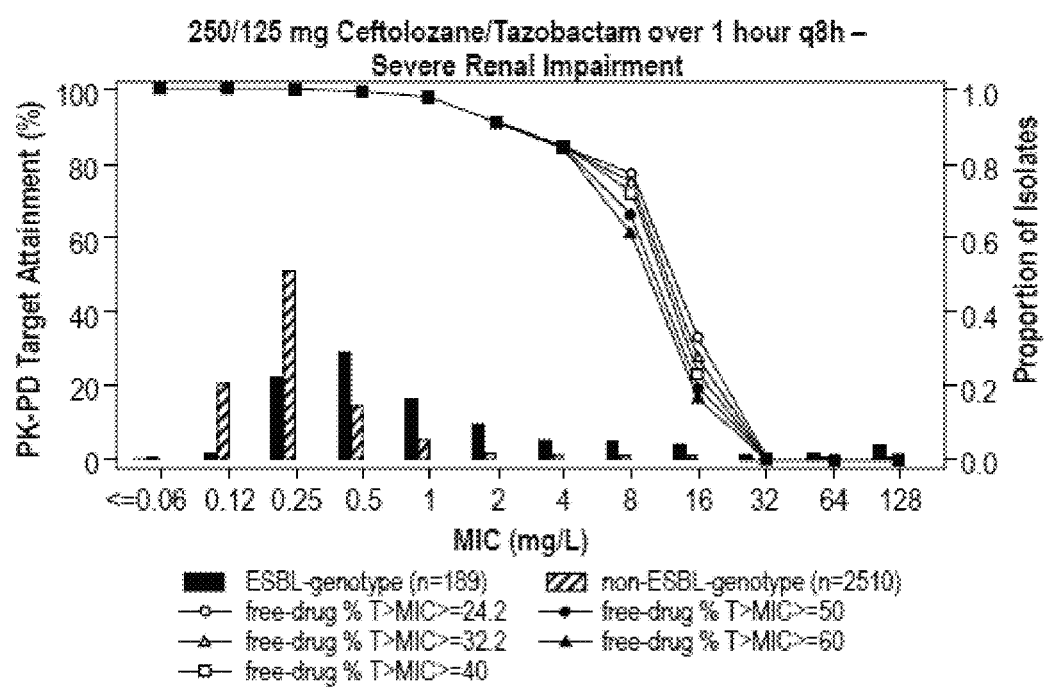
Figure 35A:
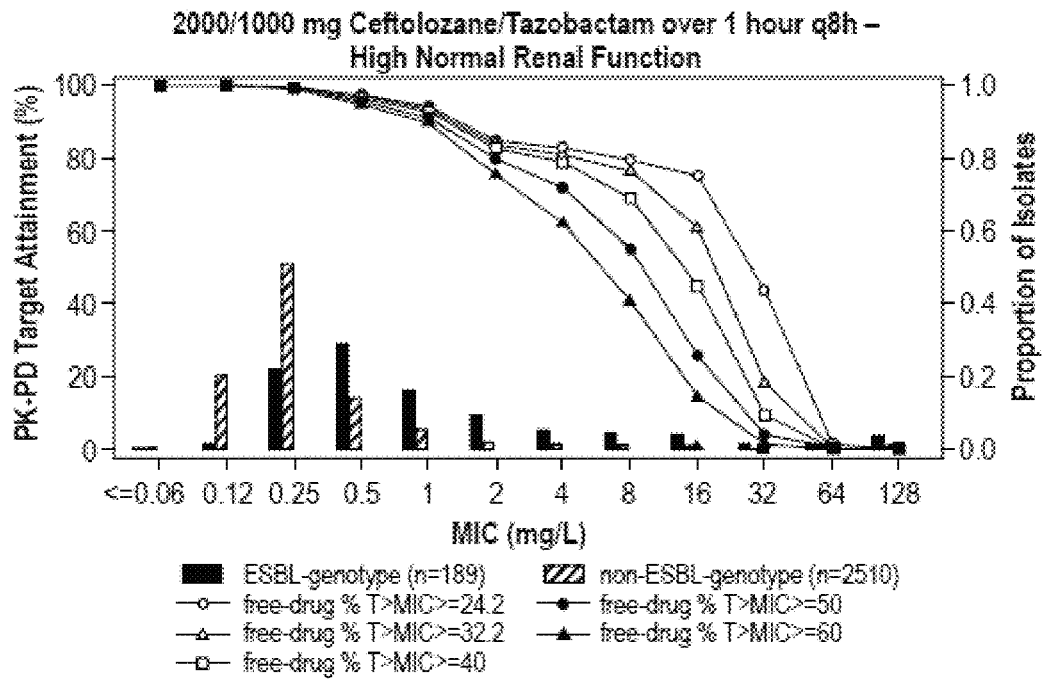
FIGS. 35A-E show the percentage of simulated patients achieving free-drug % T>MIC targets for Enterobacteriaceae by MIC at steady-state following administration of [A] 2000/1000 mg 2000/1000 mg Ceftolozane/Tazobactam over 1 hour q8h (High Normal Renal Function), [B] 2000/1000 mg Ceftolozane/Tazobactam over 1 hour q8h (Normal Renal Function), [C] 2000/1000 mg Ceftolozane/Tazobactam over 1 hour q8h (Mild Renal Impairment), [D] 1000/500 mg Ceftolozane/Tazobactam over 1 hour q8h (Moderate Renal Impairment), [E] 500/250 mg Ceftolozane/Tazobactam over 1 hour q8h (Severe Renal Impairment) dosing regimens overlaid on histograms showing the clinical trial program MIC distributions for TOL/TAZ against Enterobacteriaceae.
Figure 35B:
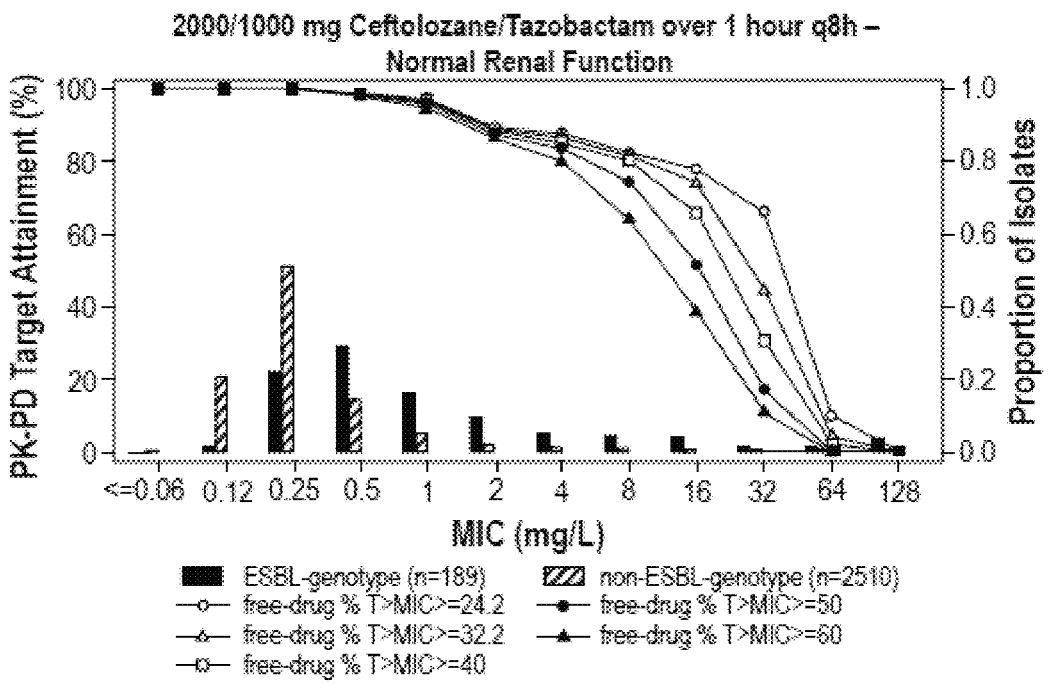
Figure 35C:
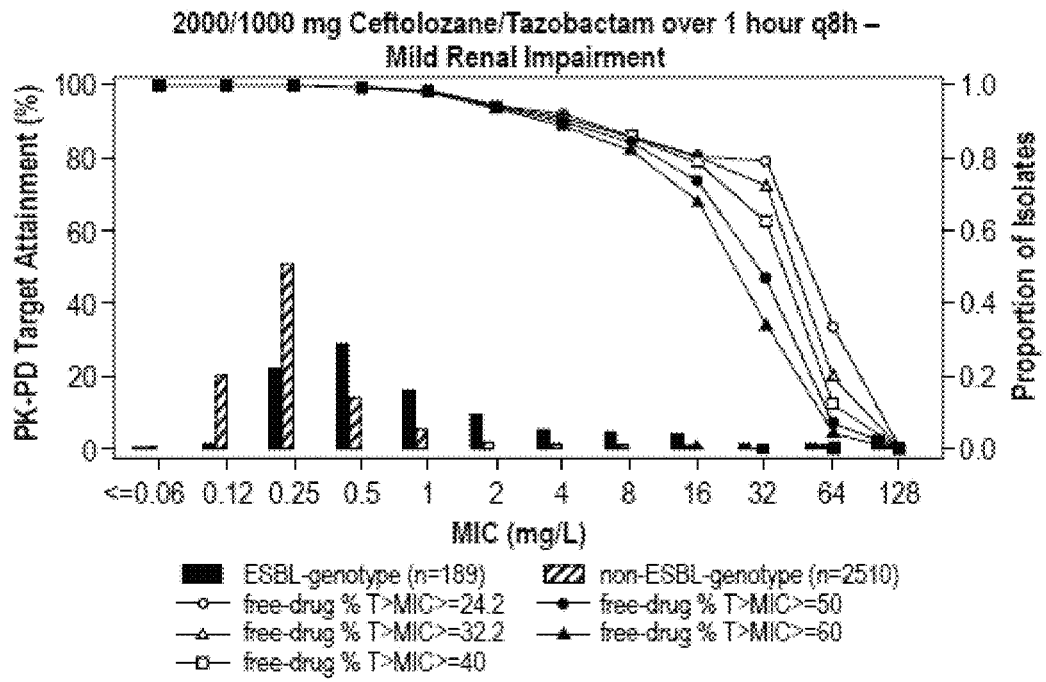
Figure 35D:
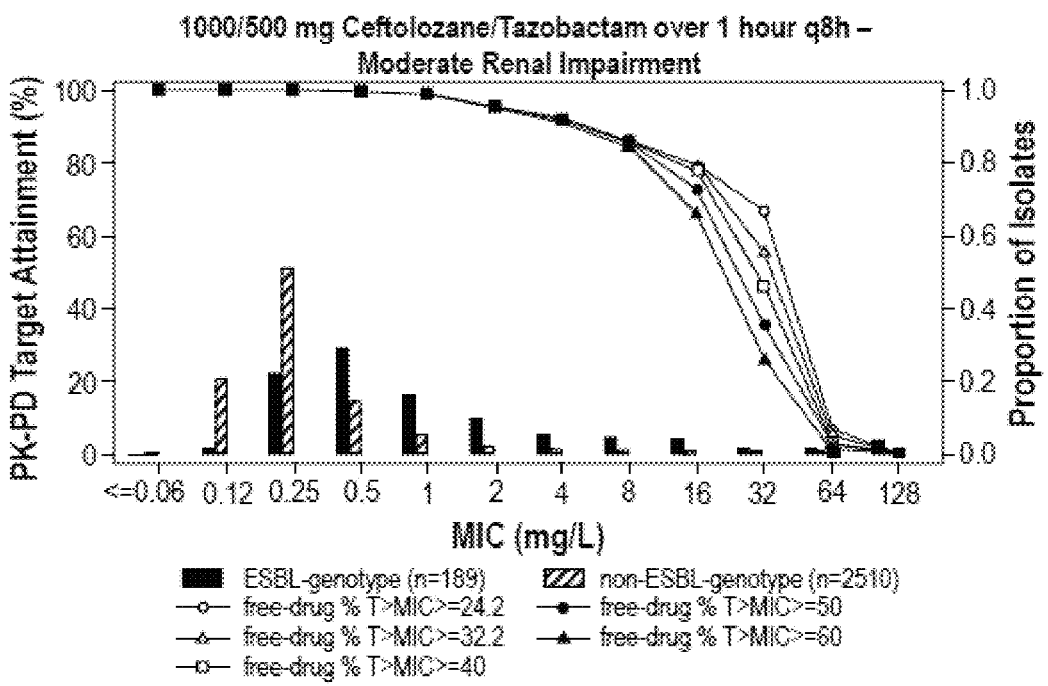
Figure 35E:
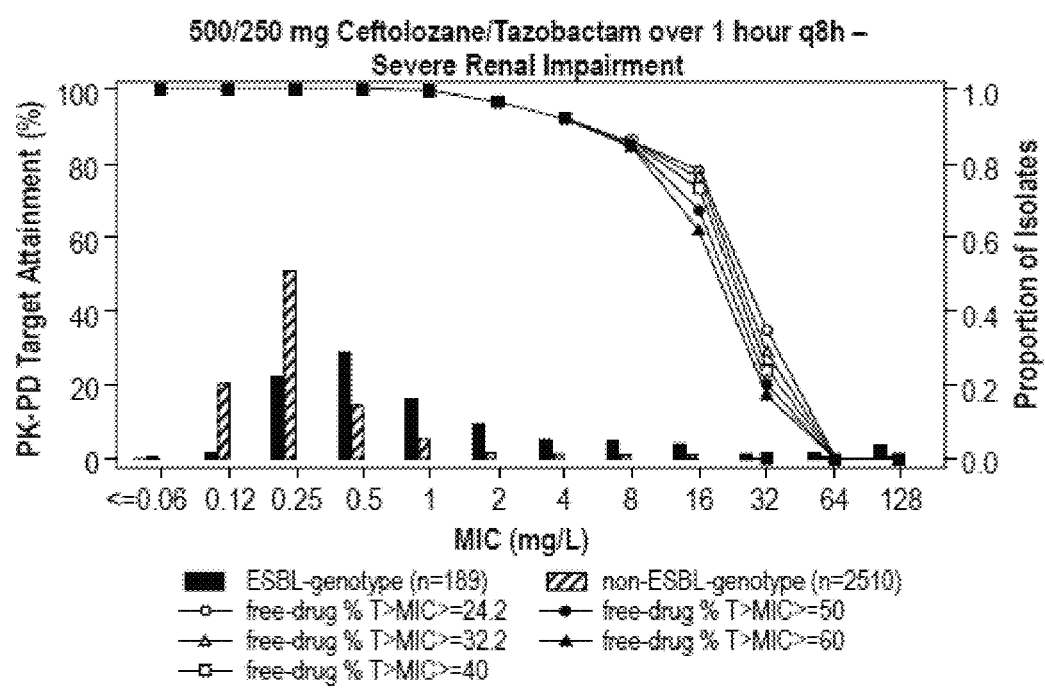

$AUC_\infty$ = area under the plasma concentration-time curve from time zero to infinity;
$AUC_{last}$ = area under the area under the plasma concentration-time curve from time zero to the last measurable concentration (plasma samples were obtained through 22.5 hours);
CL = total body clearance from plasma;
$C_{max}$ = maximum (peak) plasma drug concentration;
CV = coefficient of variation;
PK = pharmacokinetic;
$t_{1/2}$ = elimination half-life;
$t_{max}$ = time to reach maximum (peak) plasma concentration following drug administration;
$V_{ss}$ = apparent volume of distribution at steady state after intravenous administration
aMedian (minimum, maximum) presented As the sample size in this study was large, with an aim to enroll an equal number of males and females, it provided the opportunity to evaluate the effect of gender on PK. Results of the ANOVA indicated that ceftolozane AUC was 22% higher in females compared to males while tazobactam AUC was 19% higher. This increase in AUC was not considered clinically meaningful since ceftolozane/tazobactam doses up to 3 g administered every 8 hours were safe and well tolerated. Further, as shown in FIG. 33, which presents body weight adjusted CL values for 28 males and 23 females, no clinically relevant gender differences were observed in the PK of ceftolozane/tazobactam at the proposed therapeutic dose of 1.5 g ceftolozane/tazobactam. The results for M1 metabolite of tazobactam as well as at the supratherapeutic dose also were in agreement with this observation.

Pharmacokinetic Conclusions:

The $C_{max}$ and AUC were dose proportional across therapeutic and supratherapeutic doses of ceftolozane/tazobactam, with the 4.5 g supratherapeutic dose providing a large margin of safety regarding ECG changes.

Gender did not influence the PK of ceftolozane to a clinically relevant extent.

Example 14: Pharmacokinetic-Pharmacodynamic Target Attainment Analyses Supporting the Selection of In Vitro Susceptibility Test Interpretive Criteria for Ceftolozane/Tazobactam Against Enterobacteriaceae Abstract Objectives:

The objective of these analyses was to provide support for the selection of susceptibility breakpoints for ceftolozane/tazobactam (TOL/TAZ) against Enterobacteriaceae, including those isolates producing extended-spectrum beta-lactamase (ESBL).

Methods:

Using the fixed and random effects parameter estimates and variance-covariance matrix from previously-developed population PK models for TOL and TAZ, plasma concentration-time profiles were generated for simulated patients in 5 renal function categories (1000 patients/category). Using non-clinical PK-PD targets, PK-PD target attainment by MIC value was assessed for simulated patients in each renal function category in the context of MIC distributions for TOL/TAZ against the Enterobacteriaceae, including the ESBL-producing isolates, collected during the course of the clinical trial program. For TOL, free-drug % T>MIC targets of 24.8 and 32.2, which were associated with net bacterial stasis and 1–$\log_{10}$ CFU reduction from baseline in a neutropenic murine-thigh infection model, were assessed. For TAZ, a free-drug % T>threshold (½ of the TOL/TAZ MIC) of 65.9, which was identified in an in vitro infection model, was assessed. For the ESBL-negative isolates, the percentage of simulated patients that attained the above-described TOL targets was calculated. For ESBL-positive isolates, a multi-step, sequential algorithm was used to assess PK-PD target attainment that required sufficient TOL and TAZ exposures.

Results:

As expected, the percentage of simulated patients achieving free-drug PK-PD targets for TOL (% T>MIC) and TAZ (% T>threshold) increased as the MIC value or the magnitude of the target decreased. Table 32 shows the highest MIC value for which target attainment was ≥80% by renal function category and dose regimen.

Conclusions:

These data will be used as susceptibility breakpoint decision support.

Introduction

The U.S. FDA and consensus organizations, such as the Clinical Laboratory Standards Institute (CLSI) and European Committee on Antimicrobial Susceptibility Testing (EUCAST) establish in vitro susceptibility test interpretive criteria (i.e., susceptibility breakpoints).

Clinical microbiology laboratories provide physicians qualitative test results using susceptibility breakpoints (i.e., susceptible, intermediate, or resistant) as a guide to effective antimicrobial chemotherapy.

Ceftolozane/tazobactam (TOL/TAZ), which has potent in vitro activity against a wide variety of Gram-negative pathogens, including multi-drug resistant *Pseudomonas aeruginosa*, is being developed as a first-line intravenous (IV) therapy for the treatment of serious Gram-negative bacterial infections, including complicated urinary tract infections and intra-abdominal infections.

Pharmacokinetic-pharmacodynamic (PK-PD) target attainment analyses described herein were carried out to provide support for the selection of in vitro susceptibility test interpretive criteria for TOL/TAZ against Enterobacteriaceae.

Objectives

The objectives of these analyses were to conduct PK-PD target attainment analyses to provide support for the following:

TABLE 30

TOL/TAZ Dosing Regimens by Renal Function Group

| | TOL/TAZ dosing regimens (mg) | |
|---|---|---|
| Renal function group | 1000/500 TOL/TAZ | 2000/1000 TOL/TAZ |
| High normal renal function (150 < to ≤ 200 mL/min); | 1000/500 | 2000/1000 |
| Normal renal function (90 < to ≤ 150 mL/min); | 1000/500 | 2000/1000 |
| Mild renal impairment (50 < to ≤ 90 mL/min); | 1000/500 | 2000/1000 |
| Moderate renal impairment (29 ≤ to ≤ 50 mL/min); | 500/250 | 1000/500 |
| Severe renal impairment (15 ≤ to < 29 mL/min) | 250/125 | 500/250 |

TABLE 31

Parameter Estimates and Associated Precision from the Population PK Model for TOL and TAZ

| | TOL[e] | | | | TAZ[f] | | | |
|---|---|---|---|---|---|---|---|---|
| | PK parameter | | Interindividual variability | | PK parameter | | Interindividual variability | |
| Parameter | Population estimate | Relative standard error (%) | Estimate (%) | Relative standard error (%) | Population estimate | Relative standard error (%) | Estimate (%) | Relative standard error (%) |
| CL (L/hr)[a] | 5.14 | 2.30 | 34.3 | 3.91 | 18.0 | 3.39 | 50.2 | 4.98 |
| Exponent of the relationship between CLcr and CL | 0.75 | 6.01 | NA | NA | 0.67 | 11.1 | NA | NA |
| Proportional shift in CL for infected patients | 1.26 | 16.5 | NA | NA | NA | NA | NA | NA |
| $V_c$ (L)[b] | 11.8 | 2.4 | 34.0 | 4.80 | 14.2 | 4.45 | 52.5 | 6.14 |
| Exponent of the relationship between weight and CL | 0.76 | 13.9 | NA | NA | NA | NA | NA | NA |
| Proportional shift in $V_c$ for infected patients | 1.37 | 13.0 | NA | NA | 1.47 | 21.9 | NA | NA |
| $CL_d$ (L/hr)[c] | 0.884 | 3.79 | 0 (fixed) | NA | 3.13 | 4.59 | 0 (fixed) | NA |
| $V_c$ (L)[d] | 2.88 | 2.15 | 0 (fixed) | NA | 4.29 | 2.61 | 0 (fixed) | NA |
| Proportional residual error (%) | 19.3 | 1.14 | NA | NA | 26.0 | 1.64 | NA | NA |

[a]CL is the central clearance (L/hr).
[b]$V_c$ is the central volume of distribution (L). $CL_d$ is the intercompartmental clearance (L/hr).
[c]$V_c$ is the peripheral volume of distribution (L).
[e]CL (infected patients) = 5.14 · (CLcr/109)$^{0.75}$ · 1.26. $V_c$ (infected patients) = 11.8 · (weight/74)$^{0.75}$ · 1.37.
[f]CL = (8.0 · (CLcr/115)$^{0.67}$. $V_c$ (infected patients) = 14.2 · 1.47.
NA = not applicable.

Recommendations for in vitro susceptibility test interpretive criteria for TOL/TAZ against Enterobacteriaceae (beta-lactamase producers and non-producers); and Selected TOL/TAZ dosing regimens by renal function groups.

Methods

Monte Carlo Simulation

Using SAS Version 9.2, Monte Carlo simulation was conducted to generate 5,000 patients, with 1,000 in each of five renal function categories. These categories (and corresponding creatinine clearance (CLcr) ranges) are shown in Table 30.

Using the fixed and random effects parameter estimates and variance-covariance matrix from previously-developed population PK models for TOL and TAZ (Table 31), plasma concentration-time profiles were generated for simulated patients in each renal function group following administration of TOL/TAZ 1000 and 2000 mg dosing regimens over 1 h every 8 h (q8h) adjusted for renal function (Table 30).

PK-PD Target Attainment Analyses

Using non-clinical PK-PD targets, PK-PD target attainment by MIC was assessed for simulated patients in each renal function group in the context of MIC distributions for TOL and/or TOL/TAZ against the Enterobacteriaceae, including the ESBL-producing isolates, which was comprised of data from 4 studies involving patients with either complicated urinary tract infections or complicated intra-abdominal infections.

For TOL, the percentage of the dosing interval that concentrations were above the MIC (% T>MIC) was the PK-PD measure most associated with efficacy.

Results of the PK-PD analyses based on data from a neutropenic murine-thigh model demonstrated that TOL free-drug % T>MIC targets of 24.8 and 32.2 were associated with net bacterial stasis and a 1–$\log_{10}$ CFU reduction from baseline, respectively.

In addition to assessing PK-PD target attainment for these targets, free-drug % T>MIC targets of 40, 50, and 60 were also assessed.

For TAZ, the PK-PD measure associated with efficacy was the percentage of the dosing interval that TAZ concentrations were above a threshold concentration (% T>threshold).

Data from a PK-PD in vitro infection model demonstrated that the optimal value for the TAZ threshold concentration was one-half the TOL/TAZ MIC value.

For the assessment of PK-PD target attainment, the TAZ target, free-drug % T>threshold of 65.9, was evaluated.

For the ESBL-negative isolates, the percentage of simulated patients that attained the above-described TOL targets during the dosing interval at steady-state for TOL/TAZ MIC values (0.06 to ≥32 mg/L) was determined for each TOL/TAZ dosing regimen within each renal function group.

For ESBL-positive isolates, a multi-step, sequential algorithm was used to assess PK-PD target attainment by MIC value for each TOL/TAZ dosing regimen evaluated within each renal function group, which took into account both TOL and TAZ PK-PD target attainment.

Results

Results of the PK-PD target attainment analysis for TOL/TAZ 1000/500 mg q8h are shown in FIG. 34. Similar such data for simulated patients following administration of TOL/TAZ 2000/1000 mg q8h dosing regimens are shown in FIG. 35.

Potential PK-PD cutoff values based on a threshold of ≥80% PK-PD target attainment are provided in Table 32, stratified by dosing regimen and renal impairment category In order to achieve percent probabilities of PK-PD target attainment by MIC of ≥90%, PK-PD MIC cut-off values would decrease by two dilution steps.

TABLE 32

PK-PD MIC Cut-Off Values Based Upon Achieving Percent Probabilities Target Attainment by MIC Of ≥80% For TOL/TAZ Dosing Regimens Against Enterobacteriaceae by Renal Function Category

| Renal function category[a] | TOL/TAZ dosing regimen (mg)[b] | MIC (mg/L) | Percentage of simulated patients achieving free-drug % T > MIC targets ≥24.8/≥32.2[c,d] |
|---|---|---|---|
| High normal | 1000/500 | 2 | 80.8/79.3 |
|  | 2000/1000 | 4 | 83.0/81.1 |
| Normal | 1000/500 | 4 | 81.6/80.9 |
|  | 2000/1000 | 8 | 82.4/81.6 |
| Mild | 1000/500 | 8 | 81.5/81.1 |
|  | 2000/1000 | 16 | 80.4/80.2 |
| Moderate | 500/250 | 8 | 80.1/79.4 |
|  | 1000/500 | 8 | 85.6/85.6 |
| Severe | 250/125 | 4 | 84.6/84.6 |
|  | 500/250 | 8 | 85.3/85.2 |

[a]Renal function categories were defined as follows: high normal renal function = creatinine clearance (CLcr) <150 to ≤200 mL/min; normal renal function = CLcr <90 to ≤150 mL/min; mild renal impairment = CLcr <50 to ≤90; moderate renal impairment = CLcr ≤29 to ≤80; severe renal impairment = CLcr ≤15 to <29.
[b]TOL/TAZ administered via 1 h intravenous infusion: Q8h.
[c]A free-drug % T > threshold of 65.9 for TAZ was considered when required for on ESBL-producing isolate.
[d]Represents the highest MIC associated with ≥80% PK-PD target attachment.

Conclusion

The results of the PK-PD target attainment analyses for 1000/500 and 2000/1000 mg TOL/TAZ and dosing regimens adjusted for renal function provide support for in vitro susceptibility test interpretive criteria for TOL/TAZ against Enterobacteriaceae.

Example 15: Summary of Modified Methods of Administering Ceftolozane/Tazobactam in Patients with Mild, Moderate and Severe Renal Impairment Ceftolozane/tazobactam is excreted primarily by the renal route. Consistent with this observation, population pharmacokinetic (PPK) analysis showed that clearance from plasma (CL) depends on $CL_{CR}$ (creatinine clearance) and that $CL_{CR}$ is the major determinant of variability in CL.

The extent of ceftolozane exposure increases with decreasing renal function. Although exposure increases with decreasing renal function, no clinically meaningful differences are observed in the PK of subjects with mild renal impairment compared to those with normal renal function, indicating that dosage adjustment is not required in subjects with mild renal impairment. In subjects with moderate renal impairment, exposure approximately doubles relative to that in subjects with normal renal function. The results from a dedicated study in otherwise healthy subjects with severe renal impairment demonstrate that exposure in subjects with severe renal impairment is significantly increased and t½ is prolonged (Table 57).

A Monte Carlo simulation analysis was conducted with $CL_{CR}$ cut-offs similar to the Sponsor-proposed cut-off values. Based on this analysis, a 2-fold and 4-fold dose reduction to 750 and 375 mg ceftolozane/tazobactam administered as an IV 1-hour infusion every 8 hours in subjects with moderate and severe renal impairment, respectively, compared to the 1.5 g ceftolozane/tazobactam dose in subjects with normal renal function, produces sufficient drug concentrations to cover target pathogens with a Probability of Target Attainment (PTA) of more than 97% for a conservative % T>MIC of 40% above an MIC of up to 8 μg/mL. In general, with an increase in t½ as renal function declines, the PTA is increased.

Additionally, based on exposure values in subjects with severe renal impairment, a reduced dose of 375 mg ceftolozane/tazobactam results in a mean AUC for ceftolozane and tazobactam of 269 and 26.2 μg·h/mL, respectively. For tazobactam, this estimated exposure from a dose of 125 mg in subjects with severe renal impairment not on hemodialysis is similar to that achieved with 500 mg tazobactam in subjects with normal renal function (23.8 μg·h/mL). For ceftolozane, this estimated exposure (269 μg·h/mL) from a dose of 250 mg in subjects with severe renal impairment is approximately 1.4 fold higher than that achieved with doses of 1 g ceftolozane in subjects with normal renal function. This increased ceftolozane exposure is below the mean AUCτ, ss of approximately 300 μg·h/mL after q8h dosing for 10 days that is demonstrated to be safe.

With an increase in t½ as renal functional declined, the accumulation of the M1 metabolite of tazobactam (see, e.g., J Clin Pharmacol. 1994 December; 34(12): 1208-17) increased but metabolite levels were projected to still remain several fold below that observed with long-term clinical use of Zosyn (see e.g. Expert Opinion on Drug Metabolism & Toxicology 2010 6:8, 1017-1031).

From a recommended dose of 375 mg ceftolozane/tazobactam every 8 hours, the estimated AUC of the tazobactam M1 metabolite was higher than that in subjects with normal renal function receiving 1.5 g ceftolozane/tazobactam. However, the estimated steady-state Cmax and AUC of the M1 metabolite with the recommended 375 mg every 8 hours ceftolozane/tazobactam dose in subjects with severe renal impairment is still lower than that from the clinically recommended dose of Zosyn in subjects with severe renal impairment (Table 46). Accordingly, the dose in subjects with severe renal impairment should be reduced to ¼th (i.e., 375 mg ceftolozane/tazobactam every 8 hours) of that in subjects with normal renal function.

TABLE 33

Geometric Mean (CV %) Pharmacokinetic Parameters After an Intravenous 1-Hour Infusion in Subjects with Mild, Moderate, and Severe Renal Impairment, and Subjects (Subjects with Infection and Healthy Volunteers) with Normal Renal Function

| | Study CXA-101-02 | | Study CXA-201-02 | | | | Study CXA-REN-11-01 |
|---|---|---|---|---|---|---|---|
| Ceftolozane/Tazobactam Dose (mg): | Normal 1000/0 | Mild 1000/0 | Normal 1000/500 | Mild 1000/500 | Normal 1000/500 | Moderate$_{(a)}$ 500/250 | Severe$^a$ 250/125 |
| Ceftolozane PK | | | | | | | |
| $C_{max}$ (μg/mL) | 68.2 (22) | 72.1 (24) | 76.0 (13) | 98.7 (25) | 76.1 (52) | 42.5 (25) | 24.3 (28) |
| $AUC_\infty$ (μg · h/mL) | 219 (15) | 243 (17) | 244 (21) | 307 (11) | 224 (26) | 278 (38) | 263 (23) |
| $t_{1/2}$ (h) | 2.74 (7) | 2.97 (14) | 3.21 (5) | 3.24 (11) | 2.92 (17) | 5.85 (45) | 10.9 (24) |
| Tazobactam PK | | | | | | | |
| $C_{max}$ (μg/mL) | NA | NA | 16.4 (9) | 22.1 (16) | 20.0 (28) | 13.2 (7) | 7.45 (22) |
| $AUC_\infty$ (μg · h/mL) | NA | NA | 26.8 (17) | 34.5 (14) | 32.4 (16) | 32.4 (21) | 25.4 (27) |
| $t_{1/2}$ (h) | NA | NA | 1.04 (25) | 1.16 (22) | 1.04 (25) | 1.78 (20) | 2.5 (22) |
| Tazobactam M1 Metabolite | | | | | | | |
| $C_{max}$ (μg/mL) | NA | NA | 0.79 (15) | 1.2 (15) | 1.06 (44) | 1.5 (91) | 1.1 (20) |
| $AUC_\infty$ (μg · h/mL) | NA | NA | 8.57 (23) | 11.6 (8) | 9.7 (41) | 22.6 (101) | 29.0 (30) |
| $t_{1/2}$ (h) | NA | NA | 4.12 (14) | 4.0 (8) | 3.43 (22) | 6.67 (27) | 11.6 (29) |

Abbreviations: $AUC_\infty$ = area under the plasma concentration-time curve from time zero to infinity;
$C_{max}$ = maximum (peak) plasma drug concentration;
$t_{1/2}$ = elimination half-life;
TAZ = tazobactam;
TOL = ceftolozane
Note:
For Study CXA-101-02: normal impairment = $CL_{CR}$ > 80 mL/min and mild impairment = $CL_{CR}$ ≥ 50 to ≤ 80 mL/min; for Study CXA-201-02: mild impairment = $CL_{CR}$ ≥ 50 to ≤ 80 mL/min and moderate impairment = $CL_{CR}$ ≥ 30 to < 50 mL/min; for Study CXA-REN-11-01: severe impairment = $CL_{CR}$ < 30 mL/min.
$_{(a)}$Data are dose normalized to recommended dose for a 2- and 4-fold dose reduction in moderate and severe renal impairment, respectively, relative to that in subjects with normal renal function.

TABLE 34

Recommended Dosing of Ceftolozane/Tazobactam in Subjects with Renal Insufficiency (as Total g Ceftolozane/Tazobactam)

| Renal Impairment Category | Creatinine Clearance (mL/min) | Recommended Dose of Ceftolozane/Tazobactam | Frequency of Dosing |
|---|---|---|---|
| Normal and Mild | >50 | 1.5 g | q8h |
| Moderate | 30-50 | 750 mg$^{(a)}$ | q8h |
| Severe | 15-29 | 375 mg$^{(b)}$ | q8h |
| ESRD on HD | <15 | 750 mg$^a$ loading dose immediately following the first dialysis followed by 450 mg$^{(c)}$ maintenance dose q24h | q24h |

Abbreviations:
ESRD = end-stage renal disease;
HD = hemodialysis;
qxh = every x hours
$^{(a)}$500/250 mg ceftolozane/tazobactam
$^{(b)}$250/125 mg ceftolozane/tazobactam
$^{(c)}$300/150 mg ceftolozane/tazobactam

TABLE 35

Probability of Target Attainment Rates for 40% T > MIC based on MIC levels of 8 μg/mL for Various Assumptions on Dose, Dosing Interval, and Renal Function

| Ceftolozane/Tazobactam (mg) | Dosing Interval (h) | 40% T > MIC |
|---|---|---|
| Normal Renal Function ($CL_{CR}$ ≥90 mL/min) | | |
| 250/125 | 8 | 10.9 |
| 500/250 | 8 | 68.0 |
| 1000/500 | 8 | 97.6 |
| 250/125 | 12 | 0.4 |
| 500/250 | 12 | 15.9 |
| 1000/500 | 12 | 63.4 |
| Mild Renal Impairment ($CL_{CR}$ 50-89 mL/min) | | |
| 250/125 | 8 | 50.6 |
| 500/250 | 8 | 98.2 |
| 1000/500 | 8 | 100 |
| 250/125 | 12 | 7.1 |
| 500/250 | 12 | 65.3 |
| 1000/500 | 12 | 94.5 |
| Moderate Renal Impairment ($CL_{CR}$ 30-49 mL/min) | | |
| 250/125 | 8 | 90.6 |
| 500/250 | 8 | 100 |
| 1000/500 | 8 | 100 |
| 250/125 | 12 | 38.4 |
| 500/250 | 12 | 94.9 |
| 1000/500 | 12 | 99.2 |

TABLE 35

Probability of Target Attainment Rates for 40% T > MIC based on MIC levels of 8 µg/mL for Various Assumptions on Dose, Dosing Interval, and Renal Function (Continued)

| Ceftolozane/Tazobactam (mg) | Dosing Interval (h) | 40% T > MIC |
|---|---|---|
| Severe Renal Impairment (CL$_{CR}$ <30 mL/min) | | |
| 250/125 | 8 | 99 |
| 500/250 | 8 | 100 |
| 1000/500 | 8 | 100 |
| 250/125 | 12 | 81.5 |
| 500/250 | 12 | 99.5 |
| 1000/500 | 12 | 100 |

Abbreviations:
% T > MIC = time as percentage of dosing interval the drug concentration exceeds the MIC;
MIC = minimum inhibitory concentration

TABLE 36A

Mean (CV %) Pharmacokinetic Parameters After Intravenous 1-hour Infusion of Ceftolozane/Tazobactam in Subjects with Severe Renal Impairment and Healthy Subjects with Normal Renal Function

| Analyte PK Parameters | Severe Renal Impairment[a] CXA-REN-11-01[b] (n = 6) 250/125 mg Single Dose | Healthy Subjects CXA-QT-10-02 (n = 51) 1000/500 mg Single Dose | Healthy Subjects CXA-MD-11-07 (n = 7) 2000/1000 mg q8h |
|---|---|---|---|
| Ceftolozane | | | |
| $C_{max}$ (µg/mL) | 25 (28) | 66.5 (19) | 112 (13) |
| AUC (µg · h/mL) | 269 (23)(c) | 186 (18)[b] | 300 (10)(d) |
| $t_{1/2}$ (h) | 11.1 (24) | 2.29 (15) | 2.8 (14) |
| Tazobactam | | | |
| $C_{max}$ (µg/mL) | 7.6 (22) | 18.6 (23) | 25.8 (15) |
| AUC (µg · h/mL) | 26.2 (27)[b] | 23.8 (24)[b] | 40.5 (13)[c] |
| $t_{1/2}$ (h) | 2.6 (22) | 0.870 (18) | 1.0 (18) |
| Tazobactam M1 metabolite | | | |
| $C_{max}$ (µg/mL) | 1.1 (20) | 1.02 (54) | 1.8 (20) |
| AUC (µg · h/mL) | 26.9 (29)[b] | 7.92 (47)[b] | 11.9 (19)[c] |
| $t_{1/2}$ (h) | 12 (29) | 3.24 (29) | 4 (8) |

Abbreviations:
AUC = area under the plasma concentration-time curve;
AUC$_\infty$ = area under the plasma concentration-time curve from time zero to infinity;
AUC$_{\tau\,ss}$ = area under the plasma concentration-time curve for a dosing interval (8 hours) at steady state;
$C_{max}$ = maximum (peak) plasma drug concentration;
q8h = every 8 hours;
$t_{1/2}$ = elimination half-life: time required for a 50% decrease in the concentration of the drug

[a] Severe renal impairment = CL$_{CR}$ < 30 mL/min.
[b] Estimated from a dose of 750 mg ceftolozane/tazobactam assuming linear pharmacokinetics.
[c] AUC$_\infty$ from a single dose
(d) AUC$_{\tau\,ss}$ at steady-state on Day 10

TABLE 36B

Mean (CV %) Plasma Tazobactam M1 Metabolite Pharmacokinetic Parameters Comparison in Subjects with Severe Renal Impairment: 2.250 g Zosyn versus 250/125 mg Ceftolozane/Tazobactam

| | Tazobactam M1 metabolite | |
|---|---|---|
| PK parameters | Zosyn[a] (2.25 g) | Ceftolozane/tazobactam[b] (250/125 mg) |
| $C_{max}$ (μg/mL) | 5.2 (30) | 1.1 (20) |
| $AUC_\infty$ (μg · h/mL) | 192 (66) | 26.9 (29) |

Abbreviations:
$AUC_\infty$ = area under the plasma concentration-time curve from time zero to infinity;
$C_{max}$ = maximum (peak) plasma drug concentration;
PK = pharmacokinetic
[a]$AUC_\infty$ and $C_{max}$ for a tazobactam dose of 375 mg from Zosyn (3.375 g) dose normalized to Zosyn dose of 2.25 g in severe renal impairment
[b]From Study CXA-REN-11-01; Estimated from a dose of 750 mg ceftolozane/tazobactam assuming linear PK

Example 16: Pharmacokinetics of CXA-101, Tazobactam, and the M-1 Metabolite of Tazobactam in Subjects with End Stage Renal Disease on Hemodialysis The plasma concentration versus time plots for CXA-101, tazobactam, and the M-1 metabolite during non-HD on Study Day 1 for subjects with ESRD are shown in FIGS. 36, 37, and 38, respectively. The 0.5 and 1.0 hour plasma samples of two subjects (Subject 001-0201 and Subject 001-0205) appeared to have been mislabeled, since a higher concentration of CXA-101 and tazobactam were seen at 0.5 hours than at 1.0 hour. However, since this did not affect the PK parameters (AUC, CL etc.) to a substantial degree, the concentrations were used as reported. The concentrations of CXA-101 appeared to decline in a bi-exponential manner in most subjects and were above the LLOQ for the entire duration of the sampling interval. The concentrations of tazobactam were above the quantifiable limits for between 12 and 48 hours post-dose administration and appeared to decline in a bi-exponential manner. The plasma concentrations of the M-1 metabolite increased in plasma but did not appear to decline at the end of the sampling interval. Therefore, no PK parameters (AUC, $t_{1/2}$) for the M-1 metabolite were calculated.

The PK parameters for CXA-101, tazobactam, and the M-1 metabolite during non-HD for subjects with ESRD are presented in Table 37 below. The median $C_{max}$ of CXA-101 and tazobactam in plasma were 44.2 μg/mL and 20.2 μg/mL, respectively. The median elimination half-lives of CXA-101 and tazobactam were 40.5 and 4.21 hours, respectively. Since the sampling for CXA-101 was conducted over a period of 48 hours, which is approximately 1 half-life, the estimates of $t_{1/2}$, CL, and $V_{ss}$ parameters for CXA-101 should be interpreted with caution.

TABLE 37

Median (Range) Pharmacokinetic Parameters for CXA-101, Tazobactam, and the M-1 Metabolite of Tazobactam During Non-Hemodialysis Following Administration of the First Dose of CXA-201 on Study Day 1 in Subjects with ESRD

| Parameter (Units) | CXA-101 | Tazobactam | M-1 Metabolite |
|---|---|---|---|
| Half-Life (hr) | 40.5 (20.8-58.1) | 4.21 (3.38-9.10) | ND |
| $C_{max}$ (μg/mL) | 44.2 (30.2-60.6) | 20.2 (15.9-30.3) | 10.1 (2.9-14.2) |
| $T_{max}$ (hr) | 1.0 (0.5-1.0) | 1.0 (0.5-1.0) | 30.0 (12.0-48.0) |

TABLE 37-continued

Median (Range) Pharmacokinetic Parameters for CXA-101, Tazobactam, and the M-1 Metabolite of Tazobactam During Non-Hemodialysis Following Administration of the First Dose of CXA-201 on Study Day 1 in Subjects with ESRD

| Parameter (Units) | CXA-101 | Tazobactam | M-1 Metabolite |
|---|---|---|---|
| $AUC_{0-t}$ (μg * hr/mL) | 903 (372-1233) | 107 (45.3-169) | 389 (99.8-538) |
| $AUC_{0-\infty}$ (μg * hr/mL) | 1629 (466-2750) | 109 (46.0-170) | ND |
| CL (L/hr) | 0.3 (0.2-1.1) | 2.4 (1.5-5.4) | ND |
| $V_{ss}$ (L) | 17.9 (11.9-31.7) | 15.2 (11.5-27.1) | ND |

ND = Not determined

Since insufficient urine samples were collected following the administration of the first dose of study drug on Study Day 1 and over a limited time period, no analysis to determine the amount of CXA-101, tazobactam, and the M-1 metabolite excreted in the urine was conducted. Consequently, the $CL_R$ of CXA-101 and tazobactam in these subjects could not be determined.

The plasma concentration versus time profiles for CXA-101, tazobactam, and the M-1 metabolite in subjects with ESRD during HD following the second dose of study drug are presented in FIGS. 39, 40, and 41, respectively. Dialysis started 2 hours post-start of the infusion of study drug and lasted for 3 or 4 hours, depending on the subject. The concentrations of the 3 analytes increased following the start of the infusion and declined rapidly at the start of dialysis. The concentrations continued to decline during dialysis and rebounded slightly at the end of dialysis followed by a slow decline over the remainder of the sampling interval.

The plasma PK parameters for CXA-101, tazobactam, and the M-1 metabolite for subjects with ESRD during HD are summarized in Table 38 below. Sampling continued beyond a second HD session, but only plasma concentrations of samples collected between one dialysis period (0-44 hours) were used in the determination of the PK parameters. The median $C_{max}$ for CXA-101, tazobactam, and the M-1 metabolite were 41.1, 14.9, and 10.9 μg/mL, respectively. The median elimination half-life of CXA-101 in these subjects was 43.2 hours. Since sampling was conducted for approximately 1 half-life, other PK parameters such as $AUC_{0-\infty}$, CL, and $V_{ss}$ are not reported. Due to the nature of the plasma concentration versus time profile, the PK parameters for the M-1 metabolite ($t_{1/2}$ and AUC) were not calculated.

TABLE 38

Median (Range) Pharmacokinetic Parameters for CXA-101, Tazobactam, and the M-1 Metabolite of Tazobactam Following Administration of the Second Dose of CXA-201 on Study Day 4 in Subjects with ESRD During HD

| Parameter (Units) | CXA-101 | Tazobactam | M-1 Metabolite |
|---|---|---|---|
| Half-Life (hr) | 43.2 (32.8-56.9) | 5.0 (1.9-8.5) | 368.4[a] |
| $C_{max}$ (μg/mL) | 41.1 (17.5-56.4) | 14.9 (7.2-22.9) | 10.9 (2.2-15.7) |

TABLE 38-continued

Median (Range) Pharmacokinetic Parameters for CXA-101, Tazobactam, and the M-1 Metabolite of Tazobactam Following Administration of the Second Dose of CXA-201 on Study Day 4 in Subjects with ESRD During HD

| Parameter (Units) | CXA-101 | Tazobactam | M-1 Metabolite |
|---|---|---|---|
| $T_{max}$ (hr) | 1.0 (1.0-1.0) | 1.0 (1.0-1.0) | 1.5 (0.5-24.0) |
| $AUC_{0-t}$ (µg * hr/mL) | 298 (179-437) | 37.1 (19.9-57.8) | 181.8 (78.0-254.8) |

[a]Based on data from 1 subject.

A separate analysis was conducted to determine the PK parameters of CXA-101, tazobactam, and the M-1 metabolite from the start of the second study drug infusion to the end of dialysis. This was conducted in order to determine the contribution of HD on the removal of the 3 analytes. The plasma concentration versus time profiles for CXA-101, tazobactam, and the M-1 metabolite during this period are shown in FIGS. 42, 43 and 44, respectively.

The PK parameters for CXA-101, tazobactam, and the M-1 metabolite following administration of the second dose of CXA-201 on Study Day 4 for subjects with ESRD during HD are presented in Table 39 below. Concentrations of CXA-101, tazobactam, and the M-1 metabolite declined rapidly following the start of dialysis with a median half-life of 1.13, 0.91, and 1.80 hours, respectively. Maximum concentrations of the 3 analytes decreased rapidly during HD indicating that greater than 90% of the administered dose was removed by dialysis. The concentrations at the last sampled time-point before the end of dialysis, $C_{last}$, were approximately 14-, 32-, and 26-fold lower, respectively, than the concentrations seen at $C_{max}$, indicating a significant contribution of dialysis in the removal of the administered dose.

TABLE 39

Median (Range) of Pharmacokinetic Parameters for CXA-101, Tazobactam, and the M-1 Metabolite of Tazobactam Following Administration of the Second Dose of CXA-201 on Study Day 4 in Subjects with ESRD During HD (Start of Infusion-End of Dialysis)

| Parameter | CXA-101 | Tazobactam | M-1 Metabolite |
|---|---|---|---|
| Half-Life (hr) | 1.13 (0.89-1.79) | 0.91 (0.66-1.35) | 1.80 (0.68-2.38) |
| $C_{max}$ (µg/mL) | 41.1 (17.5-56.4) | 14.9 (7.19-22.9) | 10.9 (1.26-15.7) |
| $T_{max}$ (hr) | 1 (1-1) | 1.00 (1.00-1.00) | 1.50 (0.50-1.50) |
| $C_{last}$ (µg/mL) | 2.88 (1.23-4.48) | 0.46 (0.13-1.14) | 0.41 (0.26-1.11) |
| $AUC_{0-t}$ (µg * hr/mL) | 97.1 (39.2-115) | 28.9 (14.0-44.0) | 26.8 (3.77-32.0) |
| $AUC_{0-\infty}$ (µg * hr/mL) | 99.8 (46.9-122) | 29.4 (15.7-45.2) | 31.0 (23.4-34.9) |

TABLE 39-continued

Median (Range) of Pharmacokinetic Parameters for CXA-101, Tazobactam, and the M-1 Metabolite of Tazobactam Following Administration of the Second Dose of CXA-201 on Study Day 4 in Subjects with ESRD During HD (Start of Infusion-End of Dialysis)

| Parameter | CXA-101 | Tazobactam | M-1 Metabolite |
|---|---|---|---|
| $CL_{ss}$ (L/hr) | 5.01 (4.11-10.7) | 8.53 (5.53-15.9) | ND |
| $V_{ss}$ (L) | 7.26 (5.71-20.5) | 10.4 (6.61-25.1) | ND |

ND = Not determined

The summary of $CL_D$ of CXA-101, tazobactam, and M-1 metabolite in subjects with ESRD during HD is provided in Table 40. Briefly, the total amount of analyte recovered in the dialysate was computed and the ratio of the total amount recovered in the dialysate and the plasma AUC during the period of dialysis yielded the $CL_D$. Dialysate concentrations and the corresponding volumes were available from 0-3 hours in Subject 001-0201, Subject 001-0202, and Subject 001-0204. In these subjects, the plasma AUC from 0-3 hours was used in the computation of the $CL_D$. In the remaining three subjects, plasma AUC from 0-4 hours was utilized.

The median $CL_D$ for CXA-101, tazobactam, and the M-1 metabolite was 5.75, 4.39, and 4.59 L/hr, respectively. In 3 subjects (Subjects 001-0201, 001-0202, and 001-0204), the cumulative amounts of CXA-101 recovered in the dialysate were greater than the administered dose. The total volumes of dialysate collected are an approximation. Any differences in the volume of dialysate collected can impact the calculated recovery of the drug from the dialysate. Additionally, since the plasma concentrations reflect any carryover from the previously administered dose on Day 1, the amount in the dialysate can fluctuate significantly.

TABLE 40

Summary of Dialysis Clearance for CXA-101, Tazobactam, and the M-1 Metabolite of Tazobactam Following Hemodialysis in Subjects with ESRD on HD (Median and Range)

| Analyte | Dose (mg) | Amount in Dialysate (mg) | $AUC_{t0-t1}$ (µg * hr/mL) | $CL_D$ (L/hr) |
|---|---|---|---|---|
| CXA-101 | 500 | 438 (131-709) | 87 (39-102) | 5.75 (1.78-8.88) |
| Tazobactam | 250 | 111 (33-185) | 26.4 (13.9-40.5) | 4.39 (1.36-6.29) |
| M-1 Metabolite | — | 136 (36-220) | 27.5 (3.8-32.7) | 4.59 (1.44-11.6) |

The percent reduction in plasma concentrations for CXA-100, tazobactam, and the M-1 metabolite and is shown in Table 41 below. The median RDHD for CXA-101, tazobactam, and the M-1 metabolite was 92%, 95%, and 93%, respectively, indicating significant removal by HD.

TABLE 41

Summary of Percent of CXA-101, tazobactam, and the M-1 Metabolite of Tazobactam Removed During Hemodialysis in Subjects with ESRD on HD (Median and Range)

| Analyte | Concentration before HD (µg/mL) | Concentration after HD (µg/mL) | Change in Concentration | Percent Removed |
|---|---|---|---|---|
| CXA-101 | 34.4 (13.2-49.3) | 2.9 (1.2-4.5) | 32.3 (10.2-44.8) | 91.5 (72.3-96.3) |
| Tazobactam | 10.8 (3.9-18.7) | 0.5 (0.1-1.1) | 10.5 (3.6-17.6) | 95.3 (83.8-98.6) |
| M-1 Metabolite | 9.4 (1.4-14.9) | 0.4 (0.3-1.1) | 9.1 (0.5-14.5) | 93.4 (38.1-97.7) |

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material set forth herein is only incorporated to the extent that no conflict arises between that incorporated material and the present disclosure material.

What is claimed is:

1. A method of treating pneumonia in a human patient with end stage renal disease on hemodialysis, said method comprising administering to the patient a single loading dose comprising ceftolozane or a pharmaceutically acceptable salt thereof and tazobactam or a pharmaceutically acceptable salt thereof that provides a 2:1 ratio of ceftolozane active to tazobactam active, followed by administering to the patient maintenance doses comprising ceftolozane or a pharmaceutically acceptable salt thereof and tazobactam or a pharmaceutically acceptable salt thereof that provides a 2:1 ratio of ceftolozane active to tazobactam active, wherein the amount of the ceftolozane or pharmaceutically acceptable salt thereof in the loading dose is greater than the amount of the ceftolozane or pharmaceutically acceptable salt thereof in the maintenance doses, and the amount of the tazobactam or pharmaceutically acceptable salt thereof in the loading dose is greater than the amount of the tazobactam or pharmaceutically acceptable salt thereof in the maintenance doses.

2. The method of claim 1, wherein the maintenance doses are delivered intravenously about every 8 hours.

3. The method of claim 1, wherein the loading dose and maintenance doses are administered over a dosing schedule that provides an unbound concentration of ceftolozane active of at least 8 micrograms/mL for at least 30% of the time between successive treatment days.

4. The method of claim 3, wherein the dosing schedule provides an unbound concentration of tazobactam active of at least 1 microgram/mL for at least 20% of the time between successive treatment days.

5. The method of claim 3, wherein the dosing schedule provides an unbound concentration of tazobactam active of at least 0.5 micrograms/mL for at least 50% of the time between successive treatment days.

6. The method of claim 1, wherein the loading dose and maintenance doses are administered over a dosing schedule that provides an unbound concentration of ceftolozane active of at least 8 micrograms/mL for at least 40% of the time between successive treatment days.

7. The method of claim 6, wherein the dosing schedule provides an unbound concentration of tazobactam active of at least 1 microgram/mL for at least 20% of the time between successive treatment days.

8. The method of claim 6, wherein the dosing schedule provides an unbound concentration of tazobactam active of at least 0.5 micrograms/mL for at least 50% of the time between successive treatment days.

9. The method of claim 3, wherein the daily AUC of ceftolozane is less than 1,100 µg·hr/mL.

10. The method of claim 1, wherein the first maintenance dose following completion of hemodialysis is administered to the patient within 3 hours following completion of hemodialysis.

11. The method of claim 1, wherein the first maintenance dose following completion of hemodialysis is administered to the patient within 2 hours following completion of hemodialysis.

12. The method of claim 1, wherein the first maintenance dose following completion of hemodialysis is administered to the patient within 1 hour following completion of hemodialysis.

13. The method of claim 1, wherein the pharmaceutically acceptable salt of ceftolozane is ceftolozane sulfate.

14. The method of claim 1, wherein the pharmaceutically acceptable salt of tazobactam is tazobactam sodium.

15. A method of treating pneumonia in a human patient with end stage renal disease on hemodialysis, said method comprising administering to the patient a single loading dose comprising ceftolozane or a pharmaceutically acceptable salt thereof and tazobactam or a pharmaceutically acceptable salt thereof that provides a 2:1 ratio of ceftolozane active to tazobactam active, followed by administering to the patient maintenance doses comprising ceftolozane or a pharmaceutically acceptable salt thereof and tazobactam or a pharmaceutically acceptable salt thereof that provides a 2:1 ratio of ceftolozane active to tazobactam active, wherein the ratio of ceftolozane active in the loading dose to ceftolozane active in the maintenance doses is 5:1 by weight, and the ratio of tazobactam active in the loading dose to tazobactam active in the maintenance doses is 5:1 by weight.

16. The method of claim 15, wherein the maintenance doses are delivered intravenously about every 8 hours.

17. The method of claim 15, wherein the loading dose and maintenance doses are administered over a dosing schedule that provides an unbound concentration of ceftolozane active of at least 8 micrograms/mL for at least 30% of the time between successive treatment days.

18. The method of claim 17, wherein the dosing schedule provides an unbound concentration of tazobactam active of at least 1 microgram/mL for at least 20% of the time between successive treatment days.

19. The method of claim 17, wherein the dosing schedule provides an unbound concentration of tazobactam active of at least 0.5 micrograms/mL for at least 50% of the time between successive treatment days.

20. The method of claim 15, wherein the loading dose and maintenance doses are administered over a dosing schedule that provides an unbound concentration of ceftolozane active of at least 8 micrograms/mL for at least 40% of the time between successive treatment days.

21. The method of claim 20, wherein the dosing schedule provides an unbound concentration of tazobactam active of at least 1 microgram/mL for at least 20% of the time between successive treatment days.

22. The method of claim 20, wherein the dosing schedule provides an unbound concentration of tazobactam active of at least 0.5 micrograms/mL for at least 50% of the time between successive treatment days.

23. The method of claim 17, wherein the daily AUC of ceftolozane is less than 1,100 µg·hr/mL.

24. The method of claim 15, wherein the first maintenance dose following completion of hemodialysis is administered to the patient within 3 hours following completion of hemodialysis.

25. The method of claim 15, wherein the first maintenance dose following completion of hemodialysis is administered to the patient within 2 hours following completion of hemodialysis.

26. The method of claim 15, wherein the first maintenance dose following completion of hemodialysis is administered to the patient within 1 hour following completion of hemodialysis.

27. The method of claim 15, wherein the pharmaceutically acceptable salt of ceftolozane is ceftolozane sulfate.

28. The method of claim 15, wherein the pharmaceutically acceptable salt of tazobactam is tazobactam sodium.

29. The method of claim 1, wherein the pneumonia is nosocomial pneumonia.

30. The method of claim 1, wherein the pneumonia is caused by one or more microorganisms selected from the group consisting of *Enterobacter cloacae, Escherichia coli, Haemophilus influenzae, Klebsiella oxytoca, Kiebsiella pneumoniae, Proteus Pseudomonas aeruginosa*, and *Serratia marcescens*.

31. The method of claim 30, wherein the pneumonia is caused by *Pseudomonas aeruginosa*.

32. The method of claim 15, wherein the pneumonia is nosocomial pneumonia.

33. The method of claim 15, wherein the pneumonia is caused by one or more microorganisms selected from the group consisting of *Enterobacter cloacae, Escherichia coli, Haemophilus influenzae, Klebsiella oxytoca, Kiebsiella pneumoniae, Proteus mirabilis, Pseudomanas aeruginosa*, and *Serratia marcescens*.

34. The method of claim 33, wherein the pneumonia is caused by *Pseudomonas aeruginosa*.

\* \* \* \* \*